(12) United States Patent
Jia

(10) Patent No.: US 12,038,445 B2
(45) Date of Patent: Jul. 16, 2024

(54) LIVER DISEASE-RELATED BIOMARKERS AND METHODS OF USE THEREOF

(71) Applicant: Human Metabolomics Institute, Inc., Guangdong (CN)

(72) Inventor: Wei Jia, Honolulu, HI (US)

(73) Assignee: HUMAN METABOLOMICS INSTITUTE, INC., Shenzhen (CN)

(*) Notice: Subject to any disclaimer, the term of this patent is extended or adjusted under 35 U.S.C. 154(b) by 812 days.

(21) Appl. No.: 16/305,718

(22) PCT Filed: May 30, 2017

(86) PCT No.: PCT/US2017/034915
§ 371 (c)(1),
(2) Date: Nov. 29, 2018

(87) PCT Pub. No.: WO2017/210147
PCT Pub. Date: Dec. 7, 2017

(65) Prior Publication Data
US 2020/0378991 A1 Dec. 3, 2020

Related U.S. Application Data

(60) Provisional application No. 62/343,010, filed on May 29, 2016.

(51) Int. Cl.
G01N 33/68 (2006.01)
G01N 30/72 (2006.01)
G01N 30/02 (2006.01)

(52) U.S. Cl.
CPC ..... *G01N 33/6893* (2013.01); *G01N 30/7233* (2013.01); *G01N 2030/025* (2013.01);
(Continued)

(58) Field of Classification Search
CPC .... C08F 210/02; C08F 212/08; C08F 255/02; C08F 4/65912; C08F 4/6592; C08F 212/36; C08F 297/02; C08F 110/06; C08F 210/00; C08F 212/34; C08F 255/00; C08F 2800/10; C08F 2800/20; C08F 295/00; C08F 4/65927; B41J 2/1603; B41J 2/1631; B41J 2/1642; B41J 2/14129; B41J 2/1628; B41J 2/1629; B41J 2/1645; B41J 2/1646; B41J 2/14072; B41J 2/14088; B41J 2/1433; B41J 2/1601; B41J 2/1626; B41J 2/1634; B41J 2/1639; B41J 2/1643; B41J 2002/14387; B41J 2202/03; B41J 2/0455; B41J 2/0458; B41J 2/05; B41J 2/1412; B41J 2/162; B41J 2/1632; B41J 2/1635; B41J 2/1637; B41J 2002/14403; B41J 2202/13; C08L 51/06; C08L 53/00; C08L 23/10; C08L 25/08; C08L 51/003; C08L 53/025; C08L 2207/04; C08L 23/04; C08L 55/02; C08L 71/12; C08L 71/123; C08L 101/00; C08L 23/02; C08L 23/12; C08L 25/06; C08L 2666/02; C08L 2666/06; C08L 51/00; C08L 51/04; C08L 53/02; C08L 91/00; C08J 3/24; C08J 2371/12; C08J 3/22; B32B 27/32; B32B 2274/00; B32B 2307/584; B32B 2509/00; B32B 2535/00; B32B 2605/00; B32B 27/08; B32B 27/30; B32B 27/302; B32B 27/18; B32B 27/28; B32B 7/02; C04B 41/009; C04B 35/565; C04B 38/0615; C04B 2111/00405; C04B 2111/00431; C04B 2111/00793; C04B 2111/2084; C04B 2111/343; C04B 2235/428; C04B 2235/96; C04B 35/20; C04B 35/22; C04B 35/515; C04B 38/0009; C04B 38/0625; C04B 41/5027; C04B 41/5096; C04B 41/51; C04B 41/85; C04B 41/87; C04B 41/88; C09K 5/16; B22D 41/02; B60R 13/02; B41M 1/18; B41M 3/14; B41M 3/144; C08K 3/00; C08K 3/04; C09D 11/50; H04N 21/439; H04N 21/44; H04N 21/4402; H04N 21/442; H04N 5/14; H04N 5/57; A61P 1/16; G01N 2030/025; G01N 2030/027; G01N 2800/085; G01N 2800/52; G01N 30/7233; G01N 33/6893; B64C 2001/0081
See application file for complete search history.

(56) References Cited

U.S. PATENT DOCUMENTS 10,073,077 B2 * 9/2018 Matsuura ............ H01J 49/0036
2011/0092592 A1 4/2011 Yano
(Continued)

FOREIGN PATENT DOCUMENTS

CA 2662987 A1 8/2007
CN 106520888 * 3/2020 .............. C12P 33/00
(Continued)

OTHER PUBLICATIONS

Kuiper et al. HEPATOLOGY 2010, vol. 52: pp. 1334-1340.*
(Continued)

*Primary Examiner* — Bao Q Li

(57) ABSTRACT

The present invention provides biomarker and biomarker panels useful for diagnostic methods evaluating liver disease status in a subject, monitoring liver disease, distinguishing between liver diseases, treating subjects evaluated by diagnostic methods of the invention, providing diagnostic tests for evaluating liver disease status in a subject, and kits therefor.

9 Claims, 69 Drawing Sheets

(52) U.S. Cl.
CPC . *G01N 2030/027* (2013.01); *G01N 2800/085* (2013.01); *G01N 2800/52* (2013.01)

(56) References Cited

U.S. PATENT DOCUMENTS

| | | | |
|---|---|---|---|
| 2015/0355197 | A1 | 12/2015 | Kamp et al. |
| 2015/0377910 | A1 | 12/2015 | McCreedy et al. |
| 2016/0169862 | A1* | 6/2016 | Matsuura ............... G01N 33/50 435/7.92 |

FOREIGN PATENT DOCUMENTS

| | | | | |
|---|---|---|---|---|
| JP | 2010500566 | A | 1/2010 | |
| JP | 2011232164 | A | 11/2011 | |
| JP | 2013533471 | A1 | 8/2013 | |
| TW | 2007/45556 | A | 12/2007 | |
| WO | 2009151125 | A1 | 12/2009 | |
| WO | WO 2012/049874 | A1 | 4/2012 | |
| WO | WO2015/019976 | * | 2/2015 | ............. G01N 33/52 |
| WO | WO201509976 | A * | 2/2015 | ............. G01N 33/50 |
| WO | WO 2015/106129 | A1 | 7/2015 | |
| WO | 2016081534 | A1 | 5/2016 | |
| WO | WO 2017/210147 | A1 | 12/2017 | |

OTHER PUBLICATIONS

May 19, 2020 European Extended Search Report issued by European Patent Office for European Patent Application No. 17807309.4.
Jun. 22, 2021 First Office Action issued by European Patent Office for European Patent Application No. 17807309.4.
Mar. 21, 2022 Second Office Action issued by European Patent Office for European Patent Application No. 17807309.4.
May 17, 2021 Notice of Refusal issued by the Japanese Patent Office for Japanese Patent Application No. 2019-514204 and its English translation.
Jiang-Shan Lian et al, "A serum metabonomic study on the difference between alcohol- and HBV-induced liver cirrhosis by ultraperformance liquid chromatography coupled to mass spectrometry plus quadrupole time-of-flight mass spectrometry", Chinese medical journal, China, doi:10.3760/cma.j.issn.0366-6999.2011.09.018, (May 1, 2011), pp. 1367-1373, URL.
Habtom W. Ressom et al, "Utilization of metabolomics to identify serum biomarkers for hepatocellular carcinoma In patients with liver cirrhosis", Analytica Chimica Acta, Amsterdam, NL, (20120901), vol. 743, doi:10.1016/j.aca.2012.07.013.
Yang F et al, "Evaluation of the protective effect of Rhei Radix et Rhizoma against alpha-naphthylisothiocyanate induced liver injury based on metabolic profile of bile acids", Journal of Ethnopharmacology, Elsevier Ireland Ltd, IE, (Feb. 1, 2013), ISSN 0378-8741, pp. 599-604.
Baohong Wang et al, "Metabonomic Profiles Discriminate Hepatocellular Carcinoma from Liver Cirrhosis by Ultraperformance Liquid Chromatography-Mass Spectrometry", Journal of Proteome Research, (Jan. 18, 2012), vol. 11, No. 2, doi:10.1021/pr2009252, ISSN 1535-3893, pp. 1217-1227.
Masubuchi Noriko et al, "Oxidative stress markers, secondary bile acids and sulfated bile acids classify the clinical liver injury type: Promising diagnostic biomarkers for cholestasis", Chemico-Biological Interactions, Elsevier Science Irland, IR, (Aug. 30, 2015), vol. 255, doi:10.1016/J.CBI.2015.08.016, ISSN 0009-2797, pp. 83-91.
Ferslew Brian C et al, "Altered Bile Acid Metabolome in Patients with Nonalcoholic Steatohepatitis", Digestive Diseases and Sciences, Springer New York LLC, US, vol. 60, No. 11, doi:10.1007/S10620-015-3776-8, ISSN 0163-2116, (Jul. 3, 2015), pp. 3318-3328.
Sai Praneeth R. Bathena et al, "Urinary Bile Acids as Biomarkers for Liver Diseases II. Signature Profiles in Patients", Toxicological Sciences, (Oct. 24, 2014), vol. 143, No. 2, doi:10.1093/toxsci/kfu228, ISSN 1096-6080, pp. 308-318.
Beyoglu Diren et al, "The metabolomic window into hepatobiliary disease", Journal of Hepatology, Elsevier, Amsterdam, NL, (May 25, 2013), vol. 59, No. 4, doi:10.1016/J.JHEP.2013.05.030, ISSN 0168-8278, pp. 842-858.
International Search Report dated Sep. 21, 2017 in connection with PCT International Application No. PCT/US2017/034915.
Mekhtiev, S.N. et al., "Modern concepts of liver fibrosis and methods of its correction, " *FARMATEKA*, 2014, No. 6.
Miethke, A.G. et al., "Pharmacological inhibition of ASBT changes bile composition and blocks progression of sclerosing cholangitis in mdr2 knockout mice, " *Hepatology*, Feb. 2016.
Written Opinion of the International Searching Authority dated Sep. 21, 2017 in connection with PCT International Application No. PCT/US2017/034915.
Xiao, J.F. et al., "LC-MS based serum metabolomics for identification of hepatocellular carcinoma biomarkers in Egyptian cohort, " *J Proteome Res*, Dec. 7, 2012.
Feb. 15, 2023 3rd European Office Action issued in European Patent Application No. 17807309.4.
Mar. 28, 2023 Notice of Reasons for Refusal issued in Japanese Patent Application No. 2022-032114.
Yunpeng Qi et al., Bile acid signaling in lipid metabo lism: metabolomicand lipidomic analysis of lipid and bile acid markerslinked to anti-obesity and anti-diabetes in mice, Biochim Biophys Acta, Jan., 2015, 1851(1), 19-29.
Xie Guoxiang et al., Serum metabolite profiles are associated with the presence of advanced liver fibrosis in Chinese patients with chronic hepatitis B viral infection, BMC Medicine, Jun. 5, 2020, 18(144), 1-15, doi.org/10.1186/s12916-020-01595-w.

* cited by examiner

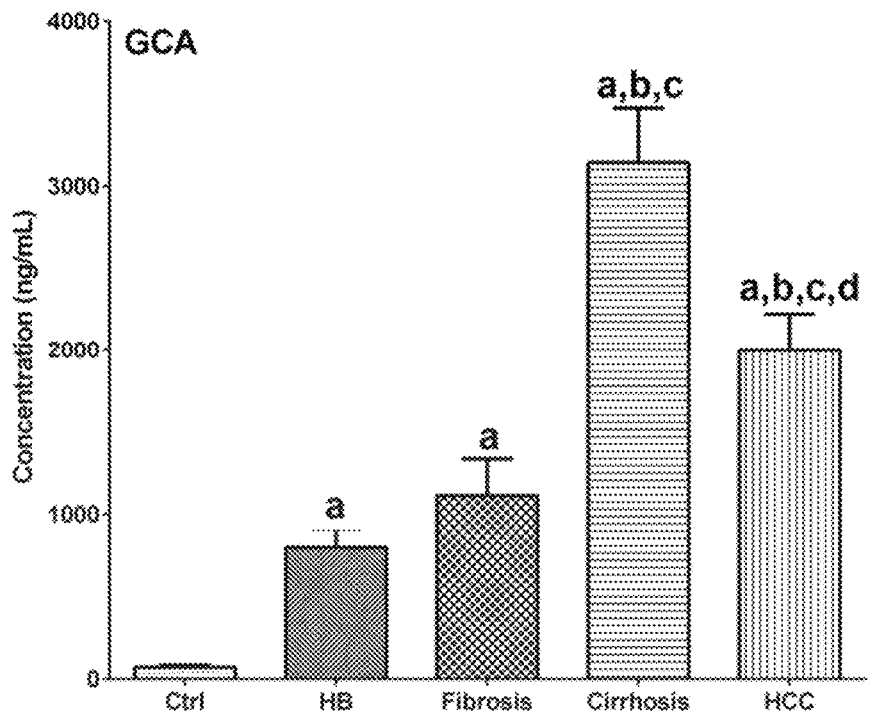
Fig. 17E1
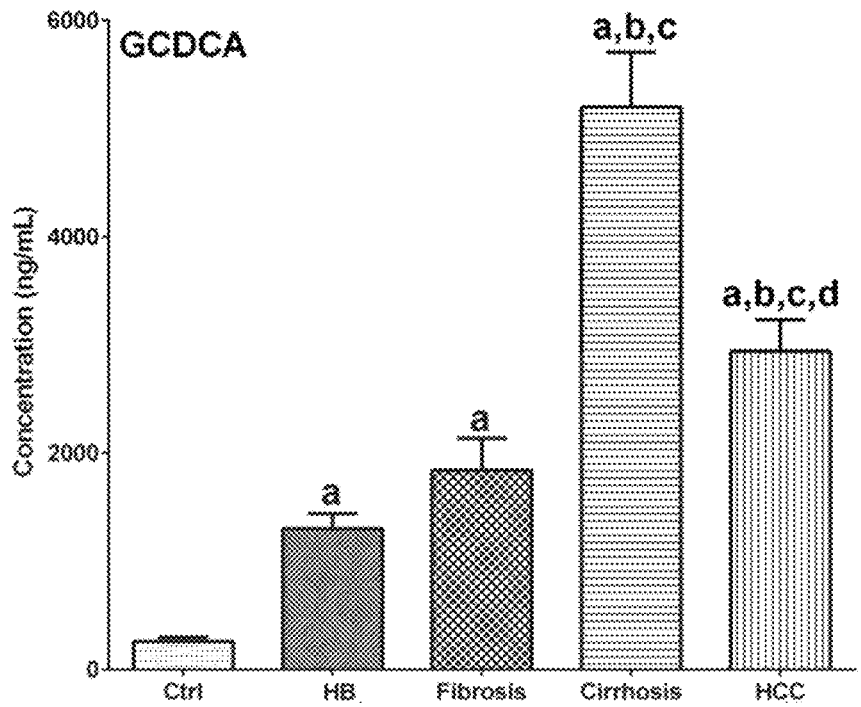
Fig. 17E2

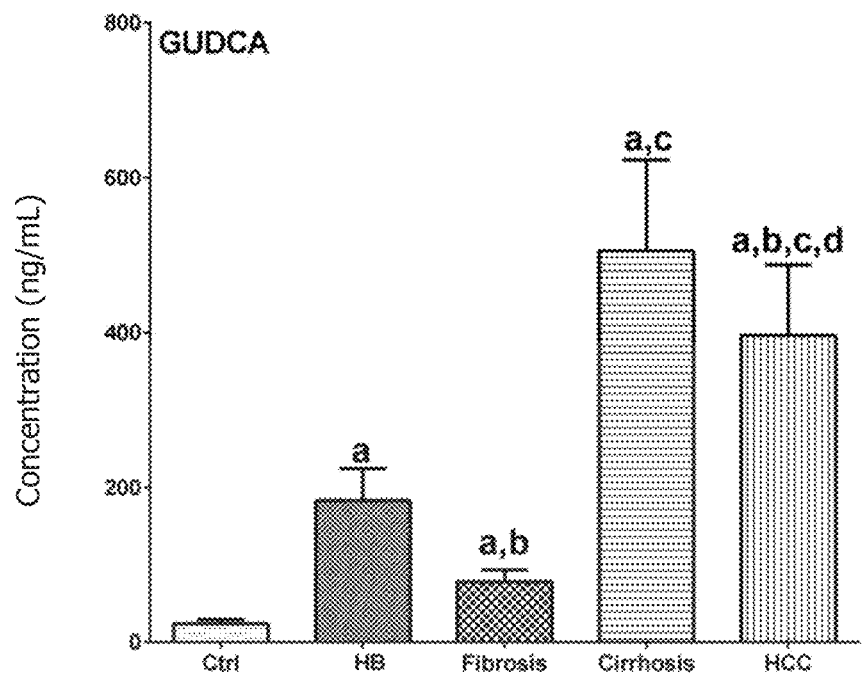
Fig. 17E3
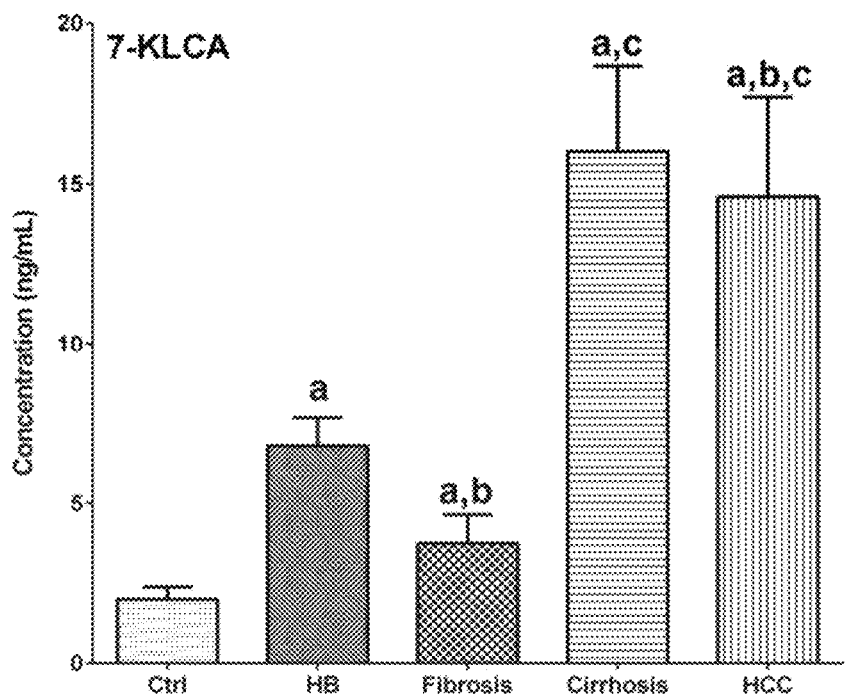
Fig. 17E4

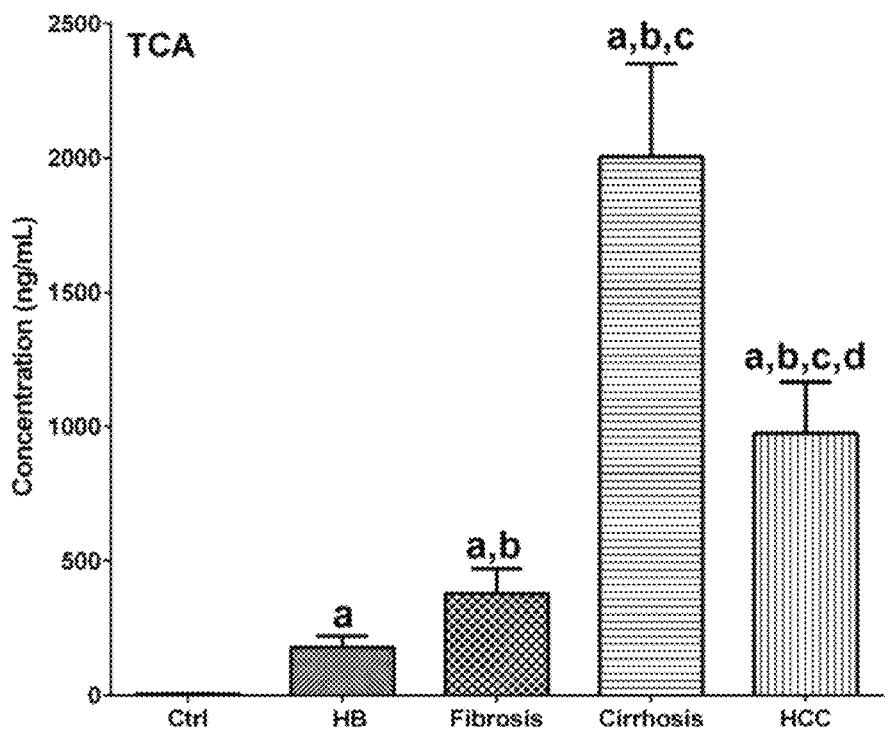
Fig. 17E5
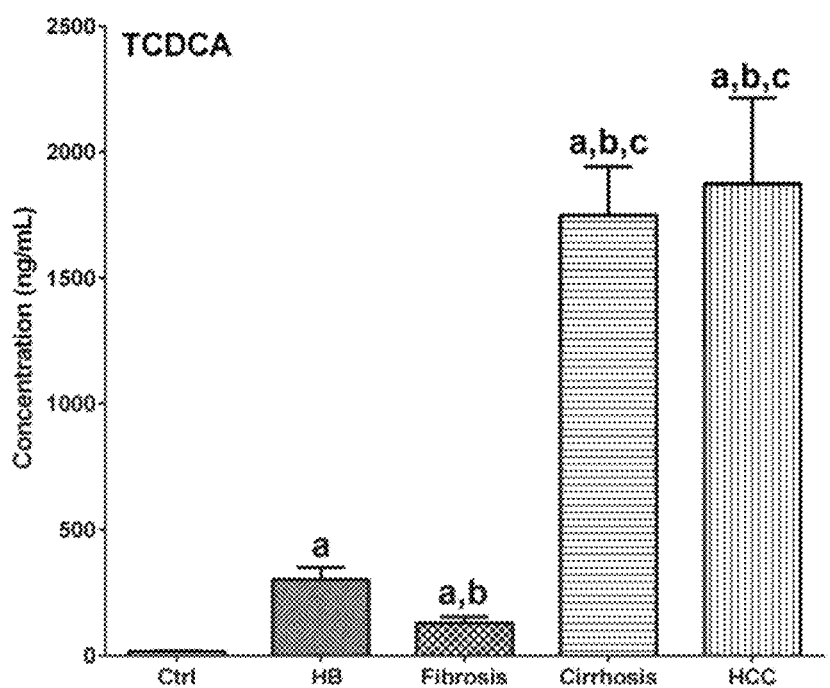
Fig. 17E6

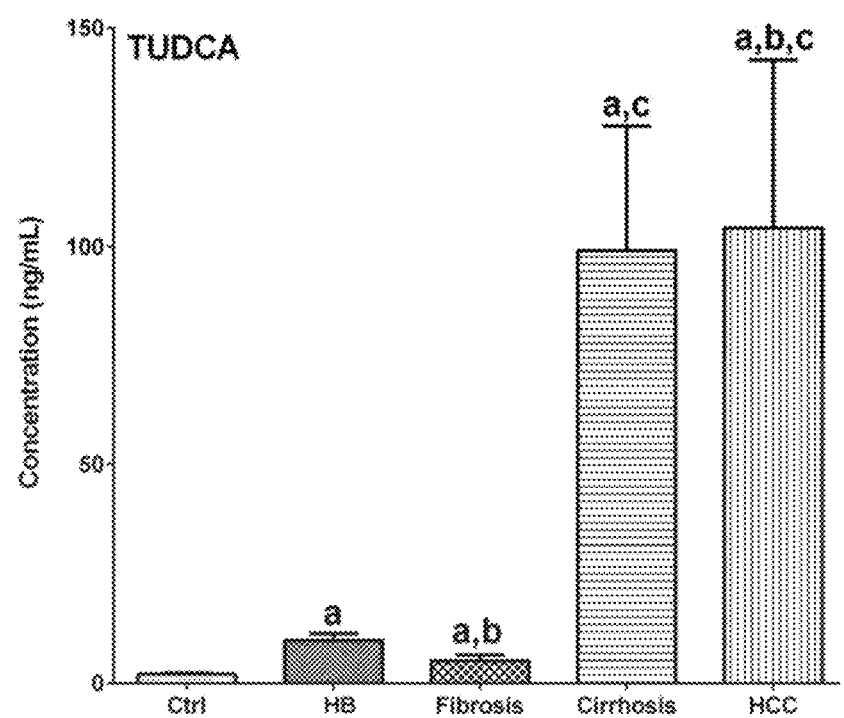
Fig. 17E7

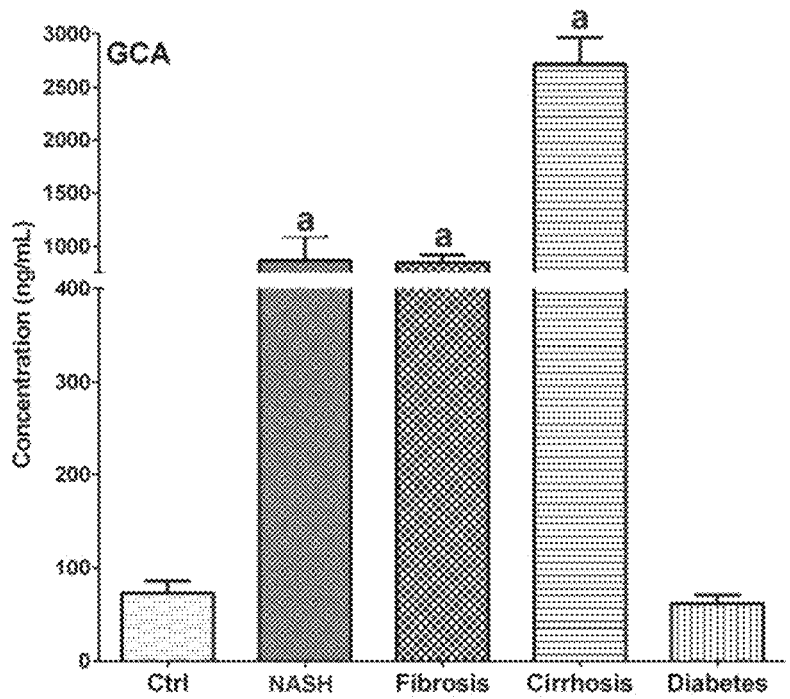
Fig. 19A1
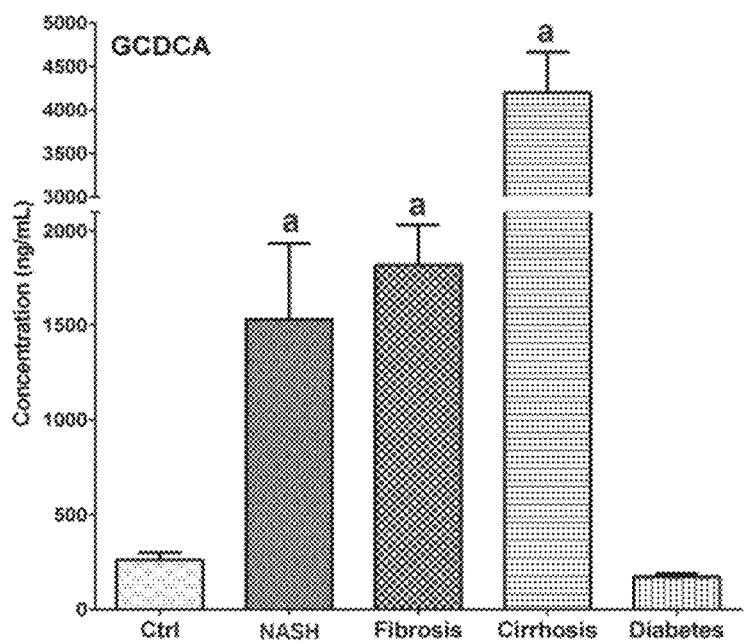
Fig. 19A2

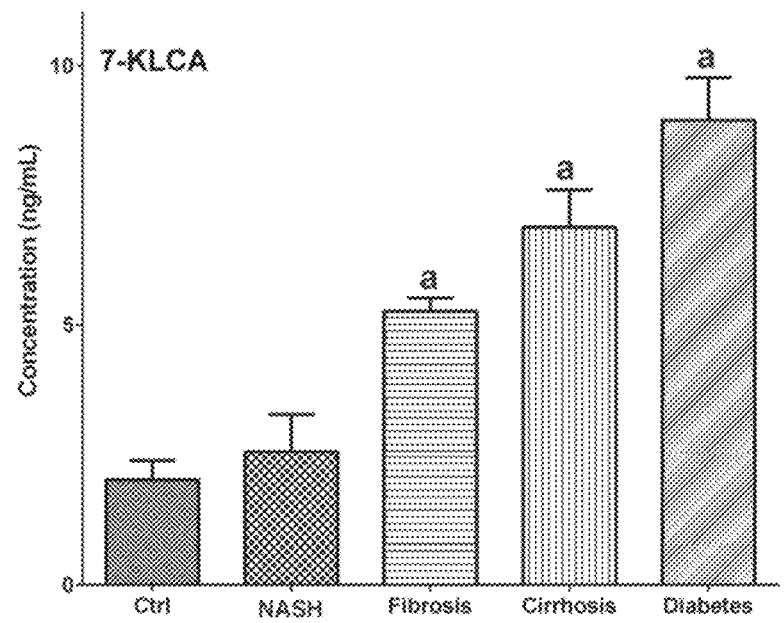
Fig. 19A3
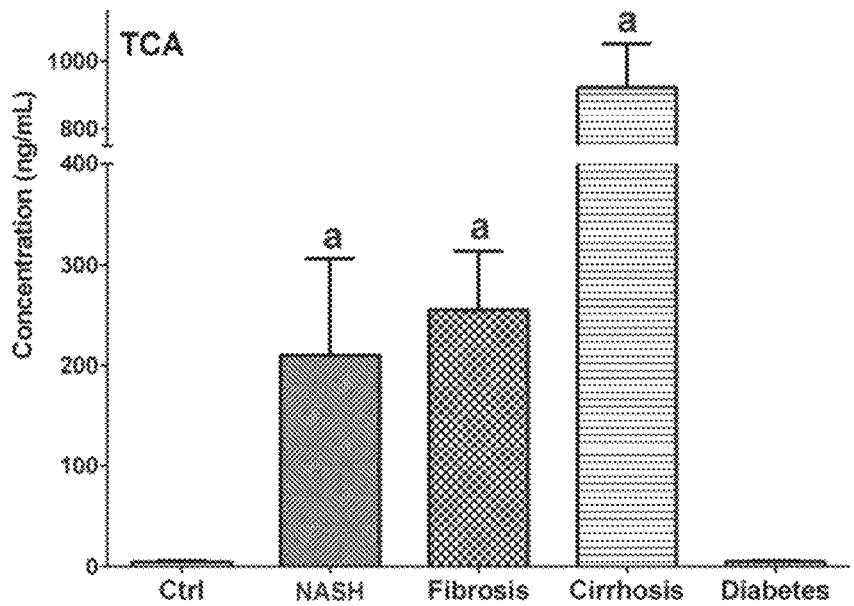
Fig. 19A4

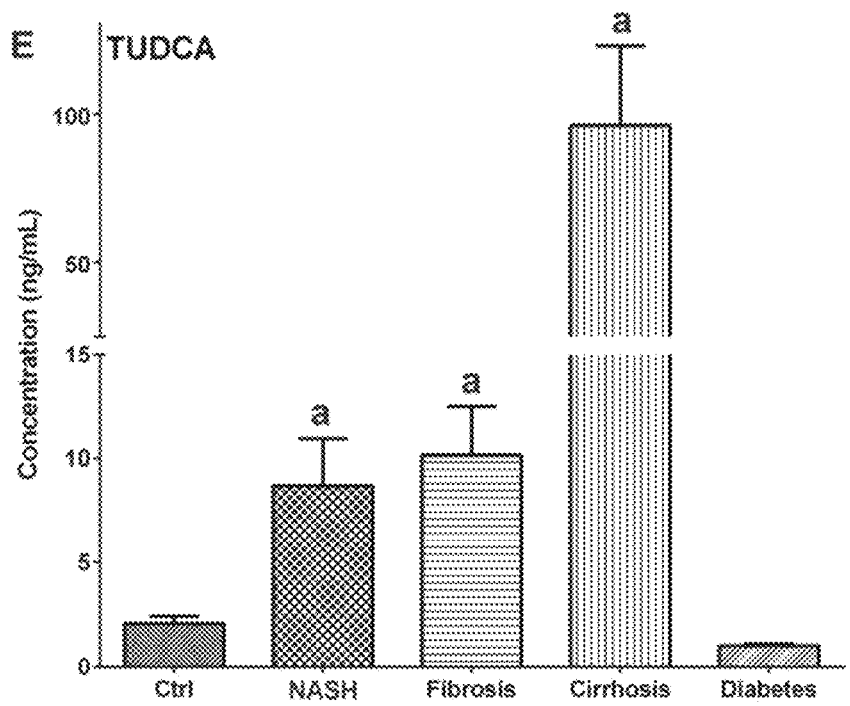
Fig. 19A5
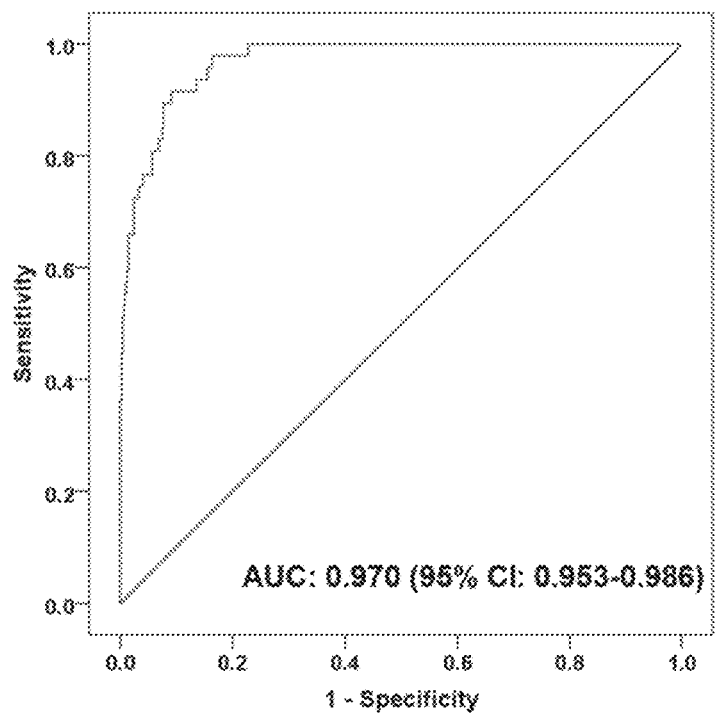
Fig. 19B

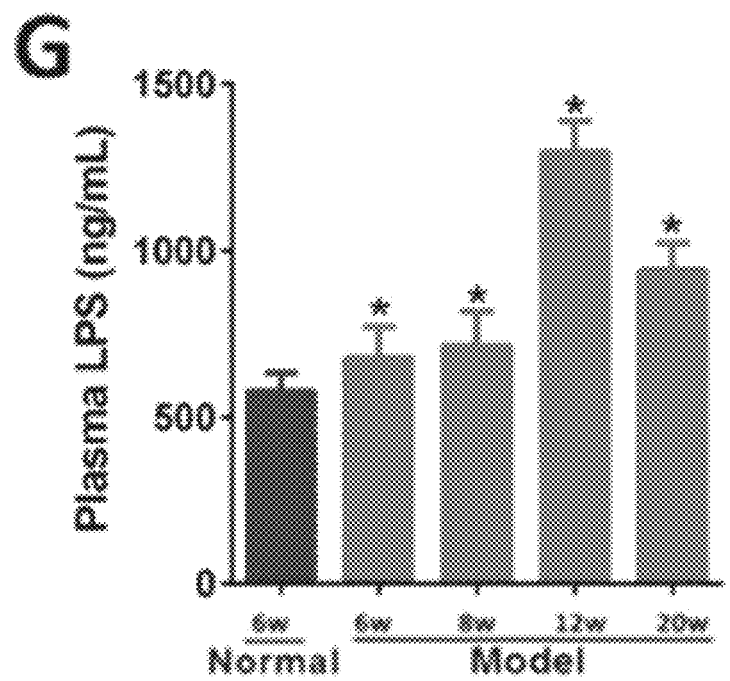
Fig. 23G
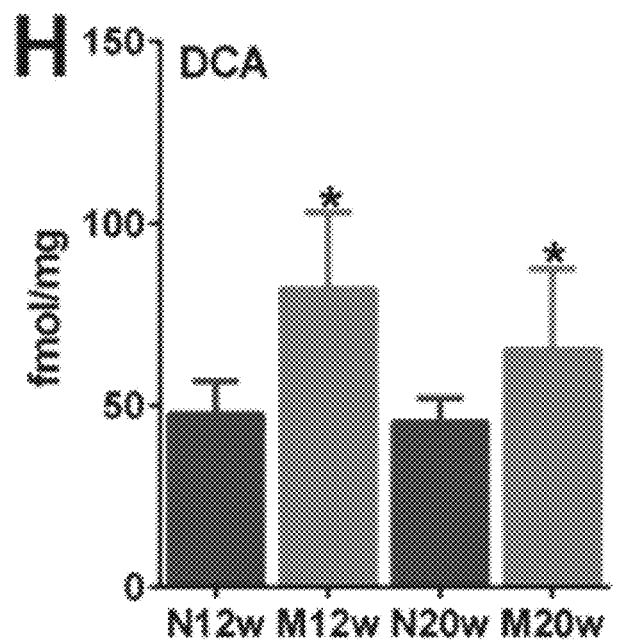
Fig. 23H1

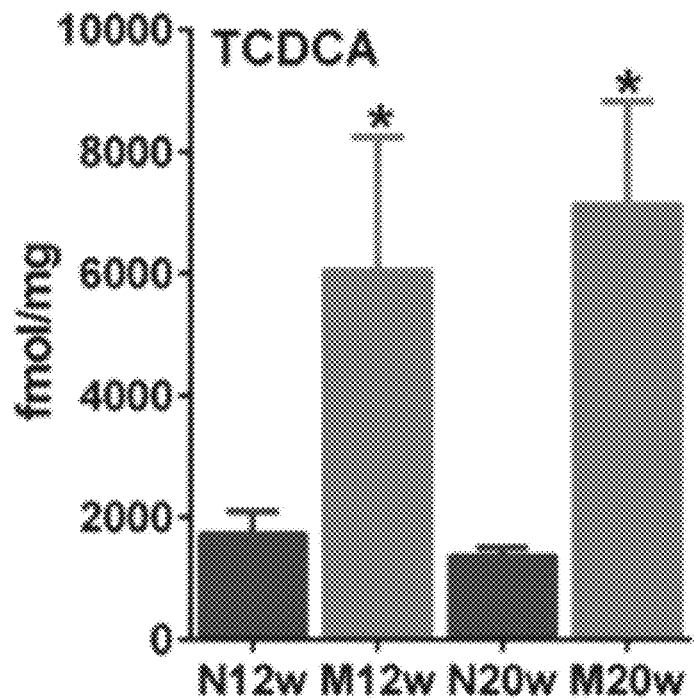
Fig. 23H2
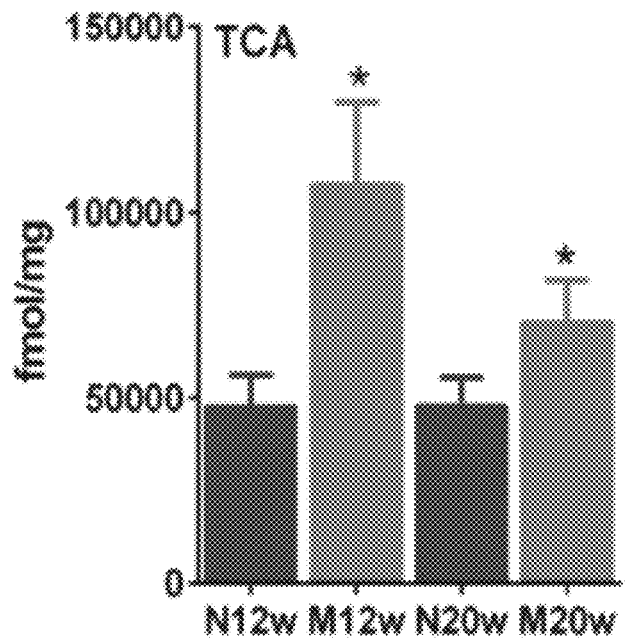
Fig. 23H3

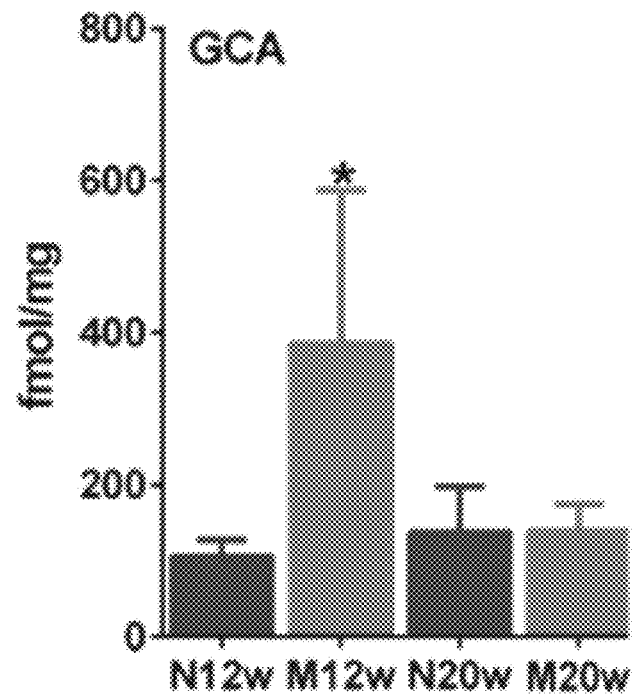
Fig. 23H4
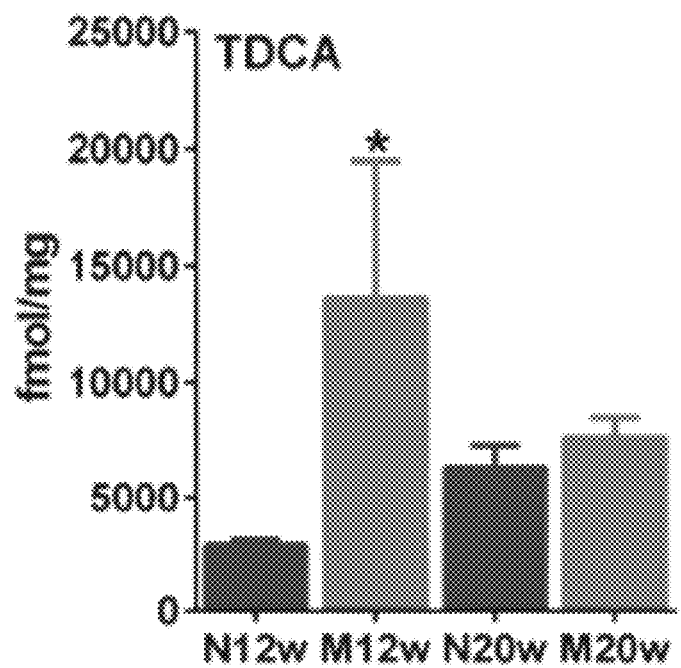
Fig. 23H5

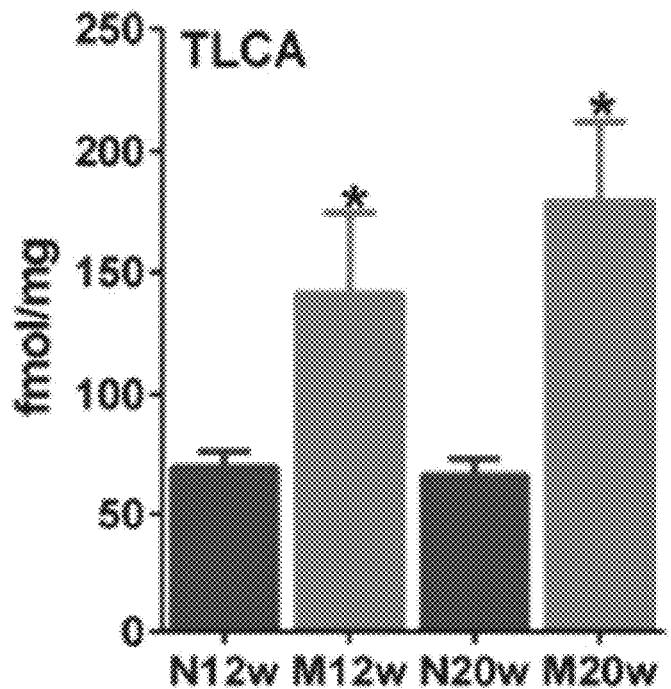
Fig. 23H6
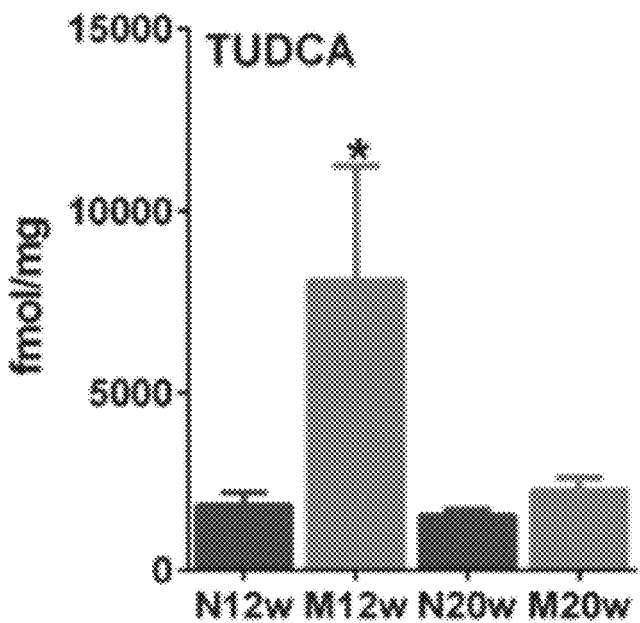
Fig. 23H7

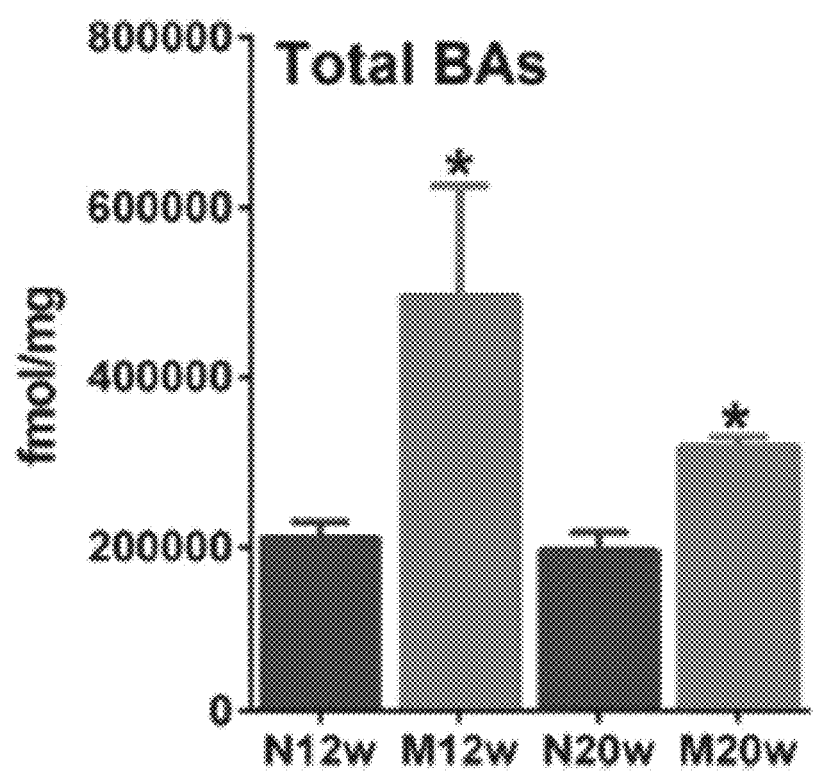
Fig. 23H8

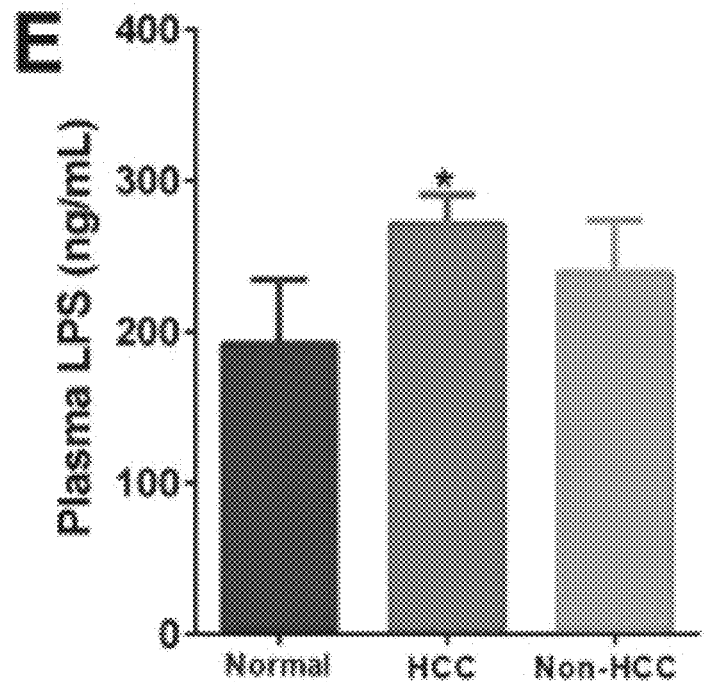
Fig. 24E
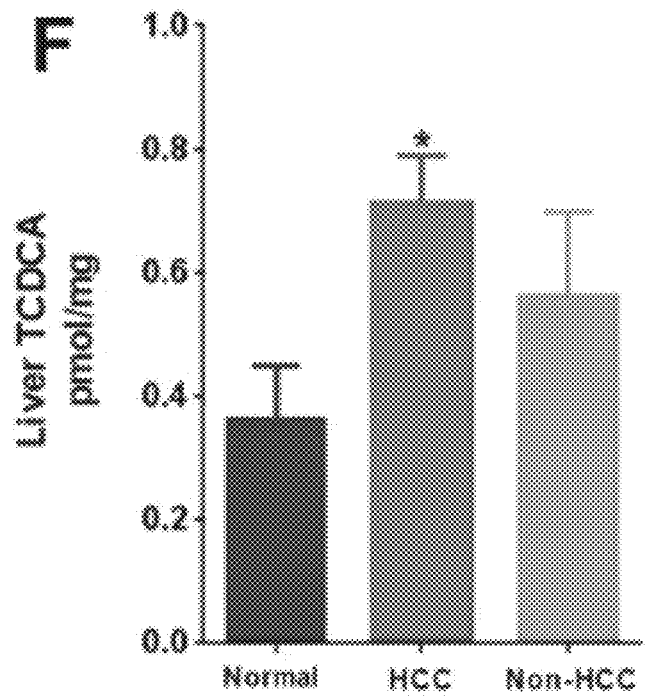
Fig. 24F1

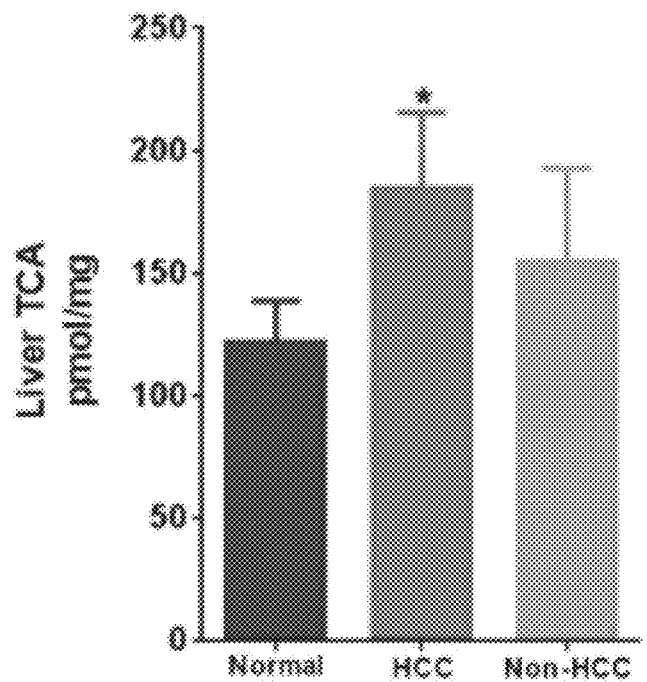
Fig. 24F2
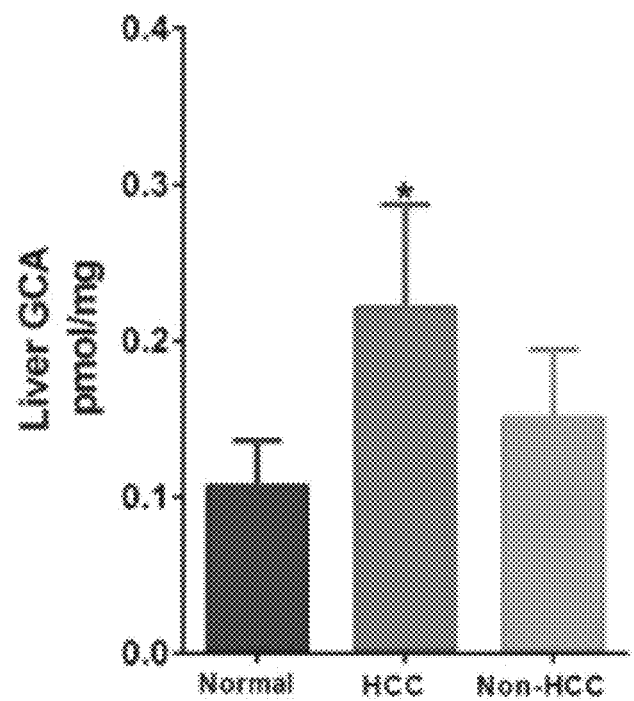
Fig. 24F3

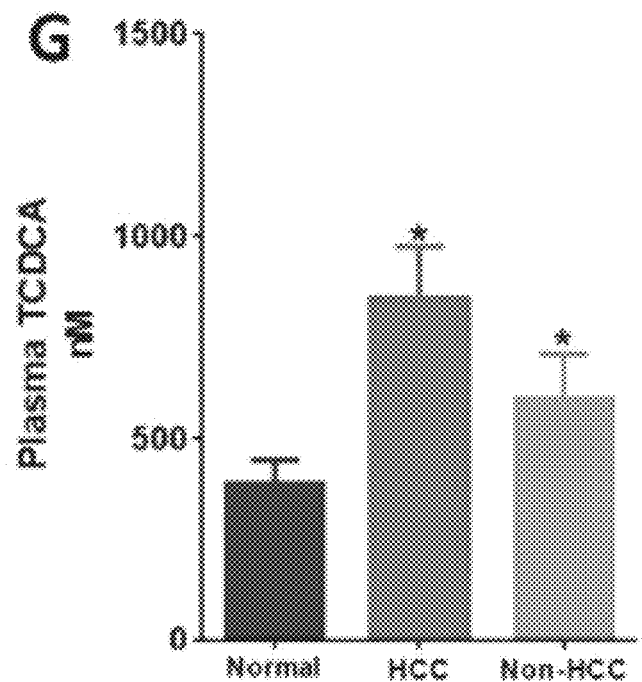
Fig. 24G1
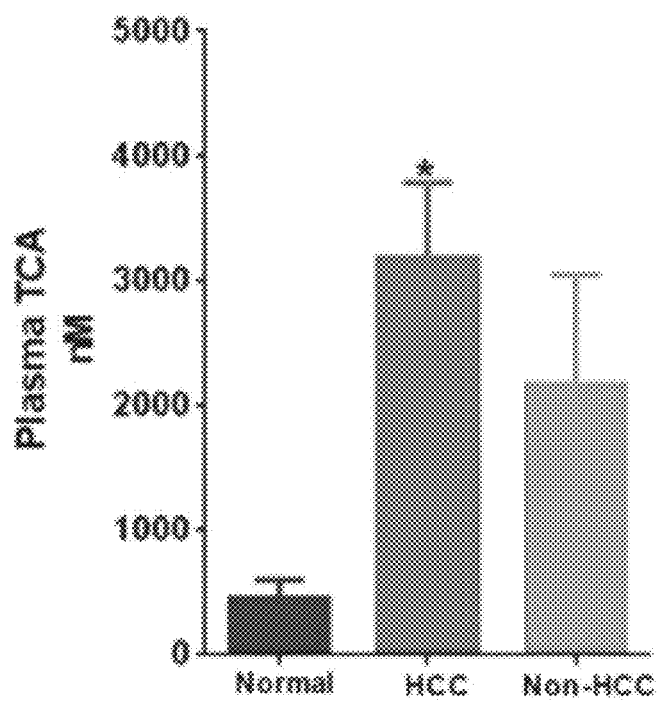
Fig. 24G2

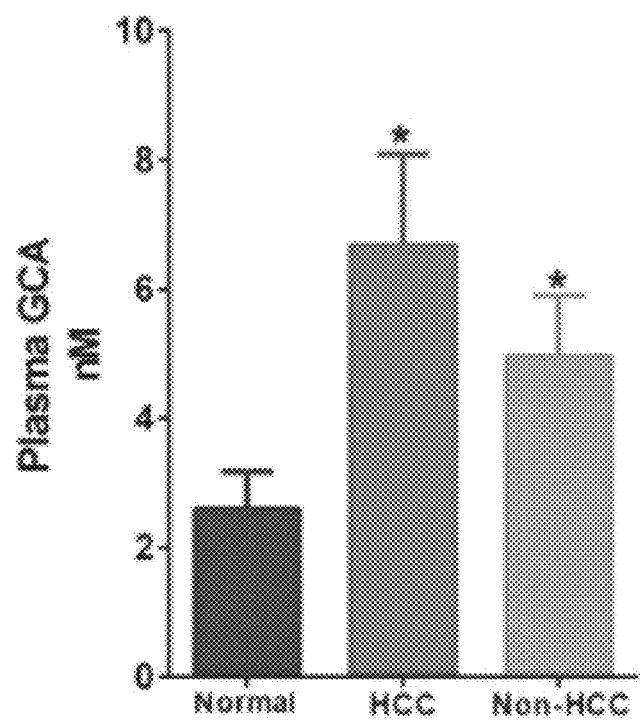
Fig. 24G3

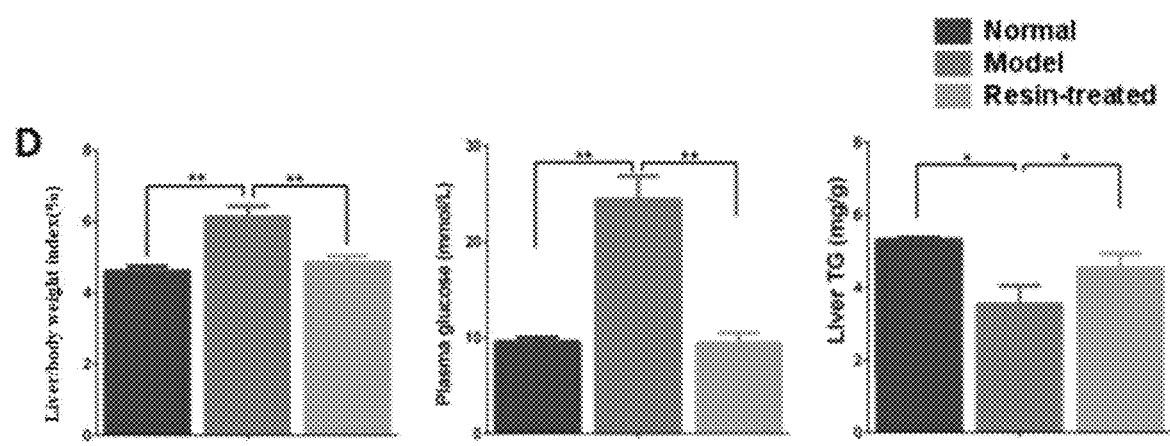
Fig. 25D
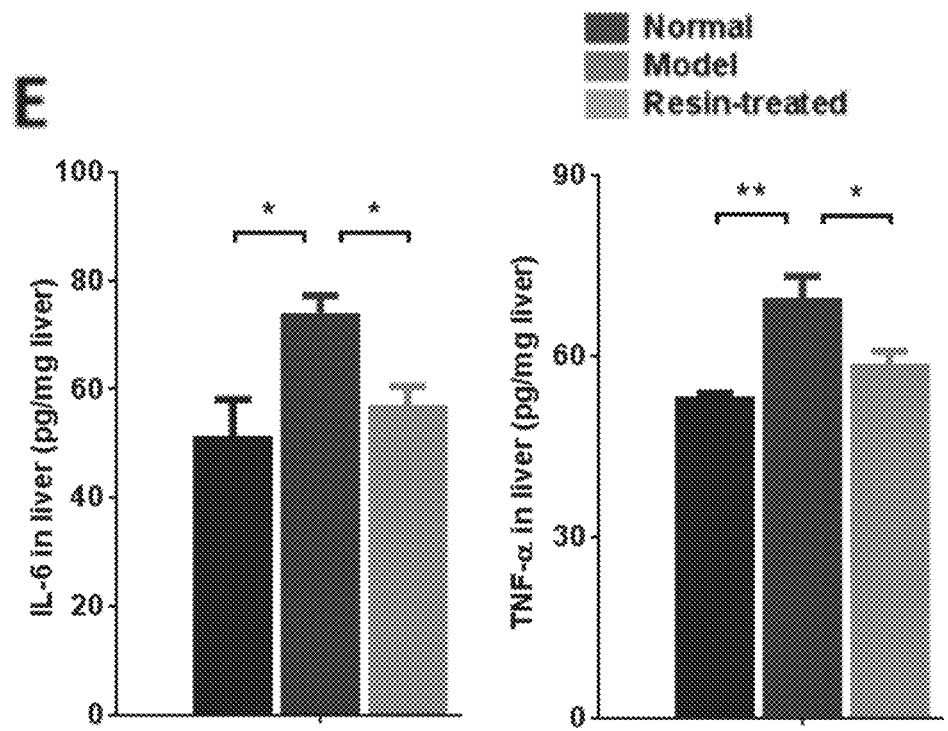
Fig. 25E1

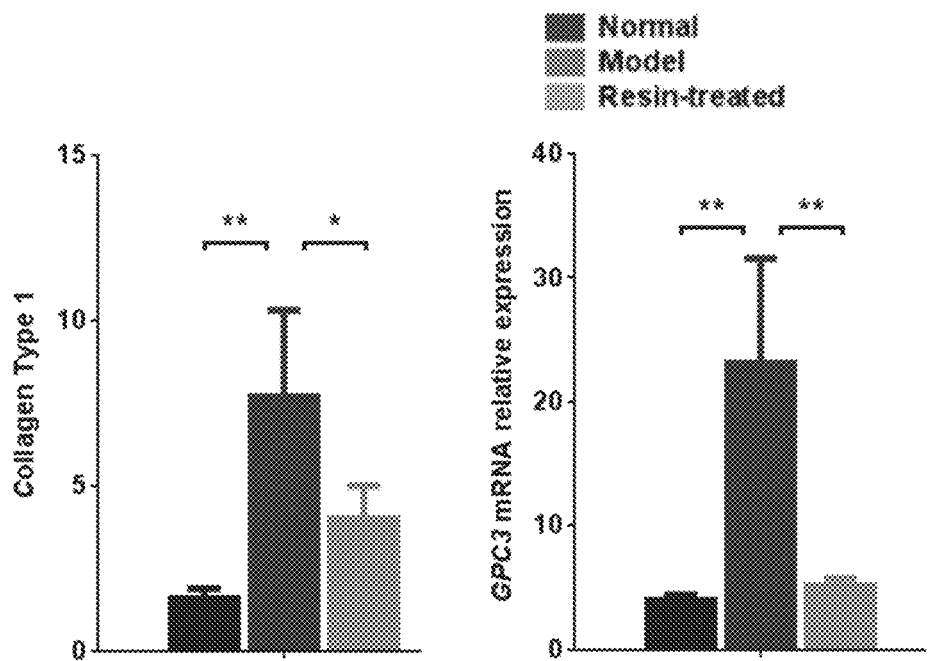
Fig. 25E2
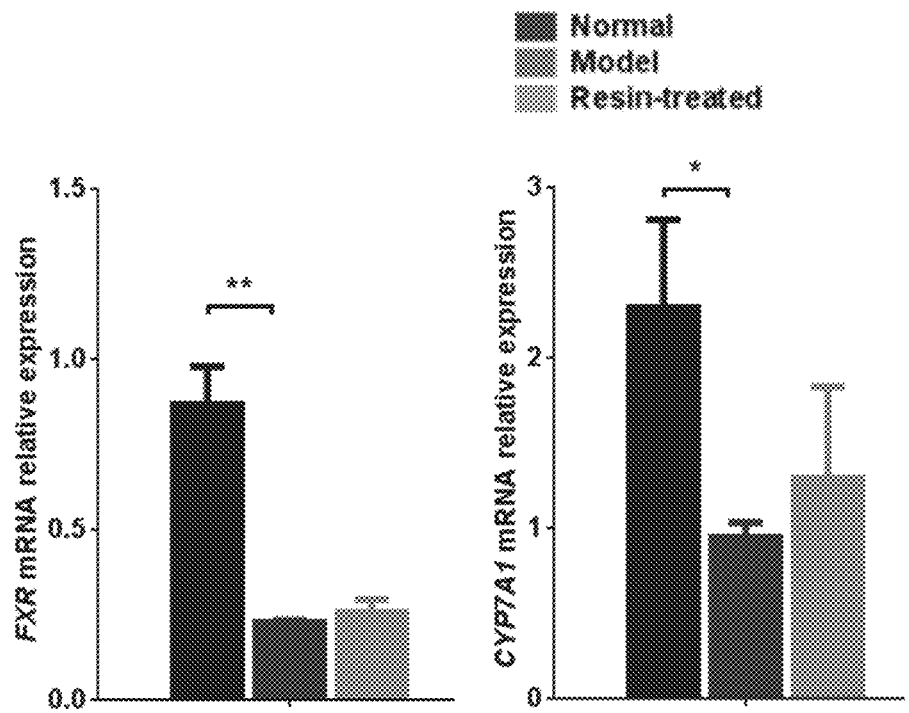
Fig. 25E3

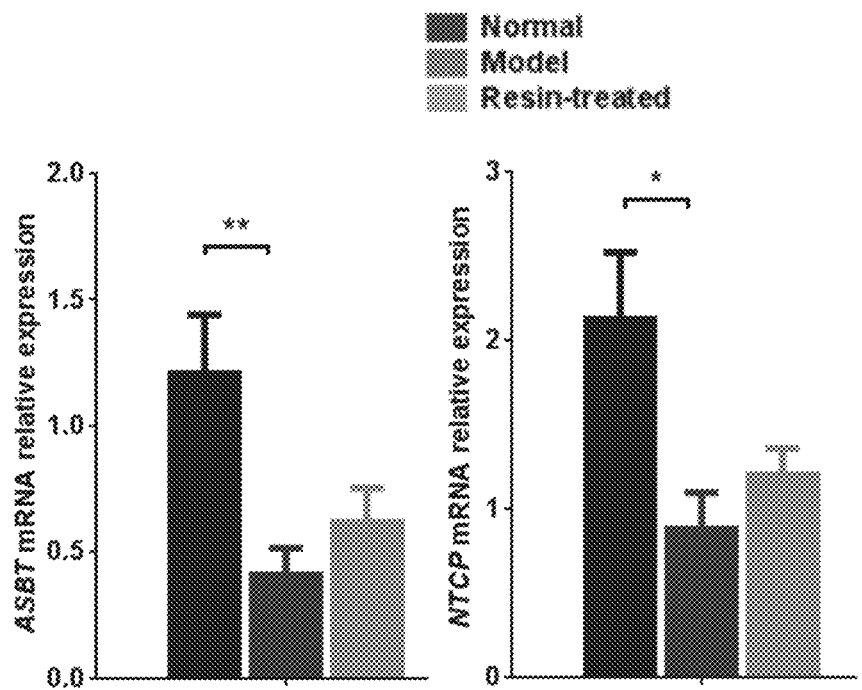
Fig. 25E4
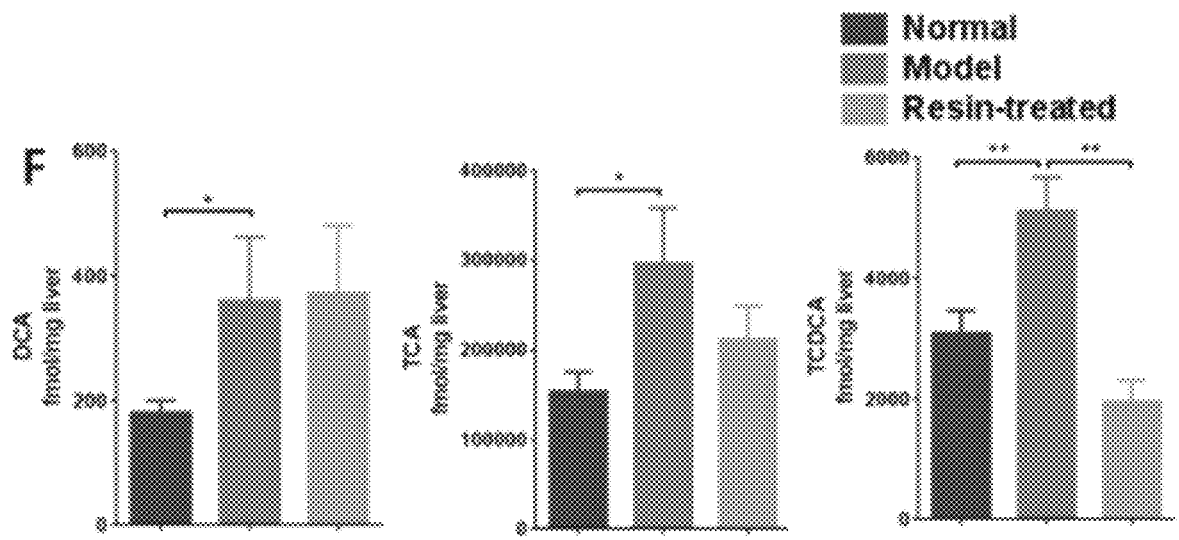
Fig. 25F

| Compound | Chemical structure | Formula |
|---|---|---|
| 264W94 | 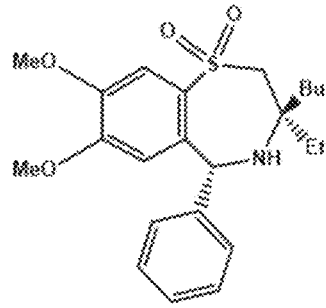 | C₁₉H₂₃N O₃S |
| SC-435 | 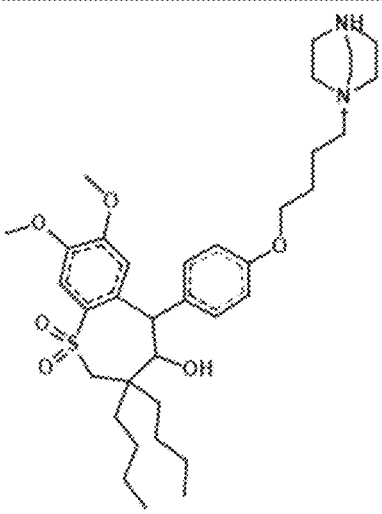 | C₃₁H₄₅N ₂O₅S⁺ |
| R-146224 | 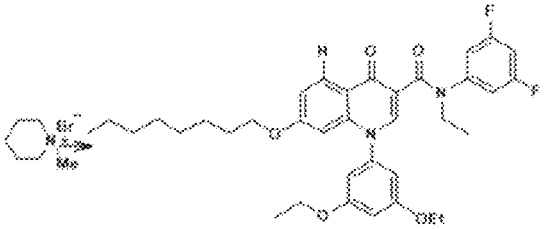 | |
Fig. 32A

| | | |
|---|---|---|
| colestipol | | $(C_4H_{10}N_3)$ $_m(C_3H_6O)_n$ |
| obeticholic acid (OCA) | | $C_{26}H_{44}O_4$ |

Fig. 32C

LIVER DISEASE-RELATED BIOMARKERS AND METHODS OF USE THEREOF

CROSS-REFERENCE TO RELATED APPLICATIONS

This application is a § 371 national stage of PCT International Application No. PCT/US2017/034915, filed May 29, 2017, claiming the benefit of U.S. provisional application No. 62/343,101 filed May 29, 2016, each of which is hereby incorporated by reference.

TECHNICAL FIELD

The present invention relates to biomarkers associated with liver disease, methods of using the biomarkers to diagnose liver disease, monitor liver disease progression, stratify a liver disease, or distinguish between liver diseases, kits there for, and the treatment of a subject diagnosed by a method of invention.

BACKGROUND

Liver fibrosis can be a wound-healing response resulting from liver injury (Chang T T, et al. *Long-term entecavir therapy results in the reversal of fibrosis/cirrhosis and continued histological improvement in patients with chronic hepatitis B. Hepatology* 52, 886-893 (2010); George S L, Bacon B R, Brunt E M, Mihindukulasuriya K L, Hoffmann J, Di Bisceglie A M. *Clinical, virologic, histologic, and biochemical outcomes after successful HCV therapy: a 5-year follow-up of 150 patients. Hepatology* 49, 729-738 (2009)) and is a common cause of chronic failure of liver function and also a main risk factor for hepatocellular carcinoma. Hepatitis B and C virus infections, autoimmune and biliary diseases, alcohol abuse and nonalcoholic steatohepatitis are the most frequent causes of chronic liver disease worldwide, and can lead to liver fibrosis and cirrhosis over years or decades of time (Bataller R, Brenner D A. *Liver fibrosis. The Journal of clinical investigation* 115, 209-218 (2005)). Approximately 15-20% of the patients with fatty liver will progressed to fibrosis and cirrhosis in industrialized countries; among them, around 30-40% will eventually die of liver failure, cancer or recurrence after liver transplantation (Shneider B L, Gonzalez-Peralta R, Roberts E A. *Controversies in the management of pediatric liver disease: Hepatitis B, C and NAFLD: Summary of a single topic conference. Hepatology* 44, 1344-1354 (2006)). Detection and staging of liver fibrosis and progression to cirrhosis have been a longstanding challenge in hepatology. Recent studies indicate that liver fibrosis can be reversed (Chang T T, et al.), thus highlighting the need for long-term monitoring and surveillance for response to therapy in these patients.

An objective assessment of the severity of liver disease in chronic liver disease patients has become increasingly important, such as in decision making prior to treatment and for evaluating patients with mild disease who are not being treated but are rather being followed up expectantly. As liver fibrosis/cirrhosis prevalence increases, it challenges clinicians to identify its progression. In daily clinical routine a reliable serum biomarker for the surveillance of liver fibrosis/cirrhosis status would be desirable. Prognosis and management of chronic liver diseases greatly depend on the amount and progression of liver fibrosis.

Currently, liver biopsy is the gold standard for evaluating the presence and the degree of liver fibrosis. However, its limitations such as invasiveness, sampling errors, and intra- and inter-observer variability create a long felt need for accurate non-invasive tests. Presence of significant fibrosis is an indication for antiviral treatment, and presence of cirrhosis is an indication for specific monitoring of complications related to portal hypertension and to the increased risk of HCC.

Developing simple and reliable noninvasive markers of hepatic disease is an important goal in clinical hepatology and will facilitate the design of clinical trials. However, despite several attempts, the field has failed to produce an acceptable noninvasive solution. These attempts to provide noninvasive methods are usually classified into three categories: (i) serological markers that are composed of routine laboratory tests associated with liver function, (ii) fibrosis biomarkers composed of products of extracellular matrix synthesis and degradation and enzymes involved in those processes, and (iii) imaging techniques that span the spectrum from common liver nonspecific techniques, such as ultrasonic (US), computed tomography (CT) and magnetic resonance imaging (MRI) (Taouli B, Ehman R L, Reeder S B. Advanced MRI methods for assessment of chronic liver disease. AJR American journal of roentgenology 2009; 193:14-27; Brancatelli G, Federle M P, Ambrosini R, et al. Cirrhosis: CT and MR imaging evaluation. European journal of radiology 2007; 61:57-69.), to liver-specific techniques, such as transient elastography (TE) (FibroScan) (Talwalkar J A. Elastography for detecting hepatic fibrosis: options and considerations. Gastroenterology 2008; 135:299-302. Sandrin L, Fourquet B, Hasquenoph J M, et al. Transient elastography: a new noninvasive method for assessment of hepatic fibrosis. Ultrasound in medicine & biology 2003; 29:1705-13. Meng F, Zheng Y, Zhang Q, et al. Noninvasive Evaluation of Liver Fibrosis Using Real-time Tissue Elastography and Transient Elastography (FibroScan). J Ultrasound Med 2015; 34:403-10). However, imaging modalities have limited accuracy in patients with ascites, elevated central venous pressure, and obesity. Among those three categories, the usual serological markers seem to be appealing because of their widespread availability and relatively low cost, but again, have not provided an acceptable solution. These include scoring systems composed of haematological and chemistry laboratory tests, such as the FibroTest (Imbert-Bismut F, Ratziu V, Pieroni L, Charlotte F, Benhamou Y, Poynard T. Biochemical markers of liver fibrosis in patients with hepatitis C virus infection: a prospective study. Lancet 2001; 357:1069-75) the AST to ALT ratio (Sheth S G, Flamm S L, Gordon F D, Chopra S. AST/ALT ratio predicts cirrhosis in patients with chronic hepatitis C virus infection. Am J Gastroenterol 1998; 93:44-8. Park S Y, Kang K H, Park J H, et al. [Clinical efficacy of AST/ALT ratio and platelet counts as predictors of degree of fibrosis in HBV infected patients without clinically evident liver cirrhosis]. Korean J Gastroenterol 2004; 43:246-51) and the APRI index (Wai C T, Greenson J K, Fontana R J, et al. A simple noninvasive index can predict both significant fibrosis and cirrhosis in patients with chronic hepatitis C. Hepatology 2003; 38:518-26) were developed during the past few years and validated as good predictors for the degree of liver fibrosis among HCV patients. However, findings obtained in those studies have been inconsistent. Accordingly, there is still a need for a non-invasive test for liver disease status.

What is needed in the art are biomarker panels capable of determining the presence of a liver disease in a subject, distinguishing between liver diseases, staging liver disease, and monitoring the progression of a liver disease. The literature on the diagnosis of NASH, liver fibrosis, and cirrhosis, and other liver diseases has not disclosed heretofore such a biomarker panel.

SUMMARY OF THE INVENTION

The present invention relates to the identification of biomarkers associated with subjects having a liver disease. The present invention provides panels of biomarkers useful for diagnostic methods, diagnostic kits, and therapeutic methods. A diagnostic method of the invention optionally comprises any of: diagnosing liver disease in a subject, monitoring liver disease progression in a subject, stratifying a liver disease by stage or severity, or distinguishing liver diseases in a subject. A therapeutic method of the invention comprises treating a subject identified by a diagnostic method of the invention. A kit of the invention comprises one or more reagents for performing a diagnostic method of the invention.

A first aspect of the invention provides a panel of biomarkers. The biomarker of the panel can be measured and used to perform a diagnostic method of the invention. The panel comprises a set of one or more biomarkers that can be employed for methods, kits, computer readable media, systems, and other aspects of the invention which employ a panel of biomarkers.

A second aspect of the invention provides a diagnostic method. A diagnostic method of the invention comprises measuring, in a biological sample ('sample') obtained from a subject, the level of each biomarker of a panel taught herein, and evaluating a liver disease status based on the measured level.

Optionally, the step of evaluation can comprise diagnosing a liver disease or progression state thereof, monitoring liver disease progression, or distinguishing between two or more liver diseases or fibrosis stages.

Optionally, the step of evaluating comprises correlating the measured level of each biomarker (e.g. individually or collectively) with a liver disease status. For example, correlating can comprise:
a. comparing the measured level of each biomarker of the panel to a comparator level (e.g. a level indicative of liver disease status indicative of a lack there of), and evaluating the subject based on the comparison;
b. evaluating the subject based on an output from a model (e.g. algorithm), wherein the model is executed based on an input of the measured level of each biomarker of the panel, or
c. providing a spectrum generated by mass spectrometry analysis of a biological sample taken from a subject, extracting data from the spectrum and subjecting the data to univariate and multivariate analysis that is keyed, e.g. to a pair of peaks, corresponding to a respective biomarker of the panel.

Optionally, the liver disease status is the presence of steatohepatitis (e.g. NASH), liver fibrosis, or cirrhosis, or a stage or grade thereof. For example, the liver disease status can be a stage of fibrosis (e.g. early, intermediate, or late stage based reflective of metabolic function) or stage of cirrhosis (e.g. a Child-Pugh ('CP') grade of cirrhosis).

Optionally, the subject is any of: a subject that that has not been previously diagnosed as having a liver disease or liver fibrosis, a subject that has not been treated for a liver disease, or a subject that has undergone treatment for a liver disease.

Optionally, the sample is blood, plasma, or serum. In a particular embodiment, the sample is serum.

Optionally, the method of measuring comprises mass spectrometry ('MS'). Optionally, the MS comprises time-of-flight mass spectrometry ('TOFMS'), triple quadrupole mass spectrometry ('TQMS'), or quadrupole-time-of-flight mass spectrometry ('QTOFMS'). The MS can be performed following, for example, a separate technique such as gas chromatography ('GC') or liquid chromatography ('LC') such as Ultra Performance Liquid Chromatography ('UPLC'). As such the invention can employ GC-MS, LC-MS, UPLC-MS. Optionally, the invention employs GC-TOFMS, UPLC-QTOFMS, or LC-TQMS.

A third aspect of the invention provides a method of treatment comprising administering or recommending (hereinafter collectively and independently referred to as 'administering') to a subject that has been evaluated as having a liver disease by a diagnostic method of the invention, a treatment for the liver disease.

Optionally, the treatment is a treatment that reduces the deviation between the level of one or more biomarkers of the panel exhibited by the subject and a comparator level that is indicative of reduced liver damage or reduced severity or progression of liver disease.

Optionally, the treatment comprises administering a therapeutic agent, e.g. a small molecule therapeutic agent.

Optionally, the method further comprises, following administering the treatment, measuring the level of each biomarker of the panel in a sample obtained from the subject post-treatment, and comparing the post-treatment level to the pre-treatment level, and evaluating whether the treatment has reduced liver damage in the subject or reduced severity or progression of liver disease. Optionally, the method further comprises modifying the treatment following a determination that the liver damage or the severity or progression of liver disease has not been reduced by the treatment or produces poor efficacy (e.g. progression or severity has not been reduced by a pre-determined threshold amount).

A fourth aspect of the invention provides a kit comprising one or more reagents for detecting a panel of one or more biomarkers taught herein. The one or more reagents comprise one or more internal standards, wherein, collectively, the one or more internal standards provide at least one internal standard for each biomarker of the panel. Optionally, the kit comprises a mixture of said internal standards. Optionally, the one or more or more internal standards are lyophilized. Optionally, the one or more or more internal standards are deposited on a filter. Optionally, one or more reagents are provided in a container. Optionally, the kit comprises instructions for detecting the biomarkers, for example, to evaluate a liver disease status (e.g. diagnose liver fibrosis).

A fifth aspect of the invention provides a non-transitory computer readable medium comprising software for evaluating a liver disease status based on a measured level of one or more biomarkers of a panel taught herein. The software comprises an algorithm for analyzing data extracted from a spectrum generated by mass spectroscopic analysis of a biological sample taken from a subject, wherein said data relates to biomarkers of the panel.

In any aspect of the invention, the panel comprises one or more bile acids, one or more free fatty acids, one or more amino acids, and/or one or more carbohydrates (e.g. as listed in Table 1).

Optionally, the one or more bile acids are selected from the bile acids listed in Table 1.

Optionally, the one or more one or more free fatty acids are selected from the bile acids listed in Table 1.

Optionally, the one or more one or more amino acids are selected from the amino acids listed in Table 1.

Optionally, the panel comprises one or more bile acids selected from the bile acids listed in Table 1, one or more one or more free fatty acids selected from the bile acids listed in Table 1, one or more one or more amino acids selected from the amino acids listed in Table 1, and one or more carbohydrates selected from the carbohydrates listed in Table 1.

Optionally, the one or more bile acids are selected from the bile acids listed in Table 2.

Optionally, the one or more one or more free fatty acids are selected from the bile acids listed in Table 2.

Optionally, the one or more one or more amino acids are selected from the amino acids listed in Table 2.

Optionally, the panel comprises one or more bile acids selected from the bile acids listed in Table 2, one or more one or more free fatty acids selected from the bile acids listed in Table 2, one or more one or more amino acids selected from the amino acids listed in Table 2, and one or more carbohydrates selected from the carbohydrates listed in Table 2.

Optionally, the panel is a panel listed in Table 3 (i.e. in Table 3A or Table 3B).

BRIEF DESCRIPTION OF THE DRAWINGS

FIGS. 16A-16K depict charts demonstrating the diagnostic power of biomarkers of the invention.

FIGS. 17A-17F depict charts demonstrating the diagnostic power of biomarkers of the invention.

FIG. 19A1-FIG. 19A5 depict bar charts of GCA, GCDCA, TCA, TUDCA, and 7-KLCA (ng/mL, mean±SEM) in liver disease patients with NASH, fibrosis, and cirrhosis, and diabetes patients and controls. FIG. 19B depicts a ROC curve in the CLD patients from the testing set and in the diabetes patients using the established BA panel.

FIG. 23A-FIG. 23H8 depict data from a study of bile acid modulators as treatment for liver cancer.

FIG. 24A-FIG. 24G3 depict data from a study of bile acid modulators as treatment for liver cancer.

FIG. 25A-FIG. 25H depict data from a study of bile acid modulators as treatment for liver cancer.

FIG. 32A-FIG. 32C depict examples of useful compounds for treating or preventing liver disease.

DETAILED DESCRIPTION OF THE INVENTION

Figure 1:
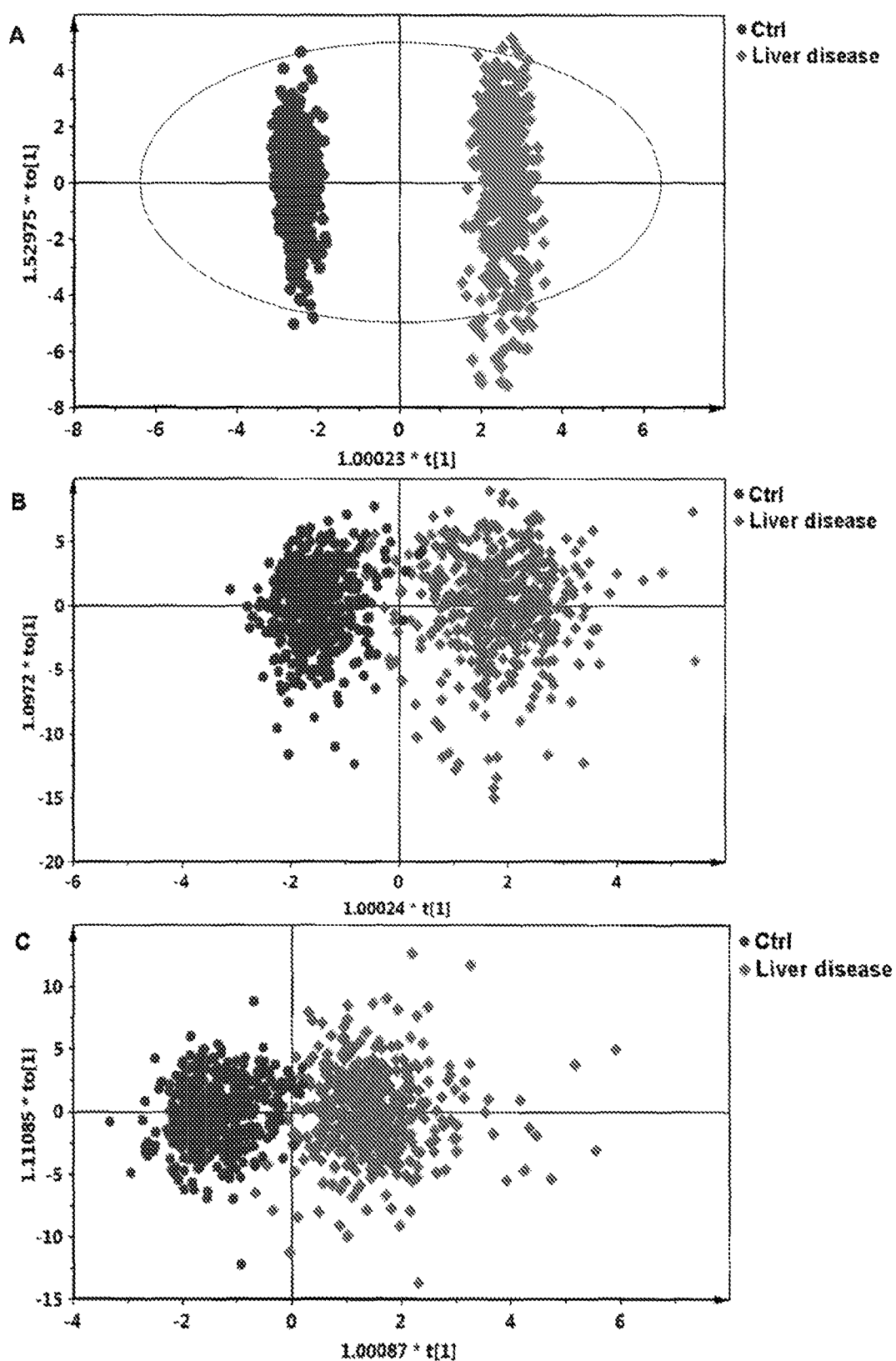
FIG. 1 depicts OPLS-DA scores plot established with all identified differential bile acids (A), free fatty acids (B) and amino acids (C) in liver disease patients and healthy controls (Ctrl).

Methods
Overview

One embodiment of the invention provides diagnostic methods comprising evaluating liver disease status in a subject. Liver disease status can optionally be evaluated by measuring, in a sample obtained from the subject, the level of one or more biomarkers of a panel taught herein and correlating the measured level of the level of one or more biomarkers with disease status. Based on the correlation, the invention can identify subjects having a liver disease status. For example, the liver disease status can be the presence of a liver disease (e.g. fibrosis), or the severity or progression of a liver disease (e.g. stage or grade, such as discriminating between stages of fibrosis such as between non-cirrhosis fibrosis and cirrhosis). Methods of the invention can optionally be used to diagnose a liver disease or progression or severity thereof (e.g. progression of liver fibrosis or cirrhosis), monitor a liver disease progression (e.g. progression of liver fibrosis or cirrhosis), or distinguish between two or more liver diseases.

To illustrate one non-limiting example of carrying out the invention, the present invention teaches the use of LC-MS or GC-MS and multivariate statistical analysis to detect molecular changes in human blood serum samples by comparing the metabolic profiles of patients with liver disease and healthy controls, to identify a metabolite profile of liver disease, and biomarkers for liver disease, as well as methods for monitoring the progression of liver disease. Further illustrative examples provide monitoring diagnostic methods that are tests based on panels of biomarkers that have been selected as being effective in detecting liver disease as well as the progression of liver fibrosis and cirrhosis. The tests have high degrees of clinical sensitivity and specificity. The tests are optionally based on biological sample classification methods that use a combination of MS techniques. More particularly, the present invention optionally takes advantage of LCMS and GC-MS to identify small molecule metabolites comprising a set of metabolite biomarkers found in a patient serum sample.

Optionally, subjects identified as having as having a liver disease are selected to receive treatment for the liver disease, for example, according to a method of treatment taught herein.

Optionally, the diagnostic method comprises monitoring the level of the one or more biomarkers of the panel. Methods of monitoring can comprise providing a first biological sample can be provided from the subject at a first time (e.g. prior to undergoing treatment or following a first period of treatment) and a second biological sample can be provided from the subject at a later time (e.g. following the treatment or following a second period of treatment), measuring the level of the one or more biomarkers in the first sample and the second sample, and comparing the levels measured in the first sample and the second sample.

Optionally, a method of the invention comprises diagnosing or monitoring a liver disease by measuring a panel comprising one or more bile acid metabolites in a sample from a subject, and correlating the level of the one or more metabolites with the presence or absence of the liver disease. Optionally, the panel further comprises metabolites such as fatty acids, amino acids, and/or carbohydrates (e.g. as listed in Table 1). Optionally, the metabolites are selected from the biomarkers listed in Table 1. Alternatively, the metabolites are selected from the biomarkers listed in Table 2. Additionally or alternatively, the panel is a panel listed in Table 3 (i.e. in Table 3A or Table 3B).

Subject

Methods of the invention can measure the level of one or more biomarkers in a biological sample obtained from a subject. The subject can be any subject, e.g. a human subject.

Optionally, the subject is any warm-blooded animal, for example, a member of the class Mammalia such as, without limitation, a human or a non-human primates such as a chimpanzee, an ape, or a monkey; a farm animal such as a cow, a sheep, a pig, a goat, or a horse; a domestic mammal such as a dog or a cat, a laboratory animal such as a mouse or a rat.

The subject can be any age or sex. For example the subject can be an adult, a non-adult, an infant, a mature animal, or an immature animal.

Optionally, the subject is a male.

Optionally, the subject is female.

Embodiments of the present invention can optionally comprise comparing the level of a panel of biomarkers to that of a control sample. Optionally, the control is a healthy control sample or a sample comprising biomarker levels equivilant to a healthy control. As used herein, a healthy controls means healthy subject who is clinically free of liver disease (e.g. as identified by a liver biopsy). A healthy control sample refers to a sample of biofluid that has been obtained from a healthy control subject.

The invention is surprisingly useful for correlating liver disease status in a subject, e.g., subjects that do or do not exhibit typical phenotypes of liver disease.

Optionally, the present invention can be implemented to evaluate liver disease status in a subject that is not suspected or predisposed to having a liver disease.

Optionally, the subject is any of: a subject that that has not been previously diagnosed as having a liver disease, a subject that that has not been previously diagnosed as having a liver disease wherein a sample of the subject is obtained and a method of the invention is used to evaluate the sample for the liver disease, a subject that that has not been previously or recently (e.g. within one year) undergone a liver biopsy, a subject that has not been previously diagnosed with hepatitis B or C virus, a subject that has not been diagnosed with or does not have alcoholism or heavy alcohol consumption, a subject that has not been diagnosed with or does not have non-alcoholic liver disease (NALD), a subject that has not been diagnosed with or does not have diabetes or obesity, a subject that has not been diagnosed with exposure to aflatoxins, or a metabolically healthy subject (e.g. based on HBA1c levels or other diagnosis of metabolism as taught in PCT/US16/57538), a subject expressing a serological marker profile associated with healthy liver function, a subject that does not express a clinically significant amount fibrosis biomarkers composed of products of extracellular matrix synthesis and degradation and enzymes involved in those processes, a subject that does not, if tested, present test results indicative of liver disease selected from ultrasonic (US), computed tomography (CT) and magnetic resonance imaging (MRI) or transient elastography (TE) (FibroScan), or a subject that would not, if tested, present a test result indicative of liver fibrosis wherein the test is selected from a FibroTest, a AST to ALT ratio, and an APRI index.

Optionally, the present invention can be implemented to evaluate liver disease status of a subject suspected, confirmed, or at risk of having a liver disease.

Optionally, the subject is any of: a subject that has been previously diagnosed with or has hepatitis B or C virus, a subject diagnosed with or having alcoholism or heavy alcohol consumption, a subject that has been diagnosed with or has non-alcoholic liver disease (NALD), a subject diagnosed with or having diabetes or obesity, a subject that has been exposed to aflatoxins, a subject expressing a serological marker profile associated with poor liver function, a subject expressing a clinically significant amount fibrosis biomarkers composed of products of extracellular matrix synthesis and degradation and enzymes involved in those processes, a subject presenting test results indicative of liver disease selected from ultrasonic (US), computed tomography (CT) and magnetic resonance imaging (MRI), to liver-specific techniques, such as transient elastography (TE) (FibroScan), or a subject that presents a test results indicative of liver fibrosis wherein the test is selected from a FibroTest, a AST to ALT ratio, and an APRI index.

Optionally, the subject does not have hepatocellular carcinoma (HCC). Alternatively, the subject optionally has HCC.

While examples taught herein detail the production of scoring models and biomarker signatures of liver disease status (e.g. steatohepatitis, NASH, fibrosis, or cirrhosis) from a population of subjects having hepatitis B, the present inventor believes that the biomarker levels are a picture of the metabolic state of the liver that is governed by presence of hepatitis (e.g. steatohepatitis), fibrosis or cirrhosis, not governed by the mere presence of a virus. Accordingly, the present invention can be implemented on subjects with or without hepatitis B infection. Similarly, while examples taught herein detail the production of scoring models and biomarker signatures of steatohepatitis from a population of subjects having NASH, the present inventor believes that the biomarker levels are a picture of the metabolic state of the liver that is governed by presence of hepatitis (e.g. steatohepatitis), and that the biomarkers are useful to diagnose fibrosis or hepatitis resulting from any cause (alcoholism or non-alcoholism). Accordingly, the present invention can be implemented on alcoholic or non-alcoholic subjects, e.g. to identify a subject as having alcoholic steatohepatitis or NASH.

Sample

Methods of the invention can measure the level of one or more biomarkers in a biological sample ('sample') obtained from a subject.

Optionally, the sample comprises or consists of blood, plasma, or serum. For example, any of such samples can be obtained from a subject following a period of fasting. The collection of fasting samples is well-known in the art.

Optionally, the sample comprises or consists of serum. As used herein, "serum" refers to the fluid portion of the blood obtained after the removal of the fibrin clot and blood cells, distinguished from the plasma in circulating blood.

Internal Standards

Methods of the invention optionally comprise the use of an internal standard for one or more (e.g. each) of the biomarkers that are measured. An internal standard can optionally be mixed with the sample at any time prior to measurement.

Optionally, the internal standard, having a known initial level in the sample prior to sample preparation, can provide a measurement signal used to normalize the signal of the respective biomarker.

Steps of sample preparation can sometimes induce substantial loss of biomarker prior to measurement. While the development of a predictable sample preparation technique and use of the same separation and measurement instruments (e.g. the same LCMS machine) can increase accuracy and precision of measurement, the use of different sample preparation mediums, methods, and measurement machines (e.g. by different laboratories) can induce unpredictable changes in biomarker recovery and/or measurement signal. Accordingly, an internal standard can optionally be used in the present invention to correct for loss (i.e. recovery inconsistencies) and/or signal level variation of a respective biomarker during sample preparation and measurement.

Optionally, an internal standard is the same compound as the corresponding biomarker of the panel, except it has one or more of its atoms replaced with a stable isotope of the one or more atoms (e.g. (2)H, (13)C, (15)N, or (18)O). For example, a set of internal standards for a given panel of biomarkers can be provided by providing an isotope-labeled variant of each biomarker.

Optionally, an internal standard compound is chemically similar, but not identical to the respective one or more biomarkers that are measured such that the internal standard exhibits similar behavior during sample preparation but can be uniquely identified during the measurement step. Optionally, the internal standard is selected such that effects of sample preparation on the measurement signal level of internal standard are the same relative to the measurement signal level of the respective biomarker.

Optionally, the internal standard is mixed with the sample prior to one or more steps of preparation (e.g. extraction or other purification), and biomarker separation steps.

Optionally, the panel comprises a plurality of biomarkers and a different internal standard for each biomarker (e.g. a labeled biomarker identical to the respective biomarker other than the label) or, alternatively, at least one internal standard is provided for normalization of a plurality of biomarkers (e.g. a biomarker of the same compound class one or more respective biomarkers such as a labeled steroid acid or bile acid for a plurality of bile acids, a labeled fatty acid for a plurality of fatty acid biomarkers, and/or a labeled amino acid for a plurality of amino acids). For example, nonadecanoic-d37 acid can optionally be provided as an internal standard for all of the free fatty acids of a panel taught herein.

Optionally, the internal standard is an isotope-labeled compound. Alternatively, the internal standard is any compound not found in the sample, e.g. not found in blood, plasma, or serum.

Optionally, the internal standard is a stable isotope labeled compound (e.g. labeled variant of the biomarker or labeled variant of a compound with similar properties as the biomarker). Optionally, the stable isotope is (2)H, (13)C, (15)N, or (18)O.

Optionally, one or more internal standards are selected from a labeled steroid acid (e.g. bile acid) (e.g. used for a bile acid biomarker), a labeled fatty acid (e.g. used for a fatty acid biomarker) and/or a labeled amino acid (e.g. used for an amino acid biomarker).

Optionally, useful internal standards are any stable-isotope labeled metabolite with respect to the biomarkers to be determined in the real samples as the internal standards. Optionally, the internal standards have the same chemical properties as the metabolite biomarkers to be measured from the panel. For example, with respect to a corresponding biomarker of the panel, the internal standard produces the recovery percent when extracted by protein precipitation (e.g. by Ammonium sulfate, trichloroacetic acid (TCA), acetone, or ethanol) and/or filtration (e.g. using filters taught herein) from the sample. Given a particular biomarker panel, the skilled artisan can readily select internal standards that have the same or shared chemical properties as a corresponding biomarker, wherein the same or shared chemical properties are those that influence the recovery percentage of a biomarker and internal standard (e.g. molecular weight, polarity, shared, shared R-groups, etc.). Optionally, each internal standard is an internal standard that has a rate of recovery of no greater or less than (+/−) 10%, 7%, 5%, 4%, 3%, 2%, 1%, or 0.5% relative to the corresponding biomarker.

For example, the following illustrate useful internal standards of corresponding biomarkers measurement in the present invention:

cholic acid (CA)-d4 (e.g. used for hypochloric acid (HCA)
ursodeoxycholic acid (UDCA)-d4 (e.g. used for glycohyodeoxycholic acid (GHDCA), taurochenodeoxycholic acid (TCDCA), taurodeoxycholic acid (TDCA), glycohyocholic acid ('GHCA'), and/or taurohyocholic acid (THCA))
lithocholic acid (LCA)-d4 (e.g. used for taurolithocholic acid (TLCA))
tridecanoic-d25 acid (e.g. used for monounsaturated free fatty acids)
nonadecanoic-d37 acid (e.g. used for saturated free fatty acids)
Valine-d8 (used for valine)
Leucine-5,5,5-d3 (used for leucine)
Isoleucine-2-d1 (used for isoleucine)
Tyrosine-3,3-d2 (used for tyrosine)
Phenylalanine-3,3-d2 (used for phenylalanine)

Optionally, the internal standards configured for GC-MS or LC-MS.

With the teachings provided herein, the skilled artisan can readily select useful internal standards based on the selection of a biomarker panel.

Sample Preparation

The biomarkers measured in the present invention can optionally be extracted from the sample. For example, the method can comprises steps of contacting the sample with an extraction medium, extracting the biomarkers from the sample and measuring the extracted lipids (e.g. by mass spectrometry following separation of the biomarkers by chromatography).

The extraction medium can be any medium that allows the extraction on biomarkers from one or other components of the sample that are not measured in the measuring step. Optionally, the extraction medium comprises a solution (e.g. protein precipitating solution), a filter, or both.

Measurement

Methods of the invention detect one or more biomarkers in a biological sample by measuring the level of one or more biomarkers in the biological sample. The step of measuring can be performed in any manner useful to measure the biomarkers taught herein. For example, any in-vitro method of measuring biomarker levels in a biological sample (e.g. blood, plasma, or serum) can be used Optionally, the method of measuring comprises mass spectrometry ('MS'). The MS can be performed following, for example, a separate technique such as gas chromatography ('GC') or liquid chromatography ('LC'). Optionally, the MS comprises GC-MS, LC-MS, or ultra-performance liquid chromatography ('UPLC-MS'). Optionally, the MS is time-of-flight, ion trap, quadrupole, magnetic sector, ion cyclotron resonance, electrostatic sector analyzer or a combination or hybrid thereof. Optionally, the MS comprises time-of flight mass spectrometry ('TOFMS'), triple quadrupole mass spectrometry ('TQMS'), or quadrupole-time-of-flight mass spectrometry ('QTOFMS'). Optionally, the invention employs GC-TOFMS, UPLC-QTOFMS, or LC-TQMS.

Optionally, the step of measurement is preceded by steps of extraction (e.g. filtration) and/or separation (e.g. chromatography). Chromatography is a method of separating components in a sample based on differences in partitioning behavior between a mobile phase and a stationary phase. Typically, a column holds the stationary phase and the mobile phase carries the sample through the column. Sample components that partition strongly into the stationary phase spend a greater amount of time in the column and are separated from components that stay predominantly in the mobile phase and pass through the column faster. As the components elute from the column, they can be measured, e.g. using a mass spectrometer.

Optionally, each of the biomarkers of a panel is measured from the same aliquot of sample following instruction of the aliquot in a chromatography column. Such an embodiment can separate all of the biomarkers from a single aliquot and provides an efficient method by eliminating the need for parallel sample preparation, extraction, and separation steps.

Such a simultaneous running of all biomarkers can be provided by tailoring the chromatographic conditions, e.g. including the column temperature, the composition of mobile phase, flow rate, eluent condition of mobile phase, analytical time as well as the mass fragmentation pattern (parent ion and daughter ion of the biomarker to be measured) of metabolites to get adequate separation.

When the biomarker of interest is an analyte (e.g. palmitic acid or stearic acid), the step of "measuring" can include measuring the level (e.g. measuring a signal indicative of the level) of the analyte. When biomarker of interest is a calculation based on the level of a plurality of analytes such as ratio (e.g. (C22:4 n-6)/(C20:4 n6) ratio), the step of measuring can include measuring the levels of each of the plurality of analytes and calculating the level of the biomarker of interest based on the measured analyte levels.

The term "level", as used herein with respect to a biomarker, can be any quantitative or qualitative representation of the presence of the biomarker in the sample, e.g. the amount (e.g. mass) or concentration (e.g. w/w, w/v, or molarity). When expressed as a concentration, the level can be expressed with respect to the original volume (or weight) of the obtained sample prior to sample preparation (e.g. extraction).

Liver Disease Status

Methods of the present invention can be used to evaluate a liver disease status, e.g. by correlating biomarker levels of a panel to the liver disease status. Accordingly, a method of the invention can optionally be used to identify a subject as having a liver disease status.

The liver disease status evaluated can be any liver disease status, for example, liver damage, liver impairment, or abnormal liver condition. Optionally, the liver disease status is liver inflammation, liver steatosis (e.g. alcoholic or nonalcoholic), hepatitis, steatohepatitis (e.g. alcoholic or nonalcoholic), hepatocyte damage, NASH, fibrosis, cirrhosis, chronic liver disease, or a stage, progression, or severity thereof.

Steatosis without steatohepatitis or fatty liver is characterized, for example, by fat infiltration with little or no inflammation.

Steatohepatitis, such as Nonalcoholic steatohepatitis ('NASH'), is a liver condition characterized by steatosis and inflammation causing damage to liver cells. Chronic inflammation in steatohepatitis sometimes causes the progression to fibrosis with scar tissue formation.

Fibrosis can optionally be classified (e.g. stratified) by stage or progression. For example, fibrosis stages can include S0-S4 stages S0 can optionally be characterized by an absence (or substantial absence or minor presence) of fibrosis such as steatohepatitis in S0. S1 can optionally be characterized by mild fibrosis or fibrosis only present (or only substantially present) at the portal area ('portal fibrosis'). S2 can optionally be characterized by moderate fibrosis, or fibrosis present between portal areas, or periportal or portal septa but having intact architecture, or such fibrosis without the substantial damage to the lobular structure. S3 can optionally be characterized as severe fibrosis, or fibrosis bridging between portal areas and between portal areas and center veins, or architectural distortion but no obvious cirrhosis. S4 can optionally be characterized as cirrhosis, or the formation of pseudo-lobules, or the deformation of liver structure. Prior to the present invention, such classification of liver fibrosis was only possible with substantial certainty using invasive tests such as liver biopsy. Surprisingly, however, certain biomarker panels taught can be measured to provide a profile useful for diagnosing and classifying liver fibrosis. While pre-existing definitions for certain classifications of fibrosis exist (e.g. S0-S4 stage), these classifications were historically defined in a manner that allows them to be identified by liver biopsy. As fibrosis can progress in a gradual increase in fibrosis, the present invention can optionally be used to provide new fibrosis classifications (e.g. by severity or progression) that are defined according to changes in biomarker levels (e.g. by a model score) and that might not necessarily directly correspond to the biopsy-based stage classifications. For example, fibrosis can optionally be stratified into two stages, e.g. mild (e.g. S0-S2 or a stage somewhat coextensive with S0-S2) and severe (e.g. S3-S4 or a stage somewhat coextensive with S3-S4). Alternatively, fibrosis can optionally be stratified into three stages, e.g. including early (e.g. S0-S1 or a stage somewhat coextensive with S0-S1), intermediate (e.g. S2 or a stage somewhat coextensive with S2), and late stages of fibrosis (e.g. S3-S4 or a stage somewhat coextensive with S3-S4). Alternatively, fibrosis can be classified using a model stratifying into 4 or more discrete stages, or classified using a continuous stage model (e.g. wherein a higher score indicates a greater degree of fibrosis but with no discrete stages separated by cutoffs).

Cirrhosis can optionally be classified by progression or severity. For example, cirrhosis classified by Child-Pugh grade (e.g. A, B and C). Similar to the explanation of fibrosis above, the present invention can stratify cirrhosis in a manner that corresponds to previously formed classification schemes (e.g. Child-Pugh grade) or can stratify cirrhosis using a different scheme identified, e.g. by biomarker score. For example, cirrhosis can be classified using a model stratifying into 2 discrete stages, 3, discrete stages, or 4 or more discrete stages, or classified using a continuous stage model (e.g. wherein a higher score indicates a greater degree of cirrhosis but with no discrete stages separated by cutoffs).

Surprisingly, panels taught herein can be used to identify or discriminate subjects by liver disease status. For example, a panel taught herein can be used to discriminate between fibrosis and non-fibrosis, between cirrhosis and non-cirrhosis, between liver disease (e.g. steatohepatitis) and non-liver disease. Prior the present invention, invasive methods of the liver biopsy were required to identify such subjects.

Optionally, a panel taught herein is used to discriminate between fibrosis and non-fibrosis. For example, the non-fibrosis can be any non-fibrosis, or can be a healthy liver or a Steatohepatitis (e.g. NASH) liver.

Optionally, a panel taught herein is used to discriminate between cirrhosis and non-cirrhosis. The non-cirrhosis can be any non-cirrhosis, e.g. a healthy liver, non-cirrhosis fibrosis (e.g. S3 fibrosis), or non-cirrhosis liver damage (e.g. steatohepatitis).

Optionally, a panel taught herein is used to discriminate between liver disease and non-liver disease.

For example, the liver disease can be Steatohepatitis (e.g. NASH) or fibrosis (e.g. both cirrhosis and non-cirrhosis fibrosis), or can be a liver disease status defined by the subject having either Steatohepatitis or fibrosis.

Optionally, a panel taught herein is used to discriminate between stages or severity of fibrosis.

Optionally, a panel taught herein is used to discriminate between severity of cirrhosis.

Correlation

Methods of the invention can comprise evaluating liver disease status by correlating the measured level of one or more biomarkers of the panel with liver disease status. Based on the correlation, a subject can be identified as having a liver disease status, for example, diagnosed with a liver disease, classified (e.g. by liver disease type, stage, progression, or severity), or monitored for a change in liver disease status (e.g. progression or severity). Subjects identified as having a liver disease, liver disease classification, or change in liver disease status can be selected to receive liver disease treatment.

Optionally, the step of correlating comprises comparing one or more measured biomarker levels to a respective comparator level (e.g. a level indicative of or equivalent to a healthy control subject). Additionally or alternatively, measured levels of one or a plurality of biomarkers can be inputted into a model (e.g. mathematical formula or algorithm performed by a computer) that computes a score based on the measured levels.

A biomarker level (e.g. measured level) or a score (e.g. computed by model) can compared to a comparator level or comparator score, respectfully, utilizing techniques such as reference limits, discrimination limits, or diagnosis or classification defining thresholds to define cutoff points and abnormal values for a status such as the presence or severity of a liver disease. The comparator level of a biomarker or combined biomarker score can be a level or score, respectively, typically found in a subject not having a given liver status. Such comparator level and cutoff points may optionally vary based on whether a biomarker is used alone or in a formula combining with other biomarkers into a score. Alternatively, a comparator level or score can be determined from previously tested subjects that were diagnosed with a liver disease status (e.g. based on liver biopsy) or a threshold that was determined to distinguish subjects who presented a given liver disease status from those who did not (e.g. as taught in the Examples). Optionally, the comparator level or comparator score is the level or score, respectively, that distinguishes between the severity or progression of a liver disease. Additionally or alternatively, several liver disease classifications (e.g. stages) can be provided, wherein each classification is identified by a given level or score range. Additionally or alternatively, an equation (e.g. curve) can be provided that correlates level or score to classification of liver disease status (e.g. relative stage or severity or absolute stage or severity).

Optionally, a profile is provided comprising each of the measured levels of a biomarker panel and the measured profile is compared to a comparator biomarker profile. The biomarkers of the present invention can be used to generate a comparator biomarker profile. A comparator biomarker profile can be a negative control, e.g. obtained from healthy control subjects who do not have the liver disease status or have a classification of a lesser stage or severity of liver disease. Alternatively, a comparator profile can be a positive control comparator, e.g. obtained from subjects who have the liver disease status or have the classification of or evaluated stage or severity of liver disease. Optionally, the different comparator profiles can be compared, wherein each comparator profile corresponds to subjects that exhibit different liver disease classifications (e.g. stage or severity) in order to provide a basis for to monitor liver disease, e.g. by progression of disease, or to monitor the effectiveness of treatment. The negative comparator profile and/or positive comparator profile can optionally be stored on a non-transitory computer readable memory.

Optionally, a method of the invention uses a model (e.g. algorithm) to correlate measured biomarkers levels with liver disease status. Such correlation using a model can be performed on a system configured there for, e.g. computer having a program (e.g. stored on on-transitory computer readable memory and executed by a controller such as a microprocessor) that implements the model and calculates a score based on the input of measured marker levels. Optionally, measurements of a biomarker panel of the present invention serve as inputs to a computer or microprocessor thereof programmed with a model that implements an algorithm that computes a liver disease status score. If some factors (e.g. physiological factors) in addition to the biomarkers tested in the system are used to calculate the final score, then these factors can be supplied to the model so that it can complete the score calculation, or the algorithm can produce a preliminary score that will reported and externally combined with the other factors to calculate a final score.

A scoring model can produce a score that indicates a binary decision, e.g. a score threshold or cutoff that distinguishes the presence or absence of a particular liver disease status, or can be a score that classifies a liver disease status, e.g. based on severity, stage, or progression (e.g. wherein a higher score indicates a more severe stage of liver disease such as fibrosis).

The liver disease status which is evaluated can be any liver condition (e.g. associated with fibrosis) and can be identified by any endpoint exhibited by subjects having the liver disease status. The liver disease status endpoint can include, for example, liver biopsy results showing the presence of fibrosis or a particular level of fibrosis. Other endpoints of liver disease are well-known endpoints of clinical diagnosis, and the skilled artisan will appreciate that such endpoints can be varied and produce a liver disease status endpoint useful according to the invention.

In one embodiment, evaluation of liver disease status comprises calculating a score. While certain scoring methods of the invention are exemplified using Logistic Regression-based correlation (e.g. as detailed in the Examples), the invention contemplates any method of correlation. For example, after selection of a set of biomarkers as disclosed in the instant invention, well-known techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, or other mathematical and statistical methods can be used to develop an algorithm for calculation of liver disease status score.

As one example a scoring model can comprise a logistic function, the end value of which is indicative of the presence (or severity) of liver fibrosis. For example, a method of the invention using such a scoring model can optionally comprise a) measuring the levels of each biomarker of a panel taught herein, in the serum or plasma of a subject, b) combining said measured levels through a logistic function including said biomarkers and, c) analyzing the end value of said logistic function in order to determine the presence of a liver disease status (e.g. liver fibrosis) or the severity thereof. Such analysis of the end value of the logistic function can comprise correlating the end value to end values obtained from applying the model to a population of test subjects Optiona lly, the logistic function is obtained by i) classification of the patients in differe nt gro ups according to their liver disease status (e.g. severity of fibrosis) ii) logistic reg ression analysis to assess the independent discriminative value of biomarkers of the panel for the diagnosis of liver disease status, and iii construction of the logistic function by combining the biomarkers of the panel. Examples of such are detailed in Example 1 through Example 16 Example 19, and Example 20.

Useful methods of producing scoring model are also disclosed in WO 2002/016949; WO 2002/016949: WO 2010/149767, WO 2006/10357, WO 2006/082522, WO 2003/073822, WO 2011/039321, WO 2005/116901, WO 2010/058295, WO 2010/097472.

Generally, a selected population of individuals is used, where historical information is available regarding the values of biomarkers in the population and their clinical endpoints such as can be determined by liver biopsy (e.g. as detailed in the Examples). To calculate a liver disease status score for a given individual, biomarker values are obtained from one or more samples collected from the individual and used as input data, i.e. input into a model fitted (e.g. algorithm) to the actual historical data obtained from the selected population of individuals.

The performance and thus absolute and relative clinical usefulness of the invention may be assessed in multiple ways as noted above. Amongst the various assessments of performance, the invention is optionally intended to provide accuracy in diagnosis of liver disease status and treatment monitoring. Accuracy can concern the ability of the test, assay, or method to distinguish between subjects that have or do not have the liver disease status, and is based on whether the subjects have an effective level or a substantial alteration in the level of one or more biomarkers, or score calculated there from. By effective level or substantial alteration it is optionally meant that the measurement of the biomarker is different than the predetermined cut-off point (or threshold value) for that biomarker or change in level there of, respectively, and therefore indicates that the subject is determined to have a particular liver disease status or has undergone a change in liver disease status (e.g. in methods of monitoring). The difference in the level of biomarker between the presence of a liver disease status and the absence of the liver disease status is preferably statistically significant and may be an increase in biomarker level or a decrease in biomarker level, as is readily apparent from the Examples taught herein. While the invention contemplates the use of a one-biomarker panel, for some populations (e.g. exhibiting a specific genetic, physiological, or clinical state), achieving statistical significance, and thus the preferred analytical and clinical accuracy, many include combinations of several biomarkers to be used together in a panel and combined with mathematical models (e.g. algorithm) in order to achieve a statistically significant score.

As with the categorical diagnosis of a liver disease status, changing the cut point or threshold value of a test for the liver disease status according to the present invention may change the sensitivity and specificity, but often in a qualitatively inverse relationship. Therefore, in assessing the accuracy and usefulness of a proposed method one may optionally take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is sometimes preferred for liver disease status evaluation using the invention.

Using such statistics, an acceptable degree of diagnostic accuracy using a method of the invention to evaluate liver disease status in which the AUC (area under the ROC curve for the test or assay) is at least 0.60, or greater such as at least 0.65, at least 0.70, at least 0.75, at least 0.80, or at least 0.85. Optionally, the AUC is even greater, e.g. 0.875, at least 0.90, or at least 0.95.

Optionally, by defining the degree of diagnostic accuracy, i.e., cut points on a ROC curve, defining an acceptable AUC value, and determining the acceptable ranges in relative concentration of what constitutes a level (or score) of the biomarkers (individually or collectively) that distinguishes the presence of a liver disease status from the absence of the liver disease status, the invention allows one of skill in the art to use a biomarker taught herein to identify subjects that that have the liver disease status with high accuracy.

Models can also be developed and/or used as detailed below.

Development of a Scoring Model

While the Examples taught herein provide details of the development of a model for carrying out the invention, the skilled artisan will appreciate that, using the biomarkers identified herein and the relationships taught herein, a mathematical model used to calculate a correlation or score can be produced in any manner, and need not rely on the data collected and presented herein.

For example, the model can be produced by obtaining biomarker level data from a representative population including data from both those who do and do not exhibit a particular clinical endpoint of a liver disease status (e.g. identified by liver biopsy), e.g. as detailed in the Examples. Such data can be obtained from the teachings provided herein (e.g. biomarker data detailed in the Examples) or other means of obtaining such as first-hand from the population, prospective (longitudinal) and/or from a retrospective epidemiological data storage containing the results from previous studies, such as a private or public database. The biomarker data may be derived from a single study or multiple studies, and generally includes data pertaining to the desired indication and endpoint of the representative population, including values of the biomarkers described herein, clinical annotations (which may include endpoints), and most particularly the desired endpoints for training an algorithm for use in the invention, across many subjects. The biomarker level data is then optionally stored on non-transitory computer-readable memory.

The representative population data set can then be prepared as needed to meet the requirements of the model or analysis that will be used for biomarker selection, as described below. For example, data set preparation may include preparing the biomarker level values from each subject within the representative population, or a chosen subset thereof. However, the raw biomarker level data alone may not be entirely useful for the purposes of model training. As such, various data preparation methods may be used to prepare the data, such as gap fill techniques (e.g., nearest neighbor interpolation or other pattern recognition), quality checks, data combination using of various formulae (e.g., statistical classification algorithms), normalization and/or transformations, such as logarithmic functions to change the distribution of data to meet model requirements (e.g., base 10, natural log, etc.). Again, the particular data preparation procedures are dependent upon the model or models that will be trained using the representative population data. The particular data preparation techniques for various different model types are known, and need not be described further.

The particular biomarkers are selected to be subsequently used in the training of the model used to evaluate a liver disease status. Biomarker selection may involve utilizing a selection model to validate the representative population data set and selecting the biomarker data from the data set that provides the most reproducible results. Examples of data set validation may include, but are not limited to, cross-validation and bootstrapping. From the biomarker selection, the model to be used in evaluating a liver disease status may be determined and selected. However, it is noted that not all models provide the same results with the same data set. For example, different models may utilize different numbers of biomarkers and produce different results, thereby adding significance to the combination of biomarkers on the selected model. Accordingly, multiple selection models may be chosen and utilized with the representative population data set, or subsets of the data set, in order to identify the optimal model for liver disease status evaluation. Examples of the particular models, including statistical models, algorithms, etc., which may be used for selecting the biomarkers have been described above.

For each selection model used with the data set, or subset thereof, the biomarkers are optionally selected based on each biomarkers statistical significance in the model. When input to each model, the biomarkers are optionally selected based on various criteria for statistical significance, and may further involve cumulative voting and weighting. Tests for statistical significance may include exit-tests and analysis of variance (ANOVA). The model may include classification models (e.g., LDA, logistic regression, SVM, RF, tree models, etc.) and survival models (e.g., cox), many examples of which have been described above.

It is noted that while biomarkers may be applied individually to each selection model to identify the statistically significant biomarkers, in some instances individual biomarkers alone may provide less predictive power than desired, in which case combinations of biomarkers may be applied to the selection model. For example, rather than utilizing univariate biomarker selection, multivariate biomarker selection may be utilized. That is, a biomarker may not be as good of an indicator when used as a univariate input to the selection model, relative to when it is used in combination with other biomarkers (e.g., a multivariate input to the model), because each biomarker may bring additional information to the combination that would not be indicative if taken alone.

The model to be used for evaluating liver disease status is optionally selected, trained and validated. In particular, leading candidate models may be selected based on one or more performance criteria, examples of which have been described above. For example, from using the data set, or data subsets, with various models, not only are the models used to determine statistically significant biomarkers, but the results may be used to select the optimal models along with the biomarkers. As such, the evaluation model used to evaluate liver disease status may include one of those used as a selection model, including classification models and survival models. Combinations of models markers, including biomarker subsets, may be compared and validated in subsets and individual data sets. The comparison and validation may be repeated many times to train and validate the model and to choose an appropriate model, which is then used as a model for evaluating liver disease status.

Use of a Scoring Model

While the Examples taught herein provide models for carrying out the invention, the skilled artisan will appreciate that, using the biomarkers identified herein and the relationships taught herein, any mathematical model using the biomarker panels taught herein can be used to evaluate liver disease status.

For example, a mathematical model can be provided that can calculate a liver disease status score based on an input of one or more biomarkers of a panel taught herein. Biomarker level data is obtained from a subject and optionally stored on non-volatile memory). The subject biomarker data may be initially derived through a variety of means, including self-reports, physical examination, laboratory testing and existing medical records, charts or databases. The subject biomarker level may be prepared using calculations, transforms, logs, combinations, normalization, etc. as needed according to the model type selected and trained (e.g. as detailed in the methods of developing a scoring model taught herein). Once the data has been prepared, the subject biomarker data can be input into the model. The model can then output a liver disease status score (e.g. wherein the score is indicative of the presence or absence of a particular liver disease status or the stage or severity of a liver disease). The liver disease status determined by the score and other evaluation steps can be, for example, steatohepatitis (e.g. NASH), liver fibrosis, cirrhosis, or stages or seventies thereof.

Treatment

In one embodiment, a method of the invention comprises treating a subject that has been identified as having a liver disease status (e.g. steatohepatitis, liver fibrosis, cirrhosis, or a stage or severity thereof).

Useful treatments include a treatment that ameliorates or reduces the liver disease status, prevents or slows the progression of the liver disease status, or prevents or slows the development of another condition that can be caused by the liver disease status (e.g. hepatic encephalopathy, or liver cancer such as Hepatocellular carcinoma).

The use of a therapy in the treatment of a subject identified as having a liver disease status by a diagnostic method of the invention, can involve any therapy, any liver disease status, and any biomarker panel taught herein.

Optionally, the treatment comprises administering a therapeutic agent, performing surgery (e.g. liver transplantation), discontinuing administration of a therapeutic agent that the subject has previously received (e.g. a liver-damaging agent), prescribing a diet (e.g. lowering calorie or carbohydrate intake), discontinuing alcohol consumption, prescribing exercise, or prescribing a therapeutic regimen for weight-loss.

Optionally, the treatment comprises a therapeutic agent.

Therapeutic agents useful in the present invention can include, for example, Apical sodium-dependent bile acid transporters (ASBT)-inhibitors, Bile acid-binding resins, steroid acid (e.g. Bile acid), Bile acid derivatives, anti-cholesterol agents, and anti-diabetic agents.

Optionally, a useful therapeutic agent inhibits bile acid reuptake in the distal ileum, decreases secondary bile acid production, accelerates bile acid excretion from intestine, or inhibits bile acid synthesis.

Optionally, the treatment comprises an Apical sodium-dependent bile acid transporters (ASBT)-inhibitor such as benzothiepin derivative SC-435 (see Bhat B G, et al. Inhibition of ileal bile acid transport and reduced atherosclerosis in apoE−/− mice by SC-435. *Journal of lipid research* 44, 1614-1621 (2003)) or 264W94 (see Root C, Smith C D, Sundseth S S, Pink H M, Wilson J G, Lewis M C. Ileal bile acid transporter inhibition, CYP7A1 induction, and antilipemic action of 264W94. *J Lipid Res* 43, 1320-1330 (2002)), Quinoline derivative R-1446224 (see Kurata H, et al. A novel class of apical sodium-dependent bile acid transporter inhibitors: the amphiphilic 4-oxo-1-phenyl-1,4-dihydroquinoline derivatives. *Bioorganic & medicinal chemistry letters* 14, 1183-1186 (2004)), or a naphthol derivative such as S-8921 (see Hara S, et al. S-8921, an ileal Na+/bile acid cotransporter inhibitor decreases serum cholesterol in hamsters. *Life sciences* 60, PI 365-370 (1997)). Other useful ASBT inhibitors include any of Formulas I-VI disclosed in US 2014/0323412 A1 (Gedulin et al., application no: U.S. Ser. No. 14/354,553), which is hereby incorporated by reference. Without being bound by theory, it is believed that ASBT-inhibitors can inhibit the reabsorption of bile acids from ileum to liver hepatocytes, thus, reducing the bile acids in circulation so as to prevent or treat the degree or severity of liver fibrosis, cirrhosis or other associated liver damage or diseases.

Optionally, the treatment comprises a bile acid-binding resin, such as colesevelam (see Aldridge M A, Ito M K. Colesevelam hydrochloride: a novel bile acid-binding resin. *The Annals of pharmacotherapy* 35, 898-907 (2001)) or cholestyramine or colestipol ((see Einarsson K, et al. Bile acid sequestrants: Mechanisms of action on bile acid and cholesterol metabolism. *European Journal of Clinical Pharmacology* 40, S53-S58). Without being bound by theory, it is believed that bile acid-binding resins can remove intestinal bile acids, leading to decreased bile acid enterohepatic circulation, thus, reducing the bile acids so as to prevent or treat the degree or severity of liver fibrosis, cirrhosis or other associated liver damage or diseases.

Optionally, the treatment comprises a steroid acid. Useful steroid acids include unconjugated and conjugated forms thereof. Optionally, the steroid acid is a bile acid such as ursodeoxycholic acid. Many other steroid acids are known in the art for the treatment of liver disease.

Optionally, the treatment comprises a bile acid derivative, such as obeticholic acid (OCA) (see Trivedi P J, Hirschfield G M, Gershwin M E. Obeticholic acid for the treatment of primary biliary cirrhosis. *Expert review of clinical pharmacology* 9, 13-26 (2016)). Without being bound by theory, it is believed that bile acid derivatives can inhibit bile acid synthesis, thus, reducing the bile acids so as to prevent or treat the degree or severity of liver fibrosis, cirrhosis or other associated liver damage or diseases.

Optionally, the treatment comprises administration of an anti-cholesterol agent. Examples include a statin, a bile acid binding resin (e.g. cholestyramine, colestipol, or colesevelam), a fibrates, ezetimibe, lomitapide, a phytosterol, or orlistat.

Optionally, the treatment comprises administration of any therapeutic agent (e.g. ASBT inhibitor or Absorption Inhibitor) disclosed in US 2014/0323412 A1 (Gedulin et al., application no: U.S. Ser. No. 14/354,553), which is hereby incorporated by reference.

Optionally, the treatment comprises administration of bile acid or derivative thereof, as taught in PCT application PCT/US16/57538 to Jia, U.S. Pat. No. 6,060,465 to Miljkovic et al, EP 0417725 A2 to Kramer et al, or U.S. Pat. No. 8,445,472 to Pellicciari which are hereby incorporated by reference for treatments compounds taught therein.

A Bile Acid Binding Resin

Optionally, the treatment comprises administration of any compound of Formula I taught in PCT application PCT/US16/57538 to Jia, which is hereby incorporated by reference for compounds of formula I taught therein.

Optionally, the treatment is any standard care for subject having the liver disease status.

Optionally, the treatment comprises administration of a therapeutic agent selected from *Artemisia absinthium*, Boceprevir, bumetanide, cholestyramine, colestipol, furosemide, Harvoni, hydrochlorothiazide, lactulose, mycophenolate mofetil, spironolactone, Technivie, telaprevir, a thiazide, triamterene, hydrochlorothiazide, Viekira Pak, vitamin K, phytonadione, a corticosteroid, a bile acid, a diuretic, albumin, and an antibiotics.

Treatments useful in the present invention can include, for example, anti-diabetic agents (e.g. metformin, rosiglitazone, or pioglitazone), weight-loss agents, diet prescriptions (e.g. calorie or carbohydrate restrictions), or exercise. Such treatments can be provided to as subject having steatohepatitis, for example, with little or no fibrosis (e.g. stage S0 or S1).

Without being bound by theory, it is believed it is believed that these treatments can make a subject more sensitive to insulin and may help reduce liver injury in patients with steatohepatitis such as NASH.

Treatments useful in the present invention can include the discontinuation of a therapeutic agent that the subject has previously taken or withholding of a therapeutic agent. Without being bound by theory, it is believed that many therapeutic agents can over work the liver and progress liver disease status towards fibrosis or greater stages thereof.

Without being bound by theory, it is believed that treatments taught herein are effective in reducing or reversing the liver disease or reducing or preventing the progression of the liver disease, and optionally modify the biomarker levels in the subject to levels indicative of reduced liver disease, e.g. according to a measured biomarker level or calculated score based on measure biomarker levels.

Optionally, a method of the invention comprises evaluating a liver disease subject in a subject using a panel of the invention, wherein the step of evaluation comprises discriminating between two or more liver disease statuses of different stages or severities, and the method further comprises selecting a treatment based on the evaluation or differentially selecting treatment based on the stage or severity identified.

For example, a treatment is optionally selected only for subjects in whom their liver diseases status has been evaluated as a more severe liver disease status stage or severity.

Alternatively, a first treatment is optionally selected for subjects in which their liver diseases status has been evaluated as a more severe liver disease status stage or severity and a second treatment is selected for subjects in whom their liver diseases status has been evaluated as a less severe liver disease status stage or severity. The first treatment and second treatment can be treatments with different severities of side effects, invasiveness, or mortality rates.

For example, liver transplantation is optionally selected for subjects having more severe stage or severity of fibrosis (e.g. late stage cirrhosis such as CP stage C) while administration of a therapeutic agent (e.g. small molecule therapeutic agent, ASBT inhibitor, Absorption Inhibitor, bile acid or derivative thereof, anti-diabetic agent, steroid acid, or bile acid-binding resin) is optionally selected for subjects having the less severe stage or severity of fibrosis.

As another example, a first treatment such as administration of a therapeutic agent (e.g. small molecule therapeutic agent, ASBT inhibitor, Absorption Inhibitor, bile acid or derivative thereof, steroid acid, or bile acid-binding resin) is optionally selected for subjects having the more severe stage or severity of fibrosis and a second treatment such as administration of an anti-diabetic agent or weight loss agent, or prescription of lifestyle changes (e.g. calorie or carbohydrate restrictions or exercise) is selected as treatment for subjects having ae severe stage or severity of fibrosis (e.g. S0 or steatohepatitis without substantial fibrosis).

Optionally, the method can reserve treatments with greater severity of side effects, invasiveness, or mortality for those subjects having more severe or late stage fibrosis. For example, a liver transplant can be reserved for subjects having the most relatively severe or latest stage fibrosis (e.g. late stage cirrhosis), stronger therapeutic agents (e.g. having greater side effects or mortality rates) for subjects having relatively moderate stage or severity of fibrosis, weaker therapeutic agents (e.g. having less side effects or mortality rates) for relatively early stage or less severity of fibrosis, and lifestyle changes for subjects exhibiting relatively even less fibrosis or steatohepatitis without fibrosis.

While the invention contemplates each of the aforementioned examples, the skilled artisan can readily select between two (or more) treatments with different severities of side effects, invasiveness, or mortality rates for use in treating subjects in which their liver disease status as been evaluated based on stage or severity.

Monitoring

In one embodiment, a method of the invention comprises monitoring the level of one or more biomarkers of a panel taught herein. A method of monitoring according to the present invention comprises providing a first biological sample and a second sample, wherein the first sample is obtained from the subject at a first time and the second biological sample is obtained from the subject at a second time, wherein the second time is later than the first time, measuring the level of the one or more biomarkers in each of the first sample and second sample, and either comparing the measured levels from the first sample to the measured levels of the second sample to determine a change in liver disease status, or correlating the levels measured in each sample with liver disease status and comparing the liver disease status correlated (or identified) from the first sample to the liver disease status correlated (or identified) from the second sample.

Optionally, the first time is prior to the subject receiving a treatment and the second time is following the subject receiving the treatment. Accordingly, measuring the levels of biomarkers according to the present invention optionally further allows for the liver disease status of a subject to be monitored or a course of treatment to be monitored.

Optionally, the treatment is modified if the comparison of the levels of the one or more biomarkers from the first sample and second sample do not indicate a predetermined (e.g. substantial) reduction in liver disease status or stage or severity or do not indicate a predetermined (e.g. substantial) change in the level of the one or more biomarker levels.

Accordingly, a method of evaluating liver disease status can optionally be used to identify a subject having a liver disease status and can be used and to enable the selection and initiation of various treatment regimens or therapeutic interventions (hereinafter 'treatments') in order to treat the subject. Measuring the levels of biomarkers optionally further allows for the course of treatment to be monitored. In this method, a first biological sample can be provided from the subject prior to undergoing treatment and a second biological sample can be provided from the subject following the treatment.

Kits

In one embodiment, a method of the invention provides a kit for detecting biomarkers of a panel of the invention. Included in the kit are one or more internal standards for detecting one or more biomarkers of a panel of the invention. Collectively, the one or more internal standards provide at least one internal standard for each biomarker of the panel taught herein.

Figure 14A:
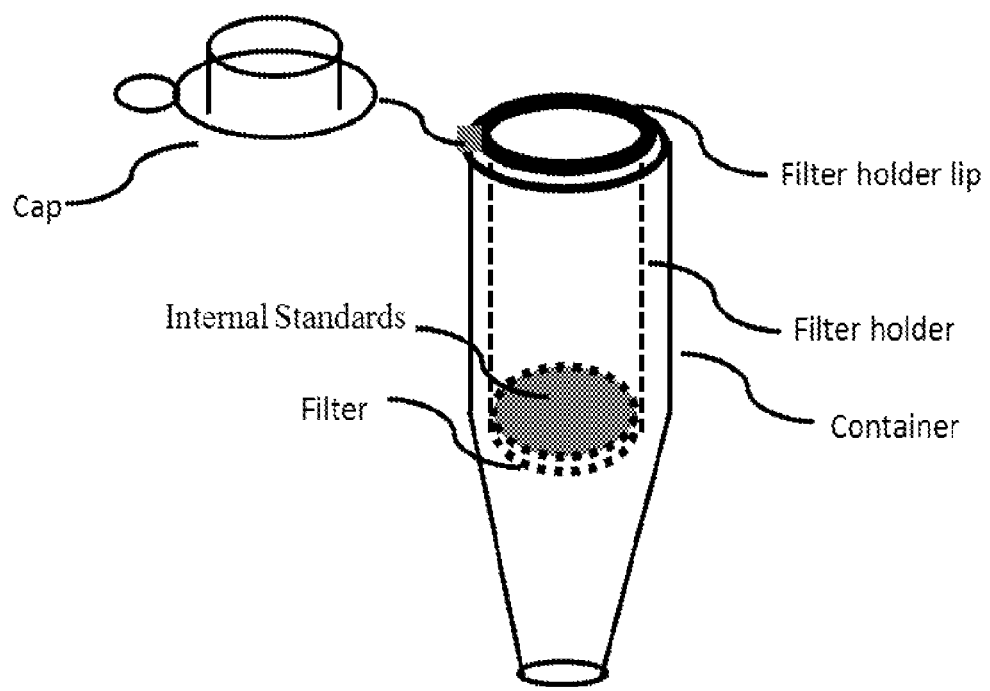
FIG. 14A and FIG. 14B depict a kit of the invention.
Figure 14B:
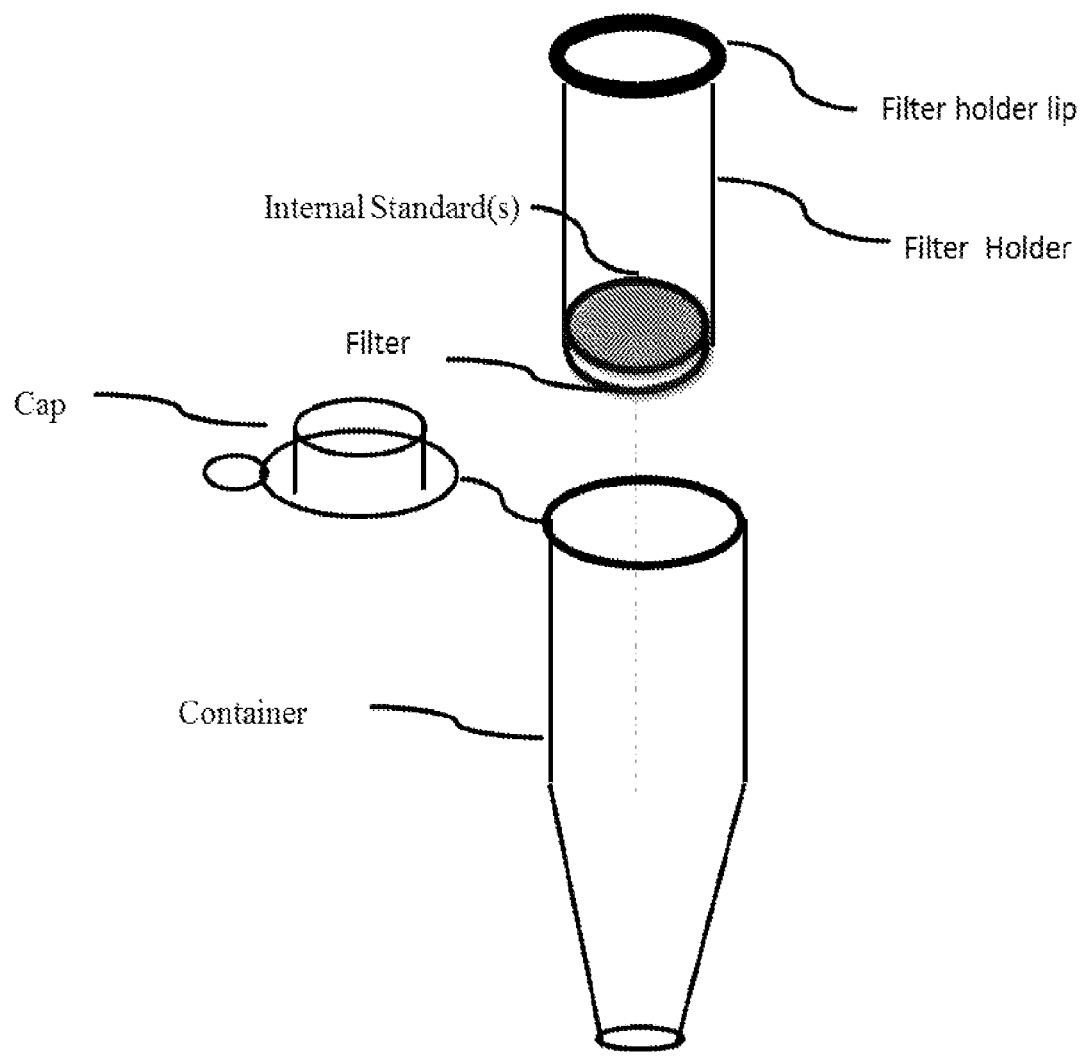
Figure 15:
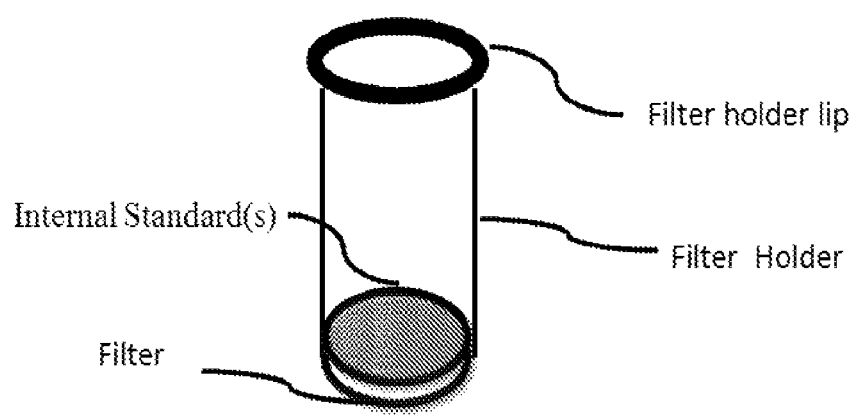
FIG. 15 depicts a kit of the invention.

Optionally, the kit comprises a container, a filter, or both (e.g. a filter in a container). Optionally the container comprises the one or more internal standards. Additionally or alternatively, a filter comprises the one or more internal standards (e.g. the standards are deposited on the filter). Examples of such kits are depicted in FIGS. 14A, 14B, and 15.

Optionally, the internal standards configured for GC-MS or LC-MS.

Optionally, optionally, the one or more internal standards are a plurality of internal standards. Optionally, the internal standards are provided in a mixture. Alternatively, one or more of the plurality of internal standards can be separated from each other.

Optionally, the one or more internal standards are provided in solid or liquid form. Optionally, the one or more internal standards dehydrated or freeze-dried (e.g. by lyophilization). Solid internal standards can be, for example, suspended into solution prior to use of the kit.

Optionally, the internal standards are any taught herein.

Optionally, the one or more internal standards comprise a labeled steroid acid (e.g. bile acid), a labeled fatty acid, and/or a labeled amino acid. The label can be, e.g. an isotope such as (2)H or (13)C.

Optionally, each internal standard is the same compound as a corresponding biomarker of the panel, except it has one or more of its atoms replaced with a stable isotope of the one or more atoms (e.g. (2)H, (13)C, (15)N, or (18)O). For example, a set of internal standards for a given panel of biomarkers can be provided by providing an isotope labeled variant of each biomarker. Optionally, the panel comprises any panel of Table 3 (i.e. Table 3A or Table 3B).

Optionally, the kit comprises a filter. Optionally, the one or more internal standards are deposited on the filter (e.g. as depicted in FIG. 14 and FIG. 15). Optionally, the filter is provided in a container or is configured for placement in or on the container (e.g. as depicted in FIG. 14 and FIG. 15). Optionally, the filter is removable from the container (e.g. as depicted in FIG. 14A). Optionally, the filter is mounted to a filter holder, e.g. a filter holder that can be placed in a container (e.g. a cylindrical filter holder and/or a filter holder having a lip as depicted in FIG. 14 and FIG. 15), for example a filter holder that is itself a container (with solid side walls) that can be placed inside another container, e.g. as depicted in FIG. 14A. Optionally, when the filter is in the container, the container can hold a volume of liquid on each side of the filter, e.g. by providing a void or cavity on each side of the filter (e.g. as depicted in FIG. 14B). Such a kit allows the container to be centrifuged to force a solution from a first side of the filter through the filter to a second side of the filter. The filter can be configured such that the filtrate includes the internal standards and biomarkers supplemented to the first side of the filter. The filtrate can then be analyzed (e.g. via GCMS or LCMS) to measure the biomarkers and internal standards, e.g. by removing the filter. Optionally, the filter is any filter with a pore size that allows the passage of biomarkers of the panel and internal standards to pass through but retains other components such as proteins (e.g. precipitated proteins). For example, the filter can be a 0.22 μm filter. Optionally, the filter is a Polyvinylidene Fluoride, cellulose (e.g. Cellulose acetate), or nylon filter. Optionally, the filter comprises an antioxidant such as butylated hydroxytoluene (BHT).

Optionally, the one more internal standards are mixed with an antioxidant such butylated hydroxytoluene (BHT). Such an anti-oxidant can be provided, e.g. to product internal standards such as fatty acids from degradation, thus extending the shelf life of the kit.

Optionally, the kit comprises at least container comprising the one or more internal standards therein. Optionally, the container is a tube, vial or multi-welled or multi-chambered plate. The kit may have a single container (e.g. well or chamber), or may have multiple containers (e.g. wells or chambers). For example, the kit can comprise a multi-welled plate (e.g., a microtiter plate such as a 96-well microtiter plate). Other analogous containers are also appropriate. In some kits, the container may be appropriate for use in measurement of the internal standards and quantitation of the one or more metabolites to be assessed in a subject sample. In some kits, the container used for measurement of internal standards and quantitation of one or more metabolites in a subject sample is configured to be used for spectral analysis such as, for example, chromatography-mass spectrometry. For example, the container may be configured for GC-TOFMS and/or LC-TQMS. In other kits, the container may be configured for other analytical tests specific for one or more of the metabolites to be assessed in a subject sample (e.g., enzymatic, chemical, colorimetric, fluorometric, etc.).

Some kits optionally include a plurality of containers. For example, some kits include one or more containers having the internal standards. In addition, some kits include one or more containers having the internal standards and an additional container to be used in measurement of the internal standards and quantitation of the one or more metabolites to be assessed in a subject sample (e.g., a multi-welled plate or another tube or vial). In some kits, there is a single container that is used to contain the one or more internal standards and used in measurement of the internal standards and quantitation of the one or more metabolites to be assessed in a subject sample.

In kits comprising a multi-welled, multi-chambered, or other multi-container device, the internal standards may optionally located in one or more wells or chambers upon distribution of the kit for use. In some kits, the internal standards are provided outside of the container and must be dispersed into the container(s) using the kits.

The container of the kit can also be configured to accept a biological sample from at least one subject. For example, where the kit includes multiple chambers or wells, a biological sample from a subject may be distributed into one or more chambers or wells. In some instances, one or more amounts of a subject sample may be distributed into a plurality of chambers or wells. The container of the kit is generally configured to accept fluid samples (e.g., fluid biological samples or solid biological samples that have been processed to obtain a fluid for analysis).

Some kits also include reagents useful for measurement of the internal standards and quantitation of the one or more metabolites to be assessed in a subject sample. These reagents may be included in the kit in one or more additional containers.

An exemplary (non-limiting example) kit may comprise an internal standard each provided in the same or a separate container. The container is optionally provided in the form of a microtiter plate, e.g., configured for use with either a GC-MS or LC-MS device. The microtiter plate can have a sufficient number of wells to receive at least one internal standard. The internal standards have known concentrations and will be already in the container or used to dispense a known amount of each internal standard into separate wells of the microtiter plate. After dispensing the internal standards into the analytical container, a portion of the subject sample can also be dispensed into the microtiter plate. Either a single portion of a subject sample is dispensed or a plurality of portions can be dispensed. If a plurality of portions is dispensed into the microtiter plate, each portion may be dispensed into a separate well. In addition, if a plurality of portions is dispensed into the microtiter plate, each portion may be of a different amount.

Computers and Modules and Automated Systems

Methods of the invention can be implemented through the use of a computer, and optionally associated hardware, configured to perform one or more steps of measuring, correlating, and reporting. Accordingly, one embodiment of the present invention provides a computer readable non-transitory (e.g. non-volatile) memory comprising a module (e.g. program) configured for measurement (e.g. converting measurement signals from an analytical machine into biomarker levels), evaluating (e.g. correlating the biomarker levels with liver disease status or inputting the biomarker levels into a mathematical model that computes a score), and/or reporting the result of the evaluation. Optionally, the invention provides a computer comprising a microprocessor and the memory, wherein the microprocessor is configured to carry out the module.

The steps of measurement and/or evaluating (e.g. correlating, comparing values or a calculating score), can be performed using a computer comprising a module there for (e.g. program stored on the memory and carried out by a microprocessor). For example, a measurement module can be provided that interprets a signal indicative of biomarker level from a connected measuring device (e.g. 'MS') and calculates the level of the of the biomarker there from. Optionally, the measurement module is configured to normalize the level of the biomarker by comparing the signal to a signal obtained (e.g. via MS) from a respective internal standard. As another example, an evaluation module can be provided that makes a determination of liver disease status using the biomarker level as an input into an algorithm (e.g. an algorithm that computes a liver disease status score or that compares biomarker levels to comparator levels).

Optionally, the module is configured to report the results of the evaluation. Examples of reporting mechanisms include visible display, a link to a data structure or database, or a printer. The reporting mechanism can optionally be a data link to send test results to an external device, such as a data structure, data base, visual display, or printer.

Methods of the present invention can be automated using diagnostic test systems that utilize a computer or an analog machine. Tests to measure biomarkers and biomarker panels can be implemented on a wide variety of diagnostic test systems. Diagnostic test systems can be apparatuses that typically include means for obtaining test results from biological samples. Examples of such means include modules that automate the testing (e.g., detection assays). Diagnostic test systems can optionally be configured to handle multiple biological samples and can be programmed to run the same or different tests on each sample. Diagnostic test systems optionally include means for collecting, storing and/or tracking test results for each sample, usually in a data structure or database. Examples include physical and non-volatile storage devices (e.g., hard drives, flash memory, magnetic tape, or paper print-outs). Optionally, diagnostic test systems included a means for reporting test results. Examples of reporting means include visible display, a link to a data structure or database, or a printer. The reporting means can optionally be a data link to send test results to an external device, such as a data structure, data base, visual display, or printer.

Biomarker Panels

The invention provides biomarker panels useful for methods, kits, and other aspects of the invention.

Optionally, the panel comprises one or more biomarkers of Table 1.

Optionally, the panel comprises one or more biomarkers of Table 2

Optionally, the panel is any panel listed in Table 3 (i.e. in Table 3A or Table 3B). Table 3 lists panels A through CJ (88 panels) which can be used to diagnose any liver disease status (e.g. hepatitis, fibrosis, or cirrhosis) or discriminate between progression stats or severity of a liver disease status (e.g. severity of fibrosis or severity of cirrhosis). Note, Table 3A is split among multiple pages, and repeats the vertically-listed biomarker names on subsequent pages (the table can be reconstructed by aligning the pages side to side); Table 3B is split among multiple pages and repeats the horizontally-listed biomarker names subsequent pages (the table can be reconstructed by aligning the pages top to bottom).

A biomarker selected for level measurement of level can optionally be an analyte (a bile acid, fatty acid, or amino acid) or it can be a calculation based on a plurality of analyte levels. For example, the calculation can be a ratio of analytes (e.g. ratio of Docosatetraenoic acid (C22:4 n-6)/Arachidonic acid (C20:4 n6)) or a relative level (e.g. percent) of one or more analytes compared to one or more analytes or the sum of analyte levels. When a first biomarker is calculated as the ratio of a second biomarker to a third biomarker, the first biomarker level can be measured by measuring the level of the second biomarker and the third biomarker and calculating the ratio from the measured levels of the second biomarker and the third biomarker.

Optionally, a panel of biomarkers according to the present invention comprises 1, 2, 3, 4, 5, 6, 7, 8, 9, or 10 biomarkers, or more.

In any aspect of the invention, the panel optionally comprises one or more bile acids, one or more amino acids, and/or one or more free fatty acids.

Optionally, the biomarker panel includes one or more other biomarkers such as AST (aspartate aminotransferase), ALT (alanine aminotransferase), AST/ALT, AST.ALT, ferritin, platelets, prothrombin index, hyaluronic acid, e.g. as described by US 2011/0313276 A1. Alternatively, the biomarker panel optionally does not comprise one or more (or each) of these biomarkers.

Optionally, the biomarker panel includes one or more other biomarkers such as alpha2-macroglobulin, haptoglobin, apolipoprotein A1, total bilirubin and/or gamma-glutamyl transpeptidase (GGT) (e.g. adjusted with sex and age), e.g. as described by EP2786287A1. Alternatively, the biomarker panel optionally does not comprise one or more of these biomarkers.

Optionally, the biomarker panel includes one or more other biomarkers such as a2-macroglobulin, AST, ALT, GGT, γ-globulin, total bilirubin, albumin, αI-globulin, 2-globulin, haptoglobin, β-globulin, aPoAI, IL10, TGF-βI, apoA2, and/o apoB, e.g. as detailed in WO 2002/016949. Alternatively, the biomarker panel optionally does not comprise one or more of these biomarkers.

While the a panel useful in the invention can be produced from any biomarkers taught herein, the following three embodiments list exemplary biomarker panels useful in the present invention.

In one embodiment, a panel of the invention comprises one or more (e.g. each of) Taurochenodeoxycholic acid (TCDCA), Glycochenodeoxycholic acid (GCDCA), Glycocholic acid (GCA), Taurocholic acid (TCA), 12-Methyltridecanoic acid (C14:0 iso), 13-Methylmyristic acid (C15:0 iso), Linoelaidic acid (C18:2 n6t), elaidic acid (C18:1 n9t), beta-alanine, valine, leucine, isoleucine. Such a panel is useful, for example, to diagnose liver disease (e.g. liver fibrosis or cirrhosis).

In one embodiment, a panel of the invention comprises one or more (e.g. each of) Taurochenodeoxycholic acid (TCDCA), Glycochenodeoxycholic acid (GCDCA), Glycocholic acid (GCA), Glycoursodeoxycholic acid (GUDCA), Taurocholic acid (TCA), 7-Ketocholic acid (7-KLCA), Tauroursodeoxycholic acid (TUDCA), Myristoleic acid (C14:1 n5), Palmitoleic acid (C16:1 n7), elaidic acid (C18:1 n9t), Erucic acid (C22:1 n9), Docosatetraenoic acid (C22:4 n-6)/ Arachidonic acid (C20:4 n6) ratio, Linoleic acid (C18:2 n6)/gamma-Linolenic acid (C18:3 n6) ratio, Palmitic acid (C16:0), Palmitic acid (C16:0)/Palmitoleic acid (C16:1 n7), Tyrosine, Fructose, Fructose/glucose ratio. Such a panel is useful, for example, to stage a liver disease is a subject (e.g. distinguish between early, intermediate, or late stage of fibrosis).

In one embodiment, a panel of the invention comprises one or more (e.g. each of) Palmitic acid (C16:0), Palmitic acid (C16:0)/Palmitoleic acid (C16:1 n7) ratio, Fructose, Fructose/glucose ratio. Such a panel is useful, for example, to stage a liver disease is a subject (e.g. distinguish between early, intermediate, or late stage of fibrosis).

TABLE 1

Markers of Liver Disease Status

Bile Acids

Glycochenodeoxycholic acid (GCDCA)
Glycocholic acid (GCA)
Chenodeoxycholic acid (CDCA)
Glycodeoxycholic acid (GDCA)
Deoxycholic acid (DCA)
Cholic acid (CA)
Ursodeoxycholic acid (UDCA)
Glycoursodeoxycholic acid (GUDCA)
Glycohyodeoxycholic acid (GHDCA)
Taurochenodeoxycholic acid (TCDCA)
Taurodeoxycholic acid (TDCA)
Taurocholic acid (TCA)
Glyco-λ-muricholic acid (G λ-MCA)
λ-muricholic acid (λ-MCA)
7-Ketocholic acid (7-KLCA)
7-Ketodeoxycholic acid (7-KDCA)
Lithocholic acid (LCA)
Tauroursodeoxycholic acid (TUDCA)
Hyodeoxycholic acid (HDCA)
3-ketocholic acid (3-KCA)
Tauro-λ-muricholic acid (T λ-MCA)
Taurolithocholic acid (TLCA)
Glycolithocholic acid (GLCA)

Free Fatty Acids

Caprylic acid (C8:0)
Capric acid (C10:0)
Lauric acid (C12:0)
Myristic acid (C14:0)
12-Methyltridecanoic acid (C14:0 iso)
Myristoleic acid (C14:1(cis-9))
Myristelaidic acid (C14:1(trans-9))
13-Methylmyristic acid (C15:0 iso)
Pentadecanoic acid (C15:0)
14-methylpentadecanoic acid (C16:0 iso)
Palmitic acid (C16:0)
Palmitoleic acid (C16:1(cis-9))
Palmitelaidic acid (C16:1(trans-9))
Hexadecadienoic acid (C16:2(Z-9,12,15,18,22))
15-Methylpalmitic acid (C17:0 iso)
Margaric acid (C17:0)
Heptadecenoic acid (C17:1(cis-10))
16-Methylmargaric acid (C18:0iso)
Stearic acid (C18:0)
Oleic acid (C18:1(cis-9))
Elaidic acid (C18:1(trans-9))
Linoleic acid (C18:2(cis-9,12))
Linoelaidic acid (C18:2(trans-9,12))
γ-Linolenic acid (C18:3(cis-9,12,15))
α-Linolenic acid (C18:3(cis-6,9,12))
Nonadecanoic acid (C19:0)
Nonadecenoic acid (C19:1(cis-10))
Arachidic acid (C20:0)
Eicosenoic acid (C20:1(cis-11))
Eicosadienoic acid (C20:2(cis-11,14))
Eicosatrienoic acid (C20:3(cis-8,11,14))
Arachidonic acid (C20:4(cis-5,8,11,14))
cis-5,8,11,14,17-Eicosapentaenoic acid (C20:5(cis-5,8,11,14,17))

TABLE 1-continued

Markers of Liver Disease Status

Erucic acid (C22:1(cis-13))
cis-13,16-Docosadienoic acid (C22:2(cis-13,16))
cis-7,10,13,16-Docosatetraenoic acid (C22:4(cis-7,10,13,16))
cis-4,7,10,13,16-Docosapentaenoic acid C22:5(cis-4,7,10,13,16))
cis-7,10,13,16,19-Docosapentaenoic acid (C22:5(cis-7,10,13,16,19))
Lignoceric acid (C24:0)
Nervonic acid (C24:1(cis-15))
cis-4,7,10,13,16,19-Docosahexaenoic acid (C22:6(cis-4,7,10,13,16,19))
cis-7-Hexadecenoic acid (C16:1(cis-7))
Octadecadienoic acid (Conjugated,9,11) (C18:2(CLA))
Docosatetraenoic acid (C22:4 n-6)/Arachidonic acid (C20:4 n6) ratio
Linoleic acid (C18:2 n6)/gamma-Linolenic acid (C18:3 n6) ratio
Palmitic acid (C16:0)/Palmitoleic acid (C16:1 n7) ratio Amino Acids 5-Oxoproline
Alanine
Aspartic acid
Beta-Alanine
Citrulline
Creatine
Cystine
Glutamic acid
Glutamine
Asparagine
N-Acetylglutamin
N-Acetyl-L-aspartic acid
Glycine
Histidine
Isoleucine
Leucine
Lysine
Methionine
N-Acetyl-L-aspartic acid
Ornithine
Phenylalanine
Proline
Pyroglutamic acid
Serine
S-Methyl-cysteine
Threonine
Tryptophan
Tyrosine
Valine Carbohydrates Fructose
Fructose/glucose ratio

TABLE 2

Markers of Liver Disease Status

Bile Acids

Glycochenodeoxycholic acid (GCDCA)
Glycocholic acid (GCA)
Chenodeoxycholic acid (CDCA)
Glycodeoxycholic acid (GDCA)
Deoxycholic acid (DCA)
Cholic acid (CA)
Ursodeoxycholic acid (UDCA)
Glycoursodeoxycholic acid (GUDCA)
Glycohyodeoxycholic acid (GHDCA)
Taurochenodeoxycholic acid (TCDCA)
Taurodeoxycholic acid (TDCA)
Taurocholic acid (TCA)
Glyco-λ-muricholic acid (G λ-MCA)
λ-muricholic acid (λ-MCA)
7-Ketocholic acid (7-KLCA)
7-Ketodeoxycholic acid (7-KDCA)
Lithocholic acid (LCA)
Tauroursodeoxycholic acid (TUDCA)
Hyodeoxycholic acid (HDCA)
3-ketocholic acid (3-KCA)

TABLE 2-continued

Markers of Liver Disease Status

Tauro-λ-muricholic acid (T λ-MCA)
Taurolithocholic acid (TLCA)
Glycolithocholic acid (GLCA)

Free Fatty Acids

Lauric acid (C12:0)
12-Methyltridecanoic acid (C14:0 iso)
Myristoleic acid (C14:1(cis-9))
Myristelaidic acid (C14:1(trans-9))
13-Methylmyristic acid (C15:0 iso)
Pentadecanoic acid (C15:0)
14-methylpentadecanoic acid (C16:0 iso)
Palmitoleic acid (C16:1(cis-9))
Palmitelaidic acid (C16:1(trans-9))
Hexadecadienoic acid (C16:2(Z-9,12,15,18,22))
15-Methylpalmitic acid (C17:0 iso)
Margaric acid (C17:0)
16-Methylmargaric acid (C18:0iso)
Oleic acid (C18:1(cis-9))
Elaidic acid (C18:1(trans-9))
Linoelaidic acid (C18:2(trans-9,12))
γ-Linolenic acid (C18:3(cis-9,12,15))
α-Linolenic acid (C18:3(cis-6,9,12))
Nonadecanoic acid (C19:0)
Nonadecenoic acid (C19:1(cis-10))
Eicosenoic acid (C20:1(cis-11))
Eicosatrienoic acid (C20:3(cis-8,11,14))
Arachidonic acid (C20:4(cis-5,8,11,14))
Erucic acid (C22:1(cis-13))
cis-13,16-Docosadienoic acid (C22:2(cis-13,16))
cis-4,7,10,13,16-Docosapentaenoic acid C22:5(cis-4,7,10,13,16))
cis-7,10,13,16,19-Docosapentaenoic acid (C22:5(cis-7,10,13,16,19))
Nervonic acid (C24:1(cis-15))
cis-7-Hexadecenoic acid (C16:1(cis-7))
Octadecadienoic acid (Conjugated,9,11) (C18:2(CLA))
Docosatetraenoic acid (C22:4 n-6)/Arachidonic acid (C20:4 n6) ratio
Linoleic acid (C18:2 n6)/gamma-Linolenic acid (C18:3 n6) ratio
Palmitic acid (C16:0)/Palmitoleic acid (C16:1 n7) ratio Amino Acids 5-Oxoproline
Alanine
Aspartic acid
Beta-Alanine
Creatine
Cystine
Glycine
Histidine
Isoleucine
Leucine
Methionine
N-Acetyl-L-aspartic acid
Proline
Pyroglutamic acid
Serine
S-Methyl-cysteine
Threonine
Tryptophan
Tyrosine
Valine Carbohydrates Fructose
Fructose/glucose ratio

TABLE 3A

| Biomarker Panels ('PANELS') | | | | | | | | | | |
|---|---|---|---|---|---|---|---|---|---|---|
| | A | B | C | D | E | F | G | H | I | J |
| Taurochenodeoxycholic acid (TCDCA) | X | | | | X | X | X | | X | X |
| Glycochenodeoxycholic acid (GCDCA) | X | | | | X | X | X | | X | X |
| Glycocholic acid (GCA) | X | | | | X | X | X | | X | X |
| Taurocholic acid (TCA) | X | | | | X | X | X | | X | X |
| Glycoursodeoxycholic acid (GUDCA) | | | | | | | | | X | X |
| Tauroursodeoxycholic acid (TUDCA) | | | | | | | | | X | X |
| Deoxycholic acid (DCA) | | | | | | | | | | |
| Chenodeoxycholic acid (CDCA) | | | | | | | | | | |
| 7-Ketocholic acid (7-KLCA) | | | | | | | | | X | X |
| Cholic Acid (CA) | | | | | | | | | | |
| Ursodeoxycholic acid (UDCA) | | | | | | | | | | |
| Glycohyodeoxycholic acid (GHDCA) | | | | | | | | | | |
| Lithocholic acid (LCA) | | | | | | | | | | |
| 3-ketocholic acid (3-KCA) | | | | | | | | | | |
| Taurolithocholic acid (TLCA) | | | | | | | | | | |
| Tauro-λ-muricholic acid (T λ-MCA) | | | | | | | | | | |
| Glycolithocholic acid (GLCA) | | | | | | | | | | |
| beta-alanine | | X | | | X | | X | | | |
| valine | | X | | X | X | X | X | | | |
| leucine | | X | | X | X | X | X | | | |
| isoleucine | | X | | X | X | X | X | | | |
| Tyrosine | | | | | | | | | | X |
| Serine | | | | | | | | | | |
| Proline | | | | | | | | | | |
| Citrulline | | | | | | | | | | |
| Methionine | | | | | | | | | | |
| Ornithine | | | | | | | | | | |
| Phenylalanine | | | | | | | | | | |
| Threonine | | | | | | | | | | |
| 12-Methyltridecanoic acid (C14:0 iso) | | | X | | X | | | X | | |
| 13-Methylmyristic acid (C15:0 iso) | | | X | | X | | | X | | |
| Linoelaidic acid (C18:2 n6t) | | | X | | X | | | X | | |
| Myristoleic acid (C14:1 n5) | | | | | | | | | | |
| Palmitoleic acid (C16:1 n7) | | | | | | | | | | |
| Erucic acid (C22:1 n9) | | | | | | | | | | |
| Arachidonic acid (C20:4(cis-5,8,11,14)) | | | | | | | | | | |
| Docosatetraenoic acid (C22:4 n-6)/ Arachidonic acid (C20:4 n6) ratio | | | | | | | | | | |
| Linoleic acid (C18:2 n6)/gamma-Linolenic acid (C18:3 n6) ratio | | | | | | | | | | |
| elaidic acid (C18:1 n9t) | | | X | | X | | | X | | |

| | K | L | M | N | O | P | Q | R | S |
|---|---|---|---|---|---|---|---|---|---|
| Taurochenodeoxycholic acid (TCDCA) | X | | X | X | | | | | |
| Glycochenodeoxycholic acid (GCDCA) | | X | X | X | | | | | |
| Glycocholic acid (GCA) | | | X | X | | | | | |
| Taurocholic acid (TCA) | | | X | X | | | | | |
| Glycoursodeoxycholic acid (GUDCA) | | | | | X | X | | | X |
| Tauroursodeoxycholic acid (TUDCA) | | | | | | | | | |
| Deoxycholic acid (DCA) | | | | | | | | | |
| Chenodeoxycholic acid (CDCA) | | | | | | | | | |
| 7-Ketocholic acid (7-KLCA) | | | | | | | | | |
| Cholic Acid (CA) | | | | | | | | | |
| Ursodeoxycholic acid (UDCA) | | | | | | | | | |
| Glycohyodeoxycholic acid (GHDCA) | | | | | | | | | |
| Lithocholic acid (LCA) | | | | | | | | | |
| 3-ketocholic acid (3-KCA) | | | | | | | | | |
| Taurolithocholic acid (TLCA) | | | | | | | | | |
| Tauro-λ-muricholic acid (T λ-MCA) | | | | | | | | | |
| Glycolithocholic acid (GLCA) | | | | | | | | | |
| beta-alanine | X | | | | | | | | |
| valine | | | X | | X | | | | |
| leucine | | | X | | X | | | | |
| isoleucine | | | X | | X | | | | |
| Tyrosine | | | | | X | | X | | X |
| Serine | | | | | | | | | |
| Proline | | | | | | | | | |
| Citrulline | | | | | | | | | |
| Methionine | | | | | | | | | |
| Ornithine | | | | | | | | | |
| Phenylalanine | | | | | | | | | |
| Threonine | | | | | | | | | |
| 12-Methyltridecanoic acid (C14:0 iso) | | | | | | | | | |
| 13-Methylmyristic acid (C15:0 iso) | | | | | | | | | |
| Linoelaidic acid (C18:2 n6t) | | | X | | | | | | |

TABLE 3A-continued

Biomarker Panels ('PANELS')

| | | | | | | | |
|---|---|---|---|---|---|---|---|
| Myristoleic acid (C14:1 n5) | | | | X | | | |
| Palmitoleic acid (C16:1 n7) | | | | X | | | |
| Erucic acid (C22:1 n9) | | | | X | | | |
| Arachidonic acid (C20:4(cis-5,8,11,14)) | | | | | | | |
| Docosatetraenoic acid (C22:4 n-6)/Arachidonic acid (C20:4 n6) ratio | | | X | | X | X | |
| Linoleic acid (C18:2 n6)/gamma-Linolenic acid (C18:3 n6) ratio | | | X | | X | X | |
| elaidic acid (C18:1 n9t) | | | | X | | | |

| | T | U | V | W | X | Y | Z | AA | AB |
|---|---|---|---|---|---|---|---|---|---|
| Taurochenodeoxycholic acid (TCDCA) | X | X | X | X | X | | | | |
| Glycochenodeoxycholic acid (GCDCA) | | X | X | X | X | | | | |
| Glycocholic acid (GCA) | | X | X | X | X | | | | |
| Taurocholic acid (TCA) | | X | X | X | X | | | | |
| Glycoursodeoxycholic acid (GUDCA) | X | | | | | X | | | |
| Tauroursodeoxycholic acid (TUDCA) | | | | | | | | | |
| Deoxycholic acid (DCA) | | | | | | | | | |
| Chenodeoxycholic acid (CDCA) | | | | | | | | | |
| 7-Ketocholic acid (7-KLCA) | | | | | | | | | |
| Cholic Acid (CA) | | | | | | | | | |
| Ursodeoxycholic acid (UDCA) | | | | | | | | | |
| Glycohyodeoxycholic acid (GHDCA) | | | | | | | | | |
| Lithocholic acid (LCA) | | | | | | | | | |
| 3-ketocholic acid (3-KCA) | | | | | | | | | |
| Taurolithocholic acid (TLCA) | | | | | | | | | |
| Tauro-λ-muricholic acid (T λ-MCA) | | | | | | | | | |
| Glycolithocholic acid (GLCA) | | | | | | | | | |
| beta-alanine | | | | | | | | | |
| valine | | | | | | | | | |
| leucine | | | | | | | | | |
| isoleucine | | | | | | | | | |
| Tyrosine | | | | | | | | | X |
| Serine | | | | | | | | | |
| Proline | | | | | | | | | |
| Citrulline | | | | | | | | | |
| Methionine | | | | | | | | | |
| Ornithine | | | | | | | | | |
| Phenylalanine | | | | | | | | | |
| Threonine | | | | | | | | | |
| 12-Methyltridecanoic acid (C14:0 iso) | | | | | | | | | |
| 13-Methylmyristic acid (C15:0 iso) | | | | | | | | | |
| Linoelaidic acid (C18:2 n6t) | | | | | | | | | |
| Myristoleic acid (C14:1 n5) | | X | | X | | | X | X | X |
| Palmitoleic acid (C16:1 n7) | | X | | X | | | X | X | X |
| Erucic acid (C22:1 n9) | | X | | X | | | X | X | X |
| Arachidonic acid (C20:4(cis-5,8,11,14)) | | | | | | | | | |
| Docosatetraenoic acid (C22:4 n-6)/Arachidonic acid (C20:4 n6) ratio | | X | | | | | | X | X |
| Linoleic acid (C18:2 n6)/gamma-Linolenic acid (C18:3 n6) ratio | | X | | | | | | X | X |
| elaidic acid (C18:1 n9t) | | | | X | X | X | X | X | X |

| | AC | AD | AE | AF | AG | AH | AI |
|---|---|---|---|---|---|---|---|
| Taurochenodeoxycholic acid (TCDCA) | | X | | | | | X |
| Glycochenodeoxycholic acid (GCDCA) | | | X | | | | |
| Glycocholic acid (GCA) | | | | | | | |
| Taurocholic acid (TCA) | | | | | | | |
| Glycoursodeoxycholic acid (GUDCA) | X | X | | X | | X | |
| Tauroursodeoxycholic acid (TUDCA) | | X | | X | | | |
| Deoxycholic acid (DCA) | | | | | | | |
| Chenodeoxycholic acid (CDCA) | | | | | | | |
| 7-Ketocholic acid (7-KLCA) | | X | | X | | | |
| Cholic Acid (CA) | | | | | | | |
| Ursodeoxycholic acid (UDCA) | | | | | | | |
| Glycohyodeoxycholic acid (GHDCA) | | | | | | | |
| Lithocholic acid (LCA) | | | | | | | |
| 3-ketocholic acid (3-KCA) | | | | | | | |
| Taurolithocholic acid (TLCA) | | | | | | | |
| Tauro-λ-muricholic acid (T λ-MCA) | | | | | | | |
| Glycolithocholic acid (GLCA) | | | | | | | |
| beta-alanine | | | | | X | | |
| valine | | | | | | | |
| leucine | | | | | | | |
| isoleucine | | X | | | | | |

TABLE 3A-continued

| Biomarker Panels ('PANELS') | | | | |
|---|---|---|---|---|
| Tyrosine | X | X | | X |
| Serine | | | | |
| Proline | | | | |
| Citrulline | | | | |
| Methionine | | | | |
| Ornithine | | | | |
| Phenylalanine | | | | |
| Threonine | | | | |
| 12-Methyltridecanoic acid (C14:0 iso) | | | X | |
| 13-Methylmyristic acid (C15:0 iso) | | | X | |
| Linoelaidic acid (C18:2 n6t) | | X | X | |
| Myristoleic acid (C14:1 n5) | X | X | | X |
| Palmitoleic acid (C16:1 n7) | X | X | | X |
| Erucic acid (C22:1 n9) | X | X | | X |
| Arachidonic acid (C20:4(cis-5,8,11,14)) | | | | |
| Docosatetraenoic acid (C22:4 n-6)/ Arachidonic acid (C20:4 n6) ratio | X | X | | X |
| Linoleic acid (C18:2 n6)/gamma-Linolenic acid (C18:3 n6) ratio | X | X | | X |
| elaidic acid (C18:1 n9t) | X | | X | |

| | AJ | AK | AL | AM | AN | AO | AP |
|---|---|---|---|---|---|---|---|
| Taurochenodeoxycholic acid (TCDCA) | | X | X | X | | | |
| Glycochenodeoxycholic acid (GCDCA) | | | X | X | | | |
| Glycocholic acid (GCA) | | | X | X | | | |
| Taurocholic acid (TCA) | | | X | X | | | |
| Glycoursodeoxycholic acid (GUDCA) | | X | | X | | | X |
| Tauroursodeoxycholic acid (TUDCA) | | | | X | | | |
| Deoxycholic acid (DCA) | | | | | | X | |
| Chenodeoxycholic acid (CDCA) | | | | | | | X |
| 7-Ketocholic acid (7-KLCA) | | | | | X | X | |
| Cholic Acid (CA) | | | | | | | |
| Ursodeoxycholic acid (UDCA) | | | | | | | |
| Glycohyodeoxycholic acid (GHDCA) | | | | | | | |
| Lithocholic acid (LCA) | | | | | | | |
| 3-ketocholic acid (3-KCA) | | | | | | | |
| Taurolithocholic acid (TLCA) | | | | | | | |
| Tauro-λ-muricholic acid (T λ-MCA) | | | | | | | |
| Glycolithocholic acid (GLCA) | | | | | | | |
| beta-alanine | | | X | | | | X |
| Valine | | | X | | | | |
| Leucine | | | X | | | | |
| Isoleucine | | | X | | | | X |
| Tyrosine | X | X | | X | | | X |
| Serine | | | | | | X | |
| Proline | | | | | | | X |
| Citrulline | | | | | | | X |
| Methionine | | | | | | | X |
| Ornithine | | | | | | | X |
| Phenylalanine | | | | | | | X |
| Threonine | | | | | | | X |
| 12-Methyltridecanoic acid (C14:0 iso) | | | X | | | | |
| 13-Methylmyristic acid (C15:0 iso) | | | X | | | | |
| Linoelaidic acid (C18:2 n6t) | | | X | | X | | |
| Myristoleic acid (C14:1 n5) | | | | X | | | X |
| Palmitoleic acid (C16:1 n7) | | | | X | | | |
| Erucic acid (C22:1 n9) | | | | X | | | |
| Arachidonic acid (C20:4(cis-5,8,11,14)) | | | | | | | X |
| Docosatetraenoic acid (C22:4 n-6)/ Arachidonic acid (C20:4 n6) ratio | | | | X | | | |
| Linoleic acid (C18:2 n6)/gamma-Linolenic acid (C18:3 n6) ratio | | | | X | | | |
| elaidic acid (C18:1 n9t) | | | X | X | | | |

| | AQ | AR |
|---|---|---|
| Taurochenodeoxycholic acid (TCDCA) | | X |
| Glycochenodeoxycholic acid (GCDCA) | | X |
| Glycocholic acid (GCA) | | X |
| Taurocholic acid (TCA) | | X |
| Glycoursodeoxycholic acid (GUDCA) | X | X |
| Tauroursodeoxycholic acid (TUDCA) | | X |
| Deoxycholic acid (DCA) | | |
| Chenodeoxycholic acid (CDCA) | | X |
| 7-Ketocholic acid (7-KLCA) | | X |
| Cholic Acid (CA) | | X |
| Ursodeoxycholic acid (UDCA) | | X |

TABLE 3A-continued

| Biomarker Panels ('PANELS') | |
|---|---|
| Glycohyodeoxycholic acid (GHDCA) | X |
| Lithocholic acid (LCA) | X |
| 3-ketocholic acid (3-KCA) | X |
| Taurolithocholic acid (TLCA) | X |
| Tauro-λ-muricholic acid (T λ-MCA) | X |
| Glycolithocholic acid (GLCA) | X |
| beta-alanine | |
| valine | |
| leucine | |
| isoleucine | |
| Tyrosine | X |
| Serine | |
| Proline | |
| Citrulline | |
| Methionine | |
| Ornithine | |
| Phenylalanine | |
| Threonine | |
| 12-Methyltridecanoic acid (C14:0 iso) | |
| 13-Methylmyristic acid (C15:0 iso) | |
| Linoelaidic acid (C18:2 n6t) | |
| Myristoleic acid (C14:1 n5) | |
| Palmitoleic acid (C16:1 n7) | |
| Erucic acid (C22:1 n9) | |
| Arachidonic acid (C20:4(cis-5,8,11,14)) | |
| Docosatetraenoic acid (C22:4 n-6)/ Arachidonic acid (C20:4 n6) ratio | |
| Linoleic acid (C18:2 n6)/gamma-Linolenic acid (C18:3 n6) ratio | |
| elaidic acid (C18:1 n9t) | |

TABLE 3B

Biomarker "PANELS"

| Panel ID | Glycochenodeoxcholic acid (GCDCA) | Glycocholic acid (GCA) | Tyrosine | Fructose | Palmitic acid (C16:0) | Palmitic acid (C16:0)/ Palmitoleic acid (C16:1 n7) ratio | Fructose/ glucose ratio |
|---|---|---|---|---|---|---|---|
| AS | X | X | X | | | X | |
| AT | X | X | X | X | | | |
| AU | X | X | X | X | X | X | X |
| AV | X | X | X | X | | | X |
| AW | X | X | X | | | X | X |
| AX | X | X | X | X | | X | X |
| AY | X | X | X | | X | X | |
| AZ | X | X | X | | | | X |
| BA | X | X | | | | X | |
| BB | X | X | | X | | | |
| BC | X | X | | X | X | X | X |
| BD | X | X | | X | | | X |
| BE | X | X | | | | X | X |
| BF | X | X | | X | | X | X |
| BG | X | X | | | X | X | |
| BH | X | X | | | | | X |
| BI | | X | X | X | | | |
| BJ | | X | X | X | X | X | X |
| BK | | X | X | X | | | X |
| BL | | X | X | | | X | X |
| BM | | X | X | X | | X | X |
| BN | | X | X | | X | X | |
| BO | | X | X | | | | X |
| BP | X | | | | | X | |
| BQ | X | | | X | | | |
| BR | X | | | X | X | X | X |
| BS | X | | | X | | | X |
| BT | X | | | | | X | X |
| BU | X | | | X | | X | X |
| BV | X | | | | X | X | |
| BW | X | | | | | | X |
| BX | | X | | | | X | |
| BY | | X | | X | | | |
| BZ | | X | | X | X | X | X |
| CA | | X | | X | | | X |

TABLE 3B-continued

| | | Biomarker "PANELS" | | | | |
|---|---|---|---|---|---|---|
| Panel ID | Glycochenodeoxcholic acid (GCDCA) | Glycocholic acid (GCA) | Tyrosine | Fructose | Palmitic acid (C16:0) | Palmitic acid (C16:0)/ Palmitoleic acid (C16:1 n7) ratio | Fructose/ glucose ratio |
| CB | | X | | | | X | X |
| CC | | X | | X | | X | X |
| CD | | X | | | X | X | |
| CE | | X | | | | | X |
| CF | | | | X | X | X | X |
| CG | | | | X | | | X |
| CH | | | | | | X | X |
| CI | | | | X | | X | X |
| CJ | | | | | X | X | |

EXAMPLES

The following examples detail the discovery of biomarker panels and their use in building predictive modes that were then used to test the accuracy of liver disease diagnosis using the biomarker panels. The biomarker panels were selected following the production of metabolite profiles from blood serum samples of a study, measured metabolite levels in a population of patient samples using LC-MS and GC-MS, and analyzed the profiles using statistical methods. These examples illustrate the use of biomarker panels of the invention to evaluate liver disease status such as the presence or classification of NASH, liver fibrosis and cirrhosis.

Example 1 Patient Population of Study

A total of 504 patients diagnosed with liver fibrosis and cirrhosis, ages 15-75, were recruited at Shuguang Hospital affiliated to Shanghai University of Traditional Chinese Medicine (Shanghai, China), and Xiamen Hospital of Traditional Chinese Medicine (Xiamen, China) from April 2013 to December 2013. Patients were clinically diagnosed with liver fibrosis or cirrhosis and infection with chronic hepatitis B according to the "Guideline on prevention and treatment of chronic hepatitis B in China (Chinese Society of Hepatology, Chinese Medical Association and Chinese Society of Infectious Diseases, Chinese Medical Association. Guideline on prevention and treatment of chronic hepatitis B in China (2005). Chin Med J (Engl) 2007; 120:2159-73). All patients were clinically stable at the time of assessment. Exclusion criteria included younger than 15 years or older than 75 years, pregnancy or breast-feeding women, co-infection with human immunodeficiency virus (HIV), hepatitis C virus (HCV), hepatitis D virus (HDV), or hepatitis E virus (HEV), diagnoses of diabetes, other liver diseases, liver transplant, gastrointestinal disorders, pancreatitis, psychoactive medication use, alcohol consumption within 6 months, antibiotic and probiotic/prebiotic within 6 weeks (ajaj J S, Neuman D M, Hylemon P B, et al. Randomised clinical trial: *Lactobacillus* GG modulates gut microbiome, metabolome and endotoxemia in patients with cirrhosis. Aliment Pharmacol Ther 2014; 39:1113-25). Additionally, we excluded patients with an unclear diagnosis of cirrhosis and those patients were unable to provide fasting blood and to complete the study.

A total of 502 participants were recruited as healthy controls from the Physical Examination Center of Shuguang Hospital. There was no significant difference in age, gender, and BMI between healthy controls and liver disease patients (Table 4). Routine biochemical tests were done at Shuguang Hospital to ensure the study subjects are free of inflammation and metabolic diseases (Table 4). B-mode ultrasound examination was done to exclude participants with fatty liver. Those individuals were excluded from participation if they were older than 75 or years younger than 15 years of age; were pregnant; lactating women; had significant cardiopulmonary, renal, gastrointestinal disease or liver disease; acute or chronic infections; active malignancy; other acute or chronic diseases requiring treatment; or used any prescription medication in previous 2 months. The study was approved by the institutional human subjects review board of the Shanghai University of Traditional Chinese Medicine and Xiamen Hospital of Traditional Chinese Medicine. All participants signed informed consent forms for the study.

The demographic characteristics and clinical data of the chronic liver disease patients were summarized in Table 4. The study population included 502 patients (72% males; mean age, 36.66±11.85 years), among which, 46 patients were diagnosed as stage 0 fibrosis, 174 were diagnosed as stage 1 fibrosis, 136 were diagnosed as stage 2 fibrosis, 57 were diagnosed as stage 3 fibrosis, 39 were diagnosed as cirrhosis at CP A, 30 at CP b and 16 at CP C. Diagnosis was obtained by liver biopsy for all patients except the decompensated cirrhosis patients. Liver disease patients have significantly elevated levels of alanine transaminase (ALT), aspartate transaminase (AST), direct bilirubin (DBIL), indirect bilirubin (IBIL), total bilirubin (TBIL), gamma-glutamyl transferase (GGT), total bile acids (TBA), mean platelet volume (MPV), plateletocrit (PCT), platelet distribution width (PDW), total protein (TP), globin (GLB), and mean corpuscular hemoglobin (MCH) and decreased levels of albumin (ALB), blood urea nitrogen (BUN), cholesterol (CHOL), hematocrit (HCT), triglyceride (TG), prealbumin (PALB), mean corpuscular hemoglobin concentration (MCHC), platelet (PLT), red blood cell (RBC) and white blood cell (WHC) compared to healthy controls. As liver function gradually aggravated with increased fibrosis stages and cirrhosis CP grade, serum levels of ALB, HCT, HGB, PALB, PCT, PLT, RBC, TP, CHE, FT3, FT4, Fib, PTA, and CHOL were decreased progressively, while serum levels of ALP, BUN, APTT, TBA, HBcAb, INR, PT, TT, TBIL, DBIL, and IBIL were significantly increased. The serum levels of GGT, GLB, and AHCV were increased with increased liver fibrosis stages while they were decreased in cirrhosis patients Ethical approval for these studies was obtained from the ethics committee of the above two hospitals and all participants signed the informed consent prior to the study.

TABLE 4

| | | | NASH | Fibrosis | | | Cirrhosis | | |
|---|---|---|---|---|---|---|---|---|---|
| Number | Control 502 | Liver disease 504 | S0 n = 46 | S1 n = 174 | S2 n = 136 | S3 n = 57 | CP A n = 39 | CP B n = 30 | CP C N = 16 |
| gender (M/F) | 367/135 | 365/139 | 40/6 | 126/48 | 95/41 | 48/9 | 25/14 | 18/12 | 10/6 |
| age (years) | 36.68 ± 0.53 | 36.66 ± 11.85 | 33.88 ± 1.41 | 32.53 ± 0.73 | 33.71 ± 0.9 | 39.16 ± 1.45 | 44.1 ± 1.7 | 54.33 ± 1.65 | 49.06 ± 3.35 |
| BMI (kg/m2) | 23.08 ± 0.14 | 22.31 ± 3.16 | 22.28 ± 0.46 | 21.84 ± 0.26 | 22.21 ± 0.27 | 22.99 ± 0.38 | 23.63 ± 0.53 | 21.86 ± 0.42 | 22.89 ± 0.69 |
| ALB (g/L) | 49.25 ± 0.12 | 40.1 ± 5.91** | 43.33 ± 0.43 | 42.41 ± 0.25 | 41.35 ± 0.3 | 39.18 ± 0.49 | 39.58 ± 0.76 | 27.97 ± 1.05 | 22.92 ± 1.12 |
| ALP (IU/L) | 85.48 ± 0.82 | 89.68 ± 75.08 | 67.13 ± 2.84 | 74.31 ± 2.02 | 93.71 ± 8.42 | 89.39 ± 3.59 | 116.38 ± 26.32 | 113.55 ± 7.33 | 167.85 ± 15.5 |
| ALT (IU/L) | 30.97± 0.7 | 172.98 ± 196.97** | 160.98 ± 23.85 | 181.89 ± 16.07 | 219.9 ± 19.33 | 179.39 ± 22.97 | 93.02 ± 13.19 | 99.91 ± 28.28 | 73.62 ± 31.59 |
| AST (IU/L) | 21.77 ± 0.3 | 91.63 ± 98.19** | 69.21 ± 9.97 | 85.61 ± 6.37 | 115.61 ± 10.39 | 100.29 ± 15.03 | 64.22 ± 10.36 | 81.67 ± 18.04 | 94.84 ± 24.69 |
| BUN (mmol/L) | 4.82 ± 0.05 | 3.85 ± 1.53** | 3.59 ± 0.11 | 3.66 ± 0.1 | 3.49 ± 0.09 | 3.8 ± 0.16 | 4 ± 0.18 | 5.42 ± 0.47 | 6.58 ± 1.08 |
| CHOL (mmol/L) | 5.17 ± 0.04 | 4.63 ± 1.16** | 4.67 ± 0.13 | 4.7 ± 0.07 | 4.68 ± 0.08 | 4.9 ± 0.13 | 4.61 ± 0.22 | 4.13 ± 0.34 | 3.17 ± 0.71 |
| DBIL (μmol/L) | 2.34 ± 0.03 | 7.4 ± 15.72** | 3.27 ± 0.25 | 4.23 ± 0.32 | 6.32 ± 0.85 | 11.49 ± 3.55 | 6.7 ± 1.66 | 10.39 ± 1.19 | 45.64 ± 12.24 |
| GGT (IU/L) | 16.83 ± 0.46 | 68.93 ± 95.97** | 45.52 ± 5.48 | 51.95 ± 4 | 77.25 ± 7.73 | 105.75 ± 12.86 | 102.86 ± 36.44 | 61.41 ± 16.86 | 56.44 ± 14.44 |
| GLB (g/L) | 29.32 ± 0.12 | 33.97 ± 4.99** | 32.25 ± 0.48 | 33.42 ± 0.33 | 33.91 ± 0.43 | 34.73 ± 0.58 | 35.41 ± 1.44 | 34.74 ± 0.89 | 35.98 ± 1.31 |
| GLU (mmol/L) | 5.31 ± 0.06 | 5.25 ± 1.2 | 5.26 ± 0.09 | 5.11 ± 0.07 | 5.13 ± 0.06 | 5.34 ± 0.18 | 5.33 ± 0.15 | 5.76 ± 0.33 | 6.22 ± 1.01 |
| HCT (%) | 44.32 ± 0.16 | 42.16 ± 5.26** | 43.88 ± 0.47 | 43.22 ± 0.34 | 43.12 ± 0.38 | 42.84 ± 0.55 | 40.85 ± 0.83 | 35.43 ± 0.96 | 30.69 ± 1.32 |
| HGB (g/L) | 141.21 ± 0.83 | 138.21 ± 22.85* | 147.1 ± 1.69 | 144.13 ± 1.21 | 143.82 ± 1.34 | 142.18 ± 1.83 | 130.41 ± 3.74 | 101.21 ± 5.1 | 77.73 ± 5.51 |
| IBIL (μmol/L) | 10.44 ± 0.19 | 20.15 ± 18.29** | 15.44 ± 0.96 | 16.59 ± 0.63 | 18.18 ± 1.11 | 21.15 ± 2.48 | 16.28 ± 1.17 | 30.2 ± 2.42 | 77.73 ± 13.58 |
| MCH (pg) | 28.03 ± 0.07 | 30.84 ± 3.58** | 31.47 ± 0.68 | 30.56 ± 0.2 | 31.24 ± 0.39 | 31.23 ± 0.39 | 30.14 ± 0.36 | 29.51 ± 0.65 | 31.62 ± 1.01 |
| MCHC (g/L) | 353.21 ± 0.41 | 333.94 ± 16.55** | 329.69 ± 5.75 | 333.02 ± 0.63 | 333.71 ± 0.61 | 332.39 ± 1.16 | 337.13 ± 2.51 | 338.26 ± 3.9 | 343.34 ± 6.14 |
| MPV (fL) | 8.26 ± 0.03 | 9.76 ± 8.46** | 8.82 ± 0.11 | 9.84 ± 0.72 | 10.02 ± 0.85 | 12.46 ± 2.14 | 9.39 ± 0.17 | 8.85 ± 0.26 | 8.7 ± 0.24 |
| PALB (mg/L) | 333.12 ± 1.58 | 199.91 ± 71.08** | 259.51 ± 10.24 | 224.66 ± 4.89 | 184.4 ± 5.22 | 165.3 ± 9.02 | 179.82 ± 9.75 | 158.62 ± 13.32 | 143.06 ± 15.63 |
| PCT (%) | 0.14 ± 0 | 0.14 ± 0.06 | 0.17 ± 0.01 | 0.16 ± 0 | 0.16 ± 0 | 0.14 ± 0.01 | 0.1 ± 0.01 | 0.02 ± 0.01 | 0.01 ± 0.01 |
| PDW (%) | 15.27 ± 0.03 | 16.56 ± 0.74** | 16.61 ± 0.07 | 16.62 ± 0.05 | 16.56 ± 0.05 | 16.64 ± 0.08 | 16.59 ± 0.13 | 16.34 ± 0.27 | 16.18 ± 0.35 |
| PLT (10^9/L) | 261.19 ± 2.93 | 163.49 ± 61.62** | 192.67 ± 6.17 | 183.99 ± 3.7 | 181.1 ± 4.1 | 146.27 ± 6.78 | 124.58 ± 10.54 | 64.27 ± 8.96 | 67.55 ± 12.15 |
| RBC (10^12/L) | 4.75 ± 0.02 | 4.54 ± 0.66** | 4.78 ± 0.05 | 4.74 ± 0.04 | 4.67 ± 0.04 | 4.59 ± 0.08 | 4.32 ± 0.08 | 3.61 ± 0.12 | 2.81 ± 0.13 |
| TBA (μmol/L) | 4.56 ± 0.14 | 28.37 ± 44.4** | 23.02 ± 8.11 | 15.67 ± 1.15 | 24.64 ± 3.97 | 28.57 ± 4.18 | 35.34 ± 6.36 | 67.92 ± 8.98 | 121.59 ± 21.21 |
| TBIL (μmol/L) | 15.45 ± 0.21 | 27.73 ± 32.62** | 18.74 ± 1.14 | 20.82 ± 0.82 | 23.89 ± 1.43 | 32.64 ± 5.99 | 22.28 ± 1.87 | 42.63 ± 3.2 | 131.86 ± 25.1 |
| TG (mmol/L) | 1.52 ± 0.03 | 1.15 ± 0.85** | 1.26 ± 0.1 | 1.35 ± 0.14 | 1.04 ± 0.05 | 1.29 ± 0.1 | 1.35 ± 0.3 | 1.04 ± 0.06 | 1.02 ± 0.09 |
| TP (g/L) | 74.41 ± 0.2 | 73.4 ± 8.5* | 75.6 ± 0.69 | 75.81 ± 0.41 | 75.35 ± 0.47 | 73.91 ± 0.6 | 73.18 ± 1.62 | 57 ± 2.03 | 53.01 ± 2.32 |
| WBC (10^9/L) | 6.8 ± 0.08 | 5.38 ± 1.68** | 5.75 ± 0.14 | 5.41 ± 0.11 | 5.59 ± 0.13 | 5.73 ± 0.27 | 5.14 ± 0.28 | 3.74 ± 0.4 | 4.75 ± 0.68 |
| AHCV II (COI) | | 0.58 ± 4.98 | 0.05 ± 0 | 0.46 ± 0.4 | 0.92 ± 0.48 | 1.54 ± 1.48 | 1.64 ± 1.59 | 0.07 ± 0.01 | 0.06 ± 0 |
| A/G (%) | | 1.21 ± 0.26 | 1.35 ± 0.02 | 1.29 ± 0.01 | 1.25 ± 0.02 | 1.17 ± 0.03 | 1.18 ± 0.05 | 0.82 ± 0.04 | 0.65 ± 0.04 |
| AFP (ng/mL) | | 10.95 ± 30.38 | 2.42 ± 0.2 | 6.25 ± 1.53 | 7.9 ± 1.17 | 38.98 ± 9.63 | 15.2 ± 6.3 | 10.97 ± 3.78 | 21.35 ± 10.91 |
| AFU (U/L) | | 31.69 ± 17.23 | 28.04 ± 1.16 | 31.07 ± 1.38 | 30.98 ± 1.23 | 35 ± 1.67 | 32.31 ± 2.07 | 37 ± 1.68 | 22 ± 0 |
| APTT (Sec) | | 37.72 ± 6.41 | 36.09 ± 0.49 | 36.05 ± 0.3 | 36.66 ± 0.31 | 37.14 ± 0.63 | 38.57 ± 0.72 | 43.96 ± 1.24 | 58.05 ± 3.89 |
| AST/ALT (%) | | 0.62 ± 0.35 | 0.55 ± 0.03 | 0.6 ± 0.02 | 0.58 ± 0.02 | 0.7 ± 0.06 | 0.73 ± 0.05 | 1.1 ± 0.13 | 1.04 ± 0.3 |
| ApoAI (g/L) | | 1.4 ± 0.41 | 1.41 ± 0.03 | 1.45 ± 0.03 | 1.49 ± 0.03 | 1.49 ± 0.07 | 1.2 ± 0.07 | 1.03 ± 0.04 | 0.82 ± 0.06 |
| ApoB | | 0.94 ± | 0.91 ± | 0.96 ± | 0.95 ± | 1.05 ± | 0.91 ± | 0.85 ± | 0.79 ± |

TABLE 4-continued

Demographic data of testing population

| Number | Control 502 | NASH Liver disease 504 | Fibrosis S0 n = 46 | S1 n = 174 | S2 n = 136 | S3 n = 57 | Cirrhosis CP A n = 39 | CP B n = 30 | CP C N = 16 |
|---|---|---|---|---|---|---|---|---|---|
| (g/L) | | 0.28 | 0.03 | 0.03 | 0.03 | 0.04 | 0.04 | 0.04 | 0.06 |
| CHE (KU/L) | | 7.43 ± 2.2 | 8.84 ± 0.19 | 8.29 ± 0.13 | 7.76 ± 0.13 | 7.1 ± 0.21 | 6.51 ± 0.3 | 3.44 ± 0.26 | 2.14 ± 0.21 |
| CREA (μmol/L) | | 72.16 ± 17.01 | 77.96 ± 2.04 | 71.86 ± 1.23 | 70.95 ± 1.2 | 72.76 ± 1.74 | 66.94 ± 2.14 | 71.15 ± 5.47 | 82.61 ± 11.55 |
| FT3 (pmol/L) | | 4.85 ± 1.55 | 4.96 ± 0.09 | 4.94 ± 0.06 | 4.85 ± 0.06 | 4.65 ± 0.1 | 4.8 ± 0.08 | 3.88 ± 0.2 | ND |
| FT4 (pmol/L) | | 15.36 ± 4.97 | 15.5 ± 0.28 | 15.71 ± 0.22 | 15.57 ± 0.17 | 14.74 ± 0.29 | 14 ± 0.3 | 14.4 ± 0.63 | ND |
| Fib (g/L) | | 2.73 ± 0.97 | 2.81 ± 0.09 | 2.72 ± 0.04 | 2.83 ± 0.07 | 2.53 ± 0.07 | 2.8 ± 0.09 | 2.35 ± 0.3 | 1.63 ± 0.24 |
| HA (ng/ml) | | 50.48 ± 54.43 | 22.38 ± 3.72 | 19.84 ± 2.98 | 45.5 ± 8.06 | 145.8 ± 53.8 | 52.66 ± 19.56 | 285.16 ± 0 | ND |
| HBVDNA (IU/ml) | | 76462726.54 ± 154851345.74 | 104757500 ± 34862060 | 79503300 ± 12617610 | 96797890 ± 19223610 | 58227680 ± 15890770 | 51886250 ± 29179040 | 1033463 ± 676325.8 | 601075.3 ± 595011.8 |
| HBVDNA 1 ( ) | | 67908616.22 ± 149738604.35 | 78958230 ± 24495910 | 80075220 ± 12695650 | 97653030 ± 19375290 | 58227650 ± 15890770 | 54429440 ± 30007430 | 2301102 ± 1218347 | 21000.25 ± 20999.75 |
| HBcAb (PEI U/ml) | | 2.61 ± 2.97 | 1 ± 0.23 | 1.55 ± 0.16 | 2.29 ± 0.18 | 2.08 ± 0.28 | 4.7 ± 0.66 | 6.85 ± 0.68 | 8.64 ± 0.74 |
| HBeAb (PEI U/ml) | | 1.61 ± 2.32 | 2.05 ± 0.32 | 2.31 ± 0.22 | 1.28 ± 0.16 | 1.42 ± 0.25 | 0.94 ± 0.22 | 0.99 ± 0.59 | 1.52 ± 1.17 |
| HBeAg (PEI U/ml) | | 183.66 ± 375.08 | 254.39 ± 63 | 335.69 ± 39.87 | 165.78 ± 30.82 | 112.39 ± 43.06 | 84.29 ± 38.16 | 21.99 ± 17.18 | 45.81 ± 44.41 |
| HBsAb (mIU/ml) | | 20.31 ± 101.99 | 35.94 ± 21.33 | 14.16 ± 5.03 | 21.33 ± 10.4 | 20.24 ± 16.92 | 25.55 ± 18.09 | 53.27 ± 31.96 | 9.32 ± 8.05 |
| HBsAb1 | | 0.01 ± 0.08 | 0 ± 0 | 0 ± 0.01 | 0.02 ± 0.01 | 0 ± 0 | 0.03 ± 0.03 | 0 ± 0 | 0 ± 0 |
| HBsAg1 | | 0.94 ± 0.35 | 0.85 ± 0.05 | 0.93 ± 0.02 | 0.94 ± 0.02 | 0.96 ± 0.03 | 0.94 ± 0.04 | 0.89 ± 0.11 | 1 ± 0 |
| HBsAgQ N (ng/mL) | | 6793.93 ± 14769.89 | 9630.59 ± 2650.75 | 12410.72 ± 1569.52 | 7102.33 ± 1344.5 | 4193.58 ± 1386.42 | 3061.05 ± 1429.18 | 1001.81 ± 423.37 | 396.91 ± 115.38 |
| HDLC (mmol/L) | | 1.17 ± 0.38 | 1.08 ± 0.03 | 1.2 ± 0.03 | 1.25 ± 0.04 | 1.32 ± 0.07 | 1.02 ± 0.06 | 0.99 ± 0.04 | 0.78 ± 0.06 |
| INR (%) | | 1.02 ± 0.19 | 0.95 ± 0.01 | 0.96 ± 0.01 | 0.99 ± 0.01 | 1.03 ± 0.02 | 1.04 ± 0.02 | 1.29 ± 0.03 | 1.61 ± 0.11 |
| LDLC (mmol/L) | | 2.96 ± 0.94 | 2.83 ± 0.09 | 2.98 ± 0.09 | 3.03 ± 0.09 | 3.22 ± 0.13 | 2.77 ± 0.14 | 2.68 ± 0.19 | 2.25 ± 0.2 |
| LN (ng/ml) | | 76.42 ± 38.58 | 57.63 ± 5.25 | 67.21 ± 3.93 | 78.83 ± 6.9 | 105.69 ± 16.06 | 111.54 ± 32.9 | 57.86 ± 0 | ND |
| PT (Sec) | | 13.64 ± 2.64 | 12.79 ± 0.09 | 12.81 ± 0.07 | 13.03 ± 0.09 | 13.46 ± 0.17 | 13.84 ± 0.27 | 17.82 ± 0.55 | 22.75 ± 1.61 |
| PTA (%) | | 99.93 ± 24.9 | 110.4 ± 1.95 | 109 ± 1.34 | 105.51 ± 1.44 | 100.31 ± 2.8 | 90.86 ± 3.52 | 55.08 ± 3.43 | 35.38 ± 5.06 |
| PTR (%) | | 0.99 ± 0.29 | 0.96 ± 0.01 | 0.97 ± 0.01 | 0.99 ± 0.01 | 1.02 ± 0.01 | 1.02 ± 0.01 | 1.24 ± 0.04 | 1.47 ± 0.13 |
| TSH (μIU/mL) | | 2.27 ± 4.56 | 1.95 ± 0.14 | 2.75 ± 0.6 | 2.03 ± 0.1 | 2 ± 0.19 | 2.17 ± 0.26 | 1.78 ± 0.56 | ND |
| TT (Sec) | | 17.7 ± 4.85 | 16.03 ± 0.13 | 16.34 ± 0.07 | 16.3 ± 0.19 | 17.15 ± 0.14 | 18.82 ± 0.52 | 24.16 ± 1.32 | 35.43 ± 2.77 |

Note:
Values are expressed as mean ± SEM.
*p < 0.05; **p < 0.01, compared to healthy controls.

Example 2 Liver Biopsy

Liver disease patients except those diagnosed as decompensated cirrhosis were received a liver biopsy directed by ultrasonography within 1 week after inclusion. The biopsy specimens were fixed with 10% formalin, routinely embedded in paraffin, and the tissue sections were processed with hematoxylin and eosin and Masson's trichrome staining. A minimum length of at least 1.5 cm of the liver biopsy and at least six portal tracts were required for diagnosis. Histological grading of necro-inflammation (G0 to G4) and staging of liver fibrosis (S0 to S4) were carried out according to Scheuer's classification (Scheuer P J, Standish R A, Dhillon A P. Scoring of chronic hepatitis. Clinics in liver disease 2002; 6:335-47, v-vi.). All of the sections were blindly and independently assessed by three pathologists from Fudan University, Shanghai, China and the observed results were processed by the Kappa concordance test.

Example 3 Serum Sample Collection

Hematological and common biochemical tests were measured according to the manufacturer's protocol using LH750 Hematology Analyzer and Synchron DXC800 Clinical System (Beckman Coulter, USA). The serum hyaluronic acid (HA) and laminin (LN) concentration were measured with chemiluminescence immunoassay analyzer (CLIA) system (LUMO, Shinova Systems, Shanghai, China). The coagulation function was measured with automatic coagulation analyzer (STAGO Compact, Diagnostica Stago, France). The serum HBV-DNA level was detected with a Real-Time polymerase chain reaction (PCR) System (LightCycler 480, Roche, USA)

Example 4 Statistical Analysis

Quantitative variables were expressed as mean±SEM; categorical variables were expressed as number. Univariate analysis (ANOVA, Student t-test, nonparametric test) was carried out to identify variables that were significantly different between patients with liver fibrosis and healthy controls and among of liver fibrosis patients at different stages. We regarded p values of <0.05 as significant. Multivariate statistical analysis, orthogonal partial least squares-discriminant analysis (OPLS-DA), was first conducted to get an overview of the bile acid profiles of the control and liver fibrosis after the dataset was introduced into SIMCA-P+ 13.0 software (Umetrics, Umeå Sweden). Next, we performed OPLS-DA to differentiate liver fibrosis patients at different stages. Predictive models were constructed by stepwise logistic regression, which identified independent factors associated with each end point (fibrosis patients at S1, S2, S3, and cirrhosis patients at CP A, CP B and CP C). The overall diagnostic performance of single markers and marker panels was evaluated by receiver operating characteristic (ROC) curve analysis. Statistical analysis was carried out using the SPSS 22.0 (IBM SPSS, USA) software. Canonical discriminant Analysis was also carried out for bile acid data using SPSS. The bar plots were drawn using the Graphpad Prism 6.0 (GraphPad software, CA, USA).

Example 5 Analysis of Serum Bile Acids

Serum Sample Preparation.

An aliquot of 50 µl of serum was mixed with 150 µl of methanol (contains 0.10 µM of CA-D4, UDCA-D4, and LCA-D4 used as the internal standard). The mixture was then vortexed for 2 min, allowed to stand for 10 min, and then centrifuged at 20000 g at 4° C. for 10 min. An aliquot of 160 µL supernatant was transferred to a clean tube and vacuum dried. The residue was redissolved with equal amount of acetonitrile (0.1% formic acid) and water (0.1% formic acid) to a final volume of 40 µL. After centrifugation, the supernatant was used for UPLC-MS/MS analysis.

Method Validation.

Each aliquot of standard stock solution was mixed to obtain a mixed stock solution. Calibration solutions containing all bile acid standards were prepared at a series of concentrations of 0.610, 1.221, 2.441, 4.883, 9.766, 19.531, 39.063, 78.125, 156.250, 312.5, 625.0, 1250.000, and 2500.00 ng/mL in naïve pooled serum depleted of BAs using activated charcoal. The calibration curve and the corresponding regression coefficients were obtained by internal standard adjustment.

Instrumentation.

Serum BAs were measured according to methods previously reported (Xie G, Zhong W, Li H, et al. Alteration of bile acid metabolism in the rat induced by chronic ethanol consumption. FASEB journal: official publication of the Federation of American Societies for Experimental Biology 2013; 27:3583-93. Garcia-Canaveras J C, Donato M T, Castell J V, Lahoz A. Targeted profiling of circulating and hepatic bile acids in human, mouse, and rat using a UPLC-MRM-MS-validated method. Journal of lipid research 2012; 53:2231-41) with some modifications. A Waters ACQUITY ultra performance LC system equipped with a binary solvent delivery manager and a sample manager (Waters, Milford, MA) was used throughout the study. The mass spectrometer was a Waters XEVO TQ-S instrument with an ESI source (Waters, Milford, MA). The entire LC-MS system was controlled by MassLynx 4.1 software. All chromatographic separations were performed with an ACQUITY BEH C18 column (1.7 µm, 100 mm×2.1 mm internal dimensions) (Waters, Milford, MA).

LC-MS Analysis.

The mobile phase consisted of 0.1% formic acid in LC-MS grade water (mobile phase A) and 0.1% formic acid in LC-MS grade acetonitrile (mobile phase B) run at a flow rate of 0.3 mL/min. The flow rate was 0.45 mL/min with the following mobile phase gradient: 0-1 min (5% B), 1-5 min (5-25% B), 5-15.5 min (25-40% B), 15.5-17.5 min (40-95% B), 17.5-19 min (95% B), 19-19.5 min (95-5% B), 19.6-21 min (5% B). The column was maintained at 45° C. and the injection volume of all samples was 5 µl.

The mass spectrometer was operated in negative ion mode with a 1.2 kv capillary voltage. The source and desolvation gas temperature was 150 and 550° C., respectively. The data was collected with multiple reaction monitor (MRM) and the cone and collision energy for each bile acid (Table 5) used the optimized settings from QuanOptimize application manager (Waters Corp., Milford, MA).

Data analysis.

UPLC-MS raw data obtained with negative mode were analyzed using TargetLynx applications manager version 4.1 (Waters Corp., Milford, MA) to obtain calibration equations and the quantitative concentration of each BA in the samples. A Student's t test was used to investigate differences between the groups in BAs measurements. The resultant p values for all metabolites were subsequently adjusted to account for multiple testing by false discovery rate (FDR) method.[26] We regarded p values of <0.05 as significant.

TABLE 5

MRM transitions and mass spectrometry parameters for the bile acids LC-MS/MS analysis.

| Compound | Parent (m/z) | Daughter (m/z) | Dwell time (s) | Cone (v) | Collision (v) |
| --- | --- | --- | --- | --- | --- |
| 12-KCDCA | 405 | 405 | 0.05 | 50 | 10 |
| 12-KLCA | 389 | 389 | 0.05 | 60 | 10 |
| 23-NDCA | 377.3 | 331 | 0.05 | 68 | 33 |
| 3-KCA | 405 | 405 | 0.05 | 65 | 10 |
| 6-KLCA | 389 | 389 | 0.05 | 60 | 10 |
| 7-KDCA | 405 | 405 | 0.05 | 65 | 10 |
| 7-KLCA | 389 | 389 | 0.05 | 60 | 10 |
| ACA | 389 | 389 | 0.05 | 60 | 10 |
| CA | 407 | 407 | 0.05 | 60 | 15 |
| CA-d4 | 411 | 347 | 0.1 | 62 | 35 |
| CDCA | 391 | 391 | 0.05 | 50 | 10 |
| DCA | 391 | 391 | 0.05 | 50 | 10 |
| DHCA | 401 | 331 | 0.05 | 64 | 26 |
| IsoLCA | 375 | 375 | 0.05 | 50 | 10 |
| GCA | 464 | 74 | 0.05 | 60 | 26 |
| GCDCA | 448 | 74 | 0.05 | 60 | 50 |
| GDCA | 448 | 74 | 0.05 | 60 | 50 |
| GDHCA | 458 | 74 | 0.05 | 60 | 43 |
| GHCA | 464 | 74 | 0.05 | 60 | 26 |
| GHDCA | 448 | 74 | 0.05 | 60 | 50 |
| GLCA | 432 | 74 | 0.05 | 50 | 50 |
| GUDCA | 448 | 74 | 0.05 | 60 | 50 |
| HCA | 407 | 407 | 0.05 | 60 | 15 |
| HDCA | 391 | 391 | 0.05 | 55 | 10 |

TABLE 5-continued

MRM transitions and mass spectrometry parameters for the bile acids LC-MS/MS analysis.

| Compound | Parent (m/z) | Daughter (m/z) | Dwell time (s) | Cone (v) | Collision (v) |
|---|---|---|---|---|---|
| isoDCA | 391 | 391 | 0.05 | 50 | 10 |
| LCA | 375 | 375 | 0.05 | 68 | 33 |
| LCA-d4 | 379 | 379 | 0.05 | 70 | 15 |
| MuroCA | 391 | 391 | 0.05 | 55 | 10 |
| TCA | 514 | 124 | 0.05 | 50 | 55 |
| TCDCA | 498 | 80 | 0.05 | 60 | 55 |
| TDCA | 498 | 80 | 0.05 | 60 | 55 |
| TDHCA | 508 | 80 | 0.05 | 60 | 65 |
| THCA | 514 | 80 | 0.05 | 63 | 63 |
| THDCA | 499 | 80 | 0.05 | 60 | 55 |
| TLCA | 482 | 80 | 0.05 | 40 | 55 |
| TUDCA | 498 | 80 | 0.05 | 60 | 55 |
| TαMCA | 514 | 80 | 0.05 | 60 | 65 |
| TβMCA | 514 | 80 | 0.05 | 60 | 65 |
| TωMCA | 514 | 80 | 0.05 | 60 | 65 |
| UDCA | 391 | 391 | 0.05 | 50 | 10 |
| UDCA-d4 | 395 | 395 | 0.03 | 60 | 30 |
| αMCA | 407 | 407 | 0.05 | 50 | 10 |
| βMCA | 407 | 407 | 0.05 | 50 | 10 |
| ωMCA | 407 | 407 | 0.05 | 50 | 10 |

Example 6 Analysis of Serum Amino Acids

Following our previous procedure, each 100 μL of serum sample spiked with two internal standards (10 μL L-2-chlorophenylalanine in water, 0.3 mg/mL; 10 μL heptadecanoic acid in methanol, 1 mg/mL) was used for metabolites extraction with 300 μL of methanol: chloroform (3:1) at −20° C. for 10 min. An aliquot of the 300 μL supernatant was used for further analysis after a 12,000 rpm centrifuge for 10 min. The samples were vacuum dried at room temperature. The residue was subjected to a two-step derivatization procedure with 80 μL methoxyamine (15 mg/mL in pyridine) for 90 min at 30° C., and 80 μL BSTFA (1% TMCS) for 60 min at 70° C. In addition to the internal standards used for quality control, another quality control sample consisting of multiple reference standards was prepared and run with each 10 samples. This QC sample was vacuum dried and derivatized using the same procedure along with the samples.

The samples were analyzed by Pegasus HT system (Leco Corporation, St Joseph, USA) coupled with an Agilent 6890N gas chromatography in an order of "control-CRC-control". A QC sample was run after each 10 serum samples. The injection volume was 1 μL with a splitless mode. The injection was set to 270° C. A DB-5MS capillary column (30 m×250 μm I.D., 0.25-μm film thickness; Agilent J&W Scientific, CA, USA) was used to separate the metabolites. Helium was used as the carrier gas, with 1.0 mL/min. The GC oven temperature started at 80° C. for 2 min, then ramped to 180° C. with 10° C./min, to 230° C. with 6° C./min, and finally to 295° C. with 40° C./min. The final temperature of 295° C. was maintained for 8 min. The temperature of transfer interface and ion source was set to 270° C. and 220° C., respectively. The m/z range was set to 30-600 with electron impact ionization (70 eV). The acquisition rate was set to 20 spectrum/seconds.

Example 7 Analysis of Serum Free Fatty Acids

Serum FFA Extraction:
A 30 μL aliquot of serum sample was spiked with the isotopically labeled internal standard solution (10 μl C19:0-d37, 5 μg/mL). The mixed solution was extracted with 500 μL of isopropanol:hexane:2M phosphoric acid (40:10:1) and vortexed for 2 min. After storing for 20 minutes at room temperature, the samples were added with 400 μl hexane and 300 μL water, vortexed for 2 min and then centrifuged at 12,000 rpm for 5 minutes. An aliquot of 400 μL supernatant was transferred to a glass sampling vial. The residue was extracted with another 400 μl hexane, followed by vortex for 2 min and centrifugation at 12,000 rpm for 5 min. An aliquot of 400 μL supernatant was transferred to the same glass sampling vial to vacuum dry at room temperature. The residue was dissolved in 80 μL methanol pending UPLC-QTOFMS analysis.

Quantitative Analysis of Serum FFA by UPLC-QTOFMS:
A 5 μL aliquot of the supernatant was injected onto a 100 mm×2.1 mm, 1.7 μm BEH C18 column (Waters, USA) held at 40° C. using an ultra performance liquid chromatography system (Waters, USA). The binary gradient elution system consisted of water (A) and acetonitrile with 20% v/v isopropanol (B) and separation was achieved using the following gradient: isocratic at 70% B (0-2 min), linear gradient from 70-75% B (2-5 min), 75-80% B (5-10.0 min), 80-90% B (10.0-13.0 min), 90-100% B (13.0-16.0 min); isocratic at 100% B (16.0-21.0 min); linear gradient from 100% to 70% B (21.0-22.5 min) and isocratic at 70% B (22.5-24.0 min). The flow rate was 0.4 mUmin. All the samples were kept at 4° C. during the analysis. The samples were run in the order of "control-disease-control", alternately, to minimize systematic analytical deviations. A pooled FFA standard was used as quality control to monitor the instrument performance and data quality.

The mass spectrometric data was collected using a Waters Q-TOF premier (Manchester, UK) equipped with an electrospray ion source operating in negative ion mode. The source temperature was set at 120° C. with a cone gas flow of 50 L/h, a desolvation gas temperature of 450° C. with a desolvation gas flow of 600 L/h. The capillary and cone voltage was set to 2.5 kV and 55 V, respectively. Leucine enkephalin was used as the lock mass (m/z 554.2615 in ES-mode) at a concentration of 100 ng/mL and flow rate of 0.1 mUmin for all analyses.

The UPLC-QTOFMS ESI-raw data were analyzed by the MarkerLynx Applications Manager version 4.1 (Waters, Manchester, U.K.). A list of the ion intensities of each peak detected was generated, using retention time (RT) and the m/z data pairs as the identifier for each ion. The resulting three-dimensional matrix contains arbitrarily assigned peak index (retention time-m/z pairs), sample names (observations), and ion intensity information (variables). The internal standard was used for data quality control (reproducibility). The identification of FFA in samples was performed by comparing with the FFA standards using retention time and accurate mass.

Example 8 Bile Acid Profiles of NASH, Liver Fibrosis and Cirrhosis Patients

A total of 23 bile acids including glycochenodeoxycholic acid (GCDCA), glycocholic acid (GCA), chenodeoxycholic acid (CDCA), deoxycholic acid (DCA), glycodeoxycholic acid (GDCA), cholic acid (CA), ursodeoxycholic acid (UDCA), glycoursodeoxycholic acid (GUDCA), glycohyodeoxycholic acid (GHDCA), taurochenodeoxycholic acid (TCDCA), taurodeoxycholic acid (TDCA), taurocholic acid (TCA), glyco λ-muricholic acid (G λ-MCA), λ-muricholic acid (λ-MCA), 7-ketolithocholic acid (7-KLCA), 7-ketodeoxycholic acid (7-KDCA), lithocholic acid (LCA), tauroursodeoxycholic acid (TUDCA), hyodeoxycholic acid (HDCA), 3-ketocholic acid (3-KCA), Tauro λ-muricholic acid (T λ-MCA), taurolithocholic acid (TLCA), and glycolithocholic acid (GLCA) were significantly increased in liver disease patients compared to healthy controls. When we compared the bile acid levels among patient of liver fibrosis and cirrhosis, there were remarkable differences in GCDCA, GCA, CDCA, CA, UDCA, GUDCA, GHDCA, TCDCA, TCA, 7-KLCA, LCA, TUDCA, 3-KCA, T λ-MCA, TLCA, and GLCA and their levels were very low in control subjects, increased significantly (p<0.01) in fibrosis patients, and were very strongly increased in patients with cirrhosis (Table 6).

TABLE 6

Serum bile acid concentrations in testing population

| Bile acids Abbreviation | Full name | Control | Liver disease | NASH S0 | Fibrosis S1 | Fibrosis S2 | Fibrosis S3 | Cirrhosis CP A | Cirrhosis CP B | Cirrhosis CP C |
|---|---|---|---|---|---|---|---|---|---|---|
| GCDCA | Glycochenodeoxycholic acid | 253.17 ± 13.72 | 2191.69 ± 4130.99** | 1530.53 ± 404.05 | 1360.82 ± 133.32 | 2408.27 ± 543.64 | 1771.7 ± 273.94 | 2563.37 ± 458.16 | 3364.13 ± 343.52 | 9741.02 ± 1492.49 |
| GCA | Glycocholic acid | 72.99 ± 6.15 | 1176.03 ± 1752.77** | 865.75 ± 229.72 | 739.92 ± 97.7 | 812.89 ± 114.89 | 1246.9 ± 227.31 | 1524.37 ± 333.61 | 3246.95 ± 354.45 | 4619.41 ± 473.24 |
| CDCA | Chenodeoxycholic acid | 123.24 ± 7.39 | 237.7 ± 426.24** | 240.61 ± 56.63 | 175.74 ± 18.94 | 163.78 ± 18.26 | 193.4 ± 39.78 | 399.52 ± 72.98 | 510.34 ± 186.66 | 812.26 ± 240.57 |
| GDCA | Glycodeoxycholic acid | 44.27 ± 2.39 | 237.69 ± 434.11** | 252.56 ± 60.24 | 232.03 ± 36.8 | 243.14 ± 33.21 | 198.46 ± 38.65 | 306.8 ± 93.19 | 154.34 ± 42.83 | 281.6 ± 158.23 |
| DCA | Deoxycholic acid | 62.01 ± 2.31 | 81.1 ± 120.56** | 122.32 ± 28 | 75.39 ± 5.84 | 78.79 ± 8.42 | 58.42 ± 11.36 | 68.32 ± 9.72 | 92.78 ± 38.89 | 127.6 ± 69.81 |
| CA | Cholic acid | 46.05 ± 3.63 | 180.89 ± 428.52** | 247.63 ± 95.97 | 117.35 ± 19.66 | 133.34 ± 23.39 | 169.03 ± 48.3 | 258.12 ± 66.34 | 379.22 ± 140.54 | 586.79 ± 237.83 |
| UDCA | Ursodeoxycholic acid | 36.92 ± 2.75 | 76.09 ± 343.61* | 47.41 ± 11.46 | 33.4 ± 3.06 | 49.1 ± 8.96 | 38.38 ± 5.76 | 72.93 ± 16.91 | 496.39 ± 228.1 | 215.04 ± 146.94 |
| GUDCA | Glycoursodeoxycholic acid | 20.59 ± 1.38 | 135.42 ± 618.99** | 53.67 ± 8.09 | 47.33 ± 4.85 | 75.25 ± 11.03 | 103.56 ± 19.58 | 179.6 ± 54.76 | 528.56 ± 218.77 | 1108.24 ± 705.63 |
| GHDCA | Glycohyodeoxycholic acid | 2.93 ± 0.47 | 8.8 ± 17.8** | 19.17 ± 0.21 | 4.54 ± 1.5 | 3.7 ± 1.46 | 8.42 ± 0.34 | 9.83 ± 1.3 | 23.58 ± 1.14 | 36.99 ± 8.98 |
| TCDCA | Taurochenodeoxycholic acid | 17.73 ± 1.24 | 614.06 ± 1696.8** | 260.3 ± 101.64 | 236.95 ± 34.15 | 555.88 ± 216.61 | 727.59 ± 173.81 | 708.89 ± 153.91 | 1748.81 ± 340.8 | 3263.26 ± 679 |
| TDCA | Taurodeoxycholic acid | 5.65 ± 0.41 | 70.93 ± 186.51** | 70.11 ± 16.43 | 60.94 ± 8.84 | 78.81 ± 24.57 | 67.83 ± 16.38 | 85.33 ± 28.18 | 46.32 ± 11.73 | 83.78 ± 50.36 |
| TCA | Taurocholic acid | 6.24 ± 1.38 | 375.36 ± 1144.35** | 210.32 ± 95.95 | 151.4 ± 31.55 | 348.07 ± 148.93 | 345 ± 77.43 | 518.73 ± 182.34 | 1007.07 ± 166.08 | 1749.49 ± 327.26 |
| G λ-MCA | Glyco-λ-muricholic acid | 3.19 ± 0.16 | 33.43 ± 188.36** | 20.15 ± 5.42 | 19.79 ± 2.71 | 58.1 ± 30.77 | 23.86 ± 2.88 | 16.28 ± 4.06 | 36.29 ± 4.95 | 59.39 ± 19.65 |
| λ-MCA | Glyco-λ-muricholic acid | 4.24 ± 0.21 | 22.07 ± 46.46** | 17.15 ± 4.89 | 19.99 ± 3.41 | 22.41 ± 4.63 | 19.88 ± 3.78 | 17.68 ± 5.3 | 31.7 ± 10.24 | 35.75 ± 18.76 |
| 7-KLCA | 7-Ketocholic acid | 2.26 ± 0.13 | 5.26 ± 5.31** | 2.56 ± 0.73 | 5.71 ± 0.32 | 4.8 ± 0.4 | 4.97 ± 0.91 | 6.26 ± 1.09 | 7.71 ± 1.08 | 6.86 ± 1.91 |
| 7-KDCA | 7-Ketodeoxycholic acid | 1.03 ± 0.07 | 3.95 ± 19.23** | 3.6 ± 0.81 | 1.82 ± 0.15 | 3.04 ± 0.81 | 9.51 ± 6.82 | 4.23 ± 1.39 | 7.63 ± 3.22 | 8.66 ± 5.61 |
| LCA | Lithocholic acid | 1.06 ± 0.04 | 1.52 ± 3.68** | 1.3 ± 0.14 | 1.1 ± 0.08 | 1.56 ± 0.08 | 1.51 ± 0.18 | 1.58 ± 0.2 | 4.35 ± 2.61 | 0.98 ± 0.32 |
| TUDCA | Tauroursodeoxycholic acid | 1.44 ± 0.08 | 24.75 ± 111.38** | 8.69 ± 2.24 | 5.57 ± 0.61 | 12.61 ± 5.7 | 18.02 ± 5.66 | 41.77 ± 23.59 | 171.93 ± 65.21 | 87.21 ± 25.42 |
| HDCA | Hyodeoxycholic acid | 2.88 ± 0.23 | 7.24 ± 18.6** | 7.98 ± 1.78 | 5.27 ± 1.06 | 6.43 ± 1.8 | 11.72 ± 3.73 | 4.3 ± 1.46 | 8.24 ± 3.26 | 8.33 ± 3.93 |
| 3-KCA | 3-ketocholic acid | 0.71 ± 0.02 | 1.32 ± 2.19** | 1.4 ± 0.22 | 0.52 ± 0.07 | 1.5 ± 0.15 | 1.37 ± 0.24 | 1.73 ± 0.21 | 2.4 ± 0.87 | 4.29 ± 1.44 |
| T λ-MCA | Tauro-λ-muricholic acid | 0.77 ± 0.02 | 13.27 ± 41.07** | 5.23 ± 1.62 | 6.67 ± 1.65 | 11.73 ± 3.15 | 12.47 ± 2.22 | 23.21 ± 14.43 | 26.21 ± 4.72 | 50.48 ± 21.54 |
| TLCA | Taurolithocholic acid | 1.11 ± 0.02 | 2.13 ± 1.95** | 1.79 ± 0.17 | 1.6 ± 0.06 | 1.94 ± 0.16 | 2.51 ± 0.38 | 3.05 ± 0.35 | 4.01 ± 0.67 | 2.9 ± 0.26 |
| GLCA | Glycolithocholic acid | 1.38 ± 0.08 | 3.17 ± 4.18** | 2.54 ± 0.42 | 2.45 ± 0.22 | 3.49 ± 0.39 | 3.31 ± 0.47 | 3.55 ± 0.48 | 4.86 ± 1.64 | 4.77 ± 1.49 |

Note:
Values are mean concentration (ng/mL) ± SEM measured using UPLC-MS/MS.
**p < 0.01 when compared to healthy controls Example 9 Fatty Acid Profiles of NASH, Liver Fibrosis and Cirrhosis Patients A total of 50 free fatty acids including were identified in liver disease patients of different progression/severity levels and healthy controls (Table 7). Based on the data, it is clear that free fatty acid levels modulate (go up or down depending on the specific fatty acid, as shown in the table) with the presence and/or progression of liver disease. The data demonstrate that these markers can be used to discriminate liver disease from healthy controls or discriminate between liver disease status (e.g. by progression or severity).

TABLE 7

Serum fatty acid concentrations in testing population

| Free fatty acids Abbreviation | Full name | Control | Liver disease | NASH | Fibrosis S1 | Fibrosis S2 | Fibrosis S3 | Cirrhosis CP A | Cirrhosis CP B | Cirrhosis CP C |
|---|---|---|---|---|---|---|---|---|---|---|
| C8:0 | Caprylic acid | 2.18 ± 0.35 | 2.51 ± 0.45 | 2.22 ± 0.37 | 1.94 ± 0.18 | 3.51 ± 1.57 | 2.32 ± 0.31 | 3.55 ± 1 | 1.25 ± 0.25 | 1.41 ± 0.39 |
| C10:0 | Capric acid | 0.49 ± 0.04 | 0.45 ± 0.02 | 0.4 ± 0.03 | 0.41 ± 0.02 | 0.43 ± 0.05 | 0.46 ± 0.04 | 0.45 ± 0.04 | 0.62 ± 0.05 | 0.88 ± 0.23 |
| C12:0 | Lauric acid | 0.64 ± 0.05 | 0.56 ± 0.02* | 0.5 ± 0.04 | 0.58 ± 0.05 | 0.52 ± 0.04 | 0.5 ± 0.04 | 0.58 ± 0.05 | 0.72 ± 0.06 | 0.85 ± 0.14 |
| C14:0 | Myristic acid | 4.54 ± 0.37 | 4.38 ± 0.12 | 3.95 ± 0.38 | 4.17 ± 0.18 | 3.95 ± 0.2 | 4.18 ± 0.35 | 5.34 ± 0.44 | 6.14 ± 0.5 | 6.41 ± 0.76 |
| C14:0 iso | 12-Methyltridecanoic acid | 0.06 ± 0 | 0.04 ± 0** | 0.04 ± 0 | 0.04 ± 0 | 0.04 ± 0.01 | 0.03 ± 0 | 0.05 ± 0.01 | 0.04 ± 0 | 0.04 ± 0 |
| C14:1 (cis-9) | Myristoleic acid | 0.18 ± 0.01 | 0.25 ± 0.01** | 0.17 ± 0.02 | 0.18 ± 0.01 | 0.19 ± 0.01 | 0.2 ± 0.02 | 0.28 ± 0.03 | 0.66 ± 0.08 | 0.92 ± 0.15 |
| C14:1 (trans-9) | Myristelaidic acid | 0.13 ± 0.02 | 0.12 ± 0.01* | 0.11 ± 0.01 | 0.1 ± 0.01 | 0.11 ± 0.01 | 0.11 ± 0.01 | 0.11 ± 0.01 | 0.17 ± 0.02 | 0.3 ± 0.1 |
| C15:0 iso | 13-Methylmyristic acid | 0.13 ± 0.01 | 0.1 ± 0** | 0.09 ± 0.01 | 0.1 ± 0 | 0.1 ± 0.01 | 0.09 ± 0.01 | 0.1 ± 0.01 | 0.12 ± 0.01 | 0.09 ± 0.01 |
| C15:0 | Pentadecanoic acid | 0.26 ± 0.02 | 0.25 ± 0.01** | 0.23 ± 0.03 | 0.25 ± 0.01 | 0.24 ± 0.01 | 0.22 ± 0.02 | 0.32 ± 0.03 | 0.28 ± 0.03 | 0.19 ± 0.03 |
| C16:0 iso | 14-methylpentadecanoic acid | 0.07 ± 0.01 | 0.06 ± 0** | 0.06 ± 0.01 | 0.06 ± 0 | 0.06 ± 0 | 0.05 ± 0 | 0.07 ± 0.01 | 0.07 ± 0.01 | 0.05 ± 0.01 |
| C16:0 | Palmitic acid | 38.46 ± 1.94 | 39.57 ± 0.79 | 37.77 ± 1.94 | 39.93 ± 1.4 | 37.59 ± 1.45 | 40.4 ± 2.21 | 41.75 ± 3.27 | 44.06 ± 2.91 | 40.89 ± 5.71 |
| C16:1 (cis-9) | Palmitoleic acid | 0.42 ± 0.03 | 0.6 ± 0.02** | 0.49 ± 0.04 | 0.56 ± 0.02 | 0.54 ± 0.03 | 0.56 ± 0.04 | 0.7 ± 0.07 | 0.94 ± 0.08 | 1.2 ± 0.18 |
| C16:1(trans-9) | Palmitelaidic acid | 0.07 ± 0.01 | 0.06 ± 0.01* | 0.06 ± 0.01 | 0.06 ± 0.01 | 0.08 ± 0.03 | 0.05 ± 0.01 | 0.05 ± 0.01 | 0.06 ± 0.01 | 0.05 ± 0.01 |
| C16:2(Z-9,12,15,18,22) | Hexadecadienoic acid | 0.1 ± 0.01 | 0.08 ± 0** | 0.08 ± 0.01 | 0.08 ± 0 | 0.08 ± 0 | 0.09 ± 0.01 | 0.09 ± 0.01 | 0.11 ± 0.01 | 0.12 ± 0.03 |
| C17:0 iso | 15-Methylpalmitic acid | 0.17 ± 0.01 | 0.14 ± 0** | 0.13 ± 0.01 | 0.14 ± 0.01 | 0.14 ± 0.01 | 0.13 ± 0.01 | 0.16 ± 0.02 | 0.16 ± 0.02 | 0.15 ± 0.02 |
| C17:0 | Margaric acid | 0.52 ± 0.03 | 0.49 ± 0.01** | 0.47 ± 0.04 | 0.51 ± 0.02 | 0.48 ± 0.02 | 0.48 ± 0.03 | 0.52 ± 0.04 | 0.52 ± 0.04 | 0.41 ± 0.06 |
| C17:1(cis-10) | Heptadecenoic acid | 0.38 ± 0.02 | 0.41 ± 0.01 | 0.36 ± 0.03 | 0.37 ± 0.01 | 0.37 ± 0.02 | 0.41 ± 0.03 | 0.47 ± 0.04 | 0.61 ± 0.04 | 0.66 ± 0.11 |
| C18:0iso | 16-Methylmargaric acid | 0.04 ± 0 | 0.04 ± 0** | 0.03 ± 0 | 0.04 ± 0 | 0.04 ± 0 | 0.03 ± 0 | 0.04 ± 0 | 0.04 ± 0 | 0.04 ± 0.01 |
| C18:0 | Stearic acid | 15.16 ± 1.03 | 15.48 ± 0.33 | 14.32 ± 1.07 | 15.51 ± 0.56 | 15.34 ± 0.66 | 16.1 ± 0.96 | 15.86 ± 0.87 | 17.65 ± 1.48 | 12.44 ± 1.81 |
| C18:1(cis-9) | Oleic acid | 45.16 ± 2.16 | 48.76 ± 0.91** | 46.82 ± 2.59 | 48 ± 1.43 | 45.61 ± 1.7 | 47.88 ± 2.64 | 52.49 ± 3.39 | 61.2 ± 3.45 | 59.49 ± 8.51 |
| C18:1(trans-9) | Elaidic acid | 0.33 ± 0.02 | 0.11 ± 0.01** | 0.1 ± 0.01 | 0.11 ± 0.01 | 0.1 ± 0.01 | 0.09 ± 0.01 | 0.17 ± 0.02 | 0.15 ± 0.02 | 0.19 ± 0.06 |
| C18:2(cis-9,12) | Linoleic acid | 49.14 ± 2.13 | 47.92 ± 0.9 | 45.83 ± 2.48 | 45.75 ± 1.33 | 45.15 ± 1.62 | 48.58 ± 2.66 | 54.16 ± 3.86 | 62.51 ± 4.11 | 55.1 ± 8.31 |
| C18:2(trans-9,12) | Linoelaidic acid | 0.11 ± 0.01 | 0 ± 0** | 0 ± 0 | 0 ± 0 | 0 ± 0 | 0 ± 0 | 0.01 ± 0 | 0.03 ± 0.01 | 0.02 ± 0.01 |
| C18:3(cis-9,12,15) | γ-Linolenic acid | 0.33 ± 0.02 | 0.3 ± 0.01* | 0.27 ± 0.02 | 0.29 ± 0.01 | 0.28 ± 0.01 | 0.3 ± 0.02 | 0.35 ± 0.03 | 0.38 ± 0.03 | 0.43 ± 0.07 |
| C18:3(cis-6,9,12) | α-Linolenic acid | 0.19 ± 0.01 | 0.15 ± 0** | 0.12 ± 0.01 | 0.13 ± 0.01 | 0.13 ± 0.01 | 0.15 ± 0.01 | 0.18 ± 0.02 | 0.22 ± 0.02 | 0.27 ± 0.05 |
| C19:0 | Nonadecanoic acid | 0.03 ± 0 | 0.03 ± 0** | 0.03 ± 0 | 0.03 ± 0 | 0.03 ± 0 | 0.03 ± 0 | 0.04 ± 0 | 0.04 ± 0 | 0.02 ± 0 |
| C19:1(cis-10) | Nonadecenoic acid | 0.05 ± 0 | 0.06 ± 0* | 0.05 ± 0 | 0.06 ± 0 | 0.06 ± 0 | 0.06 ± 0 | 0.06 ± 0.01 | 0.09 ± 0.01 | 0.09 ± 0.02 |
| C20:0 | Arachidic acid | 0.18 ± 0.02 | 0.2 ± 0.01 | 0.2 ± 0.02 | 0.22 ± 0.01 | 0.18 ± 0.01 | 0.19 ± 0.02 | 0.18 ± 0.02 | 0.22 ± 0.03 | 0.13 ± 0.04 |
| C20:1(cis-11) | Eicosenoic acid | 0.55 ± 0.04 | 0.64 ± 0.02** | 0.57 ± 0.04 | 0.59 ± 0.02 | 0.6 ± 0.03 | 0.68 ± 0.05 | 0.62 ± 0.05 | 1.06 ± 0.09 | 0.9 ± 0.13 |
| C20:2(cis-11,14) | Eicosadienoic acid | 0.9 ± 0.05 | 0.95 ± 0.02 | 0.87 ± 0.06 | 0.88 ± 0.03 | 0.89 ± 0.04 | 0.96 ± 0.05 | 1.04 ± 0.09 | 1.27 ± 0.1 | 1.35 ± 0.19 |
| C20:3(cis-8,11,14) | Eicosatrienoic acid | 0.43 ± 0.04 | 0.4 ± 0.01** | 0.38 ± 0.03 | 0.4 ± 0.02 | 0.4 ± 0.03 | 0.42 ± 0.03 | 0.41 ± 0.03 | 0.46 ± 0.04 | 0.41 ± 0.05 |

TABLE 7-continued

Serum fatty acid concentrations in testing population

| Free fatty acids Abbreviation | Full name | Control | Liver disease | NASH | Fibrosis S1 | S2 | S3 | Cirrhosis CP A | CP B | CP C |
|---|---|---|---|---|---|---|---|---|---|---|
| C20:4(cis-5,8,11,14) | Arachidonic acid | 0.42 ± 0.03 | 0.36 ± 0.01** | 0.34 ± 0.03 | 0.38 ± 0.02 | 0.35 ± 0.02 | 0.35 ± 0.02 | 0.35 ± 0.03 | 0.39 ± 0.04 | 0.34 ± 0.04 |
| C20:5(cis-5,8,11,14,17) | cis-5,8,11,14,17-Eicosapentaenoic acid | 0.48 ± 0.08 | 0.55 ± 0.03 | 0.47 ± 0.06 | 0.63 ± 0.05 | 0.54 ± 0.05 | 0.53 ± 0.09 | 0.5 ± 0.07 | 0.51 ± 0.11 | 0.42 ± 0.07 |
| C22:1(cis-13) | Erucic acid | 0.15 ± 0.05 | 0.09 ± 0.01* | 0.06 ± 0.01 | 0.07 ± 0.01 | 0.09 ± 0.01 | 0.08 ± 0.01 | 0.06 ± 0.01 | 0.27 ± 0.07 | 0.09 ± 0.01 |
| C22:2(cis-13,16) | cis-13,16-Docosadienoic acid | 0.03 ± 0 | 0.03 ± 0** | 0.03 ± 0 | 0.03 ± 0 | 0.03 ± 0 | 0.03 ± 0 | 0.03 ± 0 | 0.05 ± 0 | 0.05 ± 0.01 |
| C22:4(cis-7,10,13,16) | cis-7,10,13,16-Docosatetraenoic acid | 0.64 ± 0.04 | 0.68 ± 0.02 | 0.6 ± 0.04 | 0.63 ± 0.02 | 0.62 ± 0.03 | 0.69 ± 0.04 | 0.73 ± 0.06 | 0.98 ± 0.08 | 1.08 ± 0.17 |
| C22:5(cis-4,7,10,13,16) | cis-4,7,10,13,16-Docosapentaenoic acid | 0.28 ± 0.02 | 0.28 ± 0.01* | 0.25 ± 0.02 | 0.28 ± 0.01 | 0.27 ± 0.01 | 0.28 ± 0.02 | 0.31 ± 0.03 | 0.34 ± 0.03 | 0.34 ± 0.06 |
| C22:5(cis-7,10,13,16,19) | cis-7,10,13,16,19-Docosapentaenoic acid | 0.95 ± 0.08 | 0.92 ± 0.02** | 0.84 ± 0.06 | 0.93 ± 0.04 | 0.88 ± 0.04 | 0.91 ± 0.06 | 0.9 ± 0.07 | 1.14 ± 0.1 | 1.2 ± 0.17 |
| C24:0 | Lignoceric acid | 0.02 ± 0 | 0.02 ± 0 | 0.03 ± 0 | 0.02 ± 0 | 0.02 ± 0 | 0.02 ± 0 | 0.01 ± 0 | 0.02 ± 0 | 0.01 ± 0 |
| C24:1(cis-15) | Nervonic acid | 0.04 ± 0 | 0.04 ± 0** | 0.04 ± 0 | 0.04 ± 0 | 0.04 ± 0 | 0.04 ± 0 | 0.04 ± 0 | 0.07 ± 0.01 | 0.05 ± 0.01 |
| C22:6(cis-4,7,10,13,16,19) | cis-4,7,10,13,16,19-Docosahexaenoic acid | 6.53 ± 0.46 | 6.81 ± 0.16 | 6.33 ± 0.45 | 6.97 ± 0.29 | 6.73 ± 0.29 | 6.65 ± 0.42 | 6.85 ± 0.54 | 7.41 ± 0.6 | 6.52 ± 1.06 |
| C16:1(cis-7) | cis-7-Hexadecenoic acid | 1.08 ± 0.13 | 0.67 ± 0.04** | 0.66 ± 0.08 | 0.63 ± 0.05 | 0.55 ± 0.05 | 1.1 ± 0.23 | 0.9 ± 0.15 | 0.51 ± 0.11 | 0.33 ± 0.14 |
| C18:2(C LA) | Octadecadienoic acid (Conjugated,9,11) | 3.08 ± 0.22 | 2.86 ± 0.09** | 2.55 ± 0.24 | 2.54 ± 0.13 | 2.59 ± 0.15 | 2.82 ± 0.22 | 3.4 ± 0.35 | 4.98 ± 0.58 | 4.28 ± 0.79 |

Note:
Values are mean concentration (μg/mL) ± SEM measured using UPLC-QTOFMS.
*$p < 0.05$;
**$p < 0.01$ when compared to healthy controls.

Example 10 Amino Acid Profiles of NASH, Liver Fibrosis and Cirrhosis Patients

A total of 29 amino acids were identified in liver disease patients with different progression/severity and healthy controls (Table 8). Based on the data, it is clear that amino acid levels modulate (go up or down depending on the specific amino acid as shown in the table) with the presence and/or progression of liver disease. The data demonstrate that these markers can be used to discriminate liver disease from healthy controls or discriminate between liver disease status (e.g. by progression or severity).

TABLE 8

Serum amino acid concentrations in testing population.

| Amino acids | Control | Liver disease | NASH | Fibrosis S1 | S2 | S3 | Cirrhosis CP A | CP B | CP C |
|---|---|---|---|---|---|---|---|---|---|
| 5-Oxoproline | 14029880 ± 399239.4 | 13628294.58 ± 179932.39** | 13178240 ± 504574.3 | 13350430 ± 304172 | 13415660 ± 299975.3 | 13313040 ± 414068.6 | 14477350 ± 647893.3 | 15029940 ± 905667.4 | 16043720 ± 1942901 |
| Alanine | 46405910 ± 1767134 | 39289826.55 ± 516732.9** | 39094840 ± 1469755 | 38743230 ± 812822.4 | 38651060 ± 863491.5 | 42221040 ± 1790118 | 41187660 ± 2214198 | 36764880 ± 2821215 | 40822630 ± 3104273 |
| Aspartic acid | 854915.8 ± 34132.15 | 552667.76 ± 11148.36** | 508447 ± 26711.84 | 548908.8 ± 18166.08 | 551326.3 ± 20087.34 | 576829.7 ± 31901.03 | 676104.5 ± 48354.9 | 498593.1 ± 57625.67 | 446687.7 ± 70888.92 |

TABLE 8-continued

Serum amino acid concentrations in testing population.

| Amino acids | Control | Liver disease | NASH | Fibrosis S1 | Fibrosis S2 | Fibrosis S3 | Cirrhosis CP A | Cirrhosis CP B | Cirrhosis CP C |
|---|---|---|---|---|---|---|---|---|---|
| Beta-Alanine | 734080.2 ± 85360.53 | 88247.07 ± 9723.13** | 38711.35 ± 3439.53 | 41343.25 ± 2453.1 | 39920.66 ± 2577.71 | 42460.04 ± 3622.75 | 103928.5 ± 31999.85 | 370389.7 ± 83005.47 | 723831.3 ± 143818.9 |
| Citrulline | 1137775 ± 32161.84 | 1120379.19 ± 16859.98 | 1034677 ± 45628.84 | 1051045 ± 22645.89 | 1049429 ± 24644.94 | 1096965 ± 29854.95 | 1254259 ± 61060.78 | 1503991 ± 101506 | 1729672 ± 184092.4 |
| Creatine | 3749122 ± 138444.1 | 3402282.46 ± 40251.69** | 3541246 ± 106698.2 | 3443544 ± 63132.98 | 3450673 ± 67129.14 | 3460415 ± 138279 | 3229342 ± 131060.7 | 2950468 ± 198482.3 | 3226901 ± 419807.8 |
| Cystine | 287181 ± 12539.77 | 304986.11 ± 7385.48** | 290681 ± 12974.72 | 275316.8 ± 7240.02 | 268489.8 ± 8016.48 | 276935.8 ± 12168.55 | 320034.9 ± 20425.17 | 470522.2 ± 37537.29 | 716266.7 ± 126534.4 |
| Glutamic acid | 824394.6 ± 35439.47 | 827826.73 ± 28345.76 | 710100.6 ± 48902.52 | 776259.4 ± 38508.18 | 856998.3 ± 56130.85 | 971104.9 ± 90228.32 | 1118369 ± 127882.9 | 712934.7 ± 186083.3 | 472410.1 ± 77166.34 |
| Glutamine | 12844270 ± 333486 | 11528118.59 ± 148734.23 | 11590370 ± 435350.2 | 11524620 ± 214719.9 | 11129430 ± 269423.9 | 10691740 ± 372798.5 | 11334660 ± 572962.7 | 14038150 ± 836838.3 | 11334660 ± 572962.7 ± 14038150 ± 836838.3 |
| Asparagine | 592706.5 ± 30335.15 | 520406.62 ± 11737.77 | 515304.5 ± 26500.96 | 503029.7 ± 18441.49 | 516233.8 ± 19607.91 | 550893.1 ± 35094.54 | 471104.3 ± 54536.08 | 566755.8 ± 62954.27 | 471104.3 ± 54536.08 ± 566755.8 ± 62954.27 |
| N-Acetylglutamin | 16761.91 ± 6513.436 | 46304.24 ± 5633.13 | 47181.24 ± 17334.37 | 44073.04 ± 9728.567 | 61214.73 ± 12469.08 | 39488.56 ± 135970.76 | 41937.1 ± 21612.59 | 29764.19 ± 13988 | 41937.1 ± 21612.59 ± 29764.19 ± 13988 |
| N-Acetyl-L-aspartic acid | 5820.794 ± 2259.455 | 12603.47 ± 1256.74 | 13628.28 ± 3982.57 | 11778.95 ± 2211.557 | 15003.58 ± 2331.057 | 9590.373 ± 2575.324 | 15835.64 ± 6256.154 | 12785.62 ± 5513.845 | 15835.64 ± 6256.154 ± 12785.62 ± 5513.845 |
| Glycine | 12617290 ± 626330.3 | 10338365.55 ± 183117.11** | 9280901 ± 451755.4 | 9944226 ± 298577.2 | 10058050 ± 322662.8 | 10280690 ± 519924.8 | 11232950 ± 669607.1 | 12592930 ± 994229.6 | 13683390 ± 1292520 |
| Histidine | 268386 ± 11154.4 | 249841.52 ± 3682.07** | 233516.5 ± 10374.44 | 245375.3 ± 6475.97 | 245397.4 ± 6306.3 | 248308.8 ± 9475.23 | 258163.1 ± 12930.5 | 300035.2 ± 18758.21 | 272137.7 ± 27730.75 |
| Isoleucine | 5863133 ± 235209.8 | 5226510.94 ± 67364.49** | 5270248 ± 174881 | 5177632 ± 107429.4 | 5327641 ± 122936.6 | 5785942 ± 209899 | 5465267 ± 266787.1 | 4430232 ± 286684 | 3723139 ± 383591.8 |
| Leucine | 11301100 ± 851455.9 | 10288828.01 ± 239593.55** | 9658689 ± 800533.3 | 9742646 ± 429791.5 | 11029540 ± 415478 | 10949300 ± 807635.5 | 12238280 ± 666707.2 | 8830888 ± 885127.1 | 7336271 ± 939152.4 |
| Lysine | 4603667 ± 501347.2 | 4826290.42 ± 121812.5 | 4299170 ± 444964.5 | 4836378 ± 210458.4 | 4763243 ± 218158.3 | 4880205 ± 330100.8 | 5615803 ± 378394.3 | 4564723 ± 552825.6 | 5133582 ± 859932.4 |
| Methionine | 928537.9 ± 30160.8 | 1161644.62 ± 72863.62** | 869401.4 ± 31715.88 | 880305 ± 19808.43 | 977539.5 ± 29378.31 | 1120767 ± 51572.47 | 1296102 ± 100790.2 | 1777509 ± 268177.7 | 5175958 ± 1896530 |
| N-Acetyl-L-aspartic acid | 5820.79 ± 2259.46 | 12603.47 ± 1256.74* | 13628.28 ± 3982.57 | 11778.95 ± 2211.56 | 15003.58 ± 2331.06 | 9590.37 ± 2575.32 | 15835.64 ± 6256.15 | 12785.62 ± 5513.85 | 591.16 ± 591.16 |
| Ornithine | 4657457 ± 562551.9 | 4756825.82 ± 191233.06 | 4284541 ± 457763.2 | 4644256 ± 271158.2 | 4079428 ± 258597.3 | 4706982 ± 382216.7 | 5726340 ± 792146.7 | 6224842 ± 1719643 | 8035600 ± 1745884 |
| Phenylalanine | 2751171 ± 79128.84 | 2746353.82 ± 42306.4 | 2473839 ± 74733.58 | 2559796 ± 51875.63 | 2645718 ± 66921.98 | 2645483 ± 80016.31 | 3170173 ± 162128.9 | 3395494 ± 188323 | 4446032 ± 624428.1 |
| Proline | 20859110 ± 902143.9 | 17659433.43 ± 291317.48** | 16269660 ± 749871.6 | 16645410 ± 461759.2 | 16307700 ± 423923.1 | 19735910 ± 872295.2 | 20055730 ± 1133678 | 20137540 ± 1435123 | 25931280 ± 2566343 |
| Pyroglutamic acid | 609960.1 ± 46026.25 | 682694.69 ± 28147.4** | 600412 ± 62343.15 | 604148.4 ± 37819.54 | 727458.8 ± 58234.37 | 880600.3 ± 88988.89 | 913802.1 ± 118140.6 | 543589.9 ± 170910 | 378830.9 ± 89241.53 |
| Serine | 5816557 ± 199395.3 | 5609111.85 ± 65353.52** | 5043942 ± 149885.6 | 5416155 ± 97304.96 | 5566482 ± 110155.5 | 5971612 ± 205997 | 5968203 ± 286114.5 | 6304162 ± 367105.1 | 6181868 ± 528755.5 |
| S-Methyl-cysteine | 113606.1 ± 8011.52 | 96503.86 ± 2292.73** | 100364.6 ± 10025.94 | 95416.98 ± 4064.22 | 89810.02 ± 3632.88 | 96872.79 ± 6569.18 | 98162.08 ± 7749.83 | 119489.6 ± 9021.84 | 104513.9 ± 10817.76 |
| Threonine | 2654809 ± 79880.17 | 2714210.56 ± 35960.24** | 2487672 ± 77667.02 | 2578793 ± 51945.57 | 2770605 ± 67234.22 | 2910472 ± 97191.64 | 2913164 ± 142959.4 | 2735664 ± 160500.1 | 3111459 ± 436061.8 |
| Tryptophan | 3010817 ± 140200.4 | 2874640.86 ± 42260.73* | 2864709 ± 128086.8 | 2925291 ± 70238.52 | 2860294 ± 81421.64 | 2904867 ± 94867.77 | 3089725 ± 137400.2 | 2728389 ± 224709.1 | 2132155 ± 312774.9 |
| Tyrosine | 3619177 ± 115872.7 | 4820470.15 ± 93618.47** | 3915505 ± 129797.8 | 4026208 ± 84590.13 | 4495096 ± 110019.3 | 5167558 ± 186575.8 | 5739155 ± 316032.8 | 7863873 ± 478774.3 | 9376173 ± 1257093 |
| Valine | 22662800 ± 729463.6 | 19371741.65 ± 224209.32** | 19668530 ± 582536.9 | 19295180 ± 360516.2 | 19878710 ± 388075.3 | 21458450 ± 716157.2 | 20030100 ± 784133.3 | 15924860 ± 980014.9 | 12636000 ± 989227.6 |

Note:
Values are mean intensities ± SEM measured using GC-TOFMS.
*$p < 0.05$;
**$p < 0.01$ when compared to healthy controls.

Example 11 Biomarkers for Discriminating Fibrosis from Healthy Controls

Figure 10A:
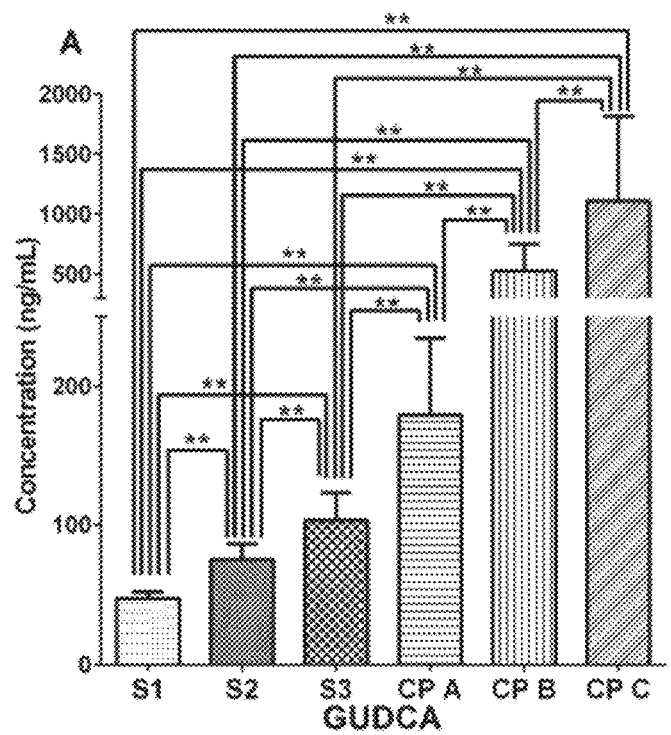
FIG. 10A-FIG. 10C depict bar charts of GUDCA (ng/mL, mean±SEM) among different stages of liver fibrosis patients and Child-Pugh A, B and C cirrhosis patients. A, all subjects; B, male subjects; and C, female subjects. GUDCA was gradually increased with the progression of liver disease. * denotes 0.05; ** denotes p<0.01, compared to each other
Figure 10B:
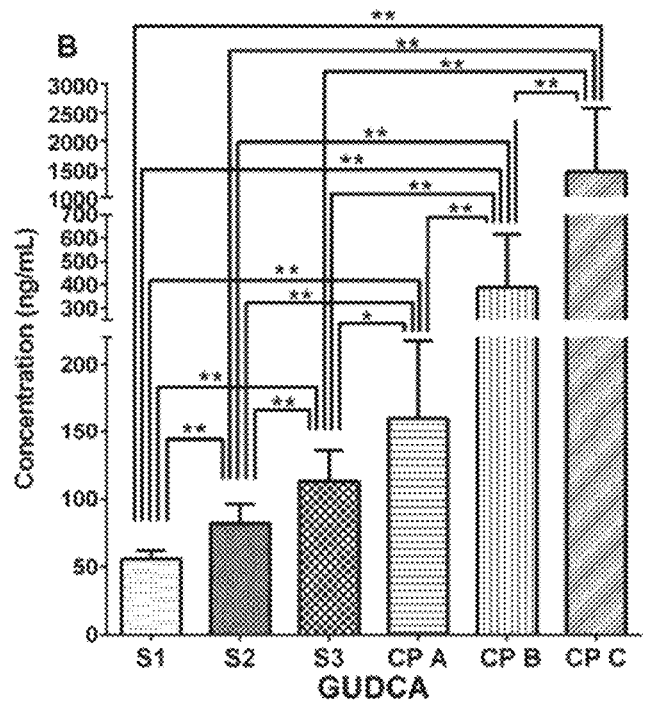
Figure 10C:
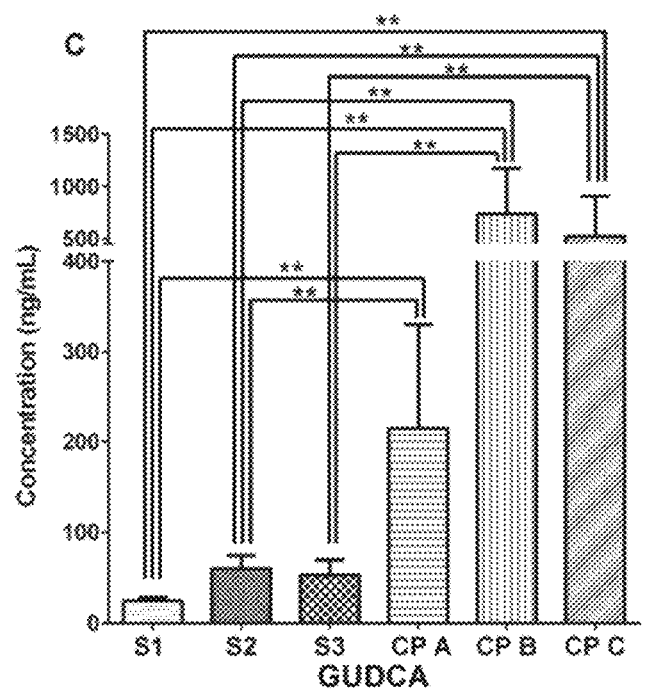
Figure 11A:
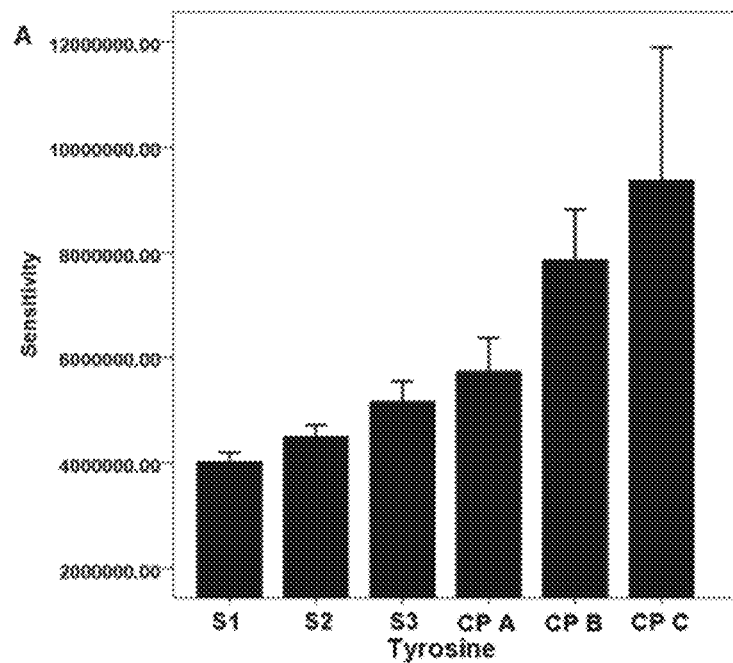
FIG. 11A-FIG. 11C depict bar charts of tyrosine (intensity, mean±SEM) among different stages of liver fibrosis patients and Child-Pugh A, B and C cirrhosis patients. A, all subjects; B, male subjects; and C, female subjects. Tyrosine was gradually increased with the progression of liver disease. * denotes p<0.05; ** denotes p<0.01, compared to each other.
Figure 11B:
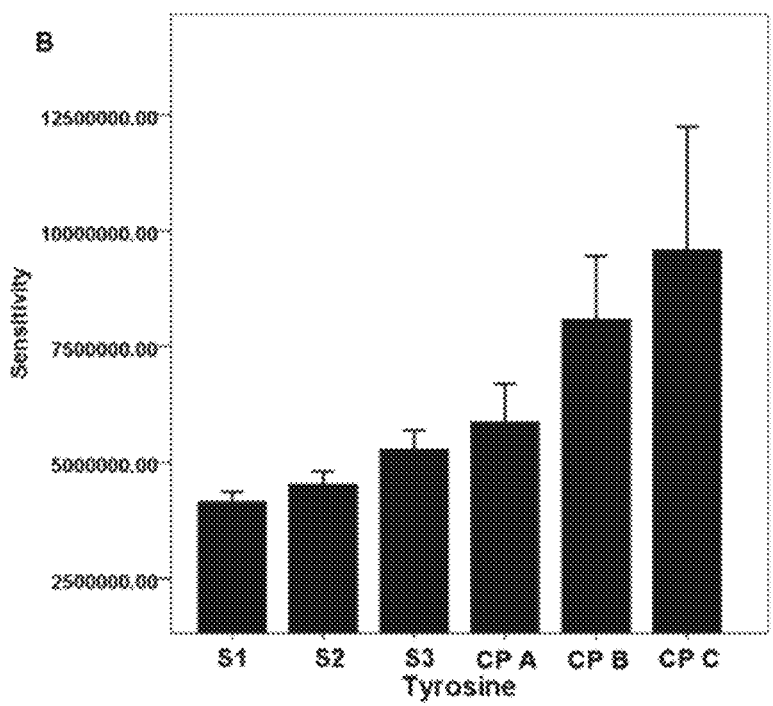
Figure 11C:
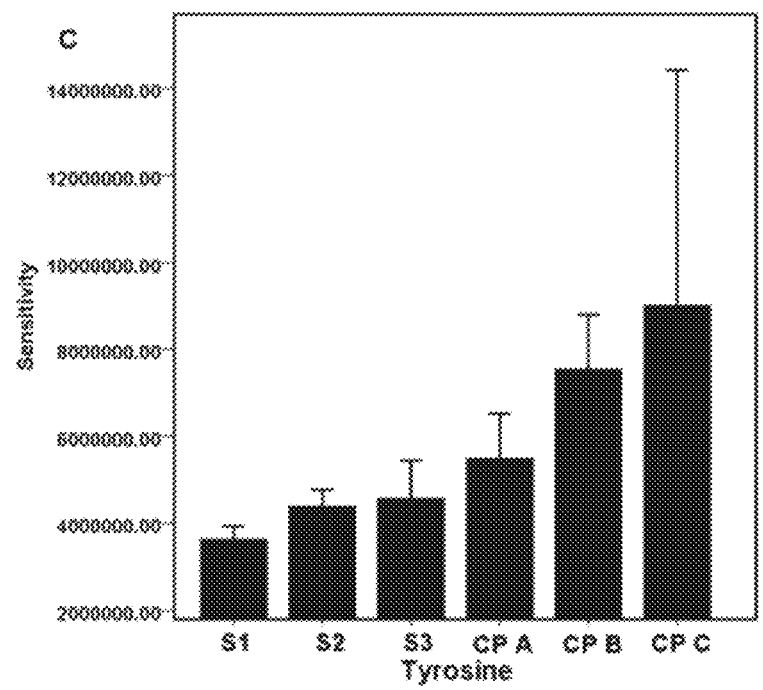

OPLS-DA revealed a separation between liver fibrosis patients and healthy controls using the 23 bile acids (FIG. 1A, R2Xcum=0.719, R2Ycum=0.778, Q2Ycum=0.744), free fatty acids (FIG. 1B, R2Xcum=0.664, R2Ycum=0.829, Q2Ycum=0.806) and amino acids (FIG. 10, R2Xcum=0.516, R2Ycum=0.793, Q2Ycum=0.785).

Example 12 Biomarkers for Discriminating NASH from Healthy Controls

To evaluate the potential utility of serum metabolites for the discrimination between NASH patients and control subjects, we developed logistic regression models based on the identified bile acids, free fatty acids and amino acids, respectively.

Through a forward stepwise analysis, we identified GCA, GCDCA, TCA, and TCDCA, were effective predictors of NASH or other steatohepatitis disease status in the regression model (Table 9). Using these metabolites, we established a regression model as follows:

$$\text{Probability} = \frac{\exp\{-2.0203 - 0.006(GCDCA) + 0.010(GCA) + 0.102(TCDCA) - 0.061(TCA)\}}{1 + \exp\{-2.0203 - 0.006(GCDCA) + 0.010(GCA) + 0.102(TCDCA) - 0.061(TCA)\}}$$

Figure 2A:
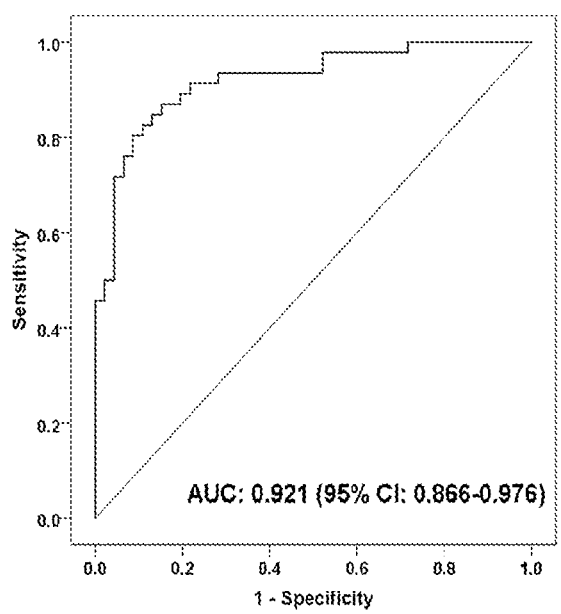
FIG. 2A depicts a receiver operating characteristic (ROC) curve in the diagnosis (i.e. distinguishing) of fibrosis at stage 0 (NASH patients) from healthy controls using GCA, GCDCA, TCA and TCDCA. The AUC is 0.921.

Next, we generated ROC curves to assess the potential usefulness of bile acid signatures as noninvasive biomarkers for the diagnosis of NASH. Our ROC analyses revealed that bile acid biomarkers were robust in discriminating patients with NASH from controls, with an area under the curve (AUC) value of 0.921 (95% CI=0.866 to 0.976) (FIG. 2A). Using a cut-off value of 0.384, the sensitivity and specificity are 84.8% and 87.0%, respectively (Table 10).

Figure 2B:
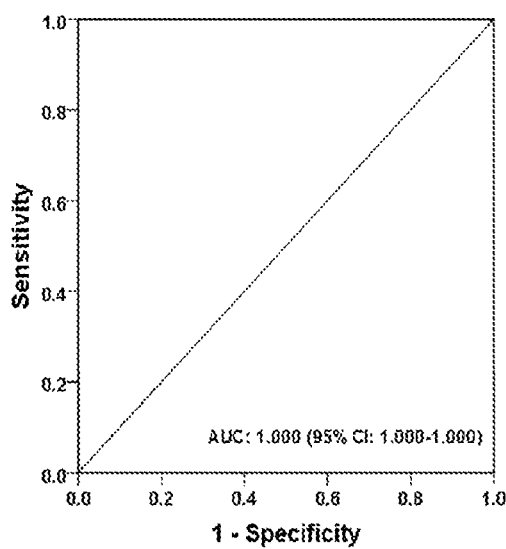
FIG. 2B depicts an ROC curve in the diagnosis (i.e. distinguishing) of fibrosis at stage 0 (NASH patients) from healthy controls using beta-alanine. The AUC is 1.000.
Figure 2C:
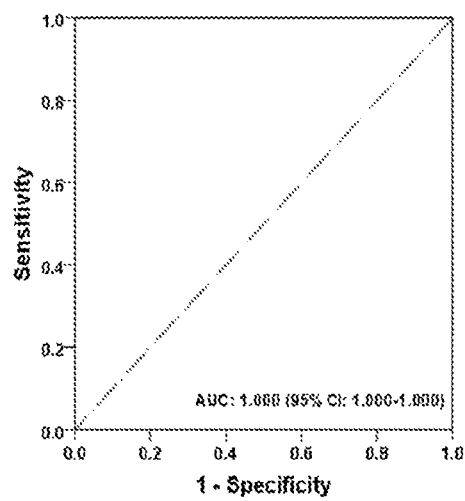
FIG. 2C depicts an ROC curve in the diagnosis (i.e. distinguishing) of fibrosis at stage 0 (NASH patients) from healthy controls using C18:2 (trans-9,12). The AUC is 1.000.

We also identified that C18:2 (trans 9,12) can discriminate patients with NASH from controls, with an area under the curve (AUC) value of 1.000 (95% CI=1.000 to 1.000) (FIG. 2C). Using a cut-off value of 0.5 µg/mL, the sensitivity and specificity reached both of 100% (Table 11).

We also identified that δ-alanine can discriminate patients with NASH from controls, with an area under the curve (AUC) value of 1.000 (95% CI=1.000 to 1.000) (FIG. 2B). Using a cut-off value of 111709, the sensitivity and specificity reached both of 100% (Table 12).

TABLE 9

Logistic regression analysis of a NASH-associated signature for a biomarker panel.

|  | Coefficient | S.E. | P value |
| --- | --- | --- | --- |
| GCDCA | −.006 | .002 | .008 |
| GCA | .010 | .004 | .020 |
| TCDCA | .102 | .027 | .000 |
| TCA | −.061 | .017 | .000 |
| Constant | −2.023 | .493 | .000 |

P values were calculated using the Wald test.

TABLE 10

Diagnosis accuracy of a biomarker panel (GCDCA, GCA, TCDCA and TCA) for the detection of patients with NASH compared to healthy controls.

| AUC (95% CI) | P value | Cutoff value 50% probability | Sensitivity (%) | Specificity (%) |
| --- | --- | --- | --- | --- |
| 0.921 (0.866-0.976) | 0.000 | 0.384 | 84.8 | 87.0 |

TABLE 11

Diagnosis accuracy of C18:2 (trans 9,12) for detection of patients with NASH compared to healthy controls.

| AUC (95% CI) | P value | Cutoff value (µg/mL) | Sensitivity (%) | Specificity (%) |
| --- | --- | --- | --- | --- |
| 1.000 (1.000-1.000) | 0.000 | 0.5 | 100 | 100 |

TABLE 12

Diagnosis accuracy of beta-alanine for the detection of patients with NASH compared to healthy controls.

| AUC (95% CI) | P value | Cutoff value (intensity) | Sensitivity (%) | Specificity (%) |
| --- | --- | --- | --- | --- |
| 1.000 (1.000-1.000) | 0.000 | 111709 | 100 | 100 |

Example 13 Biomarkers for Discriminating Patients of NASH from Fibrosis

To evaluate the potential utility of serum metabolites for the discrimination between NASH patients and fibrosis subjects, we developed logistic regression models based on the identified bile acids, free fatty acids and amino acids, respectively.

Through a forward stepwise analysis, we identified Serine, DCA, and 7-KLCA, were effective predictors of disease status in the regression model (Table 13).

Figure 3:
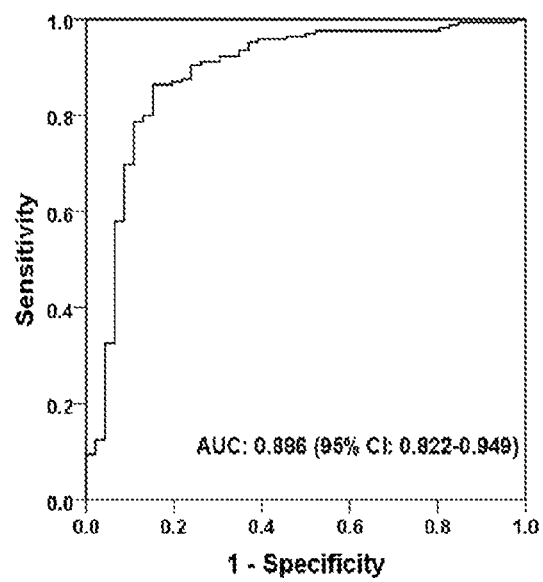
FIG. 3 depicts an ROC curve in the diagnosis (i.e. distinguishing) of fibrosis at stage 0 from fibrosis at stage 1 (NAHS vs. fibrosis) using the combination of serine, DCA and 7-KLCA. The AUC is 0.886.

Next, we generated ROC curves to assess the potential usefulness of metabolite signatures as noninvasive biomarkers for the differentiation of patients with NASH from fibrosis. Our ROC analyses revealed that metabolite biomarkers were robust in discriminating patients with NASH from fibrosis, with an area under the curve (AUC) value of 0.866 (95% CI=0.822 to 0.949) (FIG. 3). Using a cut-off value of 0.724, the sensitivity and specificity are 86.4% and 84.8%, respectively (Table 14). OPLS-DA scores plot established with Serine, DCA, and 7-KLCA showed separations between liver fibrosis patients and NASH patients (FIG. 4, R2Xcum=0.666, R2Ycum=0.654, Q2Ycum=0.643).

TABLE 13

Logistic regression analysis of metabolite signatures for discriminating NASH from S1 fibrosis subjects.

| | Coefficient | S.E. | P value |
|---|---|---|---|
| Serine | 0.000 | 0.000 | 0.041 |
| DCA | −0.014 | 0.003 | 0.000 |
| 7-KLCA | 0.678 | 0.111 | 0.000 |
| Constant | −2.067 | 1.089 | 0.058 |

P values were calculated using the Wald test.

TABLE 14

Diagnosis accuracy of a panel signatures for discriminating NASH subjects from S1 fibrosis subjects.

| AUC (95% CI) | P value | Cutoff value 50% probability | Sensitivity (%) | Specificity (%) |
|---|---|---|---|---|
| 0.866 (0.822-0.949) | 0.000 | 0.724 | 86.4 | 84.8 |

Example 14 Biomarkers for Discriminating Patients of Fibrosis from Cirrhosis To evaluate the potential utility of serum metabolites for the discrimination between fibrosis patients and cirrhosis subjects, we developed logistic regression models based on the identified bile acids, free fatty acids and amino acids, respectively.

Through a forward stepwise analysis, we identified C14.1.cis.9, C20.4 . . . cis.5.8.11.14., Beta-Alanine, Citrulline, Isoleucine, Methionine, Ornithine, Phenylalanine, Proline, Threonine, Tyrosine, CDCA, and GUDCA, were the effective predictors of disease status in the regression model (Table 15).

Figure 5:
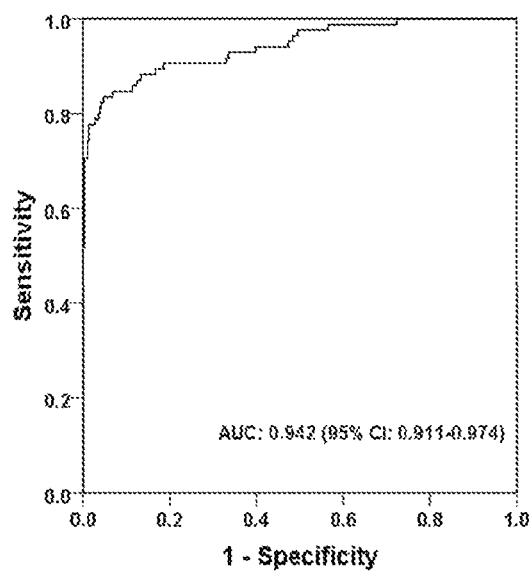
FIG. 5 depicts an a ROC curve in the diagnosis (i.e. distinguishing) of fibrosis patients from cirrhosis patients using a combination of C14: 1-cis.9, C20:4-cis.5.8.11.14, Beta-Alanine, Citrulline, Isoleucine, Methionine, Ornithine, Phenylalanine, Proline, Threonine, Tyrosine, CDCA, and GUDCA. The AUC is 0.942.
Figure 6:
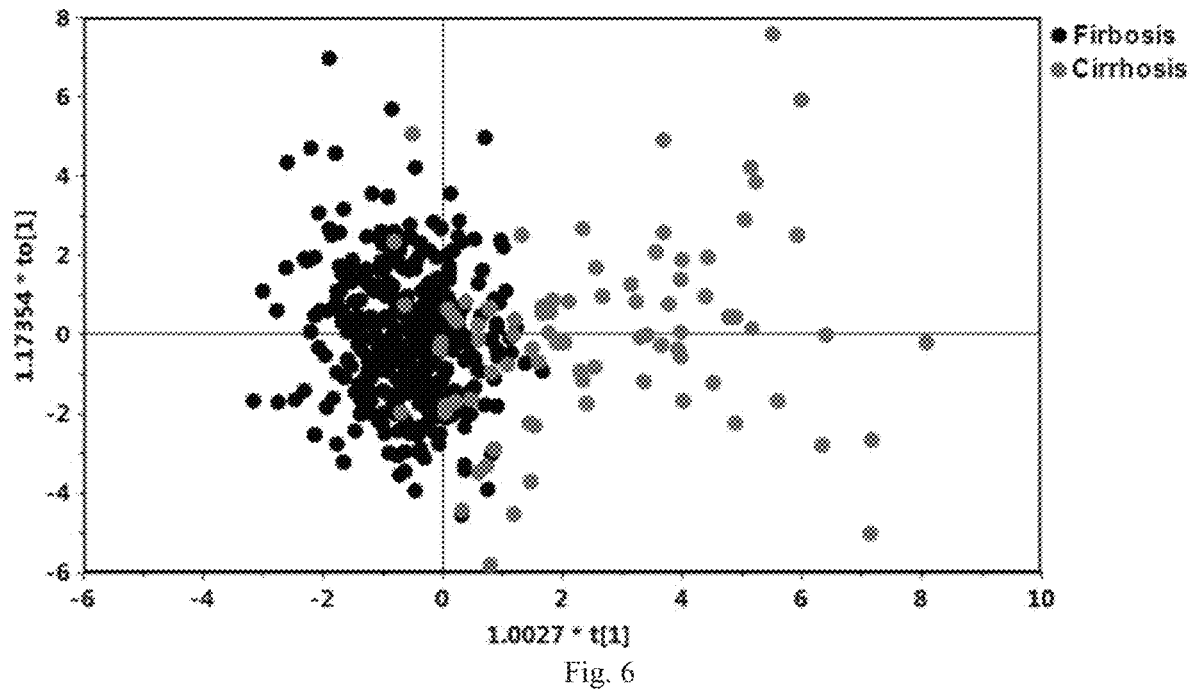
FIG. 6 depicts OPLS-DA scores plot established with C14: 1-cis.9, C20:4-cis.5.8.11.14, Beta-Alanine, Citrulline, Isoleucine, Methionine, Ornithine, Phenylalanine, Proline, Threonine, Tyrosine, CDCA, and GUDCA in patients with liver fibrosis and cirrhosis.
Figure 7A:
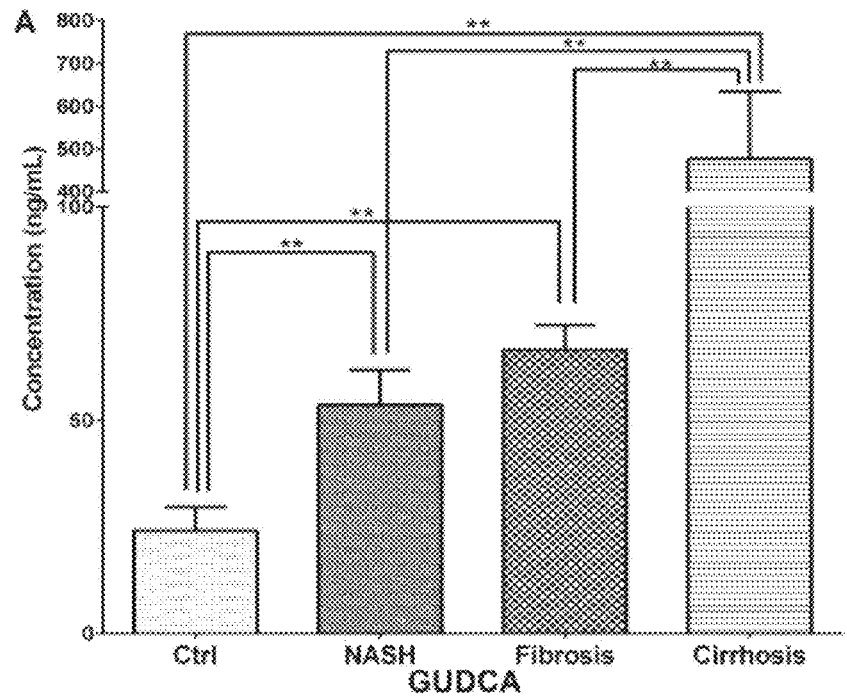
FIG. 7A-FIG. 7C depict bar charts of GUDCA (ng/mL, mean±SEM) in NASH, fibrosis, and cirrhosis patients and healthy controls. A, all subjects; B, male subjects; and C, female subjects. GUDCA was significantly increased in patients of NASH, liver fibrosis and cirrhosis compared to healthy controls and they were gradually increased with the progression of liver disease. ** denotes p<0.01, compared to each other.
Figure 7B:
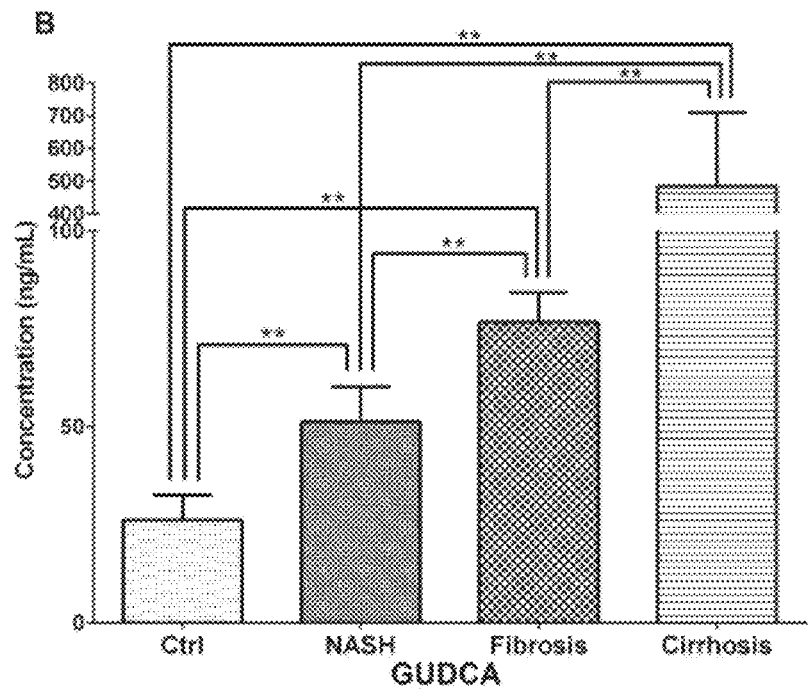
Figure 7C:
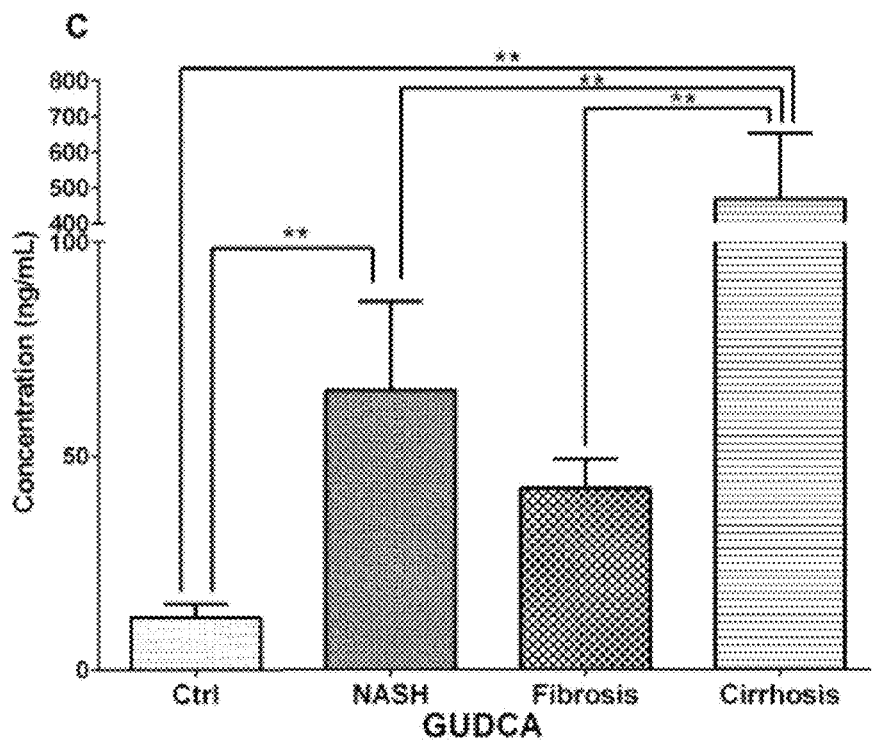
Figure 8A:
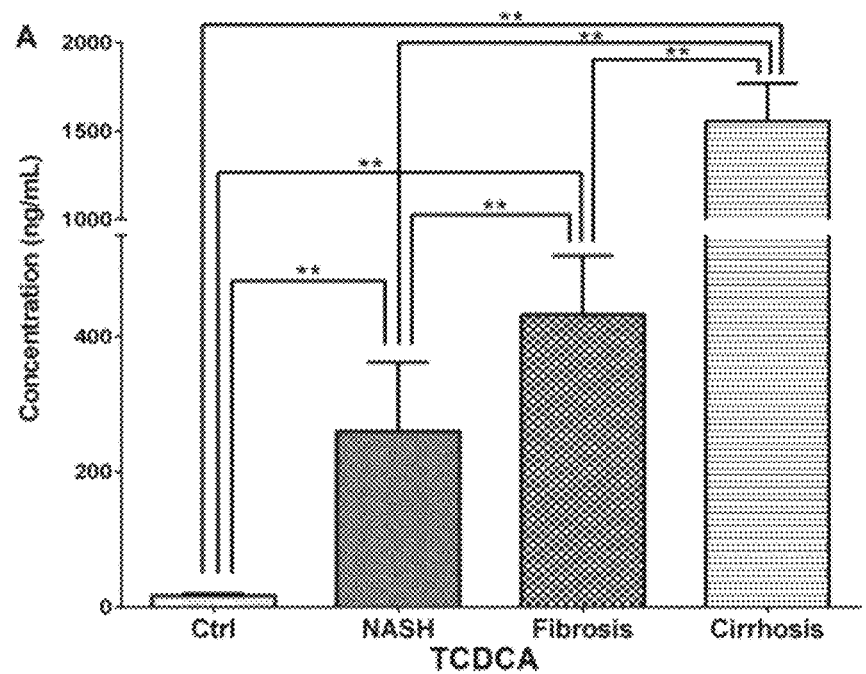
FIG. 8A-FIG. 8C depict bar charts of TCDCA (ng/mL, mean±SEM) in NASH, fibrosis, and cirrhosis patients and healthy controls. A, all subjects; B, male subjects; and C, female subjects. TCDCA was significantly increased in patients of NASH, liver fibrosis and cirrhosis compared to healthy controls and they were gradually increased with the progression of liver disease. ** denotes p<0.01, compared to each other.
Figure 8B:
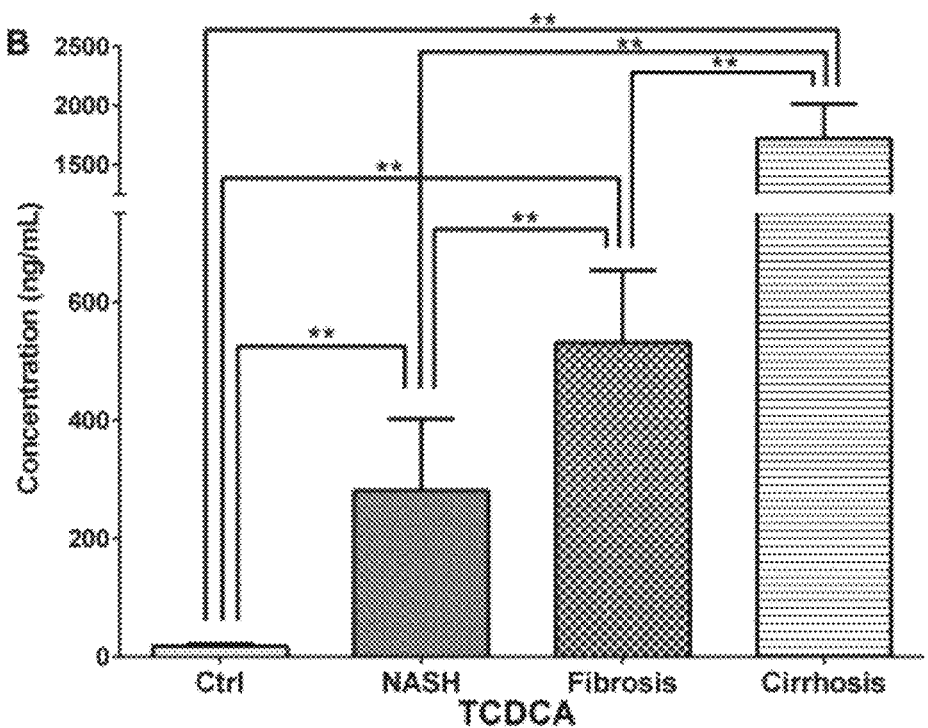
Figure 8C:
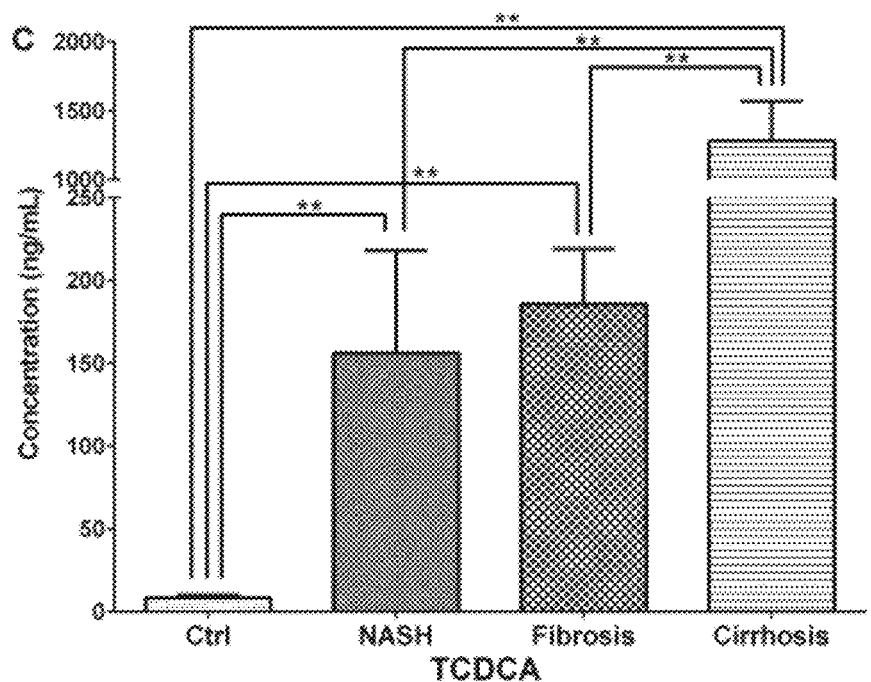
Figure 9A:
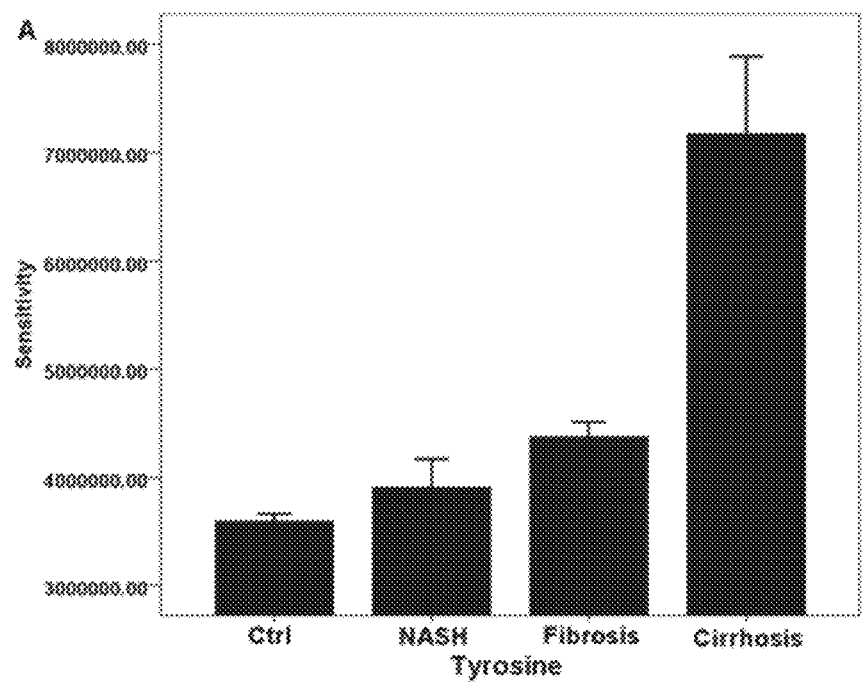
FIG. 9A-FIG. 9C depict bar charts of tyrosine (intensity, mean±SEM) in NASH, fibrosis, and cirrhosis patients and healthy controls. A, all subjects; B, male subjects; and C, female subjects. Tyrosine was significantly increased in patients of NASH, liver fibrosis and cirrhosis compared to healthy controls and they were gradually increased with the progression of liver disease. ** denotes p<0.01, compared to each other.
Figure 9B:
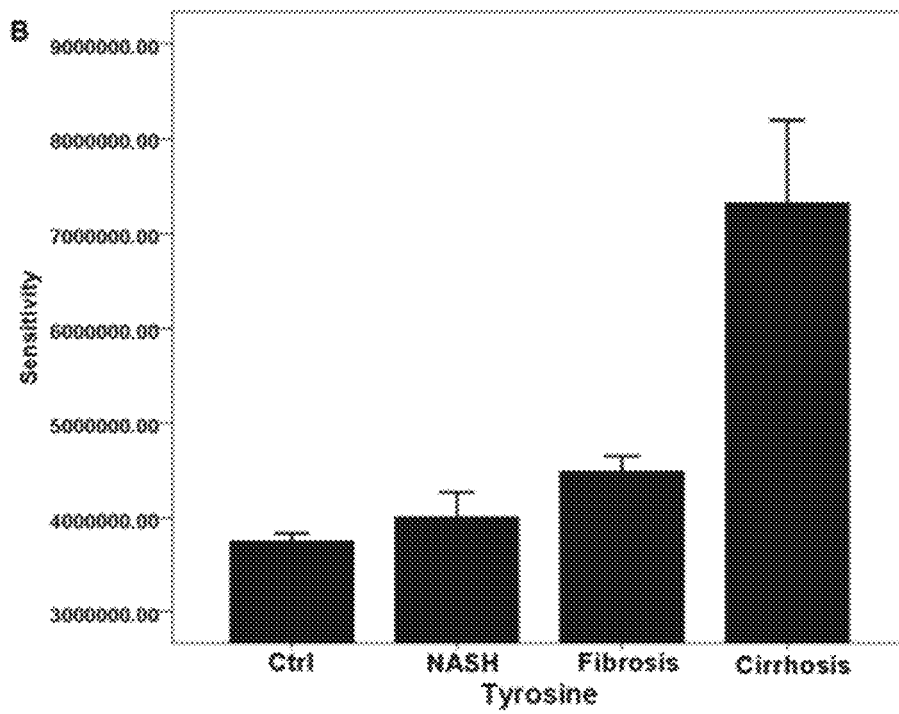
Figure 9C:
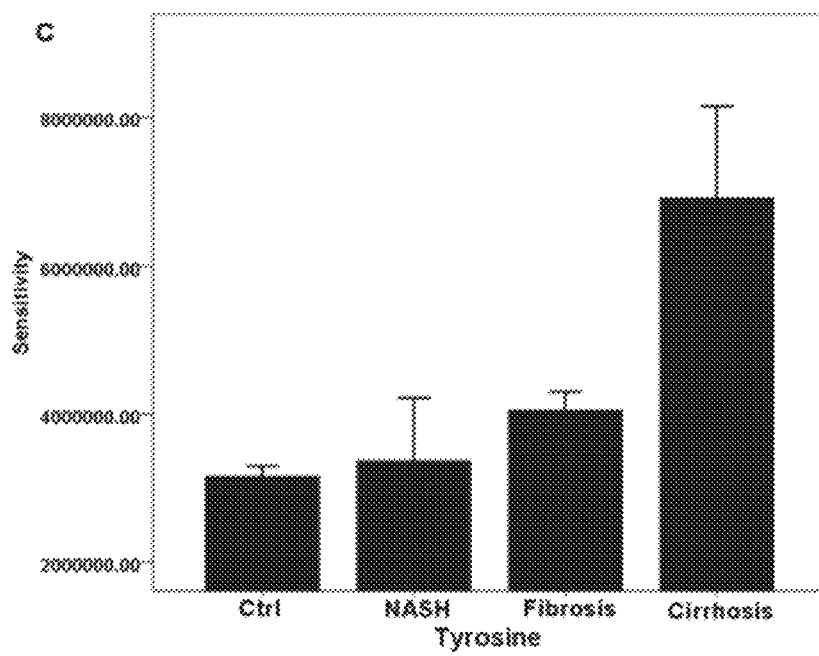

Next, we generated ROC curves to assess the potential usefulness of metabolite signatures as noninvasive biomarkers for the differentiation of patients with NASH from fibrosis. Our ROC analyses revealed that metabolite biomarkers were robust in discriminating patients with fibrosis and no cirrhosis from patients with cirrhosis, with an area under the curve (AUC) value of 0.842 (95% CI=0.911 to 0.974) (FIG. 5). Using a cut-off value of 0.256, the sensitivity and specificity are 83.5% and 95.3%, respectively (Table 16). OPLS-DA scores plot established with the metabolite biomarkers, C14.1.cis.9, C20.4 . . . cis.5.8.11.14., Beta-Alanine, Citrulline, Isoleucine, Methionine, Ornithine, Phenylalanine, Proline, Threonine, Tyrosine, CDCA, and GUDCA, showed separations between the liver fibrosis patients and the cirrhosis patients (FIG. 6, R2Xcum=0.488, R2Ycum=0.529, Q2Ycum=0.513).

TABLE 15

Logistic regression analysis of panel signature for discriminating fibrosis from cirrhosis patients.

| | Coefficient | S.E. | P value |
|---|---|---|---|
| C14.1.cis.9 | 5.785 | 1.705 | .001 |
| C20.4 . . . cis.5.8.11.14. | −4.331 | 1.469 | .003 |
| Beta-Alanine | .000 | .000 | .003 |
| Citrulline | .000 | .000 | .018 |
| Isoleucine | .000 | .000 | .007 |
| Methionine | .000 | .000 | .008 |
| Ornithine | .000 | .000 | .018 |
| Phenylalanine | .000 | .000 | .008 |
| Proline | .000 | .000 | .044 |
| Threonine | .000 | .000 | .000 |
| Tyrosine | .000 | .000 | .051 |
| CDCA | .002 | .001 | .000 |
| GUDCA | .002 | .001 | .198 |
| Constant | −6.259 | 1.285 | .000 |

P values were calculated using the Wald test.

TABLE 16

Diagnosis accuracy of metabolite signatures for detection of patients with NASH compared to fibrosis.

| AUC (95% CI) | P value | Cutoff value 50% probability | Sensitivity (%) | Specificity (%) |
|---|---|---|---|---|
| 0.842 (0.911-0.974) | 0.000 | 0.256 | 83.5 | 95.3 |

Example 15 Metabolite Profiles of Liver Fibrosis and Cirrhosis Patients at Different Stages Liver disease often progresses from steatohepatitis (e.g. NASH) to fibrosis to cirrhosis. The levels of GUDCA, TCDCA, and tyrosine were gradually increased with the liver disease progression (FIGS. 7A-7C, 8A-8C and 9A-9C). Fibrosis can also be staged by progression or severity, for example, stages 51, S2, and S3 (without cirrhosis) and S4 (i.e. cirrhosis). Similarly, late stage S4 fibrosis, i.e. cirrhosis, can be further staged by progression or severity, for example, stages CP A-C. Bile acid levels were compared among different stages of fibrosis and cirrhosis patients; as a result, GUDCA and tyrosine was differentially expressed in sera among three stages of fibrotic patients and three stages of cirrhotic patients (FIGS. 10A-10C, 11A-11C, and 13).

Figure 12A:
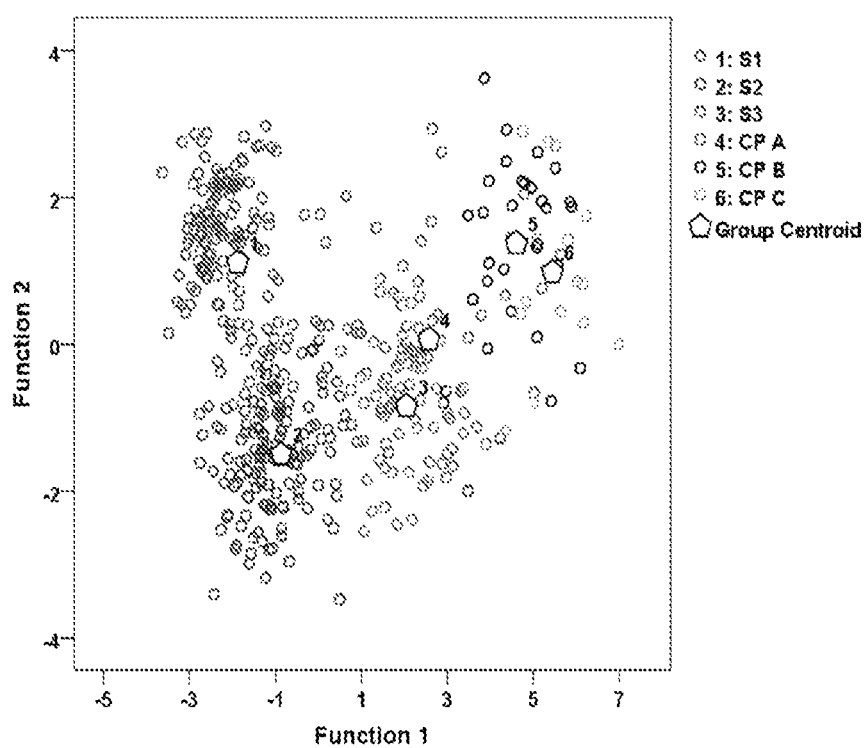
FIG. 12A depicts a plot established with functions generated with canonical discriminant analysis of all the measured bile acids.
Figure 12B:
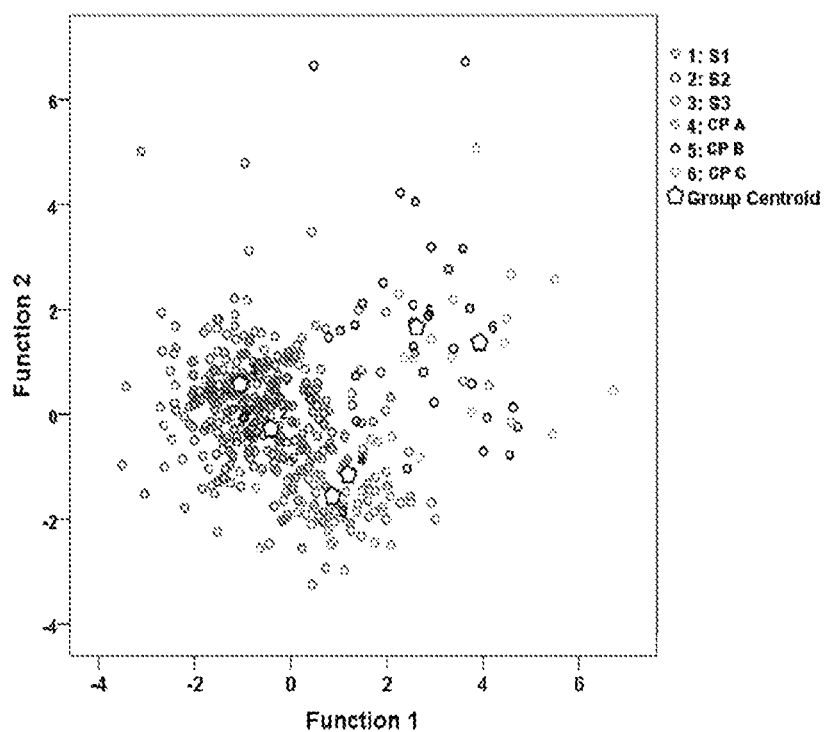
FIG. 12B depicts a plot established with functions generated with canonical discriminant analysis of all the measured free fatty acids.
Figure 12C:
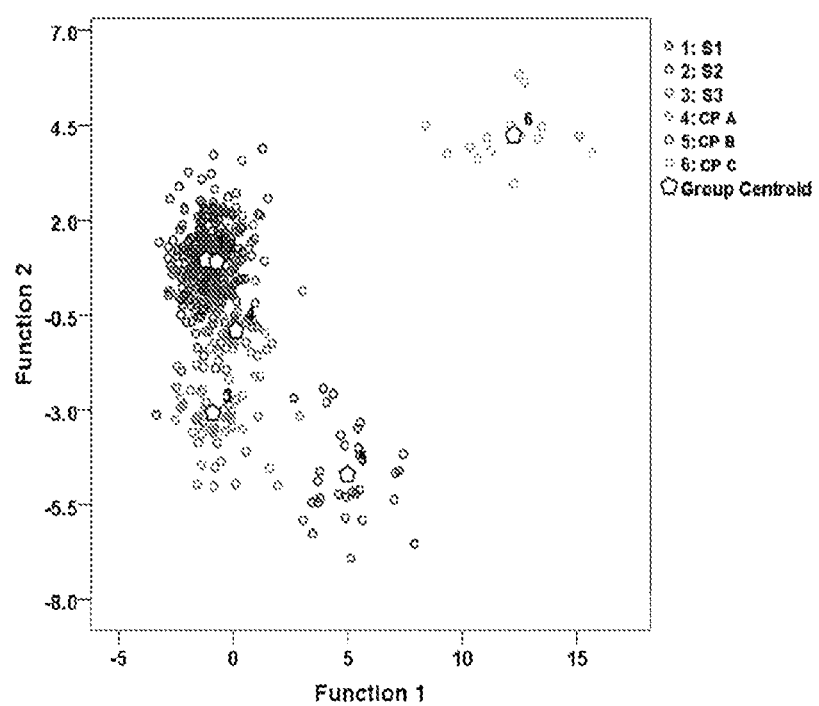
FIG. 12C depicts a plot established with functions generated with canonical discriminant analysis of all the measured amino acids.
Figure 13:
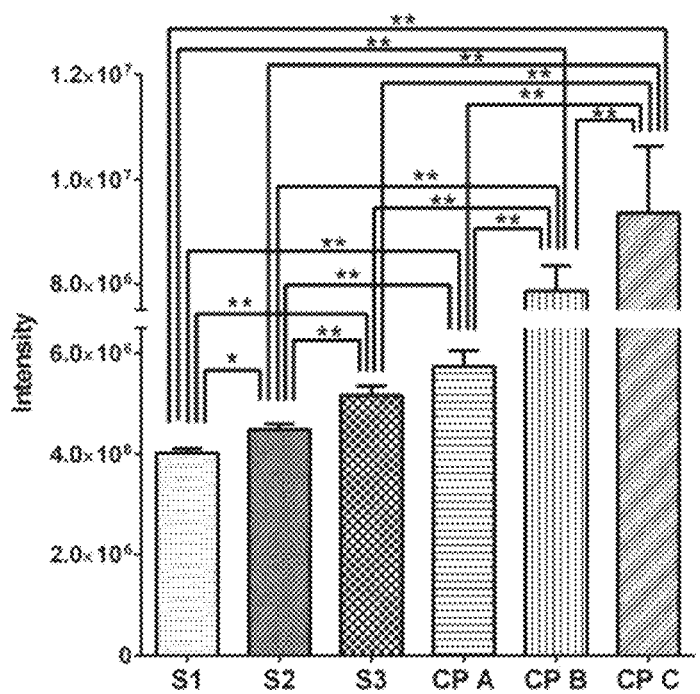
FIG. 13 depicts bar charts of tyrosine (intensity, mean±SEM) among different stages of liver fibrosis patients and Child-Pugh A, B and C cirrhosis patients. Tyrosine was gradually increased with the progression of liver disease. * denotes p<0.05; ** denotes p<0.01, compared to each other

Plots established with functions generated with canonical discriminant analysis of all the differentially expressed bile acids, free fatty acids, and amino acids showed that liver fibrosis patients at stage 1, 2, 3, and cirrhosis patients at grade CP A, B and C were clustered into six big groups (FIGS. 12A, 12B and 12C). Groups 1-6 corresponded to the respective stages 51, S2, S3, CPA, CBP, and CPC. As a result, of the 171 patients at stage 1, 145 were correctly classified, with a correct rate of 84.8%. The correct classification rate for stage 2, 3, and 4 and cirrhosis patients at grade CP A, B and C, were 91.1%, 82.5%, 82.1%, 70.0% and 93.8%, respectively (Table 17, Table 18, and Table 19).

TABLE 17

Accuracy of Stage Classification with all the measured bile acids[a]

| | | | Predicted Group Membership | | | | | | |
|---|---|---|---|---|---|---|---|---|---|
| | | Group | 1 | 2 | 3 | 4 | 5 | 6 | Total |
| Original | Count | S1 | 145 | 22 | 2 | 0 | 2 | 0 | 171 |
| | | S2 | 6 | 123 | 4 | 2 | 0 | 0 | 135 |
| | | S3 | 1 | 0 | 47 | 9 | 0 | 0 | 57 |
| | | CP A | 0 | 0 | 3 | 32 | 1 | 3 | 39 |
| | | CP B | 0 | 0 | 1 | 3 | 21 | 5 | 30 |
| | | CP C | 0 | 0 | 0 | 0 | 1 | 15 | 16 |
| | % | S1 | 84.8 | 12.9 | 1.2 | .0 | 1.2 | .0 | 100.0 |
| | | S2 | 4.4 | 91.1 | 3.0 | 1.5 | .0 | .0 | 100.0 |
| | | S3 | 1.8 | .0 | 82.5 | 15.8 | .0 | .0 | 100.0 |
| | | CP A | .0 | .0 | 7.7 | 82.1 | 2.6 | 7.7 | 100.0 |
| | | CP B | .0 | .0 | 3.3 | 10.0 | 70.0 | 16.7 | 100.0 |
| | | CP C | .0 | .0 | .0 | .0 | 6.3 | 93.8 | 100.0 |

[a]85.5% of original grouped cases correctly classified.

TABLE 18

Accuracy of Stage Classification with all the measured free fatty acids[a]

| | | | Predicted Group Membership | | | | | | |
|---|---|---|---|---|---|---|---|---|---|
| | | Group | 1 | 2 | 3 | 4 | 5 | 6 | Total |
| Original | Count | S1 | 136 | 21 | 3 | 4 | 5 | 0 | 169 |
| | | S2 | 29 | 83 | 11 | 7 | 4 | 0 | 134 |
| | | S3 | 0 | 6 | 42 | 7 | 1 | 0 | 56 |
| | | CP A | 0 | 1 | 7 | 28 | 2 | 1 | 39 |
| | | CP B | 2 | 0 | 0 | 1 | 25 | 2 | 30 |
| | | CP C | 0 | 0 | 0 | 1 | 0 | 15 | 16 |
| | % | S1 | 80.5 | 12.4 | 1.8 | 2.4 | 3.0 | .0 | 100.0 |
| | | S2 | 21.6 | 61.9 | 8.2 | 5.2 | 3.0 | .0 | 100.0 |
| | | S3 | .0 | 10.7 | 75.0 | 12.5 | 1.8 | .0 | 100.0 |
| | | CP A | .0 | 2.6 | 17.9 | 71.8 | 5.1 | 2.6 | 100.0 |
| | | CP B | 6.7 | .0 | .0 | 3.3 | 83.3 | 6.7 | 100.0 |
| | | CP C | .0 | .0 | .0 | 6.3 | .0 | 93.8 | 100.0 |

[a]74.1% of original grouped cases correctly classified.

TABLE 19

Accuracy of Stage Classification with all the measured amino acids[a]

| | | | Predicted Group Membership | | | | | | |
|---|---|---|---|---|---|---|---|---|---|
| | | Group | 1 | 2 | 3 | 4 | 5 | 6 | Total |
| Original | Count | S1 | 139 | 26 | 2 | 2 | 0 | 0 | 169 |
| | | S2 | 13 | 117 | 0 | 4 | 0 | 0 | 134 |
| | | S3 | 0 | 1 | 54 | 1 | 0 | 0 | 56 |
| | | CP A | 0 | 0 | 0 | 39 | 0 | 0 | 39 |
| | | CP B | 0 | 0 | 0 | 0 | 30 | 0 | 30 |
| | | CP C | 0 | 0 | 0 | 0 | 0 | 16 | 16 |
| | % | S1 | 82.2 | 15.4 | 1.2 | 1.2 | 0.0 | 0.0 | 100.0 |
| | | S2 | 9.7 | 87.3 | 0.0 | 3.0 | 0.0 | 0.0 | 100.0 |
| | | S3 | 0.0 | 1.8 | 96.4 | 1.8 | 0.0 | 0.0 | 100.0 |
| | | CP A | 0.0 | 0.0 | 0.0 | 100.0 | 0.0 | 0.0 | 100.0 |
| | | CP B | 0.0 | 0.0 | 0.0 | 0.0 | 100.0 | 0.0 | 100.0 |
| | | CP C | 0.0 | 0.0 | 0.0 | 0.0 | 0.0 | 100.0 | 100.0 |

[a]89.0% of original grouped cases correctly classified.

Example 16 Bile Acid Analysis

Further analysis of the data revealed other surprisingly diagnostic bile acid markers. When the bile acid ('BA') levels were compared among patients of liver fibrosis and cirrhosis, there were also remarkable differences in GCDCA, GCA, CDCA, CA, UDCA, GUDCA, GHDCA, TCDCA, TCA, 7-KLCA, LCA, TUDCA, 3-KCA, THCA, TLCA, and GLCA and their respective levels were very low in control subjects, increased significantly in fibrosis patients, and were very strongly increased in patients with cirrhosis.

This data supports the use of these markers in a diagnostic panel for diagnosis or classification (e.g. by stage or severity) of fibrosis subjects.

Example 17 Kits

An example kit of the invention included known amounts of isotope labeled (e.g. C13 labeled) internal standards corresponding to the biomarker(s) of a panel t. The kit may include a single mixture of all the internal standards to be assessed, or may include a separate amount of each internal standard. The amounts of each internal standard in the metabolite profile to be assessed can be measured and used for comparison to the corresponding amount of a corresponding biomarker in a sample from a subject. Each internal standard may be in solid form or in liquid form in the distributed kits. If the internal standards are in solid form, they are to be suspended into solution prior to use of the kit. Kits optionally comprise at least one labeled variant of each metabolite biomarker of the panel.

Example kits can include at least one container configured to contain the internal standards in the metabolite panel profile. The container may be a tube, vial or multi-welled or multi-chambered plate. The container may have a single well or chamber, or the container may have multiple wells or chambers. For example, the container may be a multi-welled plate (e.g., a microtiter plate such as a 96-well microtiter plate). Other analogous containers are also appropriate. In some kits, the container may be appropriate for use in measurement of the internal standards and quantitation of the one or more biomarkers to be assessed in a subject sample. In some kits, the container used for measurement of internal standards and quantitation of one or more metabolites in a subject sample is configured to be used for spectral analysis such as, for example, chromatography-mass spectrometry. For example, the container may be configured for GC-TOFMS and/or LC-TQMS. In other kits, the container may be configured for other analytical tests specific for one or more of the metabolites to be assessed in a subject sample (e.g., enzymatic, chemical, colorimetric, fluorometric, etc.). The container may be configured to hold an internal standard mixture, as set forth above, in one or more vials or tubes, or in one or more chambers or wells. Alternatively, the container may be configured to hold the reference amount of each internal standard to be assessed separately (e.g., one internal standard per chamber or well).

Some kits include a plurality of containers. For example, some kits include one or more containers having the internal standards. In addition, some kits include one or more containers having the internal standards and an additional container to be used in measurement of the internal standards and quantitation of the one or more metabolites to be assessed in a subject sample (e.g., a multi-welled plate or another tube or vial). In some kits, there is a single container that is used to contain the one or more internal standards and used in measurement of the internal standards and quantitation of the one or more metabolites to be assessed in a subject sample.

In kits where the container is a multi-welled or multi-chambered container, the reference amounts of the metabolites to be assessed may be located in one or more wells or chambers upon distribution of the kit for use. In some kits, the reference amounts of the metabolites to be assessed must be dispersed into one or more wells or chambers in using the kits.

The container of the kit can also be configured to accept a biological sample from at least one subject. For example, where the container of the kit includes multiple chambers or wells, a biological sample from a subject may be distributed into one or more chambers or wells. In some instances, one or more amounts of a subject sample may be distributed into a plurality of chambers or wells. The container of the kit is generally configured to accept fluid samples (e.g., fluid biological samples or solid biological samples that have been processed to obtain a fluid for analysis).

Some kits also include reagents useful for measurement of the internal standards and biomarkers and quantitation of the one or more metabolites to be assessed in a subject sample. These reagents may be included in the kit in one or more additional containers.

An example kit comprises a plurality of internal standards, each provided in a separate container or in the same container. The analytical container will optionally be a microtiter plate configured for use with either a GC-MS or LC-MS device. The microtiter plate will have a sufficient number of wells to receive at least one internal standard. The internal standards will have known concentrations and will be used to dispense a known amount (or aliquot) of each internal standard into separate wells of the microtiter plate. After dispensing the internal standards into the analytical container, a portion of the subject sample can also be dispensed into the microtiter plate. Either a single portion of a subject sample is dispensed or a plurality of portions can be dispensed. If a plurality of portions is dispensed into the microtiter plate, each portion may be dispensed into a separate well. In addition, if a plurality of portions is dispensed into the microtiter plate, each portion may be of a different amount.

Example 18 Use of Kits

Kits may be used to perform the methods of the invention to provide an evaluation of a liver disease status by enabling quantitation of the metabolites in a metabolite profile. For example, kits of the invention may be used to diagnose (e.g. determine the presence or absence of) a liver disease status. In addition, kits of the invention may be used to determine if a subject having a liver disease is responding to a treatment for a liver disease.

A biological sample obtained from a subject can be assessed using the kits of the invention. The sample may be a fluid sample (e.g., plasma or serum). In some uses of the kits, the metabolite profile in a subject sample may be assessed without processing of the sample. In other uses of the kits, the metabolite profile in a subject sample may require processing of the sample before being assessed.

A physician may optionally take a sample from a subject and send the sample to a clinical laboratory for testing using the kits of the invention. Alternatively, the physician may be located at a clinical or medical facility that can perform testing using the kits of the invention.

The kits may be used to run a variety of tests to measure the amount of one or more metabolites in a subject sample. For example, the kits may be used to run a spectral analysis of a subject sample. Some kits are configured for spectral analyses such as gas chromatography and/or liquid chromatography. For example, a kit may be configured for LC-TQMS analysis of the metabolites of interest in a subject sample. Alternatively, kits may be configured so that analytical tests specific for different types of metabolites can be conducted (e.g., enzymatic, chemical, colorimetric, fluorometric, etc.) to measure the amount of the metabolites of interest in a subject's sample. In some uses, the internal standards included in the kit are used as positive controls for the analytical test performed to measure the amount of the metabolites of interest in a subject sample. In some uses, the internal standards included in the kit are used to help calibrate and/or measure the amount of the metabolites of interest in a subject sample. Depending on the type of analytical tests to be conducted to measure the metabolites of interest in a subject sample, different components used to conduct the analytical tests can be assembled into the kit with the one or more internal standards and the container.

The data obtained from the analytical tests performed using the kits can optionally be the level (e.g. amount) of each of one or more metabolites of interest (e.g. a panel of biomarkers taught herein) in a subject sample. This data can be compared to reference biomarker levels in healthy subjects.

After the data from the analytical tests performed using the kit are obtained (i.e., metabolite profile for the subject sample (i.e., amount of each metabolite of interest)), the data can be inputted into a software program located on a computer terminal in the laboratory to generate a test result report, which can then be provided to the physician or the individual. Once the physician receives the test result report from the clinical laboratory, the physician can evaluate the subject's physical status. Based on the metabolite profile of the subject's sample assessed, which, as noted above, the test result report may indicate to the physician that the subject either does or does not have the liver disease status, or has a particular classification (e.g. stage, severity, or progression) of liver disease such as liver fibrosis, or that the subject is responding to a particular treatment for a liver disease. The physician can then, based on the individual's status indicated by the test result report, provide suggestions or select an appropriate treatment for the subject, if necessary.

Example 19 Providing a Biomarker Panel and a Diagnostic Model

From the list of 23 bile acid markers detailed in Example 8, a panel comprising a subset of markers was selected to test the diagnostic power of a smaller panel. Specifically GCA, GCDCA, TCA, TCDCA, GUDCA, TUDCA and 7-KLCA were selected based on their individual high fold changes ('FC'), area under the curve ('AUC'), and variable importance in the projection (VIP) values derived from an OPLS-DA model established between controls and all liver disease (NASH, Fibrosis, Cirrhosis) patients (Table 20).

TABLE 20

Area under the curve (AUC) of ROC curve analysis for each biomarker of a selected panel for the differentiation of liver disease patients compared to controls.

| Bile acid | AUC for ROC | P value | 95% Confidence Interval Lower Bound | 95% Confidence Interval Upper Bound | FC | VIP |
|---|---|---|---|---|---|---|
| TCA | 0.936 | .000 | .922 | .951 | 58.90 | 1.59 |
| TCDCA | 0.935 | .000 | .921 | .950 | 34.45 | 1.58 |
| GCA | 0.911 | .000 | .894 | .929 | 16.13 | 1.49 |
| GCDCA | 0.882 | .000 | .861 | .903 | 8.73 | 1.39 |
| TUDCA | 0.843 | .000 | .818 | .869 | 17.35 | 1.22 |
| 7-KLCA | 0.781 | .000 | .751 | .811 | 2.35 | 1.06 |
| GUDCA | 0.781 | .000 | .752 | .810 | 6.68 | 1.03 |

A BA panel was provided by combining the seven BAs and Logistic regression was used to create a single multi-variable. This panel is referred to as the BA panel in this example. Logistic regression (LR) was used to combine the seven bile acids into a single bile acid signature. LR model was constructed using the binary outcome of the disease (CHB) and healthy control, or disease (CHB) and disease (fibrosis), or disease (fibrosis) and disease (cirrhosis) as Dependent variables and the seven bile acids as Covariates using the "Enter" method with a Classification cutoff: 0.5; Maximum iterations: 20; and the Probability for Stepwise: Entry value of 0.05 and Removal value of 0.10. The software used was SPSS 23.0 (IBM SPSS, USA). ROC curves for the logistic model were plotted with the fitted probabilities from the model as possible cut-points for computation of sensitivity and specificity.

The following regression models for evaluating liver disease status (e.g. diagnosis and/or discrimination between disease status) were developed based on the data from the testing set. Each model trained on the training set produced a probability that indicates the likelihood the subject has the more severe liver disease status.

For the discrimination between NASH patients and healthy controls, a logistic regression model was developed based on the seven BAs (Table 21) and the regression model was as follows:

Probability=exp{−1.923−0.004(GCDCA)+0.010 (GCA)+0.116(TCDCA)−0.072(TCA)−0.035 (GUDCA)−0.122(TUDCA)+0.025(7-KLCA)}/ (1+exp{−1.923−0.004(GCDCA)+0.010(GCA)+ 0.116(TCDCA)−0.072(TCA)−0.035(GUDCA)− 0.122(TUDCA)+0.025(7-KLCA)})

TABLE 21

Logistic regression analysis of biomarker signatures of a selected panel for discriminating NASH subjects from comparison with controls.

| Bile acids | B | S.E. | p | Exp(B) | 95% C.I. for EXP(B) Lower | 95% C.I. for EXP(B) Upper |
|---|---|---|---|---|---|---|
| GCDCA | −0.004 | 0.003 | 0.197 | 0.996 | 0.990 | 1.002 |
| GCA | 0.010 | 0.005 | 0.031 | 1.010 | 1.001 | 1.019 |
| TCDCA | 0.116 | 0.034 | 0.001 | 1.123 | 1.051 | 1.201 |
| TCA | −0.072 | 0.022 | 0.001 | 0.931 | 0.892 | 0.971 |
| 7-KLCA | 0.025 | 0.141 | 0.859 | 1.025 | 0.778 | 1.352 |
| GUDCA | −0.035 | 0.031 | 0.269 | 0.966 | 0.908 | 1.027 |
| TUDCA | −0.122 | 0.339 | 0.720 | 0.886 | 0.456 | 1.720 |
| Constant | −1.923 | 0.690 | 0.005 | 0.146 | | |

P values were calculated using the Wald test.

For the discrimination of patients with NASH from those with fibrosis, a logistic regression model was developed based on the seven BAs (Table 22) and the regression model was as follows:

Probability=exp{−0.511−0.0003(GCDCA)+0.001 (GCA)+0.007(TCDCA)−0.007(TCA)−0.003 (GUDCA)+0.083(TUDCA)+0.491(7-KLCA)}/ (1+exp{−0.511−0.0003(GCDCA)+0.001(GCA)+ 0.007(TCDCA)−0.007(TCA)−0.003(GUDCA)+ 0.083(TUDCA)+0.491(7-KLCA)})

TABLE 22

Logistic regression analysis of biomarker signatures of a selected panel for discriminating NASH from fibrosis

| | B | S.E. | Sig. | Exp(B) | 95% C.I. for EXP(B) Lower | 95% C.I. for EXP(B) Upper |
|---|---|---|---|---|---|---|
| GCDCA | 0.000 | 0.000 | 0.353 | 1.000 | 0.999 | 1.000 |
| GCA | 0.001 | 0.001 | 0.092 | 1.001 | 1.000 | 1.002 |
| TCDCA | 0.007 | 0.003 | 0.012 | 1.007 | 1.002 | 1.012 |
| TCA | −0.007 | 0.003 | 0.017 | 0.993 | 0.988 | 0.999 |
| 7-KLCA | 0.491 | 0.095 | 0.000 | 1.635 | 1.357 | 1.969 |

TABLE 22-continued

Logistic regression analysis of biomarker signatures of
a selected panel for discriminating NASH from fibrosis

|  | B | S.E. | Sig. | Exp(B) | 95% C.I. for EXP(B) Lower | 95% C.I. for EXP(B) Upper |
|---|---|---|---|---|---|---|
| GUDCA | −0.003 | 0.006 | 0.544 | 0.997 | 0.986 | 1.008 |
| TUDCA | −0.083 | 0.034 | 0.015 | 0.921 | 0.861 | 0.984 |
| Constant | −0.511 | 0.399 | 0.200 | 0.600 | | |

P values were calculated using the Wald test.

For discriminating patients with fibrosis from patients with cirrhosis, a logistic regression model based on the seven BAs was built (Table 23) and the regression model was as follows:

Probability=exp{−2.514−0.0002(GCDCA)+0.001(GCA)+0.0004(TCDCA)−0.001(TCA)+0.001(GUDCA)+0.020(TUDCA)+0.020(7-KLCA)}/(1+exp{−2.514−0.0002(GCDCA)+0.001(GCA)+0.0004(TCDCA)−0.001(TCA)+0.001(GUDCA)+0.020(TUDCA)+0.020(7-KLCA)})

TABLE 23

Logistic regression analysis of biomarker signatures
of a selected panel for discriminating patients
with fibrosis from patients with cirrhosis.

|  | B | S.E. | Sig. | Exp(B) | 95% C.I. for EXP(B) Lower | 95% C.I. for EXP(B) Upper |
|---|---|---|---|---|---|---|
| GCDCA | 0.000 | 0.000 | 0.002 | 1.000 | 1.000 | 1.000 |
| GCA | 0.001 | 0.000 | 0.000 | 1.001 | 1.000 | 1.001 |
| TCDCA | 0.000 | 0.000 | 0.027 | 1.000 | 1.000 | 1.001 |
| TCA | −0.001 | 0.000 | 0.033 | 0.999 | 0.999 | 1.000 |
| 7-KLCA | 0.020 | 0.023 | 0.370 | 1.021 | 0.976 | 1.067 |
| GUDCA | 0.001 | 0.001 | 0.214 | 1.001 | 0.999 | 1.003 |
| TUDCA | 0.020 | 0.006 | 0.000 | 1.020 | 1.009 | 1.031 |
| Constant | −2.514 | 0.241 | 0.000 | 0.081 | | |

Figure 16A:
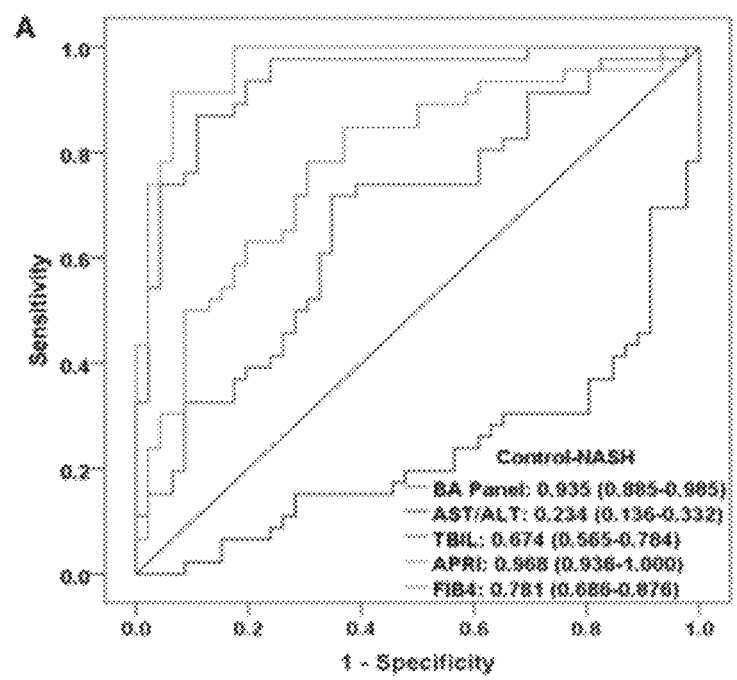
Figure 16B:
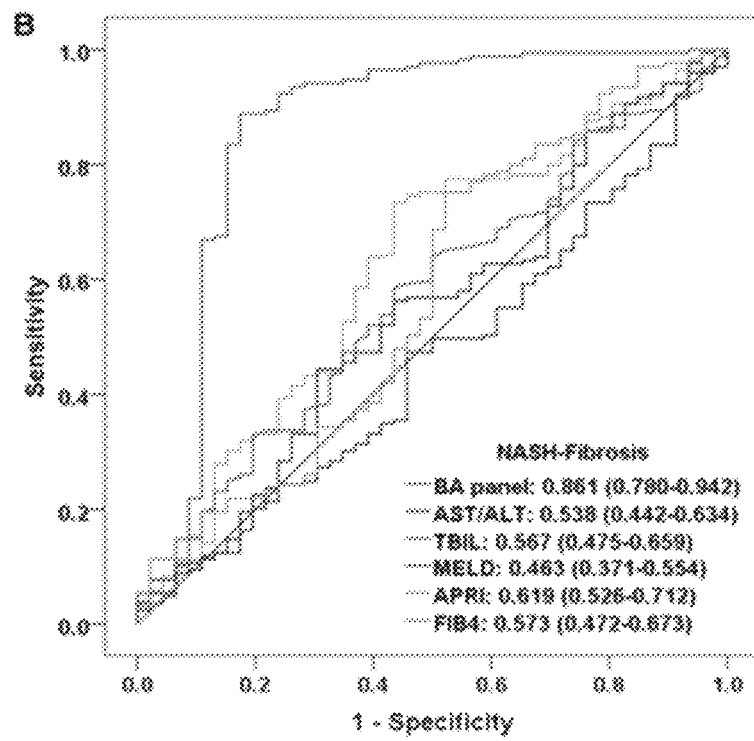
Figure 16C:
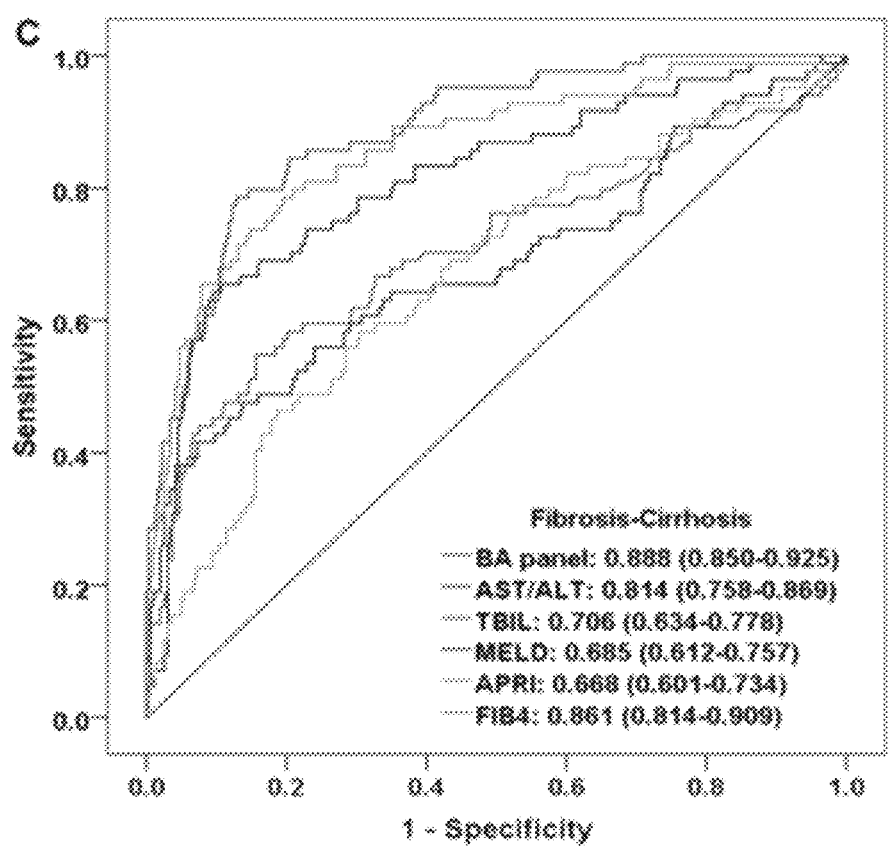
Figure 16D:
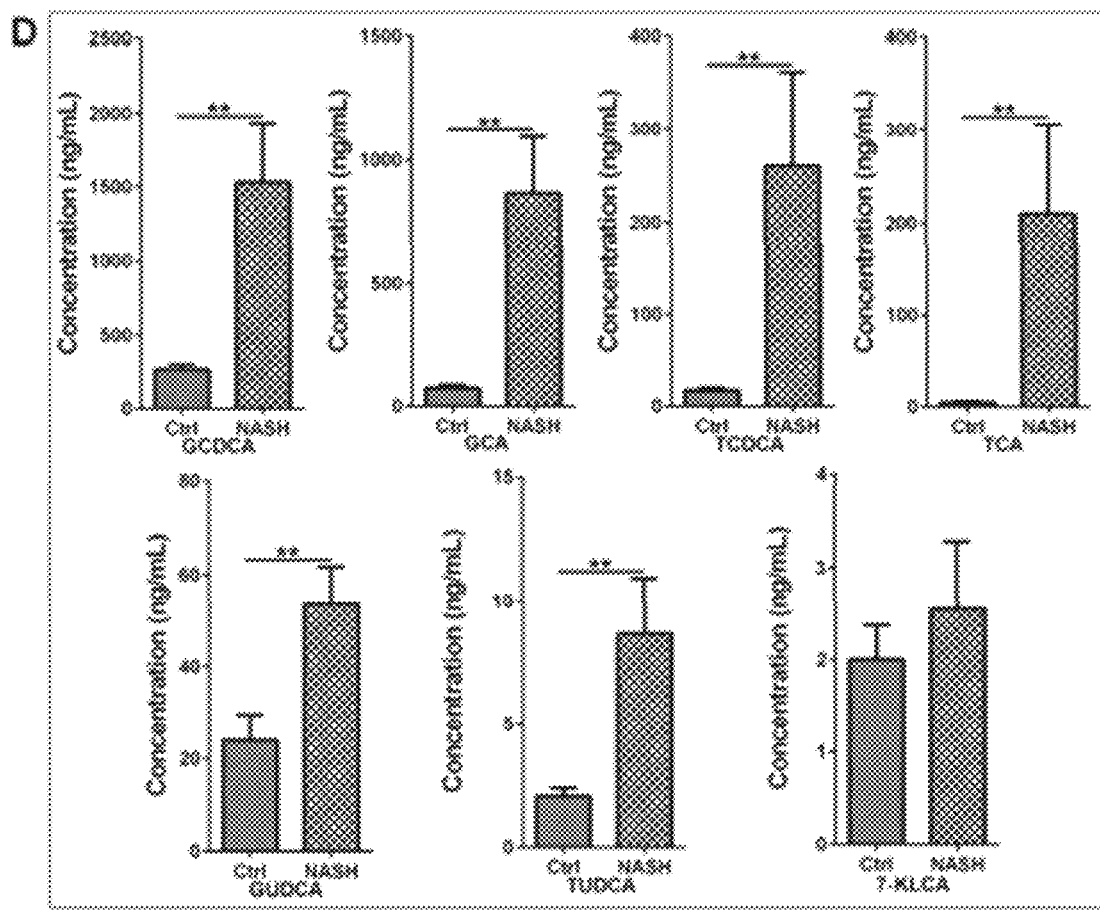
Figure 16E:
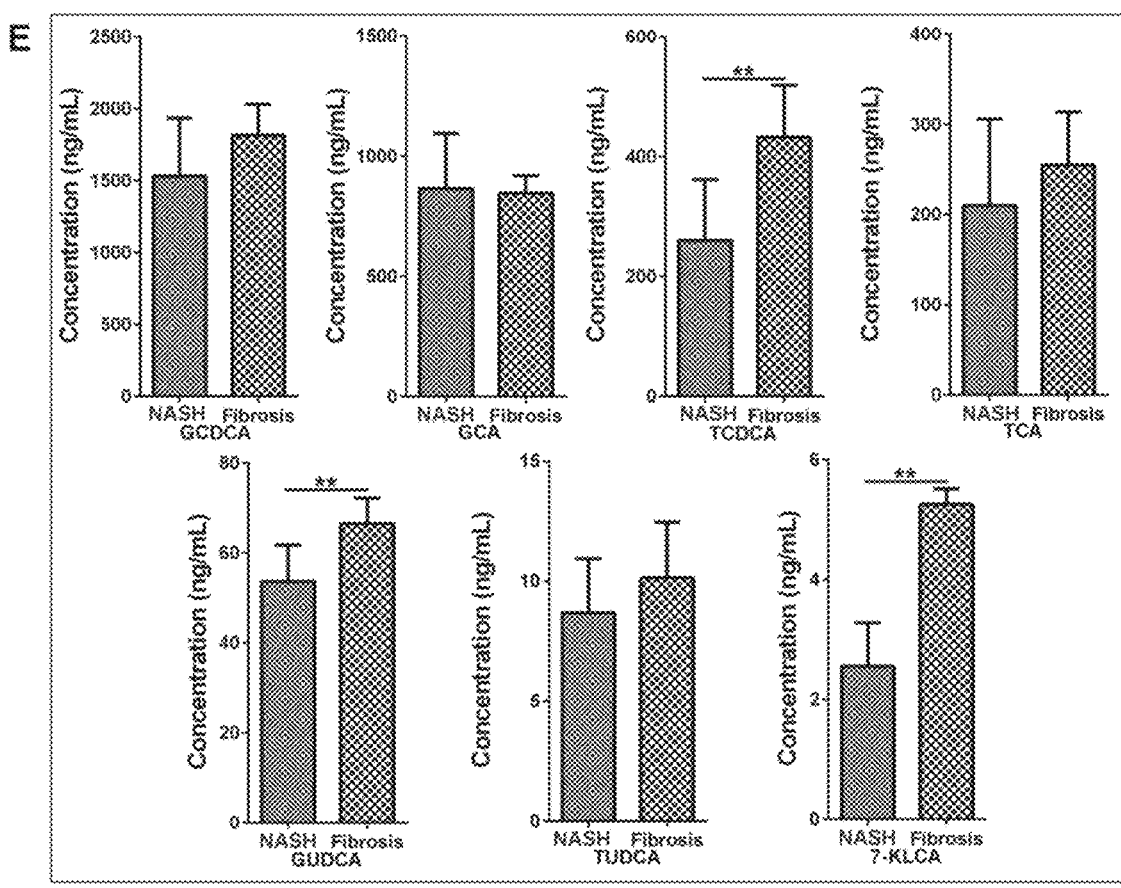
Figure 16F:
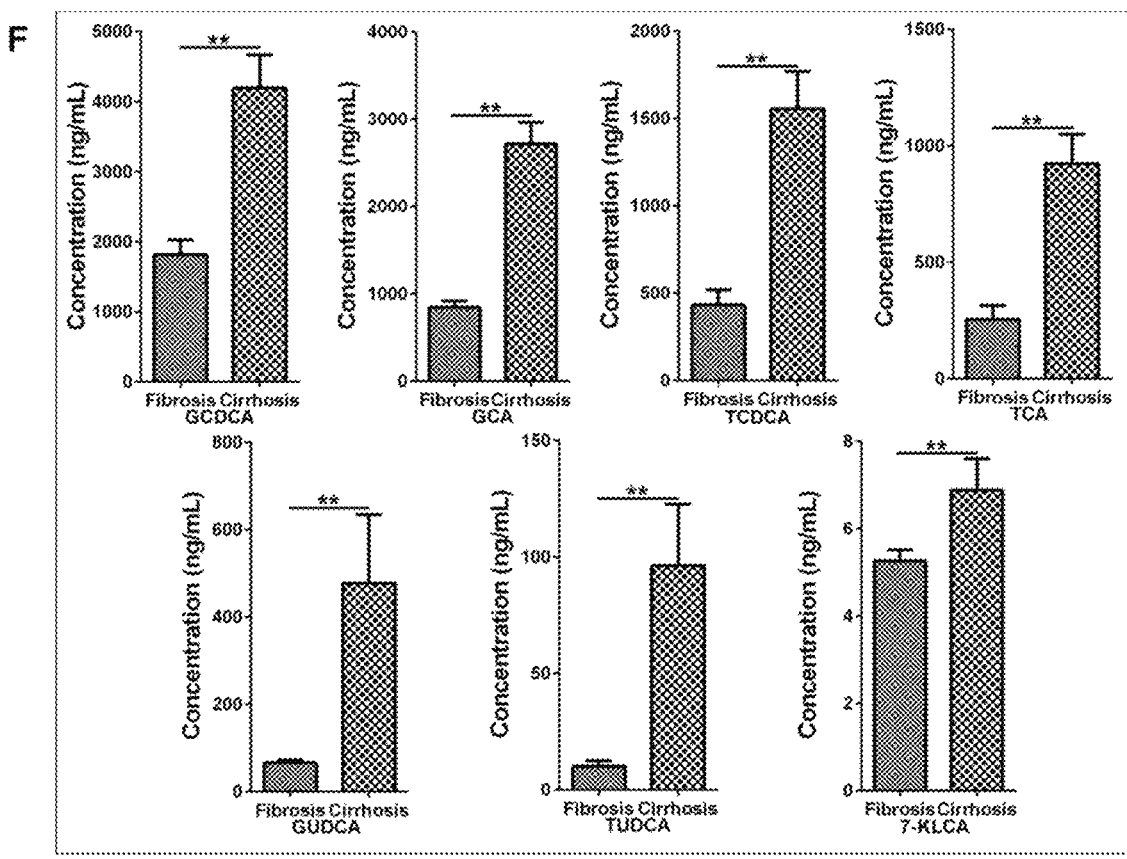

The ROC curves based on the multivariable yielded useful diagnostic power with an AUC value of 0.935 (95% confidence interval [CI]=0.855 to 0.985) (FIGS. 16A and 16D) for discriminating NASH patients from healthy controls (Table 21). Using a cut-off value of 0.429, the sensitivity of 87.0% and specificity of 89.1% are given in Table 24. The identified serum BA signatures remained significant (p<0.001) with an odds ratio of 567.635 (95% Cl, 60.667 to 5311.080) after adjustment for BMI, age and sex (Table 25). For differentiating between patients with NASH and fibrosis, the AUC value was 0.861 (95% CI=0.780 to 0.942) (FIGS. 16B and 16E, Table 22). The sensitivity and specificity were 88.8% and 82.6% using a cut-off value of 0.811, respectively (Table 24). Similarly, the identified serum BA signatures remained significant (p<0.001) and the odds ratio was 75.243 (95% Cl, 24.451 to 232.654) after adjustment for BMI, age and sex (Table 26). For discriminating patients with fibrosis from cirrhosis (Table 23), an AUC of 0.889 (95% CI=0.851 to 0.926) and a sensitivity of 78.8% and a specificity of 87.2% (FIGS. 16C and 16F, Table 24) was obtained. In addition, the identified serum BA signatures remained significant (p<0.001) and the odds ratio was 177.141 (95%01, 38.264 to 820.068) after adjustment for BMI, age and sex (Table 27).

TABLE 24

Area under the ROC Curve (AUC), Sensitivity, and
Specificity According to Different Study Groups.*

| Comparison | Area (95% CI) | P value | Cutoff value 50% probability | Sensitivity (%) | Specificity (%) |
|---|---|---|---|---|---|
| Patients with NASH vs. controls | 0.935 (0.855-0.985) | <0.001 | 0.429 | 87.00 | 89.10 |
| Patients with NASH vs. Patients with Fibrosis | 0.861 (0.780-0.942) | <0.001 | 0.811 | 88.80 | 82.60 |
| Patients with Fibrosis vs. Patients with Cirrhosis | 0.889 (0.851-0.926) | <0.001 | 0.224 | 78.80 | 87.2 |

*CI denotes confidence interval.

TABLE 25

Logistic regression analysis reveals identified BA panel signature
for the diagnosis of NASH patients from controls was independent of
the possible confounding risk factors including BMI, age and sex.

|  | Odds ratio (95% CI)[3] | S.E. | P value |
|---|---|---|---|
| NASH-associated BA signature | 567.635 (60.667-5311.080) | 1.14E+00 | 2.72E−08 |
| BMI[1] | 1.033 (0.866-1.232) | 9.00E−02 | 7.21E−01 |
| Age[1] | 1.026 (0.959-1.098) | 3.40E−02 | 4.55E−01 |
| Sex[2] | 0.560 (0.099-3.182) | 8.86E−01 | 5.13E−01 |

P values were calculated using the Wald test.
[1]BMI and age is continuous variables.
[2]male or female.
[3]Odds ratios greater than 1 correspond to a possibility of NASH as compared to the lower values of continuous variables or the reference group of categorical variables.

TABLE 26

Logistic regression analysis reveals identified BA
signature for the diagnosis of fibrosis patients from
NASH patients was independent of the possible confounding
risk factors including BMI, age and sex.

|  | Odds ratio (95% CI)[3] | S.E. | P value |
|---|---|---|---|
| Fibrosis-associated BA signature | 75.243 (24.451-232.654) | 5.75E−01 | 5.39E−14 |
| BMI[1] | 1.001 (0.895-1.119) | 5.70E−02 | 9.87E−01 |
| Age[1] | 0.993 (0.959-1.030) | 1.80E−02 | 7.20E−01 |
| Sex[2] | 0.392 (0.143-1.073) | 5.14E−01 | 6.80E−02 |

P values were calculated using the Wald test.
[1]BMI and age is continuous variables.
[2]male or female.
[3]Odds ratios greater than 1 correspond to a possibility of fibrosis as compared to the lower values of continuous variables or the reference group of categorical variables.

TABLE 27

Logistic regression analysis reveals identified BA signature for the diagnosis of cirrhosis patients from fibrosis patients was independent of the possible confounding risk factors including BMI, age and sex.

| | Odds ratio (95% CI)[3] | S.E. | P value |
|---|---|---|---|
| Cirrhosis-associated BA signature | 177.141 (38.264-820.068) | 7.82E-01 | 3.56E-11 |
| BMI[1] | 1.077 (0.979-1.186) | 4.9E-02 | 3.02E-02 |
| Age[1] | 1.086 (1.057-1.116) | 1.40E-02 | 3.11E-06 |
| Sex[2] | 0.656 (0.329-1.307) | 3.52E-01 | 4.81E-01 |

P values were calculated using the Wald test.
[1]BMI and age is continuous variables.
[2]male or female.
[3]Odds ratios greater than 1 correspond to a possibility of cirrhosis as compared to the lower values of continuous variables or the reference group of categorical variables.

Surprisingly, the results indicated that the AUC of our BA panel was higher than that of AST/ALT ratio, TBIL, MELD score, APRI and FIB-4 (FIG. 16A-C and FIG. 17A-D, further details are provided in the Supplementary materials). This demonstrates the surprisingly powerful diagnostic power of the BA panel, even compared to classic clinical parameters.

Figure 20:
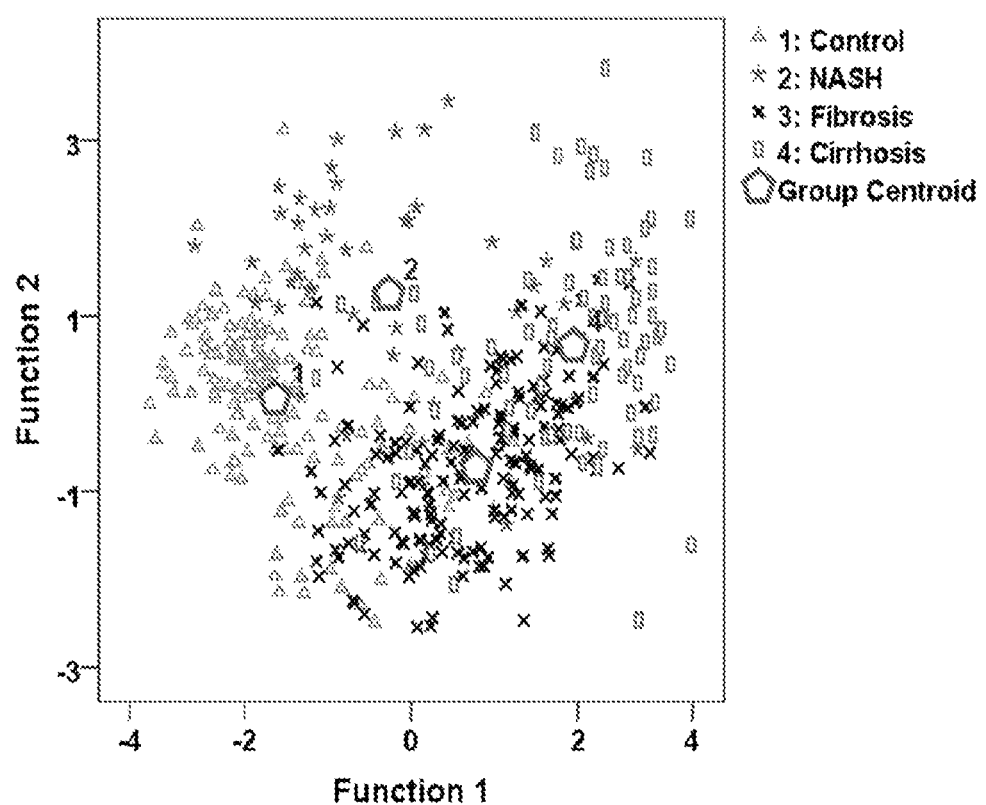
FIG. 20 depicts a plot established with functions generated with canonical discriminant analysis of GCA, GCDCA, TCA, TCDCA, GUDCA, TUDCA, and 7-KLCA among groups of control, patients with NASH, fibrosis and cirrhosis

We then established functions plots from canonical discriminant analysis using GCA, GCDCA, TCA, TCDCA, GUDCA, TUDCA, and 7-KLCA levels and showed that controls, patients with NASH, fibrosis and cirrhosis were clustered into four big groups (FIG. 20). As a result, of the 169 controls, 132 or 78.1% were correctly classified. The correct classification rates for NASH, fibrosis, and cirrhosis patients were 63.0%, 80.7%, and 70.6%, respectively (Table 28).

Figure 16G:
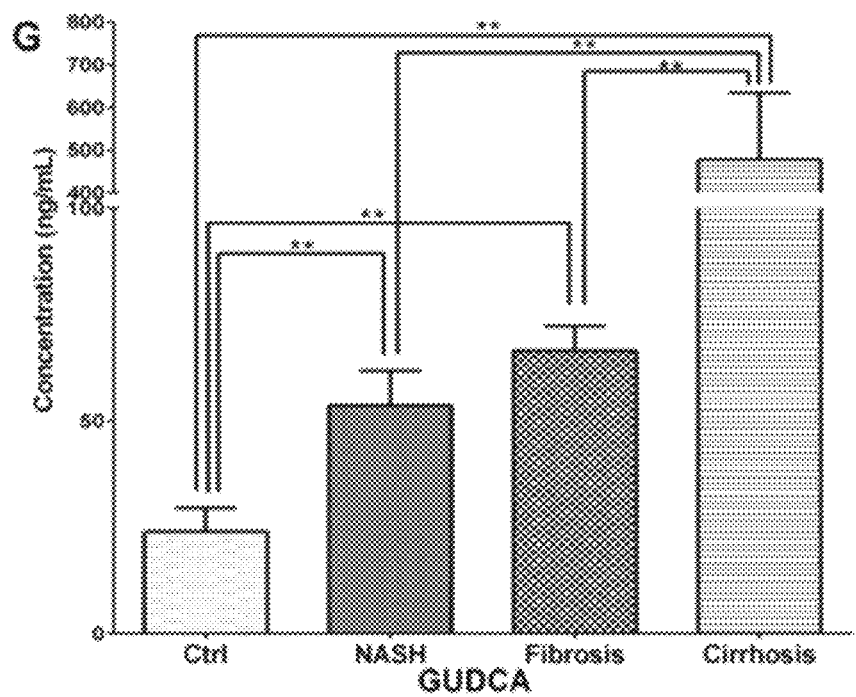
Figure 16H:
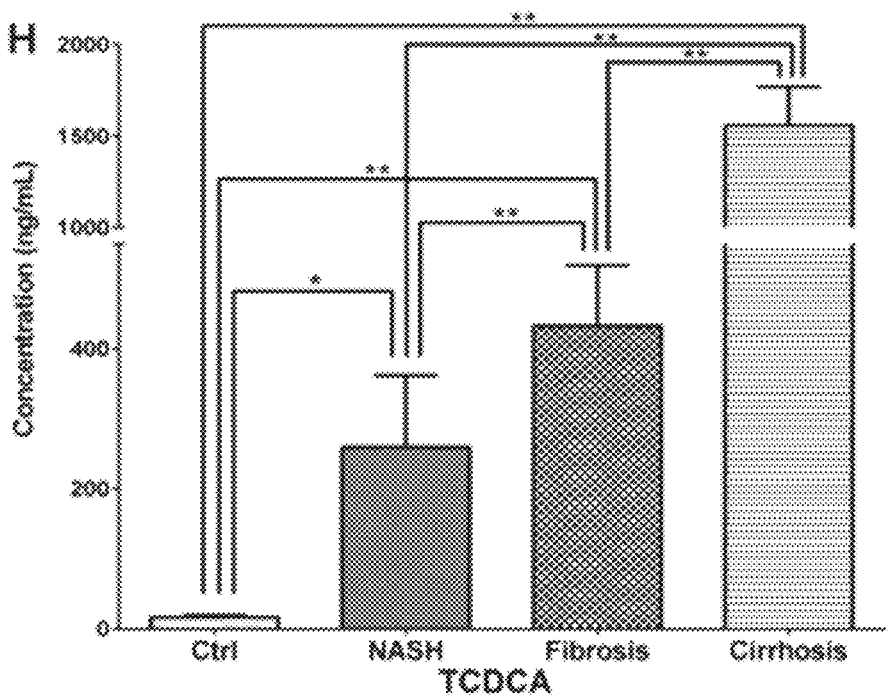
Figure 16I:
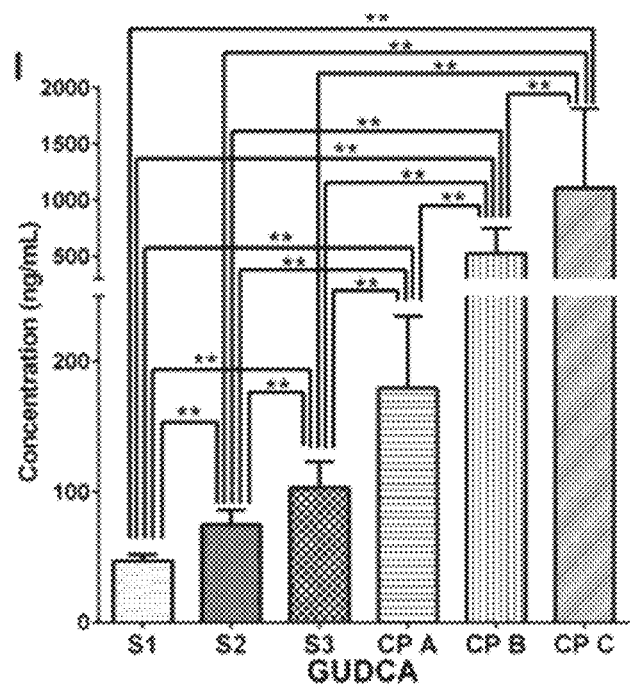
Figure 18:
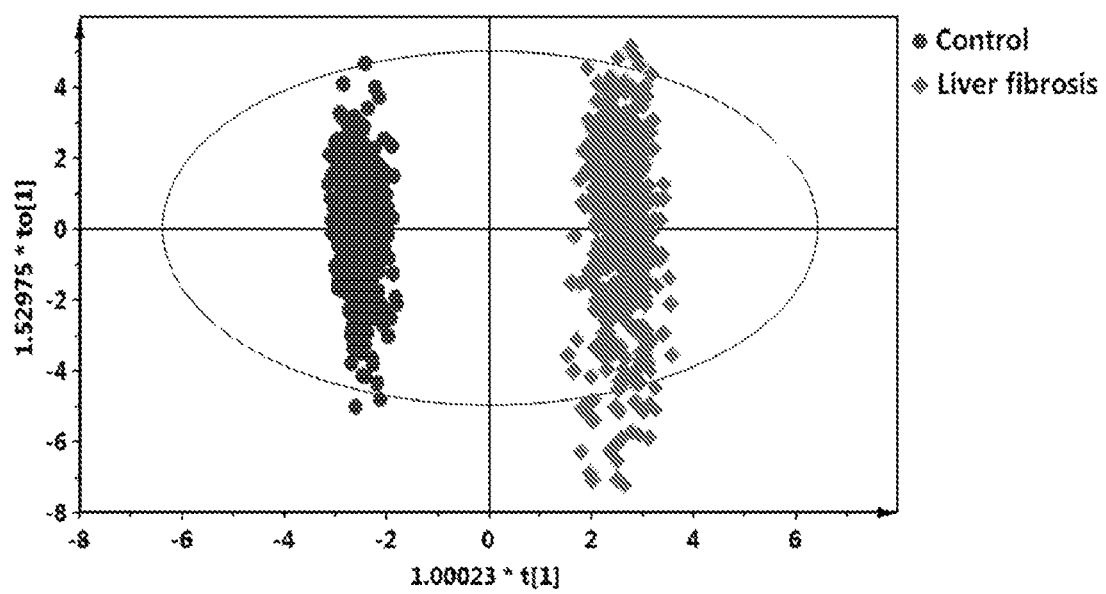
FIG. 18 depicts OPLS-DA scores plot established with all identified BAs in liver fibrosis patients and healthy controls.

Notably, patients had progressively increased serum levels of GUDCA and TCDCA that corresponded with liver disease progression from NASH to fibrosis and from fibrosis to cirrhosis (FIGS. 16G and 16H). The levels of the BA panel were also compared with those obtained from 65 patients with diabetes, which correctly differentiated diabetes patients from the liver disease patients (FIGS. 16J and 16K and FIG. 19).

TABLE 28

Classification results of patients with NASH, fibrosis, cirrhosis and controls using the bile acid levels of GCA, GCDCA, TCA, TCDCA, GUDCA, TUDCA, DCA and 7-KLCA[a]

| | | control-NASH-fibrosis-cirrhosis | Predicted Group Membership | | | | |
|---|---|---|---|---|---|---|---|
| | | | Controls | NASH | Fibrosis | Cirrhosis | Total |
| Original | Count | Controls | 132 | 9 | 28 | 0 | 169 |
| | | NASH | 6 | 29 | 6 | 5 | 46 |
| | | Fibrosis | 9 | 8 | 142 | 17 | 176 |
| | | Cirrhosis | 1 | 6 | 18 | 60 | 85 |
| | % | Controls | 78.1 | 5.3 | 16.6 | .0 | 100 |
| | | NASH | 13.0 | 63.0 | 13.0 | 10.9 | 100 |
| | | Fibrosis | 5.1 | 4.5 | 80.7 | 9.7 | 100 |
| | | Cirrhosis | 1.2 | 7.1 | 21.2 | 70.6 | 100 |

Example 20 Evaluating Liver Disease Status Using a Model for Scoring of a Multi-Biomarker Panel The selected BA panel was measured in a new set (validation set) of liver disease subjects that did not include any of the liver disease subjects tested in Example 8. The validation set included the same 502 non-diabetic, non-alcoholic, healthy subjects without liver disease, as the testing set. The data from this set of subjects is provided in Table 29. Other markers of liver disease status were also measured in these subjects for comparison (e.g. ALB, ALP, ALT, AST).

The validation set included 471 liver disease subjects (chronic liver disease, CLD) having chronic hepatitis B, none of which were in the testing set. The 471 liver disease subjects included 132 subjects with no fibrosis (HB also referred to as CHB), 30 subjects with S1 fibrosis, 26 subjects with S2 fibrosis, 20 subjects with S3 fibrosis, 49 subjects with CP A cirrhosis, 99 subjects with CP A cirrhosis, 22 subjects with CP C cirrhosis, and 93 subjects that had hepatocellular carcinoma (HCC) in addition to CP C cirrhosis. The levels of each biomarker of the panel, GCA, GCDCA, TCA, TCDCA, GUDCA, TUDCA, and 7-KLCA, was measured in the validation set. The measured levels are shown in Table 30. The measured values in the validation set were consistent with the measured values of the testing set.

TABLE 29

Demographic Data of subjects of a validation population

| Group | healthy | CLD | HB | Fibrosis S1 | Fibrosis S2 | Fibrosis S3 | Cirrhosis CP A | Cirrhosis CP B | Cirrhosis CP C | HCC |
|---|---|---|---|---|---|---|---|---|---|---|
| Characteristic | 502 | 471 | n = 132 | n = 30 | n = 26 | n = 20 | n = 49 | n = 99 | n = 22 | n = 93 |
| gender (M/F) | 367/135 | 336/135 | 83/49 | 23/7 | 16/10 | 17/3 | 33/16 | 67/32 | 17/5 | 80/13 |
| Age (years) | 36.68 ± 0.53 | 46.99 ± 0.67* | 42.2 ± 1.21 | 34.88 ± 2.31 | 36.96 ± 2.16 | 40.23 ± 1.85 | 46.51 ± 1.69 | 54.79 ± 1.29 | 47.71 ± 3.38 | 55.49 ± 1.22 |
| BMI (kg/m2) | 23.08 ± 0.14 | 22.97 ± 0.15 | 23.6 ± 0.23 | 22.58 ± 0.5 | 22.18 ± 0.82 | 21.56 ± 0.57 | 23.45 ± 0.5 | 23.14 ± 0.33 | 24.66 ± 0.89 | 21.61 ± 0.37 |
| ALB (g/L) | 49.25 ± 0.12 | 39.14 ± 0.32** | 42.62 ± 0.36 | 40.29 ± 0.77 | 40.63 ± 1.14 | 41.67 ± 0.85 | 38.3 ± 1.16 | 37.07 ± 0.68 | 27.61 ± 0.89 | 37.69 ± 0.79 |
| ALP (U/L) | 85.48 ± 0.82 | 91.38 ± 3.55* | 58.7 ± 4.51 | 76.17 ± 3.55 | 83.08 ± 3.82 | 79.45 ± 3.45 | 94.9 ± 8.66 | 90.35 ± 5.81 | 137.82 ± 23.16 | 145.13 ± 13.57 |
| ALT (U/L) | 30.97 ± 0.7 | 81.39 ± 5.38** | 87.07 ± 8.93 | 155.04 ± 25.04 | 160.87 ± 38.78 | 68.3 ± 12.9 | 65.73 ± 7.89 | 61.26 ± 12.99 | 124.88 ± 49.46 | 51.13 ± 6.03 |
| AST (U/L) | 21.77 ± 0.3 | 70.08 ± 4.13** | 65.48 ± 5.85 | 81.92 ± 12.16 | 90.5 ± 24.46 | 67.24 ± 23.62 | 51.56 ± 4.08 | 62.41 ± 8.61 | 108.82 ± 19.14 | 80.55 ± 14.88 |
| AST/ALT | | 1.26 ± 0.22 | 0.95 ± 0.09 | 0.65 ± 0.03 | 0.68 ± 0.03 | 0.80 ± 0.04 | 1.67 ± 0.07 | 2.13 ± 0.13 | 2.04 ± 0.11 | 1.56 ± 0.26 |
| CHOL (mmol/L) | 5.17 ± 0.04 | 3.98 ± 0.06** | 4.1 ± 0.09 | 5.04 ± 0.19 | 4.52 ± 0.32 | 4.57 ± 0.21 | 4.72 ± 0.24 | 3.43 ± 0.12 | 3.14 ± 0.2 | 3.56 ± 0.09 |
| PALB (mg/L) | 333.12 ± 1.58 | 152.17 ± 4.26** | 173.97 ± 8.16 | 212.75 ± 13.5 | 203.18 ± 13.17 | 201.7 ± 15.77 | 172.22 ± 13.17 | 111.78 ± 7.15 | 64.07 ± 4.82 | 121.81 ± 9.04 |
| PDW (%) | 15.27 ± 0.03 | 18.38 ± 0.71** | | 16.62 ± 0.14 | 16.59 ± 0.19 | 16.35 ± 0.34 | 18.87 ± 2.17 | 25.83 ± 8.76 | 17.22 ± 0.7 | |
| PLT (10^9/L) | 261.19 ± 2.93 | 136.26 ± 3.68 | 165.64 ± 5.16 | 208.17 ± 10.55 | 165.15 ± 10.07 | 157.38 ± 20.86 | 131.78 ± 9.67 | 87.97 ± 6.71 | 74.47 ± 9.12 | 126.73 ± 10.38 |
| TBA (umol/L) | 4.56 ± 0.14 | 34.9 ± 2.27** | 17.84 ± 1.97 | 14.42 ± 2.15 | 18.59 ± 3.36 | 14.4 ± 2.58 | 32.97 ± 4.38 | 45.85 ± 4.01 | 114.27 ± 21.03 | 50.37 ± 8.29 |
| TBIL (umol/L) | 15.45 ± 0.21 | 33.99 ± 2.99** | 17.18 ± 1.1 | 19.46 ± 1.31 | 22.83 ± 1.66 | 19.24 ± 1.09 | 24.03 ± 2.12 | 37.55 ± 4.27 | 184.8 ± 44.8 | 41.04 ± 8.56 |
| TG (mmol/L) | 1.52 ± 0.03 | 1.16 ± 0.03** | 1.38 ± 0.08 | 1.1 ± 0.1 | 1.17 ± 0.15 | 1.25 ± 0.26 | 1.09 ± 0.08 | 1.02 ± 0.07 | 1.09 ± 0.12 | 1 ± 0.05 |
| AFP (ng/mL) | | 1114.61 ± 414.88 | 26.55 ± 8.24 | 6.33 ± 1.36 | 22.61 ± 15.19 | 32.94 ± 16.46 | 42.9 ± 18.14 | 715.73 ± 691.67 | 7343.09 ± 7274.39 | 3596.19 ± 1461.11 |
| MELD score | | 9.88 ± 0.2 | 8.05 ± 0.18 | 7.58 ± 0.27 | 8.13 ± 0.32 | 9.31 ± 1.52 | 9.06 ± 0.34 | 11.25 ± 0.34 | 19.44 ± 1.37 | 10.66 ± 0.47 |
| APRI | 0.22 ± 0.05 | 1.65 ± 0.11** | 1.18 ± 0.13** | 1.04 ± 0.16* | 1.21 ± 0.20* | 1.60 ± 0.30** | 1.35 ± 0.18** | 2.18 ± 0.31** | 4.64 ± 0.71 ** | 2.20 ± 0.34** |
| FIB-4 | 0.62 ± 0.01 | 4.21 ± 0.46** | 2.17 ± 0.19** | 1.34 ± 0.36* | 1.48 ± 0.21* | 2.91 ± 0.85** | 5.94 ± 0.77** | 9.52 ± 1.17** | 11.80 ± 1.88** | 6.33 ± 0.78** |

Table notes:
Values are expressed as mean ± SEM.
*p < 0.05;
**p < 0.01, when compared to healthy controls.
ALB, Albumin;
ALP, alkaline phosphatase;
ALT, alanine transaminase;
AST, aspartate transaminase;
CHOL, cholesterol;
PALB, prealbumin;
PDW, platelet distribution width;
PLT, platelet;
TBA, total bile acid;
TBIL, Total bilirubin;
TG, triglyceride;
AFP, Alpha- Fetoprotein;
MELD, Model for End-Stage Liver Disease;
APRI, AST to Platelet Ratio Index;
FIB-4 (patient age, aspartate aminotransferase, alanine aminotransferase, and platelets)

TABLE 30

Serum BA concentrations in validation population

| Bile acids | Healthy | CLD | HB | Fibrosis | | | Cirrhosis | | | HCC |
|---|---|---|---|---|---|---|---|---|---|---|
| | | | | S1 | S2 | S3 | C PA | CP B | CP C | |
| GCDCA | 253.17 ± 13.72 | 3177.28 ± 227.55** | 1303.79 ± 136.96** | 1294.84 ± 259.63** | 2554.43 ± 772.71** | 1691.2 ± 331.47** | 4932.87 ± 736.36** | 4450.66 ± 437.83** | 10659.05 ± 3425.29** | 2944.03 ± 289.73** |
| GCA | 72.99 ± 6.15 | 1958.25 ± 150.51** | 800.53 ± 113.11** | 590.17 ± 142.37** | 1956.61 ± 559.17** | 775.59 ± 274.49** | 3097.95 ± 697.8** | 3077.65 ± 329.48** | 4591.56 ± 1658.48** | 1996.93 ± 225.44** |
| GUDCA | 20.59 ± 1.38 | 325.59 ± 49.91** | 183 ± 40.94** | 37.77 ± 4.74** | 86.67 ± 23.38** | 112.12 ± 40.62** | 384.04 ± 165.8** | 552.14 ± 147.83** | 800.07 ± 687.01** | 396.15 ± 91.04** |
| TCDCA | 17.73 ± 1.24 | 1095.09 ± 101.71** | 302.37 ± 48.41** | 100.43 ± 38.95** | 167.06 ± 52.41** | 123.19 ± 31.07** | 1200.95 ± 243.58** | 2014.23 ± 272.62** | 2648.25 ± 860.76** | 1874.03 ± 341.97** |
| TCA | 6.24 ± 1.38 | 1048.86 ± 143.34** | 178.59 ± 43.29** | 333.19 ± 180.34** | 589.34 ± 201.19** | 208.23 ± 58.19** | 2204.49 ± 877.15** | 1738.21 ± 314.31** | 3482.81 ± 1022.46** | 975.61 ± 188.96** |
| 7-KLCA | 2.26 ± 0.13 | 11.14 ± 1.21** | 6.79 ± 0.88** | 2.35 ± 0.4 | 3.92 ± 0.84 | 5.11 ± 2.59** | 16.95 ± 3.66** | 17.49 ± 4.39** | 9.49 ± 2.63** | 14.61 ± 3.09** |
| TUDCA | 1.44 ± 0.08 | 59.35 ± 12.85** | 9.86 ± 1.52** | 2.07 ± 0.34 | 4.69 ± 1.42** | 8.98 ± 3.93** | 110.24 ± 59.66** | 112.31 ± 38.49** | 27.14 ± 8.21** | 104.31 ± 38.39* |

The models developed in the previous example, which indicated that higher serum BA levels were associated with higher risk of getting liver disease, were applied to the validation population. Again, the validation study demonstrated the capacity of the seven BA panel to discriminate subjects. Specifically, the validation study performed with serum samples from the validation population successfully discriminated patients with HB from healthy controls (AUC: 0.808 (95% CI: 0.747-0.868)) using the NASH vs control model trained on training set, between patients with HB and fibrosis (AUC: 0.861 (95% CI: 0.796-0.926)) using the NASH vs fibrosis model trained on training set, and between patients with cirrhosis and fibrosis (AUC: 0.792 (95% CI: 0.705-0.879)) using the fibrosis vs cirrhosis model trained on training set, after adjustment for age, gender and BMI (FIGS. 17A-C). Further, the seven BA panel was able to discriminate between cirrhosis patients and HCC patients (AUC: 0.871 (95% CI: 0.815-0.926)) after adjustment for age, gender and BMI (FIG. 17D) using the newly established model: Probability=exp{0.503−0.001(GCDCA)−0.0002(GCA)+0.001(TCDCA)−0.001(TCA)+0.001(GUDCA)+0.0001(TUDCA)+0.029(7−KLCA)}/(1+exp{0.503−0.001(GCDCA)−0.0002(GCA)+0.001(TCDCA)−0.001(TCA)+0.001(GUDCA)+0.0001(TUDCA)+0.029(7−KLCA)}) which was trained on the validation set.

Figure 21:
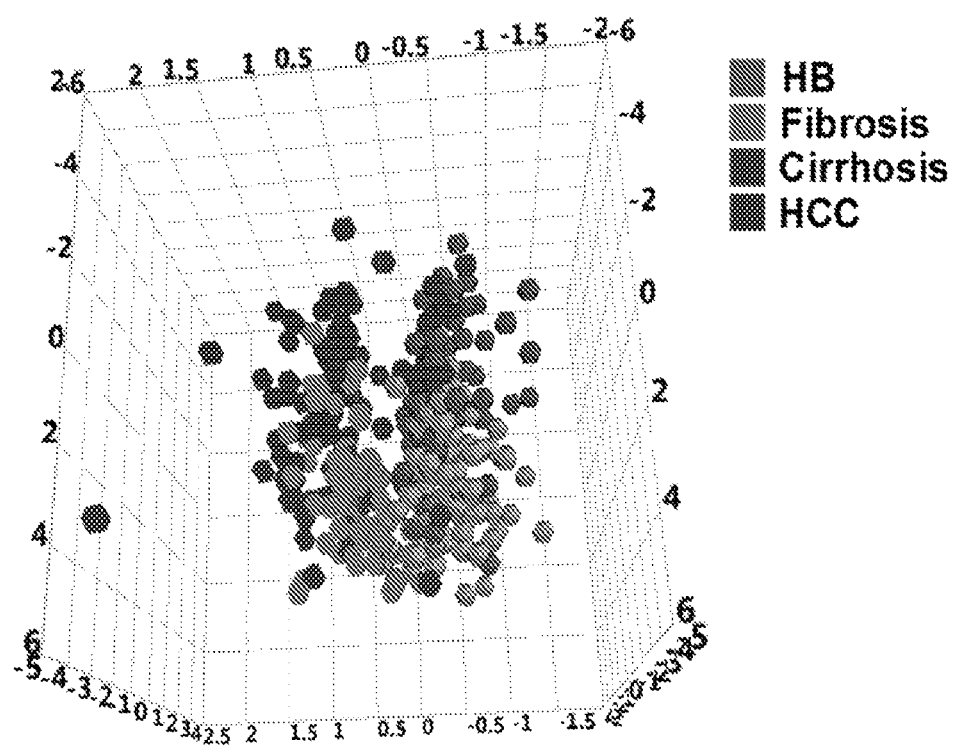
FIG. 21 depicts a OPLS-DA scores plot for patients with HB, Fibrosis, Cirrhosis and HCC were constructed using all the differentially expressed BAs
Figure 22:
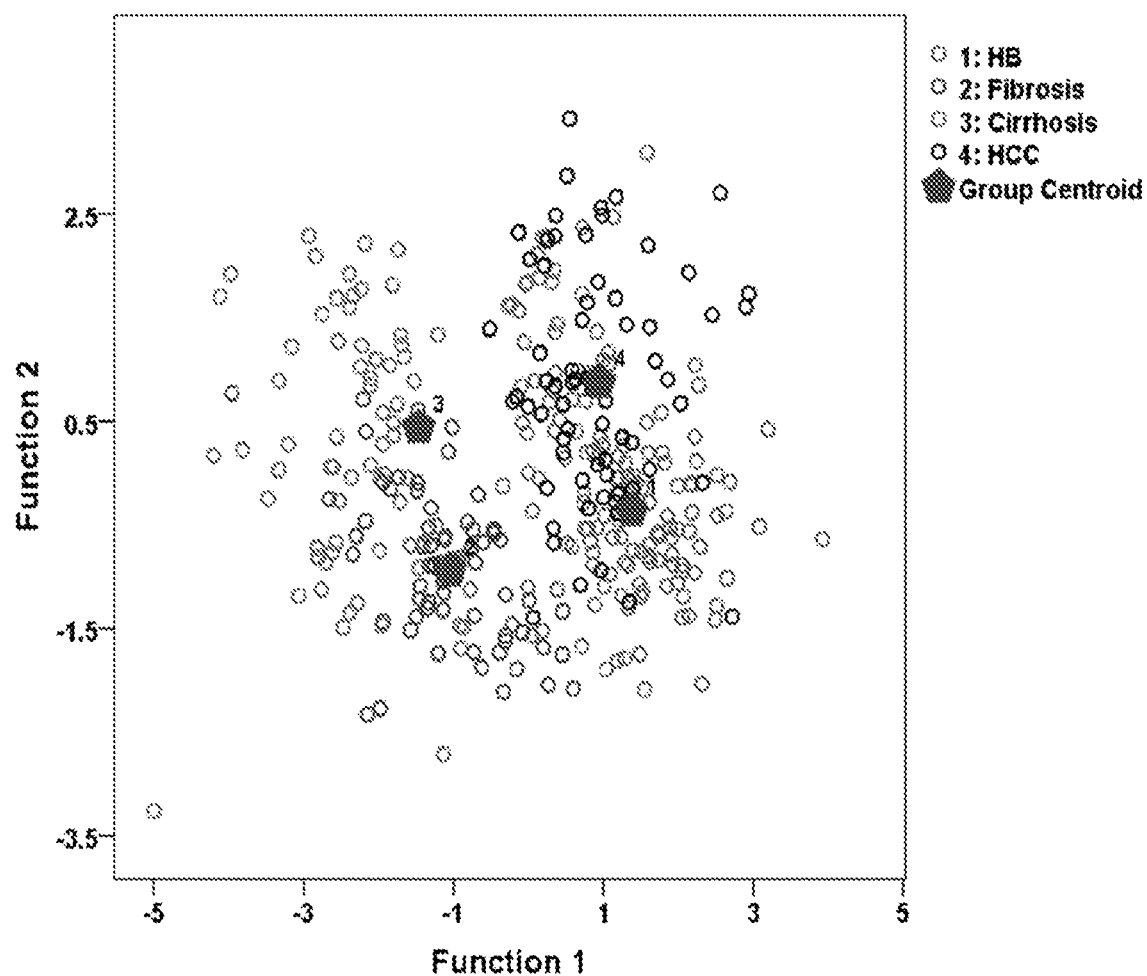
FIG. 22 depicts a plot established with functions generated with canonical discriminant analysis of GCA, GCDCA, TCA, TCDCA, GUDCA, TUDCA, and 7-KLCA among groups of patients with HB, fibrosis, cirrhosis and HCC.

Bar plots showing the alteration of serum levels of GCA, GCDCA, TCA, TCDCA, GUDCA, TUDCA and 7-KLCA in the validation set are provided in FIGS. 17E-17E7. As done previously in the testing set, we constructed functions plots using GCA, GCDCA, TCA, TCDCA, GUDCA, TUDCA, and 7-KLCA and were able to show that patients with HBV, fibrosis, cirrhosis and HCC are clustered into four big groups (FIG. 21 and FIG. 22). The GUDCA levels in patients with HBV, fibrosis at 51, S2 and S3, cirrhosis patients at CP grades A, B and C and HCC are shown in FIG. 17F.

Again, as demonstrated in the validation population, AUC of this BA panel was surprisingly found to be greater than previously reported tests AST/ALT ratio, TBIL, MELD score, APRI and FIB-4 (FIG. 17A-D). This demonstrates the remarkable power of biomarkers of this panel, when used alone or in combination with other biomarkers taught herein.

Example 21 Liver Cancer Preventable by Treatment with Bile Acid Modulator

This example details that dysregulated bile acids (BAs) are closely associated with liver diseases and attributed to altered gut microbiota. This example shows that the intrahepatic retention of hydrophobic BAs including deoxycholate (DCA), taurocholate (TCA), taurochenodeoxycholate (TCDCA), and taurolithocholate (TLCA) were substantially increased in a streptozotocin and high fat diet (HFD) induced nonalcoholic steatohepatitis-hepatocellular carcinoma (NASH-HCC) mouse model. Additionally chronic HFD-fed mice spontaneously developed liver tumors with significantly increased hepatic BA levels. Therapeutic modulation of BA levels by enhancing intestinal excretion of hydrophobic BAs in the NASH-HCC model mice by a 2% cholestyramine feeding significantly prevented HCC development. The gut microbiota alterations were closely correlated with altered BA levels in liver and feces. HFD-induced inflammation inhibited key BA transporters, resulting in sustained increases in intrahepatic BA concentrations. The study also showed a significantly increased cell proliferation in BA treated normal human hepatic cell lines and a down-regulated expression of tumor suppressor gene CEBPa in TCDCA treated HepG2 cell line, demonstrating that several hydrophobic BAs may collaboratively promote liver carcinogenesis.

It was hypothesized that intrahepatic accumulation of BAs critically induces sustained hepatocellular injuries responsible for the subsequent development of fibrosis and malignancy. A streptozotocin-high fat diet (STZ-HFD) induced nonalcoholic steatohepatitis (NASH)-HCC mouse model was used, which is highly relevant to human liver disease progression from steatosis to NASH, fibrosis, and finally HCC and nearly 100% of mice in the model group developed HCC. The hypothesis was further verified in chronic HFD-fed mice and human normal hepatic cell lines and tumor cell lines.

Figure 23A:
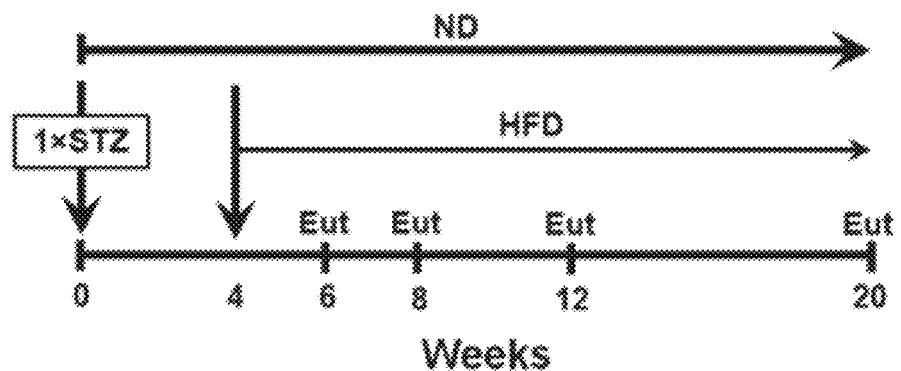

Materials and Methods
Mice and Diet
Experimental 1:
A NASH-HCC C57BU6J mice model induced by STZ coupled with HFD was developed. Pathogen-free 14-day pregnant C57BL/6J mice were purchased from CLEA Japan (Tokyo, Japan) and the new born male mice were divided into two groups: control group and model (STZ-HFD) group. The mice in control group was housed without any treatment and fed normal diet (CE-2 from CLEA Japan Inc., composed of 12 kcal % fat, 29 kcal % protein, 59 kcal % carbohydrates). The mice in STZ-HFD were subjected to a single subcutaneous injection of 200 µg STZ (Sigma, MO, USA) at 2 days after birth and fed with HFD (HFD32 from CLEA japan Inc., STZ-FHD group) ad libitum after 4 weeks of age for 16 weeks (FIG. 23A). During the experiment, the body weight of all animals was recorded once a week. At week 6, 8, 12, and 20, 6 mice in each group were euthanized and liver, plasma, and fecal samples were collected.

Experimental 2:

In addition to Experimental 1, we fed C57BL/6J male mice with HFD alone to observe the liver carcinogenesis and to further confirm that BAs will promote liver carcinogenesis. Two groups of mice were included: (1) control; (2) HFD. We sacrificed mice at different time points and at week 58, we observed HCC formation in HFD-fed mice.

Figure 26A:
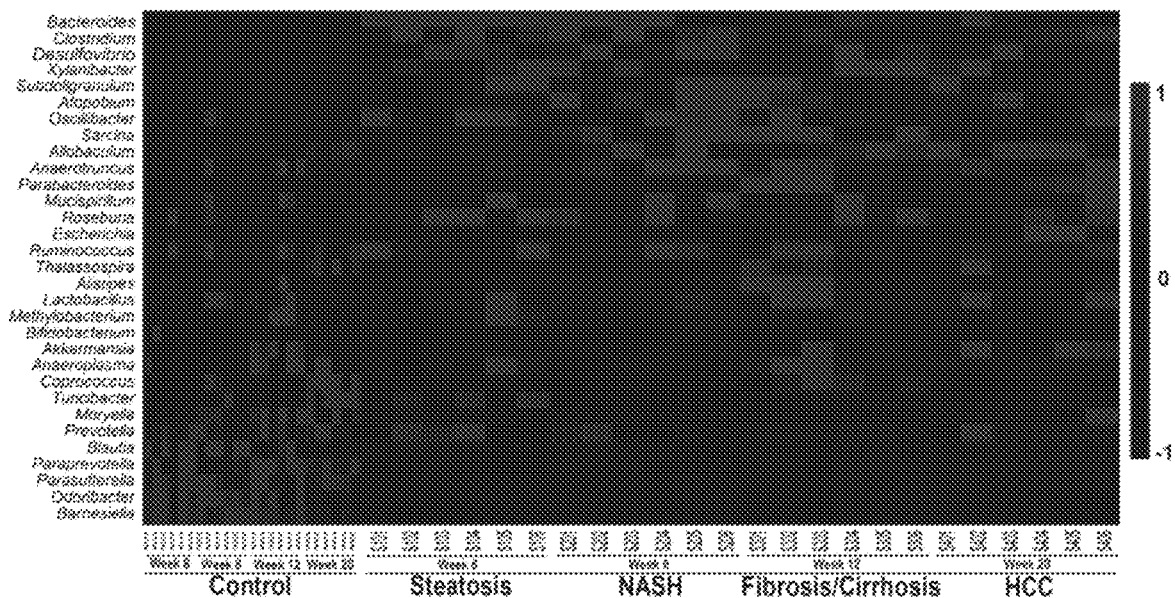
FIG. 26A-FIG. 26E depict data from a study of bile acid modulators as treatment for liver cancer.

Experimental 3:

It was found that the BA levels were significantly increased in hepatic carcinogenesis in Experimental 1; the NASH-HCC mice model was repeated to see whether the BA-binding resin, cholestyramine, can attenuate/prevent liver carcinogenesis. Three groups of mice were included: (1) control (n=9); (2) model (STZ-HFD, n=30) and (3) STZ-HFD-BA resin (n=30) group, mice were fed with HFD diet containing 2% cholestyramine. All the procedures are the same as in Experimental 1. At week 20, the mice were euthanized and liver, plasma, and fecal samples were collected (FIG. 26A).

All animal procedures were performed in accordance with the "Guide for the Care and Use of Laboratory Animals" prepared by the National Academy of Sciences and published by the National Institutes of Health (NIH publication 86-23, revised 1985).

Measurement of Serum ALT and AST

The levels of serum alanine aminotransferase (ALT) and aspartate aminotransferase (AST) were measured by FUJI DRI-CHEM 7000 (Fujifilm, Tokyo, Japan).

Histological Evaluation

Liver tissues were fixed in 10% neutral-buffered formalin, embedded in paraffin blocks, and processed by routine hematoxylin and eosin (H&E) staining. Individual NAFLD activity score was calculated.

Measurement of BAs

The BA levels in plasma, liver, and feces were quantitatively measured by ultra-performance liquid chromatography triple quadrupole mass spectrometry (UPLC-TQMS). All separations were performed with an ACQUITY BEH C18 column (1.7 µm, 100 mm×2.1 mm internal dimensions) (Waters, Milford, MA). Data acquisition was performed using MassLynx version 4.1 and BA quantification were performed using the TargetLynx applications manager version 4.1 (Waters Corp., Milford, MA). For details, see Methods in Supporting Information.

Gut Microbiota Characterization

The diversity of bacteria was characterized by using a bacterialtag-encoded FLX 16S rDNA amplicon pyrosequencing (bTEFAP) approach as previously reported.

Real-Time Quantitative Polymerase Chain Reaction

DNA and RNA were simultaneously extracted using homogenized tissue lysates in RLT Plus and the AllPrep DNA/RNA Mini kit (Qiagen, Valencia, CA) following manufacturer's protocol. RNA integrity was assessed using 1 µl of RNA on the RNA Nano 6000 chips and the 2100 Agilent Bioanalyzer. Expression of target mRNA was measured in triplicate by the comparative cycle threshold method on the Applied Biosystems 7900 FAST Real Time PCR Systems (Applied Biosystems). The forward and reverse primers were purchased from Integrated DNA Technologies (Coralville, IA). Target gene expression was normalized to ACTB levels and the relative expression of the target genes was calculated using the "dCT" a.k.a Comparative Ct approach.

Measurement of TG, IL-6 and TNF-α in the Liver

The levels of triglyceride (TG), interleukin-6 (I L-6) and tumor necrosis factor (TNF-α) in the liver were measured using Elisa kits from BlueGene Biotech, Shanghai, China.

Measurement of LPS in Plasma, Liver and Feces

The levels of lipopolysaccharides (LPS) in plasma, liver and feces were determined using a mouse LPS Elisa kit (BlueGene Biotech, Shanghai, China) according to the manufacturer's protocol.

Statistical Analysis. All statistical analyses were calculated using GraphPad Prism (version 6.0; GraphPad Software, San Diego, USA) and SPSS 22.0 (IBM SPSS, USA). Data are expressed as mean±SEM. The differences between the groups in BA measurements were analyzed by t tests with Holm-Sidak method for multiple comparisons correction. We regarded p values of <0.05 as significant. Spearman correlation analysis was made to evaluate the interactions between gut microbiota and BA levels in liver and feces, giving a value ranging from 1.0 (maximum positive correlation) to −1 (maximum anticorrelation) and 0 (no correlation).

Cell Culture and BA Treatment

Normal human hepatic cell lines WRL-68 and THLE-2 were purchased from Sigma. For BA treatment, cells were harvested, rinsed twice in PBS, resuspended in sugar-free DMEM (Life Technologies) supplemented with 10% charcoal-stripped FBS and seeded into 6-well plate at a density of $5 \times 10^4$/well. We set the glucose (Glc, Sigma) at 27.5 mM and Oleic acid (OA, Sigma) at 0.3 mM to mimic high glucose and fat conditions in vitro. Each of the 5 BAs, CA, TLCA, TCA, TCDCA, GCDCA, DCA, or LCA was added into the media at concentrations of 5 µM, 50 µM, 100 µM or 200 µM. After 14 days treatment, normal medium (DMEM-F12 containing 10% FBS) were added into each well to replace the spent media. Cell proliferation and anchorage-independent growth assays were performed in the normal medium. Additionally, western blot assay was performed to analyze the alteration of oncoprotein c-myc expression.

Human cancer cell line, HepG2, was purchased from Sigma and maintained in DMEM-F12 (Life Technologies) supplemented with 10% fetal bovine serum (FBS, Life Technologies). For BA treatment, cells were harvested, rinsed twice with PBS, seeded in sugar-free DMEM (Life Technologies) supplemented with 10% charcoal-stripped FBS and 6 mM glucose. Each of the 5 BAs, CA, UDCA, TCDCA, DCA, or LCA was added into the media at a concentration of 100 µM. The spent media was replaced by fresh normal medium (DMEM-F12 containing 10% FBS) 14 days later. And then cells were used for cell proliferation assay and western blot analysis for the tumor suppressor protein CEBPa.

Primary antibodies for c-myc (Santa Cruz), CEBPa (Santa Cruz) and Actin (Li-cor) were purchased and used with a diluted concentration as indicated by the manufacturers.

Results

Figure 23B:
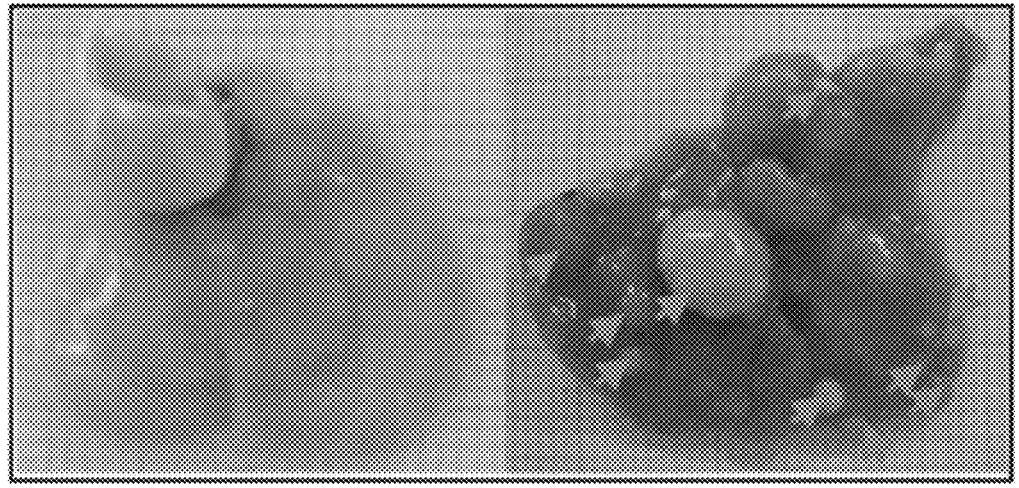
Figure 23C:
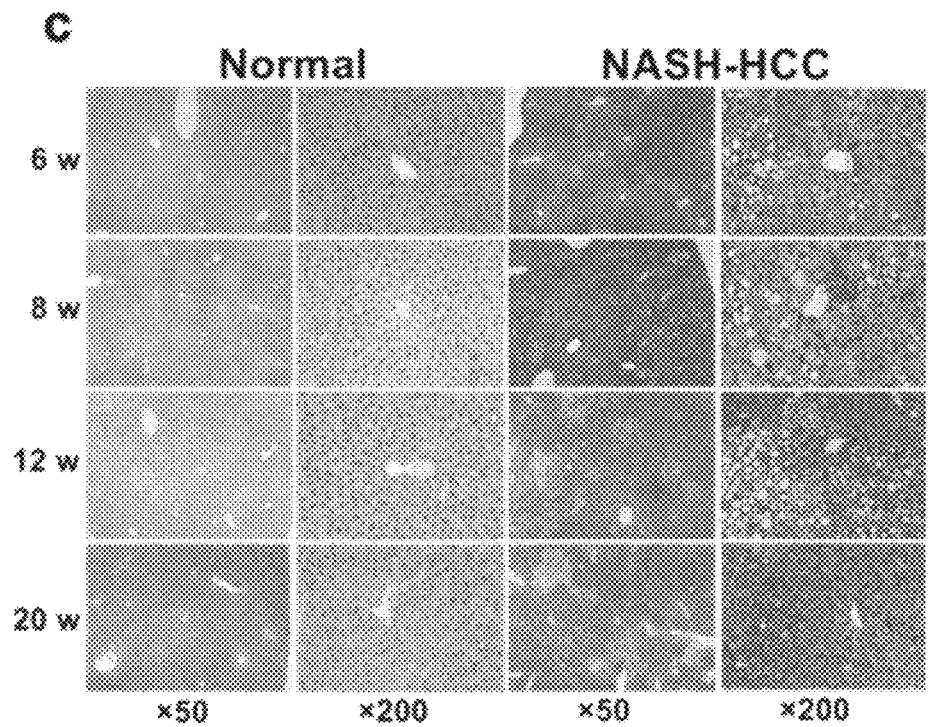

Hepatic BAs were Significantly Increased in STZ-HFD Induced NASH-HCC Mice Pathological phenotypes of steatosis, NASH, fibrosis, and HCC were successfully developed in male C57BL/6J mice. Neonatal mice injected subcutaneously with STZ induced mild islet inflammation and islet destruction. Four weeks after birth, STZ-primed mice were given with HFD, which resulted in sequential histological changes from fatty liver, to NASH, fibrosis, and HCC (FIG. 23A). Notably, all HFD-fed mice developed HCC (FIG. 23B). H&E staining (FIG. 23C) showed fatty liver, but no inflammatory foci at 6 week, fatty liver with moderate inflammatory infiltrate include neutrophils, lymphocytes and monocytes, and ballooning degeneration of hepatocytes at week 8, chronic fibrosis at week 12 and HCC at week 20 with increased NAFLD activity score.

Figure 23D:
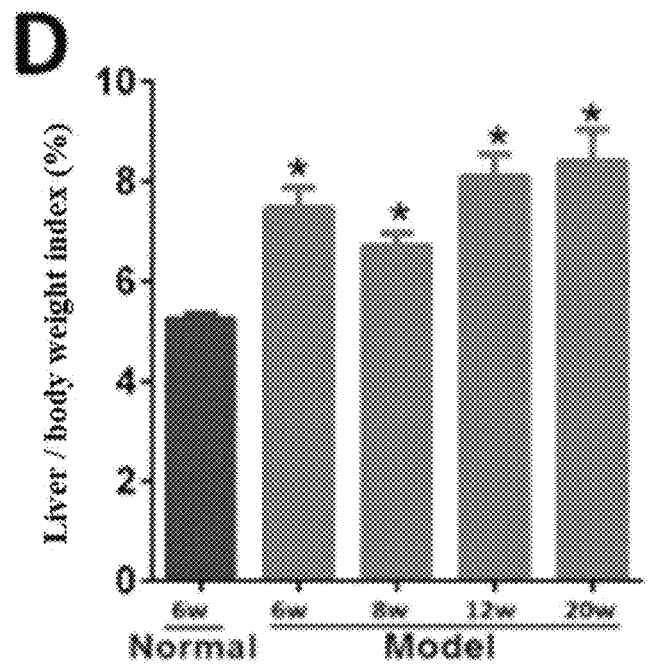
Figure 23E:
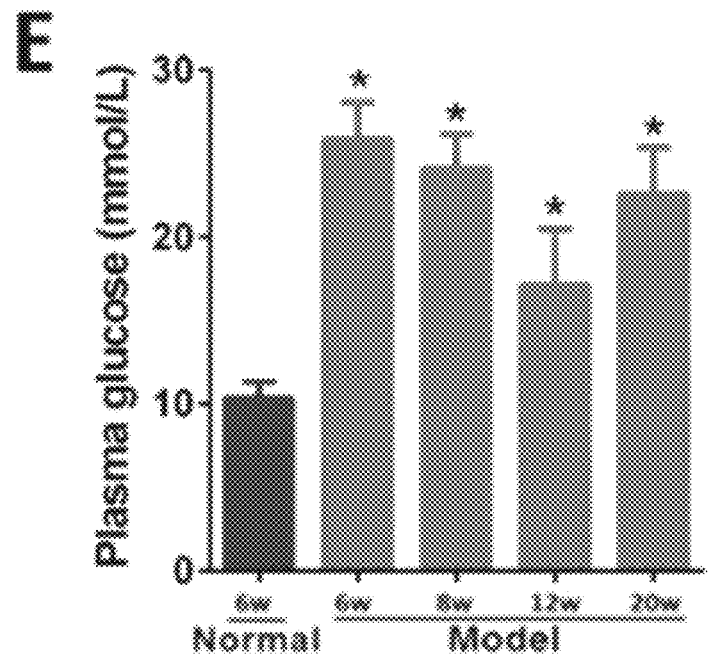
Figure 23F:
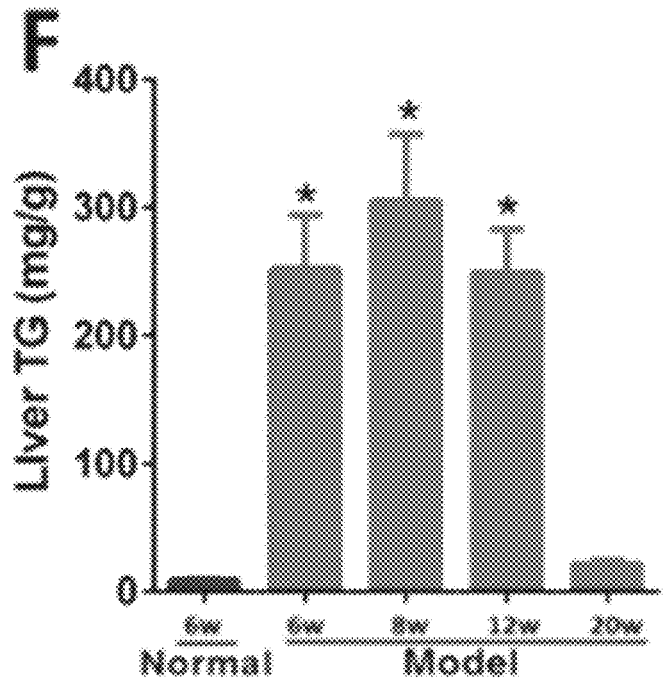

Body weight gain was observed with the aggravated liver injury in STZ-HFD mice. The liver weight was significantly increased in STZ-HFD group compared to normal mice, especially at fibrosis and HCC stages (FIG. 23D). Fasting plasma glucose and liver TG were significantly higher in the STZ-HFD group (FIGS. 23E and 23F). Mild elevation of serum ALT and AST were detectable in STZ-HFD mice. The endotoxin (lipopolysaccharides, LPS) levels in plasma, liver and feces were markedly increased in STZ-HFD group compared to controls (FIG. 23G).

Importantly, the hepatic levels of TCA, DCA, GCA, TDCA, TLCA, TUDCA, TCDCA, and total BAs were substantially increased in the model mice at week 12 and 20 (FIGS. 23H1-23H8). The hepatic accumulation of BAs occurred at liver fibrosis stage while fecal BAs were depleted at the same stage, and gradually increased at HCC stage. Notably, among all the BA species, TCDCA was the most significantly increased species in the liver of model mice compared to the controls. In addition to these BAs, LCA was increased in plasma and feces in model mice.

Interestingly, the primary BAs, CA and CDCA, in feces were decreased in fibrosis phase (week 12) in model group as compared to controls while in plasma and liver, their levels were increased. Total fecal BAs were slightly lower in model group than in controls at fibrosis stage, while at HCC stage, its level increased in plasma and liver at fibrosis and HCC stages.

Liver Tumor was Developed in Chronic HFD-Fed Mice

Figure 24A:
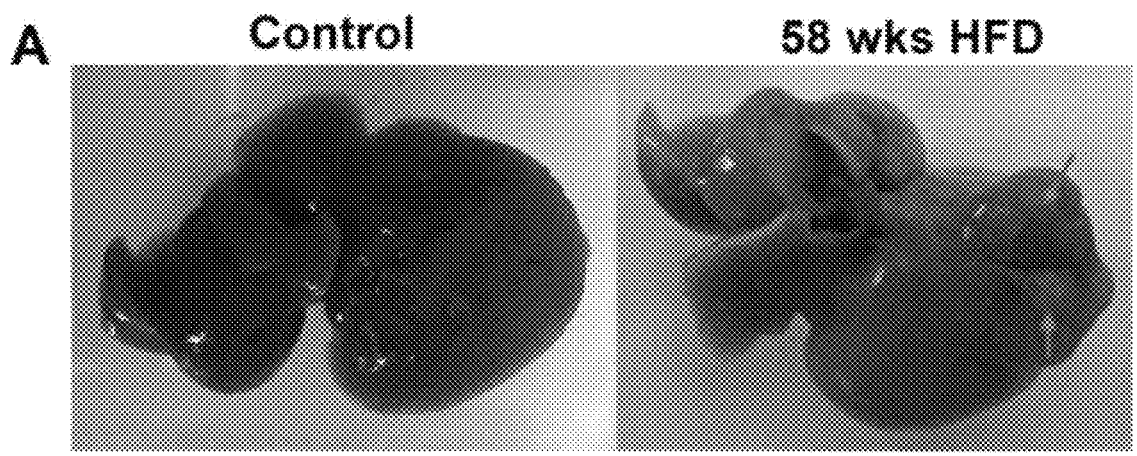
Figure 24B:
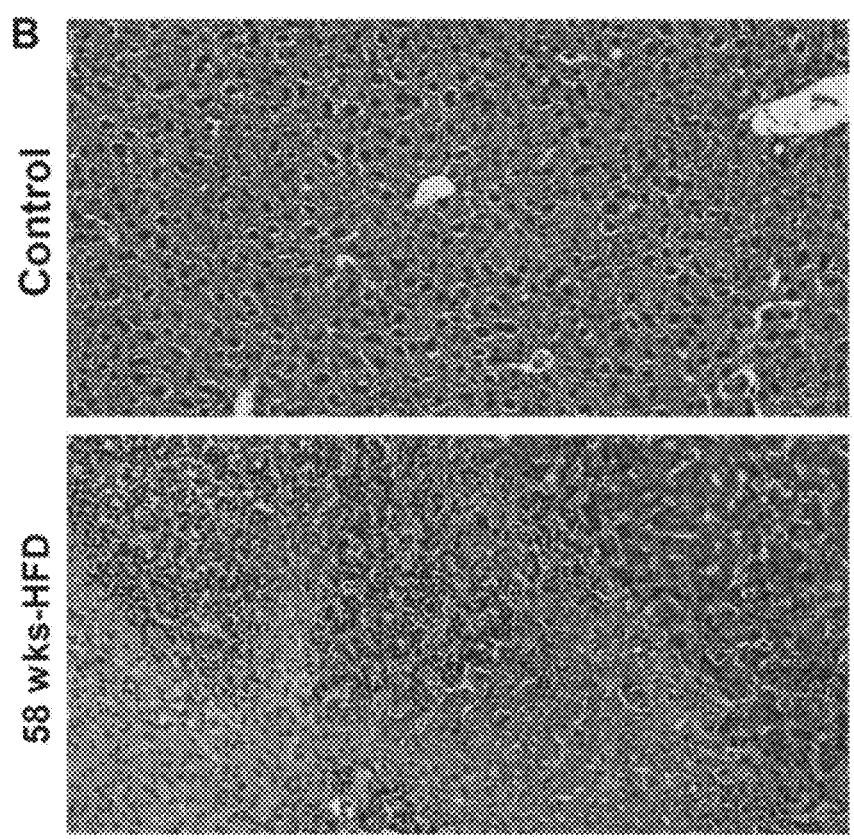
Figure 24C:
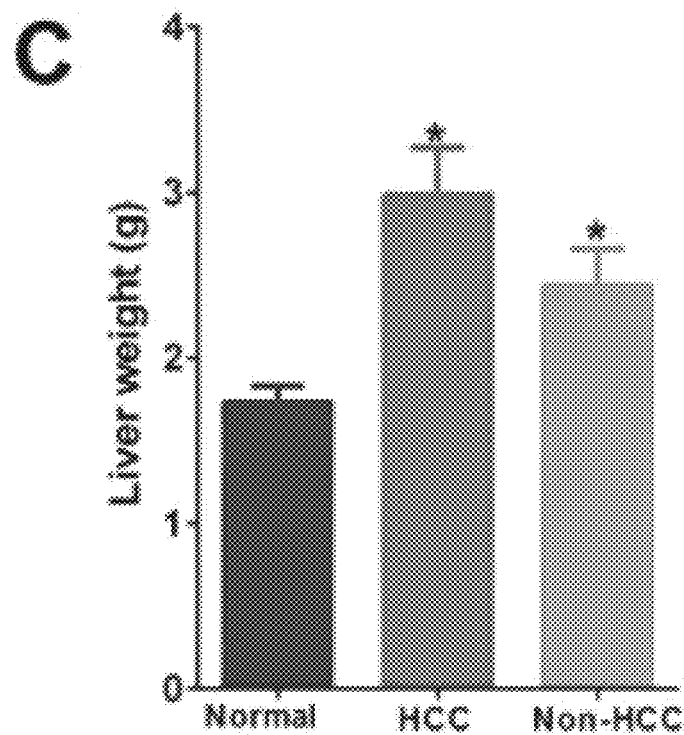
Figure 24D:
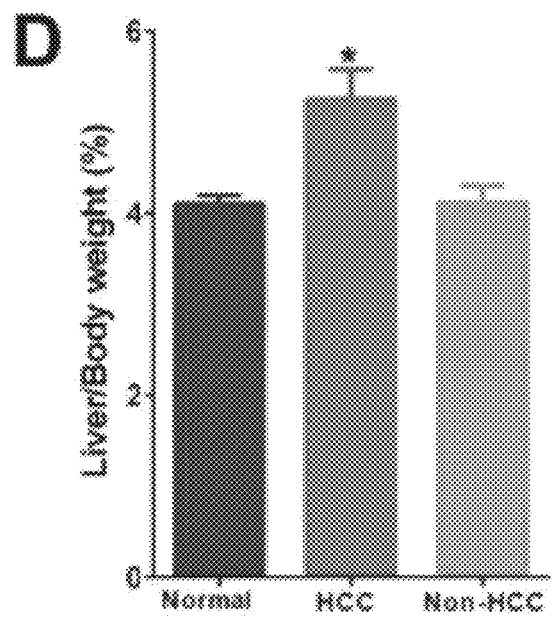

That significantly increased BAs in liver were observed in STZ-HFD treated mice leads to the hypothesis that HFD-induced high concentrations of BAs and their retention in liver may act as tumor promoters. Since STZ was classified as potential carcinogen by International Agency for Research on Cancer, we explored if HFD alone will develop liver cancer, although no HCC was observed in male mice treated with STZ alone for 20 weeks. In this long-term HFD intervention study, liver tumor was observed in more than half (6 out of 11) of the HFD-fed mice at week 58 (FIGS. 24A and 24B). Liver weight (FIG. 24C) and liver to body weight ratio (FIG. 24D) was markedly increased in HFD-fed induced HCC mice. LPS levels in plasma, liver and feces were all significantly increased in HCC mice (FIG. 24E). Notably, liver and plasma BAs, TCA, GCA and TCDCA were increased in all mice fed with HFD but with statistical significance in those mice developed HCC as compared to normal (FIGS. 24F1-24F3 and 24G1-24G3).

Enhancing intestinal excretion of hydrophobic BAs can prevent HCC development

Figure 4:
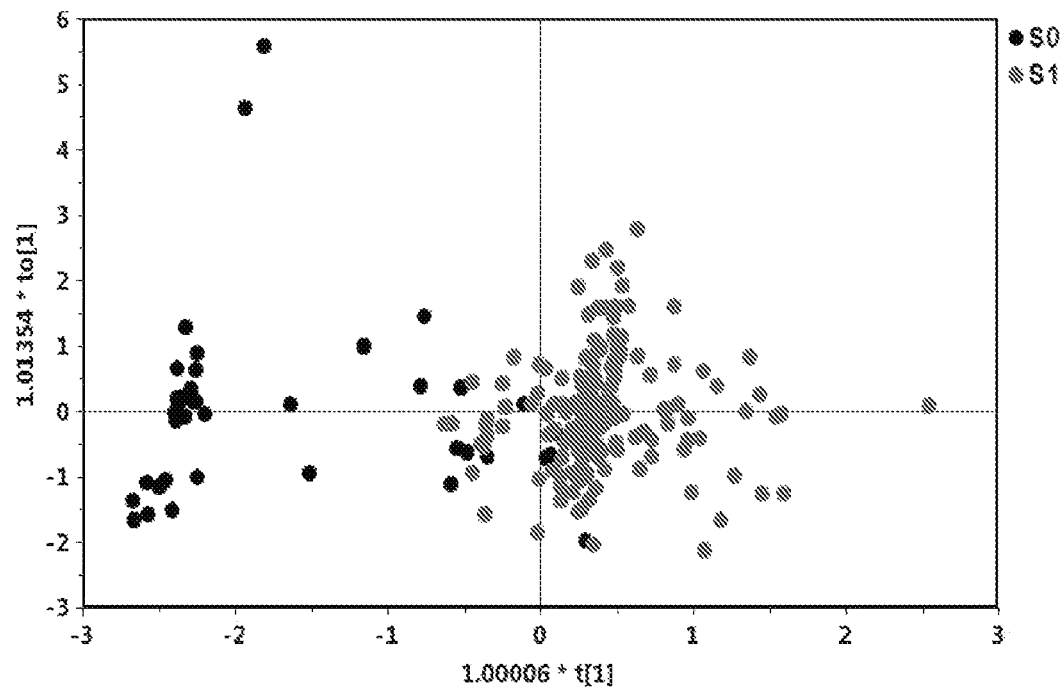
FIG. 4 depicts OPLS-DA scores plot established with serine, DCA and 7-KLCA in patients with liver fibrosis at stage 0 and 1 (NASH vs. stage 1 Fibrosis).
Figure 25A:
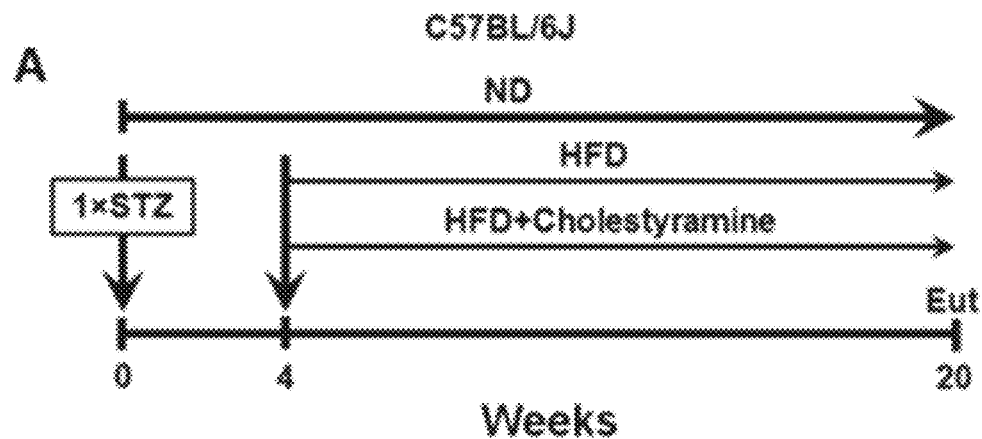
Figure 25B:
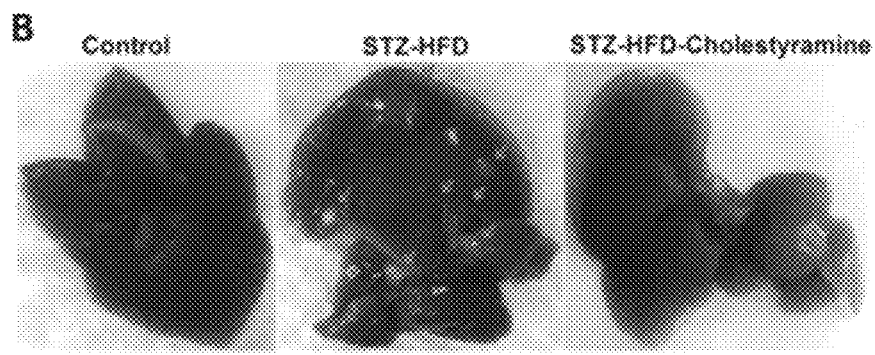
Figure 25C:
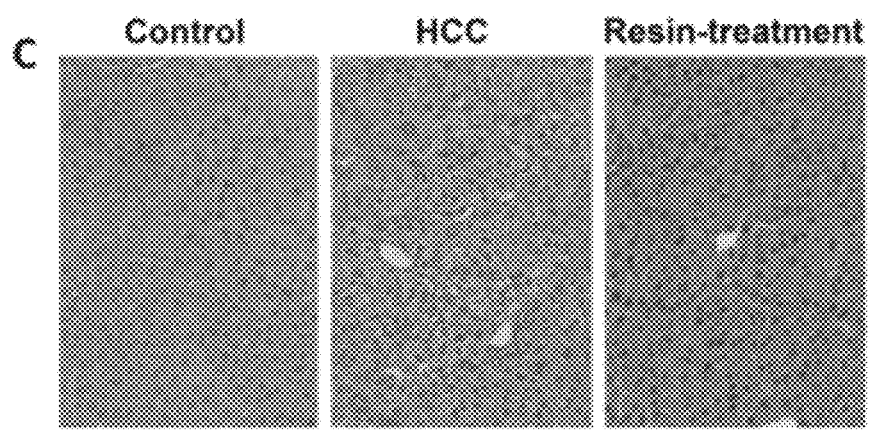
Figure 25G:
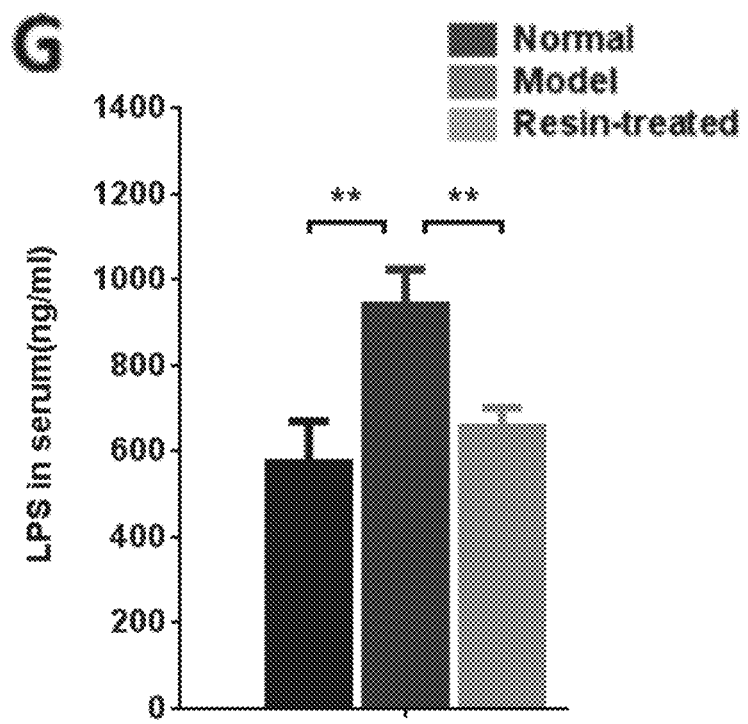
Figure 25H:
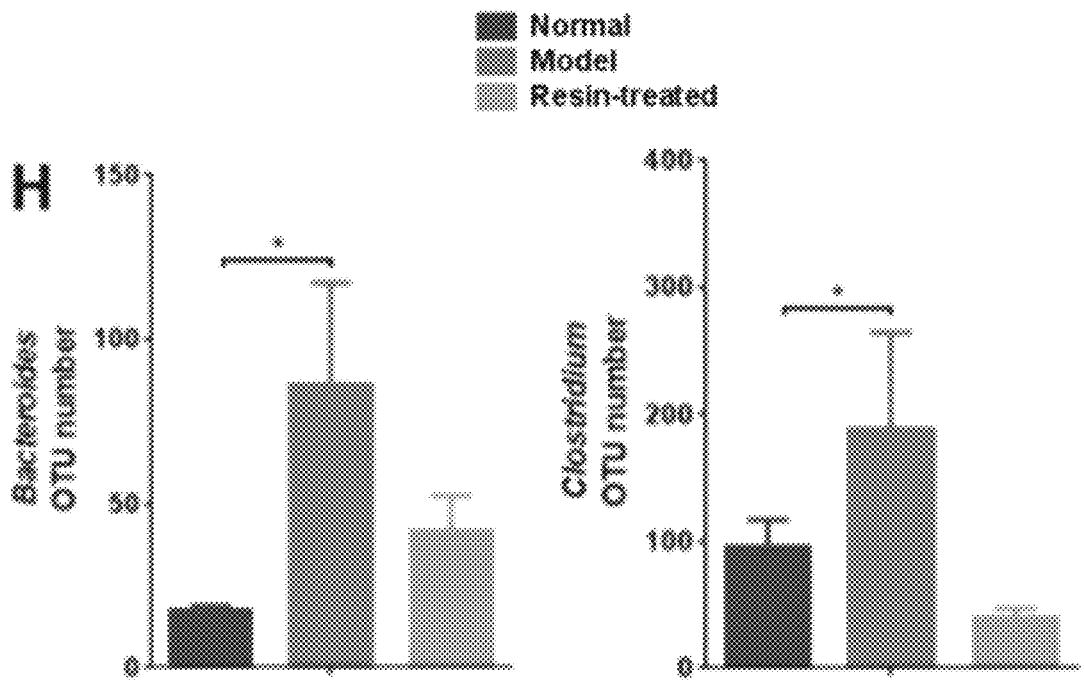

HFD-induced accumulation of hepatic BAs was shown to promote liver tumor. To ascertain the role of BAs in HCC development, we repeated the STZ-HFD mice model and reduced the amount of BAs in mice with oral administration of cholestyramine (FIG. 25A). We observed that compared with the STZ-HFD model group, cholestyramine feeding significantly reduced the incidence and size of liver malignant lesions (FIG. 25B). The histology from STZ-HFD was normalized by cholestyramine treatment, which was supported by the reversed pathological features in blood and liver tissue (FIGS. 25C and 25D). After cholestyramine administration, the levels of IL-6, TNF-α, collagen Type 1, and the expressions of cancer-related genes Glypican-3 (Gpc3) were normalized (FIGS. 25E1-25E4). Altered BA transporters (FIGS. 25E1-25E4) as well as BAs, mainly DCA, TCA, and TCDCA, in liver (FIG. 25F) and plasma were attenuated after cholestyramine intervention. Disruption of gut microbiota and the LPS levels in plasma, liver and feces in response to STZ-HFD intervention were also recovered by cholestyramine intervention (FIGS. 25G and 25H).

Figure 26B:
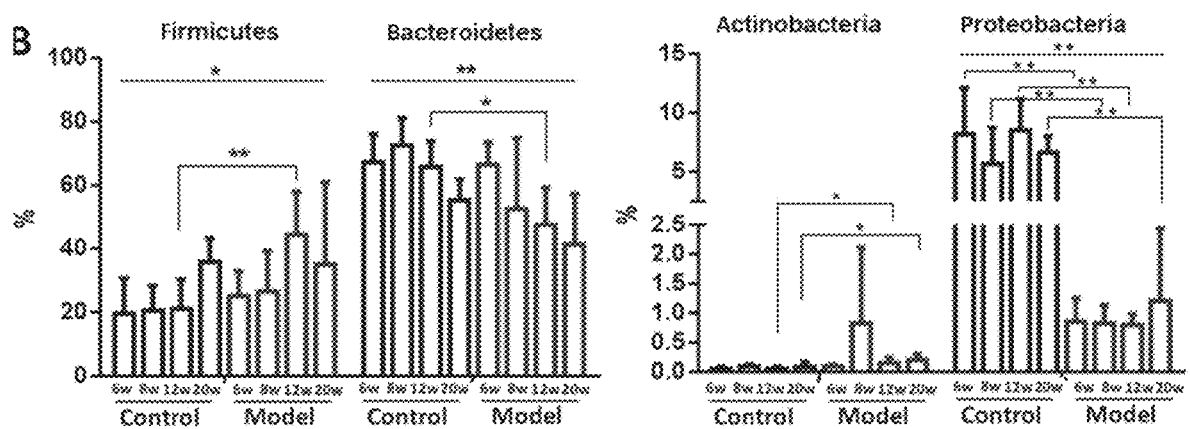
Figure 26C:
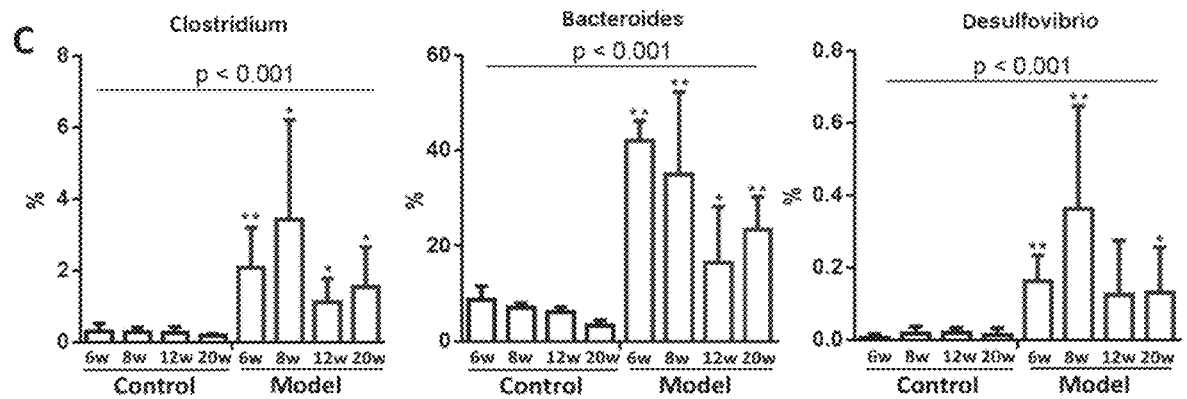
Figure 26D:
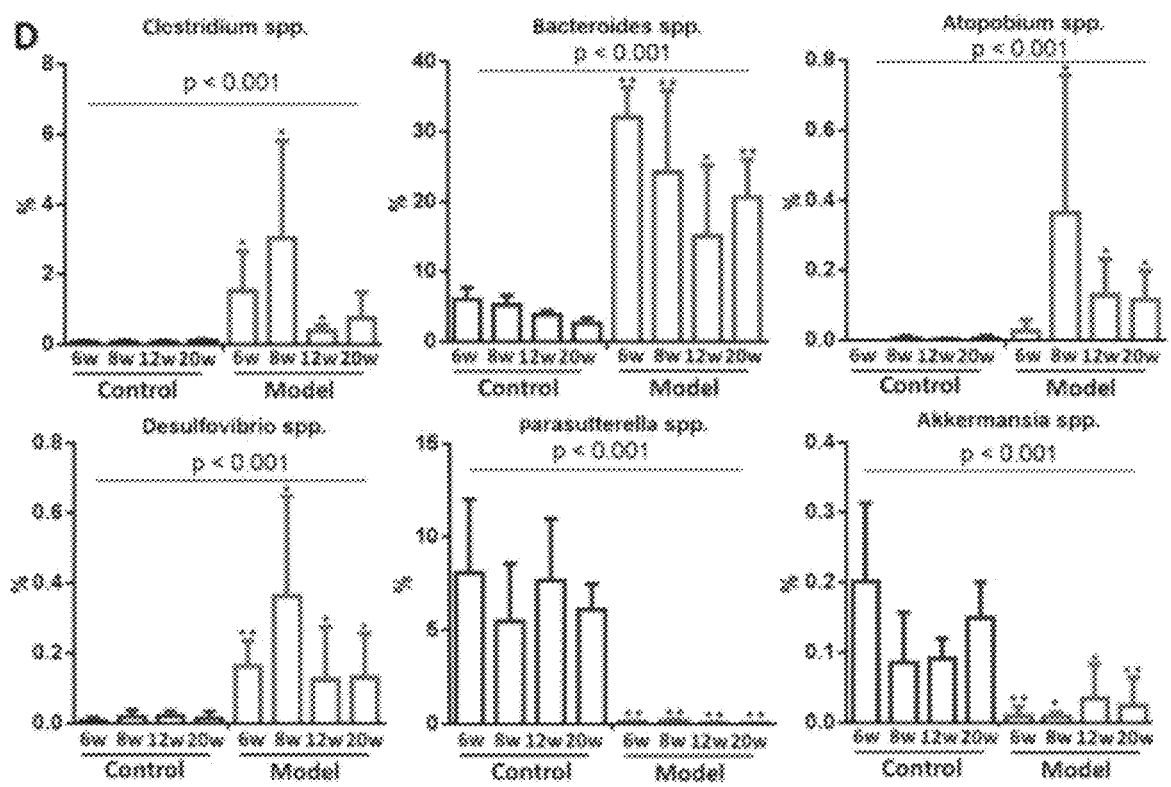

Gut microbiota was significantly altered and correlated with altered BAs during hepatocarcinogenesis Our metagenomics data showed that the gut microbiota was altered significantly in mice with STZ-HFD intervention at week 6, 8, 12, and 20 (FIG. 26A-26D). The abundance of specific microbes changed with the liver disease progression. The relative abundance of OTUs (%) in the fecal Firmicutes and Antinobacteria were significantly increased in model group, while *Bacteroides* and Proteobacteria were significantly decreased when compared to controls at the phylum level (FIG. 26B). The genus level of *Clostridium*, *Bacteroides*, and *Desulfovibrio* were significantly increased in model group (FIG. 26C). The relative abundance of OTUs (%) in the fecal *Clostridium* spp., *Bacteroides* spp., Atopobium app., and *Desulfovibrio* spp. were significantly increased, while Paasutterella spp. and Akkermansia spp were significantly decreased in model group compared to control group at the species level (FIG. 26D). All these bacteria are reported to be involved in the BA deconjugation, dehydroxylation, and BA degradation to $CO_2$ and $H_2O$.

Figure 26E:
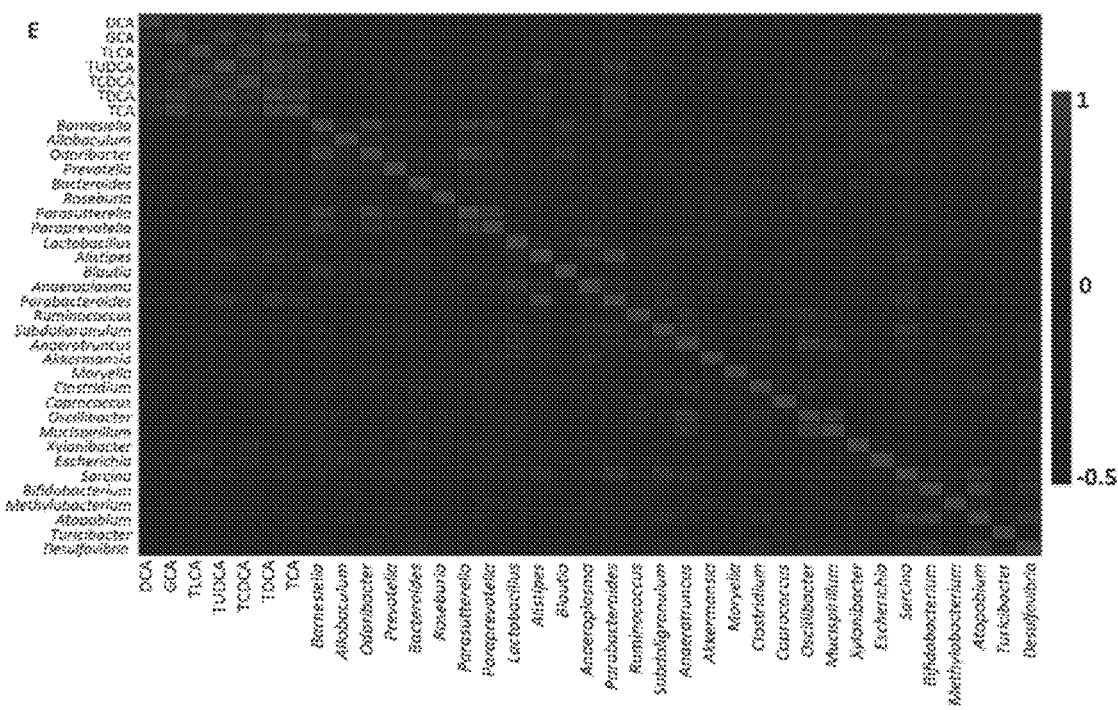

Spearman correlation analysis between the gut microbiota changes and BA concentrations in liver in FIG. 26E showed that TCDCA was significantly negatively correlated with *Barnesiella* (r=−0.31, p=0.033), *Odoribacter* (r=−0.29, p=0.047), *Parasutterella* (r=−0.34, p=0.019), and *Paraprevotella* (r=−0.48, p=0.001), and was significantly positively correlated with *Xylanibacter* (r=0.40, p=0.05) and *Escherichia* (r=0.41, p=0.004). TCA was correlated with *Parabacteroides* (r=0.46, p=0.001), *Alistipes* (r=0.40, p=0.005), and *Sarcina* (r=0.30, p=0.038). GCA was correlated with *Alistipes* (r=0.34, p=0.017) and *Parabacteroides* (r=0.30, p=0.036). TLCA was correlated with *Parasutterella* (r=−0.30, p=0.036), *Paraprevotella* (r=−0.42, p=0.003), *Parabacteroides* (r=0.29, p=0.043), and *Escherichia* (r=0.50, p=0.000). TDCA was correlated *Alistipes* (r=0.51, p=0.000) and *Parabacteroides* (r=0.58, p=0.000).

The fecal primary BAs, CDCA was positively correlated with *Oribacterium* (r=0.31, p=0.03) and *slackia* (r=0.38, p=0.009) abundance and CA was positively correlated with *stenotrophomonas* (r=0.53, p=0.0001) and was negatively correlated with *parabacteroides* (r=−0.29, p=0.046) abundance. On the other hand, *Bacteroides* was positively correlated with LCA (r=0.60, p=8.6E-06), DCA (r=0.41, p=0.005), TLCA (r=0.37, p=0.012) and TDCA (r=0.38, p=0.008). There was also a significant positive correlation between *Clostridium* and DCA (r=0.31, p=0.032) and LCA (r=0.64, p=1.1E-06), GLCA (r=0.46, p=0.001), and GDCA (r=0.48, p=0.001). *Allobaculum* was negatively correlated with TCDCA (r=−0.51, p=0.000), GCA (r=−0.55, p=0.000), TLCA (r=−0.32, p=0.027), TUDCA (r=−0.59, p=0.000) and TCA (r=−0.62, p=0.000). *Parasutterella* was negatively correlated with DCA (r=−0.38, p=0.009) and LCA (r=−0.69, p=8.6E-08). There was a significant negative correlation between *faecalibacterium* and DCA (r=−0.39, p=0.008). LCA was also significantly negatively correlated with *barnesiella* (r=−0.57, p=3.3E-05) and *odoribacter* (r=−0.58, p=4.8E-05).

Figure 27A:
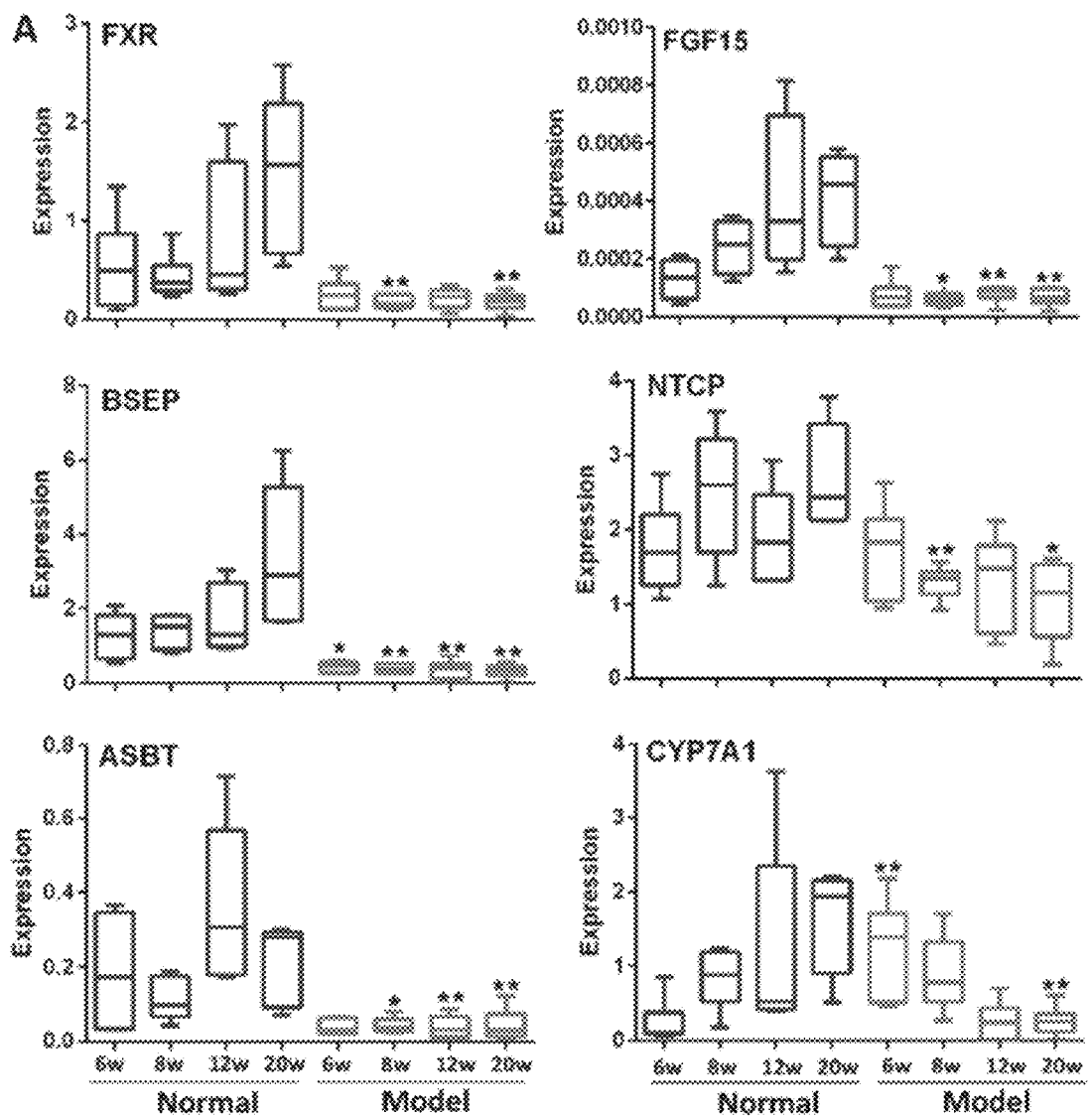
FIG. 27A-FIG. 27B depict data from a study of bile acid modulators as treatment for liver cancer.

BAs Accumulation Down-Regulated the Genes Involved in BA Transport and Synthesis Gene expression analysis showed that a down-regulation of genes involved in BA transport and synthesis in the liver (FIG. 27A). Notably, hepatic FXR expression in mouse liver was significantly decreased in the mouse model with NASH and fibrosis, suggesting a mechanism of down-regulating hepatic efflux transporters, thus leading to increased BA accumulation in hepatocytes and BA-induced liver injury. As evidenced by a significantly down-regulated BSEP at weeks 6, 8, 12, and 20, and upregulated CYP7A1 at week 6, lead to a marked increase of hepatic BA retention in the pathological development of HCC. This is consistent with the observation of abnormally high BA levels in the liver of the mouse model at weeks 6, 8, 12, and 20. All these indicated that HFD-induced fatty liver leads to a dysregulated BA synthesis and transport in the liver with significantly inhibited hepatic FXR and BSEP expressions. Expression of the uptake transporter for BAs, the sodium-taurocholate cotransporting polypeptide (NTCP), the apical sodium dependent bile acid transporter (ASBT) and the SHP was suppressed by STZ-HFD treatment.

Expression of Cytokines was Significantly Increased in Liver Carcinogenesis

Figure 27B:
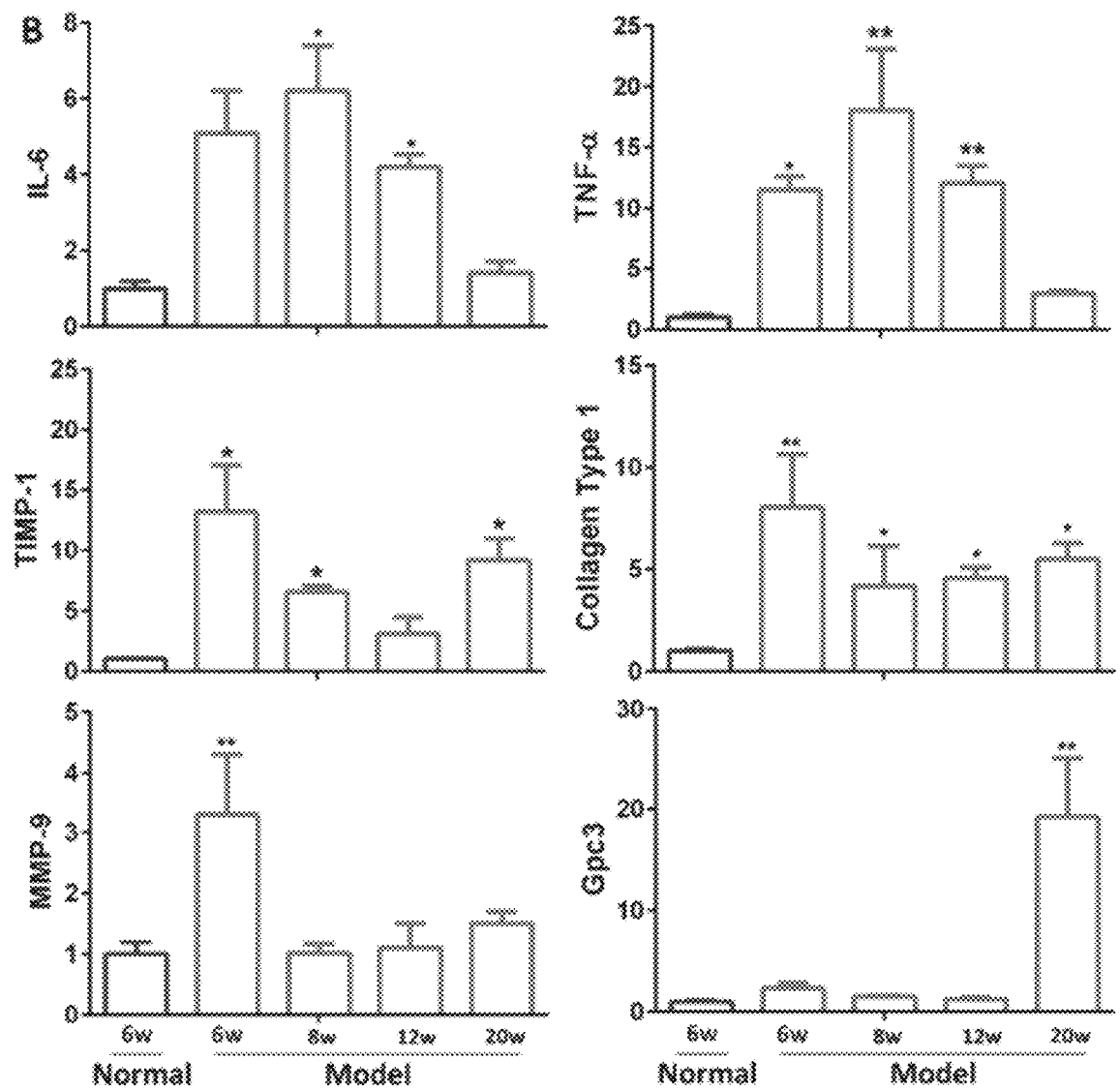

The expressions of pro-inflammation-related genes such as IL-6 and TNF-α were increased in steatosis and steatohepatitis phases, the expressions of fibrosis-related genes, TIMP metallopeptidase inhibitor 1 (TIMP-1) and collagen Type 1, were increased prior to histological evidence of collagen deposition, and the expressions of cancer-related genes (matrix metallopeptidase 9 (MMP-9) and Gpc3 were increased at the HCC stage (FIG. 27B). All these results suggest that STZ-HFD-induced inflammation and oxidative stress inhibited key BA transporters, resulting in increased intrahepatic BA concentrations (FIG. 23), which promote several important proinflammatory, fibrosis, and cancer markers.

Figure 28A:
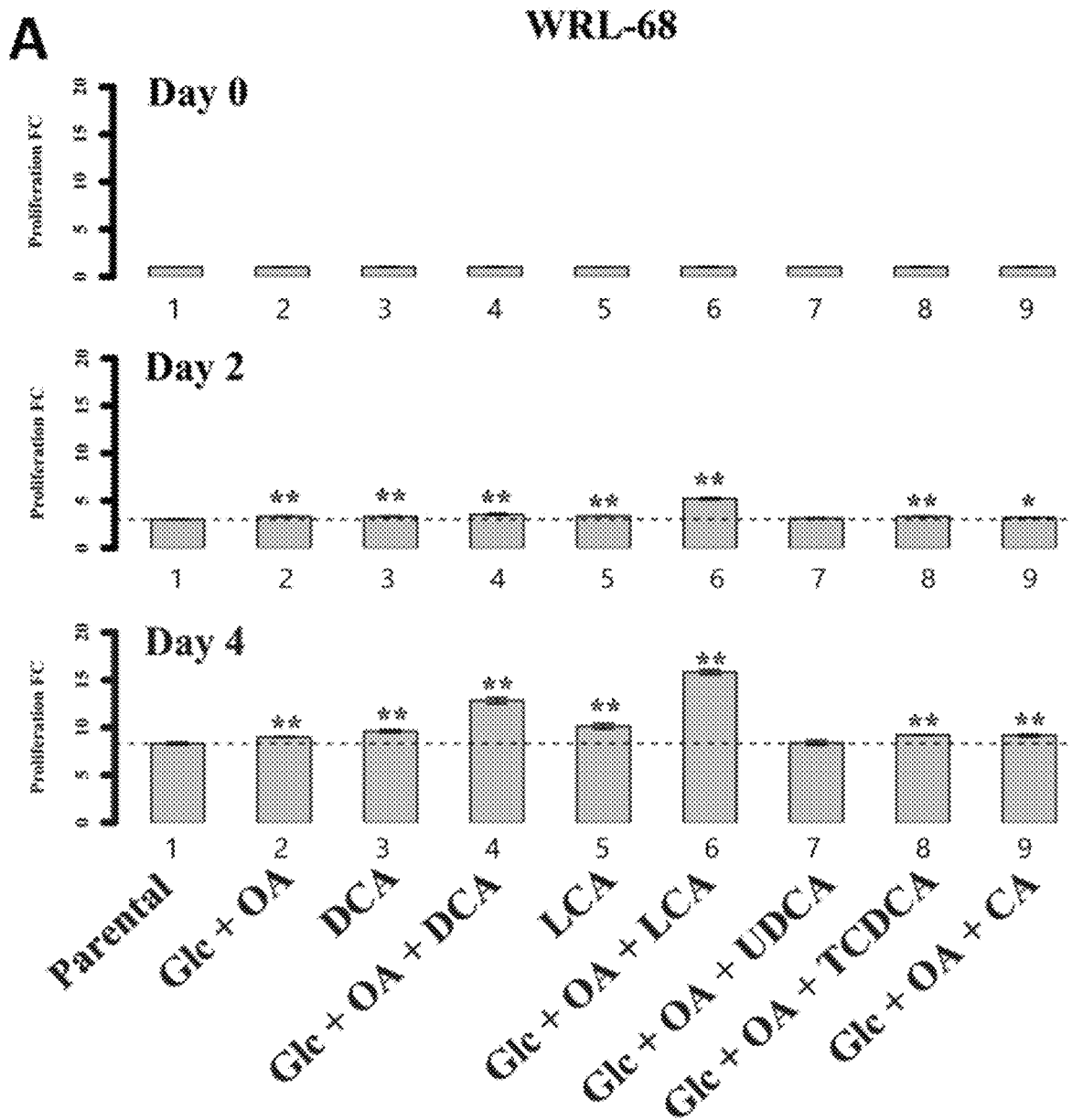
FIG. 28A-FIG. 28D depict data from a study of bile acid modulators as treatment for liver cancer.
Figure 28B:
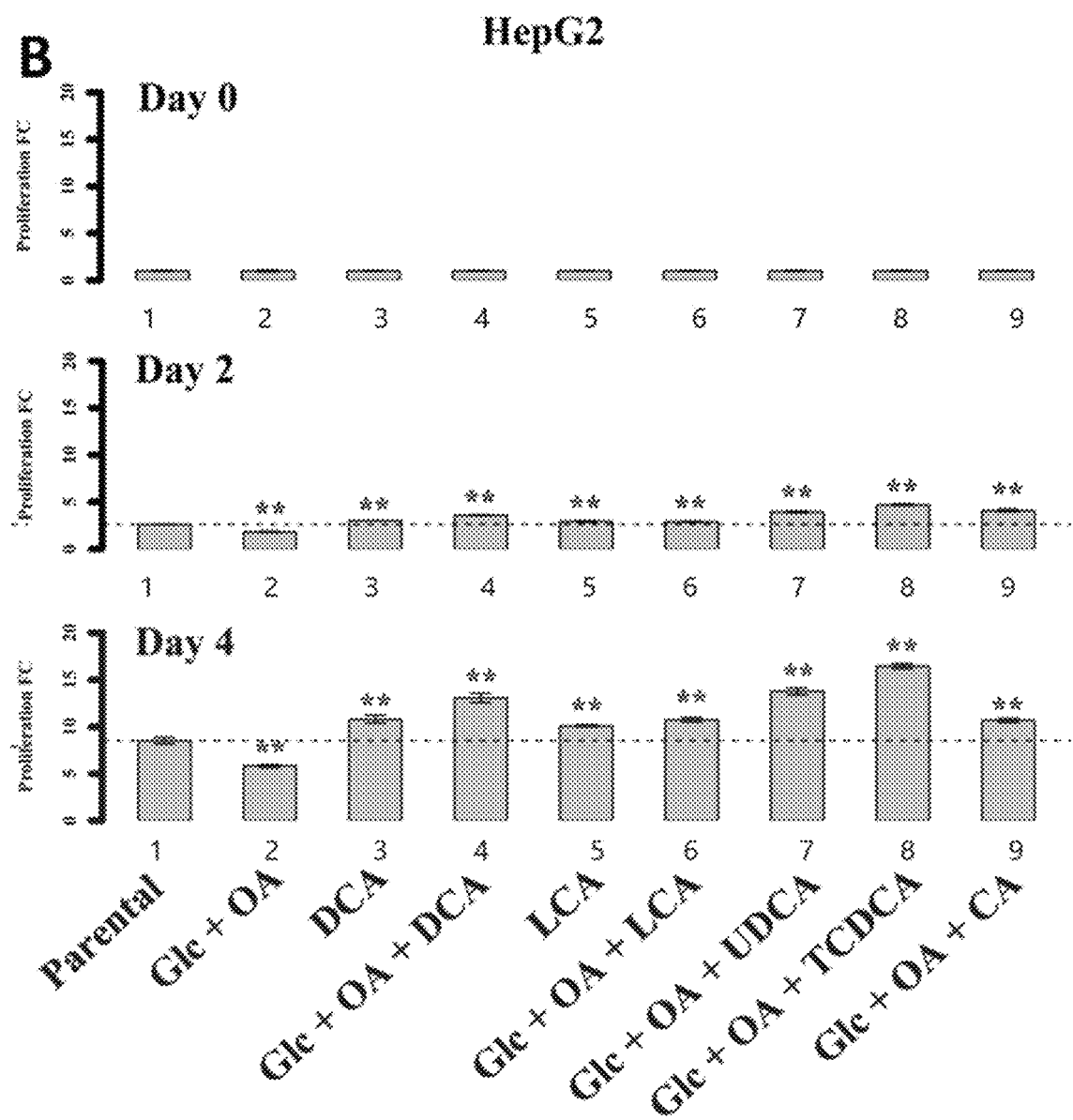

BAs Initiate the Malignant Transformation of Normal Hepatic Cells and Inhibit Tumor Suppressor Gene CEBPα in HepG2 Cell Line We further tested our hypothesis by investigating the tumor promoting effects of BAs, particularly DCA, LCA, TLCA, TCDCA, TCA, CA, UDCA and GCDCA in cultured normal human liver cells with high glucose and fatty acid concentrations. We found DCA, LCA, CA and TCDCA treatment in high glucose (27.5 mM) and oleic acid (0.3 mM) concentrations significantly promoted WRL-68 (FIG. 28A) and THLE-2 proliferation as well as HepG2 cells (FIG. 28B). However, TLCA, TCA and GCDCA treatment had very little influence on the proliferation of WRL-68 cell. These results showed that DCA, LCA or TCDCA are able to accelerate the growth rate of normal hepatic cells in a high glucose and high fat microenvironment, which may lead to malignant transformation of hepatocytes.

DCA or LCA treatment under high glucose and high fat condition didn't enhance anchorage-independent growth of WRL-68 as compared with parental cells but were significantly increased as compared to those treated with high glucose and high fat.

Figure 28C:
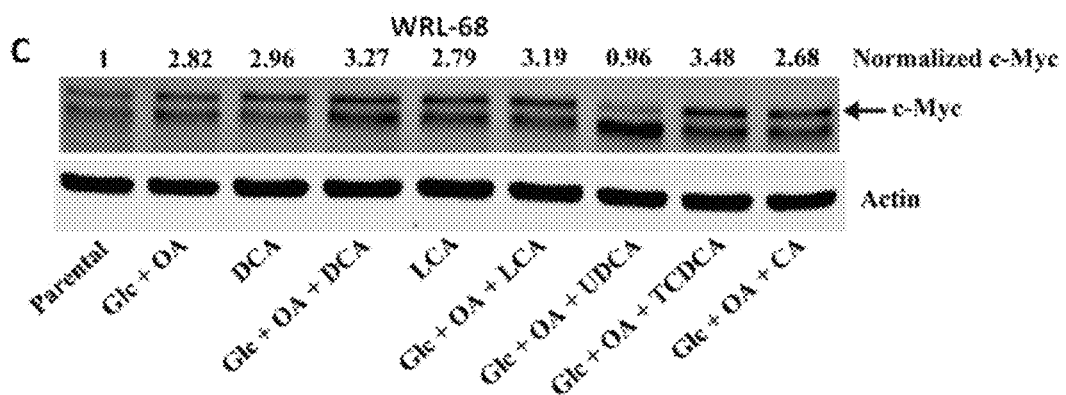
Figure 28D:
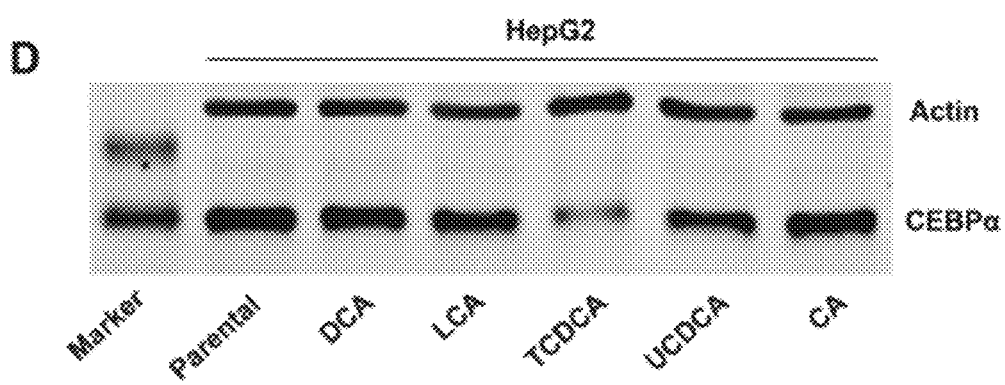

Notably, DCA, LCA and TCDCA increased the expression of oncoprotein c-myc in WRL-68 cells (FIG. 28C) and TCDCA reduced the expression of tumor suppressor gene, CEBPα in HepG2 cells (FIG. 28D).

Discussion

Definitive mechanisms underlying gut microbiota-mediated development of fatty liver disease and its progression to HCC are was lacking prior to this investigation. Our study points to a liver-BA-microbiota metabolic axis as an intrinsic link between gut microbiota and obesity-related liver carcinogenesis.

Using a unique NASH-HCC mouse model, we showed significant accumulation of a panel of hydrophobic and thus, cytotoxic BAs in liver, following the significantly altered gut microbial compositions during liver disease progression.

There are strong and bidirectional interactions between BAs and the gut microbiota through biochemical transformation of BA by microbiota (deconjugation, dehydroxylation, dehydrogenation) and, at the same time, through the antimicrobial effects of BAs. Gut microbiota has been speculated to be a determinant of bile hydrophobicity in a FXR-dependent manner. Similarly, the interactions between FXR and BAs are also bidirectional, where FXR controls BA synthesis, transport, and metabolism in liver and intestine, and BAs activate FXR. FXR contributes to the maintenance of BA homeostasis and reduction of BA toxicity. In rat liver, FXR activation causes the expressional up-regulation of BSEP and SHP. SHP interferes with the transcription genes that control BA synthesis, Cyp7a1 and Cyp8b1. SHP also affects NTCP expression, the sodium dependent BA uptake carrier from portal vein to liver. In the terminal ileum FXR activation causes the down-regulation of the ileal BA-binding protein and up-regulation of OSTα/β, intestinal BA transporters essential for BA reabsorption. The decreased expression of FXR, BSEP, SHP, and then the Cyp7a1, Cyp8b1, NTCP, and OSTα expression in our results explains the accumulation of BAs in liver due to the decreased pump rate from liver to bile and increased reabsorption of BAs from the portal vein.

The results presented here suggest that DCA may contribute to at least certain aspects of HCC development. BAs, particularly, GCA, TCA, GCDCA, TCDCA, GDCA, DCA, and TDCA are all implicated as etiologic agents in cancer of gastrointestinal tract. Continuous exposure to high levels of BAs may induce mutations and aberrant proliferation, as evidenced by enhanced proliferation of normal human cell lines WRL-68 and THLE-2 or HepG2 cells after exposure to DCA, LCA, or TCDCA. The transcription factor c-myc mediates important biological effects including cell growth, proliferation, loss of differentiation and apoptosis and overexpression of c-myc has been observed in human HCC. Previous reports showed that BAs such as DCA and CDCA can be a potent inducer of c-myc in an acid environment, and a more recent study further demonstrated that DCA and CDCA under acidic conditions increased human telomerase reverse transcriptase (hTERT) expression in human gastric cancer cells by activation of c-myc transcription. Elevated levels of serum and hepatic BAs along with an increased expression of the IL-1β and elevated β-catenin and its target gene c-myc were previously observed in the Fxr-null mice, which spontaneously develop hepatocellular lesions, adenomas and carcinomas at 12 months of age.[3]

The liver with high BA levels in model mice shows inflammation, steatohepatitis, fibrosis, and apoptosis. Inflammation is known to stimulate cell death and increase cell turnover, thus promoting liver tumorigenesis STZ intervention and continuous HFD stimulates oxidative stress and inflammation, as evidenced by continuously increased levels of TNF-α, MMP-9, Timp-1, IL-6, Collagen Type 1 and Gpc-3, a marker for HCC, as shown in other reports.

We fed C57BL/6J mice with HFD for 58 weeks to determine if HFD-induced BA overload can induce the liver tumor formation. The long-term feeding of HFD can induce liver tumor in mice in which significantly increased TCDCA, TCA and GCA in plasma and liver were also observed. TCDCA treatment to HepG2 cells markedly increased the cell proliferation and reduced the expression CEBPa, suggesting that BAs alone may have the tumor promoting effects. CEBPα is a tumor suppressor protein which is neutralized or reduced in HCC. Studies showed that the elevated expression of CEBP inhibits liver carcinogenesis in the CEBP knockin mice in which CEBP is expressed from alpha-fetoprotein It was reported that BAs activate the gene encoding SHP via a functional FXR site in its promoter where SHP can bind to CEBPa. Additionally, the primary hepatic BA sensor, FXR also inhibits the expression of gankyrin, a small proteasome subunit that mediates the downregulation of tumor suppressor proteins such as p53, HNF4α and CEBPα in the development of HCC.

Oral administration of cholestyramine significantly reduced the levels of IL-6, TNF-α, and the expressions of collagen Type 1 and Gpc3 and can prevent tumorigenesis in the mice, which gives new impetus to therapeutic efforts to reduce elevated BA levels or to counteract the pro-inflammatory and pro-carcinogenic toxicity of intestinal BAs.

Figure 29:
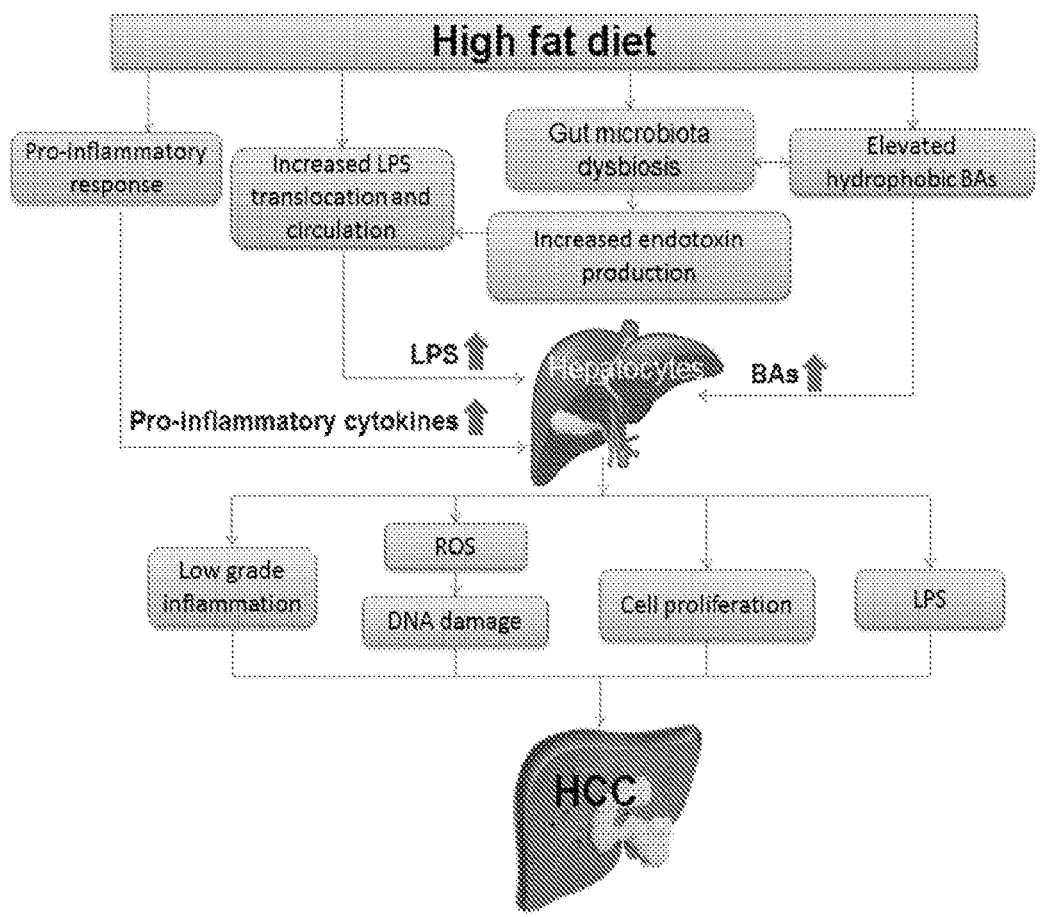
FIG. 29 depicts mechanisms through which BAs could collaboratively function to promote hepatic carcinogenesis.

Based on these results, we determined that BAs could collaboratively function to promote hepatic carcinogenesis through several mechanisms (FIG. 29). The first mechanism is that BAs slowly induce metabolic transformation of hepatocytes. Our results showed that secondary BAs and TCDCA are able to accelerate the growth rate of normal hepatic cells in a high glucose and high fat microenvironment. This is not a sufficient evidence for their tumor promoting effects. However, if we take into consideration apoptosis-inducing effect of secondary BAs, which have been extensively reported, it becomes clear that the chronic exposure to excessive amounts of BAs leads to increased and selective growth of hepatocytes that are resistant to apoptosis. The continued renewal of the hepatocytes exposed to high levels of BAs leads to continued decrease of apoptotic cells, increase of hepatocytes that are apoptosis resistant and/or cells with unrepaired DNA damage.

The second mechanism is the BA-induced cholestatic liver injury due to long-term exposure to excessive amounts of hepatic BAs which leads to increased oxidative stress that can lead to DNA damage, mitochondrial damage and disruption of cell membranes in hepatocytes, ultimately leading to HCC via mechanisms of increasing ROS levels, activating Ras and NF-κB. Our results collectively showed that a HFD-induced liver damage resulted from increased secondary BAs production in intestine and increased circulation to and retention in liver due to down-regulated BSEP.

The loss of FXR anti-inflammatory effect in liver is another mechanism of BA-promoted liver tumorigenesis. Hepatic FXR exerts anti-inflammatory activity by inhibiting activation of the pro-inflammatory transcription factor NF-κB. However, such inhibition is also bi-directional and mediated by BAs. Under inflammatory conditions, elevated pro-inflammatory cytokines, TNF-α and IL-6, modulate FXR-α2 expression with concurrent decreases in BSEP expression[48] and reduce bile canalicular contraction, leading to BA accumulation in hepatocytes. On the other hand, increased hepatic BA concentration can stimulate secretion of pro-inflammatory cytokines, TNF-α, and IL-1β from Kupffer cells (hepatic resident macrophages) that activate TNF receptor signaling and the mitogen-activated protein kinase (MAPK)/JNK pathway. Activated NF-κB in the liver inhibits hepatic FXR signaling and this in turn downregulates SHP. It is known that $Fxr^{-/-}Shp^{-/-}$ mice develop spontaneous liver tumors when exposed to chronically elevated BAs.[5]

Additionally, as our results show, BA-induced increase in LPS production in intestine may also represent an important factor contributing to obesity-related hepatic carcinogenesis. LPS has been implicated as important cofactors in the pathogenesis of liver injury and has been shown to promote hepatic fibrosis. In the pathogenesis of chronic inflammation and autoimmune diseases, dysregulated intestinal BAs may be a causal factor for increased absorption of bacterial LPS,[50] thereby promoting systemic inflammation in the organism. These processes are also bi-directionally regulated, as an increase in LPS levels involves a decrease in BA excretion and bile flow leading to further increased intestinal absorption of bacterial LPS. Our results showed that genes involved in inflammation and oxidative stress were attenuated after cholestyramine intervention together with the lowered BA accumulation in liver, indicating an improved liver pathology.

Taken together, the BA-promoted liver carcinogenesis is a complex process involving multiple mechanisms, multiple metabolic organs (liver, bile, intestine, and gut microbiome) and collaborative actions among different BA species. Tt is now clear that HFD-induced or obesity-related liver carcinogenesis can be mediated by altered gut microbiota which results in sustained retention of high concentrations of hepatic BAs.

This example demonstrates that bile acid modulators provide a useful treatment for subjects identified as having a liver disease status and prevent or slow the progression liver cancer and associated conditions.

Example 22 Discovery of Additional Biomarker Panels

Potential biomarkers were initially evaluated and selected using both univariate and multivariate analyses. The univariate analyses include parametric tests for normal-distributed variables (e.g., student's t test and ANOVA), and nonparametric tests for those that failed to follow normal distribution (e.g., Mann Whitney U test and Kruskal Wallis test). The capabilities of metabolize-type biomarkers for discriminating different stages of liver fibrosis were further evaluated using partial least squares (PLS), Pearson/Spearman correlations, clustering, multiple linear/logistic regression, and random forest. With a list of discovered potential biomarkers, a machine learning tool was developed in this invention, which is based on random forest (RF), to obtain a surprising combination of biomarkers. A panel of biomarkers including Taurochenodeoxycholic acid (TCDCA), Glycochenodeoxycholic acid (GCDCA), Glycocholic acid (GCA), Glycoursodeoxycholic acid (GUDCA), Taurocholic acid (TCA), 7-Ketocholic acid (7-KLCA), Tauroursodeoxycholic acid (TUDCA), Myristoleic acid (C14:1 n5), Palmitoleic acid (C16:1 n7), elaidic acid (C18:1 n9t), Erucic acid (C22:1 n9), Docosatetraenoic acid (C22:4 n-6)/Arachidonic acid (C20:4 n6) ratio, Linoleic acid (C18:2 n6)/gamma-Linolenic acid (C18:3 n6) ratio, Palmitic acid (C16:0), Palmitic acid (C16:0)/Palmitoleic acid (C16:1 n7), Tyrosine, Fructose, Fructose/glucose ratio are demonstrated to have the most powerful stratification ability for liver fibrosis, e.g. to distinguish between fibrosis stages and/or cirrhosis.

Figure 30:
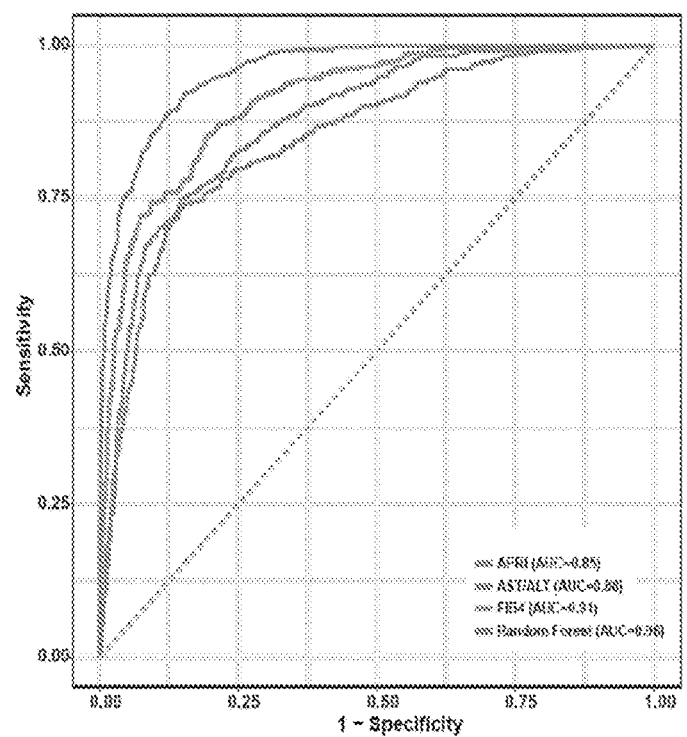
FIG. 30. depicts an ROC curve in the discrimination of three stages of liver fibrosis in using a panel of biomarkers that includes Glycocholic acid (GCA), Taurocholic acid (TCA), Palmitoleic acid (C16:1 n7), Palmitic acid (C16:0), Palmitic acid (C16:0)/Palmitoleic acid (C16:1 n7), Tyrosine, and Fructose.

A RF model built on a panel of biomarkers that includes Glycocholic acid (GCA), Taurocholic acid (TCA), Palmitoleic acid (C16:1 n7), Palmitic acid (C16:0), Palmitic acid (C16:0)/Palmitoleic acid (C16:1 n7), Tyrosine, and Fructose achieved surprising performance on discriminating three liver fibrosis stage patients according to the receiver operating characteristic (ROC) curves with the area under curve (AUC) equals to 0.96 (FIG. 30).

Figure 31:
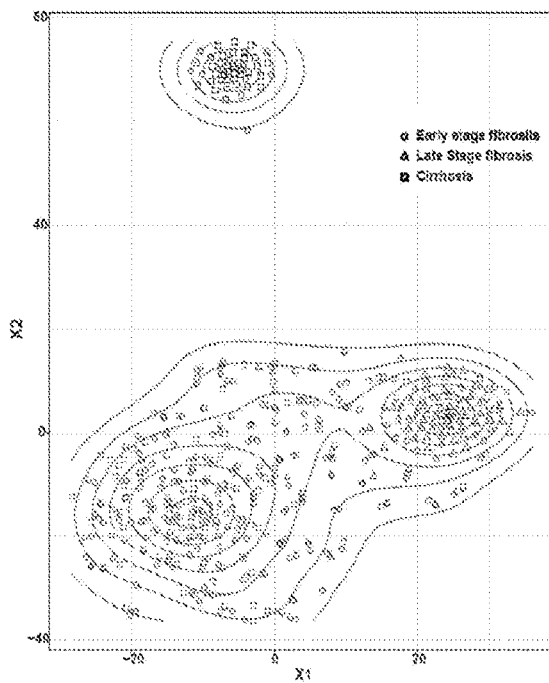
FIG. 31 depicts liver disease patients' distribution in random tree space.
Figure 32B:
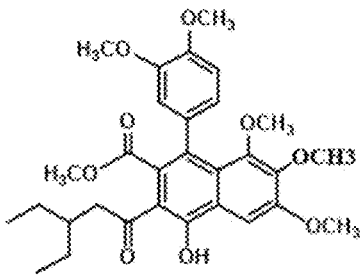

Using this RF model, the stage probability of a new sample can be predicted with these metabolite variables feeding to the model (FIG. 31).

Accordingly, the biomarker panels taught in this example provide powerful diagnosis of liver disease in subjects and/or ability to distinguish liver fibrosis stage. Additionally, any of the biomarkers can be used alone or in combination with a subset of other biomarkers of the panel (or other panel taught herein) to diagnose liver disease and/or distinguish liver fibrosis stage.

The citations provided herein are hereby incorporated by reference for the cited subject matter.

What is claimed is:

1. A method of treating a liver disease status in a subject, the method comprising:
   (a) obtaining a biological sample from the subject;
   (b) extracting from the sample each biomarker of a biomarker panel, wherein the panel comprises the following biomarkers: glycochenodeoxycholic acid (GCDCA), glycolic acid (GCA), taurochenodeoxycholic acid (TCDCA), taurocholic acid (TCA), 7-ketocholic acid (7-KLCA), glycoursodeoxycholic acid (GUDCA), and tauroursodeoxycholic acid (TUDCA);
   (c) measuring an amount of each of the biomarkers in the extract;
   (d) correlating the measured amount from each biomarker from step (c) with the subject's liver disease status by calculating:
   (i) a probability score A according to the following regression model:

Probability=exp{−1.923−0.004(GCDCA)+0.010(GCA)+0.116(TCDCA)−0.072(TCA)−0.035(GUDCA)−0.122(TUDCA)+0.025(7-KLCA)}/(1+exp{−1.923−0.004(GCDCA)+0.010(GCA)+0.116(TCDCA)−0.072(TCA)−0.035(GUDCA)−0.122(TUDCA)+0.025(7-KLCA)}, (ii) a probability score B according to the following regression model:

Probability=exp{−0.511−0.0003(GCDCA)+0.001(GCA)+0.007(TCDCA)−0.007(TCA)−0.003(GUDCA)+0.083(TUDCA)+0.491(7-KLCA)}/(1+exp{−0.511−0.0003(GCDCA)+0.001(GCA)+0.007(TCDCA)−0.007(TCA)−0.003(GUDCA)+0.083(TUDCA)+0.491(7-KLCA)}, and (iii) a probability score C according to the following regression model:

Probability=exp{−2.514−0.0002(GCDCA)+0.001(GCA)+0.0004(TCDCA)−0.001(TCA)+0.001(GUDCA)+0.020(TUDCA)+0.020(7-KLCA)}/(1+exp{−2.514−0.0002(GCDCA)+0.001(GCA)+0.0004(TCDCA)−0.001(TCA)+0.001(GUDCA)+0.020(TUDCA)+0.020(7-KLCA)};

(e) determining the subject's liver disease status based on the calculations in step (d) by comparing the score A, the score B and the score C to a threshold value associated with a subject who does not have a liver disease, and
   (i) if the score A exceeds 0.429, determining the subject has non-alcoholic steatohepatitis (NASH),
   (ii) if the score B exceeds 0.811, determining the subject has fibrosis, and
   (iii) if the score C exceeds 0.224, determining the subject has cirrhosis; and
   (f) treating the subject with NASH, fibrosis or cirrhosis based on the determination in step (e) with a treatment comprising administering a bile acid-binding resin.

2. The method of claim 1, wherein in step (c), the amount of the biomarker is measured by mass-spectroscopy ('MS').

3. The method of claim 2, wherein the MS is one or more of time-of-flight MS, ion trap MS, quadrupole MS, magnetic sector MS, ion cyclotron resonance MS, and electrostatic sector analyzer MS.

4. The method of claim 1, wherein the extracting in step (b) comprises filtering the sample to provide a filtrate, and step (c) comprises measuring the amount of each biomarker in the filtrate.

5. The method of claim 4, wherein the method comprises a step of protein precipitation prior to filtering.

6. The method of claim 1, wherein prior to step (b) the method comprises separating each biomarker from the other biomarkers.

7. The method of claim 6, wherein the separation step is effected by use of gas chromatography ('GC') or liquid chromatography ('LC').

8. The method of claim 1, wherein in step (c), the measuring is effected by use of ultra-performance liquid chromatography-triple quadrupole mass spectrometry ('UPLC-TQMS').

9. The method of claim 1, wherein in step (c) the measuring is effected by use of enzymatic analysis, chemical analysis, colorimetric analysis, or fluorometric analysis.

* * * * *